(12) United States Patent
Flechtner et al.

(10) Patent No.: US 9,765,125 B2
(45) Date of Patent: *Sep. 19, 2017

(54) **FUSED ANTIGEN VACCINES AND COMPOSITIONS AGAINST *STREPTOCOCCUS PNEUMONIAE***

(71) Applicants: Genocea Biosciences, Inc., Cambridge, MA (US); Children's Medical Center Corporation, Boston, MA (US)

(72) Inventors: Jessica Flechtner, Sudbury, MA (US); Richard Malley, Beverly, MA (US)

(73) Assignees: Genocea Biosciences, Inc., Cambridge, MA (US); Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/373,179

(22) PCT Filed: Jan. 18, 2013

(86) PCT No.: PCT/US2013/022309
§ 371 (c)(1),
(2) Date: Jul. 18, 2014

(87) PCT Pub. No.: WO2013/109995
PCT Pub. Date: Jul. 25, 2013

(65) Prior Publication Data
US 2015/0056239 A1 Feb. 26, 2015

Related U.S. Application Data

(60) Provisional application No. 61/589,267, filed on Jan. 20, 2012.

(51) Int. Cl.
*C07K 14/315* (2006.01)
*A61K 39/09* (2006.01)
*A61K 39/39* (2006.01)

(52) U.S. Cl.
CPC ........ *C07K 14/3156* (2013.01); *A61K 39/092* (2013.01); *A61K 39/39* (2013.01); *C07K 2319/00* (2013.01)

(58) Field of Classification Search
None
See application file for complete search history.

(56) References Cited

U.S. PATENT DOCUMENTS

| 7,384,775 | B2 | 6/2008 | Zagursky et al. |
| 9,393,294 | B2* | 7/2016 | Gierahn |
| 2005/0020813 | A1* | 1/2005 | Masignani ......... C07K 14/3156 530/350 |
| 2010/0015168 | A1 | 1/2010 | Maione et al. |
| 2011/0020386 | A1 | 1/2011 | Gierahn et al. |

FOREIGN PATENT DOCUMENTS

| WO | WO-02077021 A2 | 10/2002 |
| WO | WO-2011008548 A1 | 1/2011 |
| WO | WO-2012/100234 A1 | 7/2012 |
| WO | WO-2013/134656 A1 | 9/2013 |

OTHER PUBLICATIONS

Simell, B. et al., The fundamental link between pneumococcal carriage and disease, Expert Rev. Vaccines, 11(7): 841-855 (2012).
Li, Y. et al., Distinct Effects on Diversifying Selection by Two Mechanisms of Immunity against *Streptococcus pneumoniae*, PLOS Pathogens, 8(11): e1002989 1-11 (2012).
Moffitt, K.L. et al., T17-Based Vaccine Design for Prevention of Colonization, Cell Host & Microbe, 9(2): 158-165 (2010).
International Search Report for PCT/US13/22309, mailed May 24, 2013, 4 pages.
Written Opinion for PCT/US13/22309, mailed May 24, 2013, 12 pages.

* cited by examiner

*Primary Examiner* — S. Devi
(74) *Attorney, Agent, or Firm* — Choate, Hall & Stewart; Rolando Medina

(57) ABSTRACT

*Streptococcus pneumoniae* is a major health concern, especially in very young, elderly, or immunocompromised patients. The present disclosure provides, inter alia, certain highly effective vaccines and pharmaceutical compositions in *Streptococcus pneumoniae* that contain fusion proteins. The antigens may be used therapeutically or prophylactically.

20 Claims, 33 Drawing Sheets

S. PNEUMONIAE ASPIRATION CHALLENGE: SUMMARY OF STUDIES

| | SEPSIS 1 | SEPSIS 2 | SEPSIS 3 | SEPSIS 4 | PT1^ | PT2* |
|---|---|---|---|---|---|---|
| ALUM OR NRS | 20% | 10% | 30% | 20% | 0% | 20% |
| 0148 | 44% | 10% | | | 10% | |
| 1912 | | 70% | | 20% | | |
| 2108 | | | | | 30% | |
| PdT | | 50% | | 20% | | |
| PspA | | | | | 10% | 70% |
| 0148 +1912 | | 40% | 40% | | | |
| 0148 +2108 | | | | | 20% | |
| 0148 +PdT | 70% | 17% | 25% | | | |
| 0148 +PspA | | | | | 30% | 70% |
| 1912 +PdT | | | | 40% | | |
| 2108 +PspA | | | | | 67% | |
| 0148 +PdT+0641N | 90% | | | | | |
| 0148 +PdT+1912 | | 60% | 60% | | | |
| 0148 +2108+PspA | | | | | 50% | 70% |
| WCB | 70% | 100% | 100% | 100% | 90% | 90% |

°10ug PROTEIN DOSE
*PspA - PURIFIED IgG
^PspA - ASCITES

FIG. 15

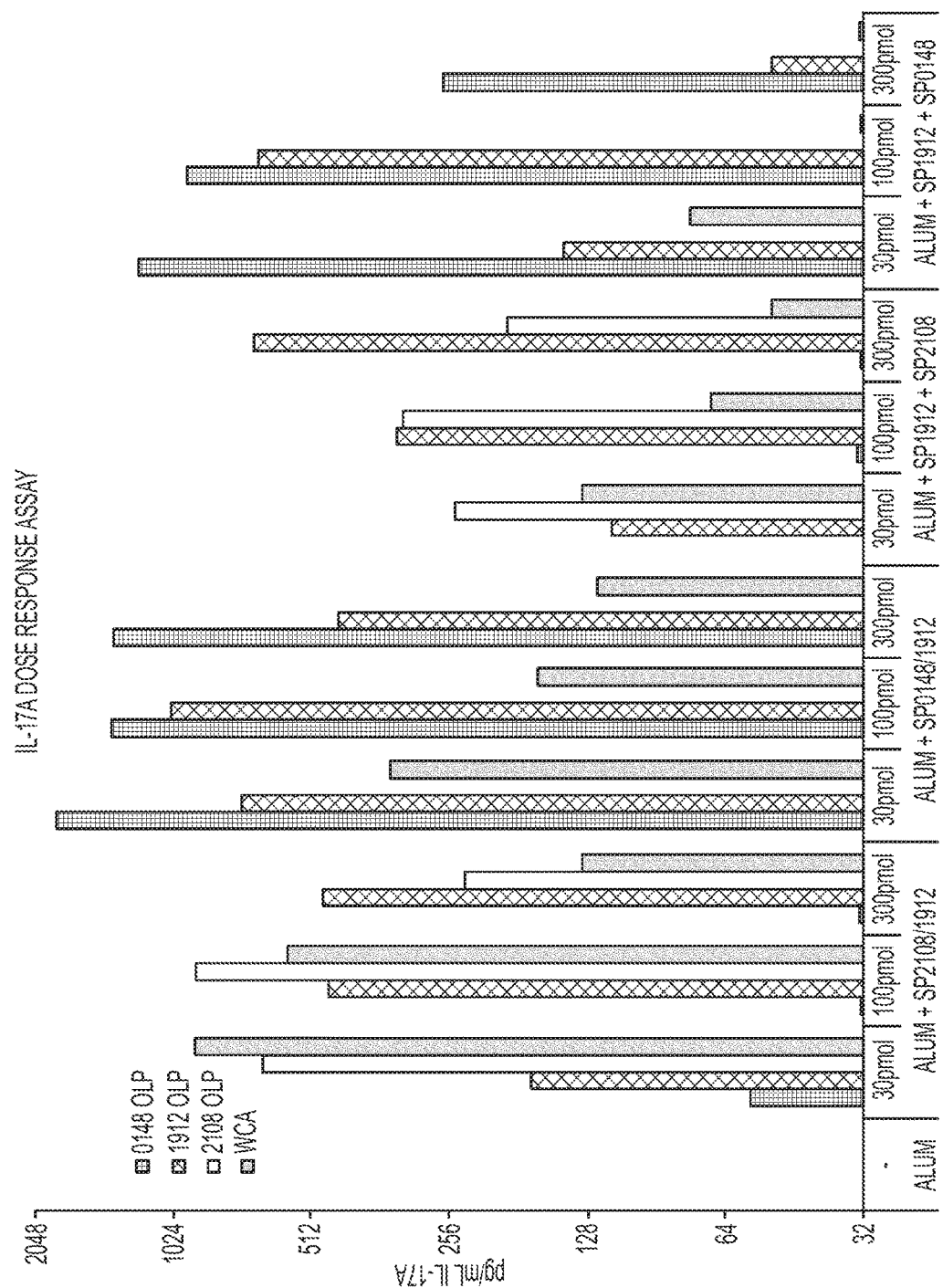

SEQUENCE LISTING

<160> NUMBER OF SEQ IDS: 144

<210> SEQ ID NO 1
<211> LENGTH: 255
<212> TYPE: PRT
<213> ORGANISM: Streptococcus pneumonia
<220> FEATURE:
<223> OTHER INFORMATION: SP0148 lacking signal sequence

<400> SEQUENCE: 1

Met Cys Ser Gly Gly Ala Lys Lys Glu Gly Glu Ala Ala Ser Lys Lys
1               5                   10                  15

Glu Ile Ile Val Ala Thr Asn Gly Ser Pro Lys Pro Phe Ile Tyr Glu
            20                  25                  30

Glu Asn Gly Glu Leu Thr Gly Tyr Glu Ile Glu Val Val Arg Ala Ile
        35                  40                  45

Phe Lys Asp Ser Asp Lys Tyr Asp Val Lys Phe Glu Leu Thr Glu Trp
    50                  55                  60

Ser Gly Val Phe Ala Gly Leu Asp Ala Asp Arg Tyr Asn Met Ala Val
65                  70                  75                  80

Asn Asn Leu Ser Tyr Thr Lys Glu Arg Ala Glu Lys Tyr Leu Tyr Ala
                85                  90                  95

Ala Pro Ile Ala Gln Asn Pro Asn Val Leu Val Lys Lys Asp Asp
            100                 105                 110

Ser Ser Ile Lys Ser Leu Asp Asp Ile Gly Gly Lys Ser Thr Glu Val
            115                 120                 125

Val Gln Ala Thr Thr Ser Ala Lys Gln Leu Glu Ala Tyr Asn Ala Glu
        130                 135                 140

His Thr Asp Asn Pro Thr Ile Leu Asn Tyr Thr Lys Ala Asp Phe Gln
145                 150                 155                 160

Gln Ile Met Val Arg Leu Ser Asp Gly Gln Phe Asp Tyr Lys Ile Phe
                165                 170                 175

Asp Lys Ile Gly Val Glu Thr Val Ile Lys Asn Gln Gly Leu Asp Asn
            180                 185                 190

Leu Lys Val Ile Glu Leu Pro Ser Asp Gln Pro Tyr Val Tyr Pro
        195                 200                 205

Leu Leu Ala Gln Gly Gln Asp Glu Leu Lys Ser Phe Val Asp Lys Arg
210                 215                 220

Ile Lys Glu Leu Tyr Lys Asp Gly Thr Leu Glu Lys Leu Ser Lys Gln
225                 230                 235                 240

Phe Phe Gly Asp Thr Tyr Leu Pro Ala Glu Ala Asp Ile Lys Glu
                245                 250                 255

<210> SEQ ID NO 2
<211> LENGTH: 277
<212> TYPE: PRT
<213> ORGANISM: Streptococcus pneumonia
<220> FEATURE:
<223> OTHER INFORMATION: SP0148 including signal sequence (277 amino
      acids with N-terminal E)

<400> SEQUENCE: 2

Met Lys Lys Ile Val Lys Tyr Ser Ser Leu Ala Ala Leu Ala Leu Val
1               5                   10                  15

Ala Ala Gly Val Leu Ala Ala Cys Ser Gly Gly Ala Lys Lys Glu Gly
            20                  25                  30

Glu Ala Ala Ser Lys Lys Glu Ile Ile Val Ala Thr Asn Gly Ser Pro
        35                  40                  45

Lys Pro Phe Ile Tyr Glu Glu Asn Gly Glu Leu Thr Gly Tyr Glu Ile
50                  55                  60

Glu Val Val Arg Ala Ile Phe Lys Asp Ser Asp Lys Tyr Asp Val Lys
65                  70                  75                  80

Phe Glu Lys Thr Glu Trp Ser Gly Val Phe Ala Gly Leu Asp Ala Asp
                85                  90                  95

Arg Tyr Asn Met Ala Val Asn Asn Leu Ser Tyr Thr Lys Glu Arg Ala
            100                 105                 110

Glu Lys Tyr Leu Tyr Ala Ala Pro Ile Ala Gln Asn Pro Asn Val Leu
        115                 120                 125

Val Val Lys Lys Asp Asp Ser Ser Ile Lys Ser Leu Asp Asp Ile Gly
    130                 135                 140

Gly Lys Ser Thr Glu Val Val Gln Ala Thr Thr Ser Ala Lys Gln Leu
145                 150                 155                 160

Glu Ala Tyr Asn Ala Glu His Thr Asp Asn Pro Thr Ile Leu Asn Tyr

```
                    165                 170                 175
Thr Lys Ala Asp Phe Gln Gln Ile Met Val Arg Leu Ser Asp Gly Gln
            180                 185                 190

Phe Asp Tyr Lys Ile Phe Asp Lys Ile Gly Val Glu Thr Val Ile Lys
            195                 200                 205

Asn Gln Gly Leu Asp Asn Leu Lys Val Ile Glu Leu Pro Ser Asp Gln
        210                 215                 220

Gln Pro Tyr Val Tyr Pro Leu Leu Ala Gln Gly Gln Asp Glu Leu Lys
225                 230                 235                 240

Ser Phe Val Asp Lys Arg Ile Lys Glu Leu Tyr Lys Asp Gly Thr Leu
                245                 250                 255

Glu Lys Leu Ser Lys Gln Phe Phe Gly Asp Thr Tyr Leu Pro Ala Glu
            260                 265                 270

Ala Asp Ile Lys Glu
        275

<210> SEQ ID NO 3
<211> LENGTH: 255
<212> TYPE: PRT
<213> ORGANISM: Streptococcus pneumonia
<220> FEATURE:
<223> OTHER INFORMATION: SP0148 consensus lacking signal sequence
<220> FEATURE:
<221> NAME/KEY: MOD_RES
<222> LOCATION: (11)..(11)
<223> OTHER INFORMATION: Glu or Gln
<220> FEATURE:
<221> NAME/KEY: MOD_RES
<222> LOCATION: (24)..(24)
<223> OTHER INFORMATION: Gly or Ser
<220> FEATURE:
<221> NAME/KEY: MOD_RES
<222> LOCATION: (27)..(27)
<223> OTHER INFORMATION: Lys or Arg
<220> FEATURE:
<221> NAME/KEY: MOD_RES
<222> LOCATION: (30)..(30)
<223> OTHER INFORMATION: Ile or Asn
<220> FEATURE:
<221> NAME/KEY: MOD_RES
<222> LOCATION: (56)..(56)
<223> OTHER INFORMATION: Asp or Asn
<220> FEATURE:
<221> NAME/KEY: MOD_RES
<222> LOCATION: (58)..(58)
<223> OTHER INFORMATION: Lys or any amino acid
<220> FEATURE:
<221> NAME/KEY: MOD_RES
<222> LOCATION: (83)..(83)
<223> OTHER INFORMATION: Leu or Ile
<220> FEATURE:
<221> NAME/KEY: MOD_RES
<222> LOCATION: (111)..(111)
<223> OTHER INFORMATION: Asp or Glu
<220> FEATURE:
<221> NAME/KEY: MOD_RES
<222> LOCATION: (159)..(159)
<223> OTHER INFORMATION: Leu or Phe
<220> FEATURE:
<221> NAME/KEY: MOD_RES
<222> LOCATION: (192)..(192)
<223> OTHER INFORMATION: Asn or Tyr
<220> FEATURE:
<221> NAME/KEY: MOD_RES
<222> LOCATION: (199)..(199)
<223> OTHER INFORMATION: Pro or Ser
<220> FEATURE:
<221> NAME/KEY: MOD_RES
<222> LOCATION: (255)..(255)
<223> OTHER INFORMATION: May or may not be present
```

```
<400> SEQUENCE: 3

Met Cys Ser Gly Gly Ala Lys Lys Glu Gly Xaa Ala Ala Ser Lys Lys
1               5                   10                  15

Glu Ile Ile Val Ala Thr Asn Xaa Ser Pro Xaa Pro Phe Xaa Tyr Glu
                20                  25                  30

Glu Asn Gly Glu Leu Thr Gly Tyr Glu Ile Glu Val Arg Ala Ile
            35                  40                  45

Phe Lys Asp Ser Asp Lys Tyr Xaa Val Xaa Phe Glu Lys Thr Glu Trp
    50                  55                  60

Ser Gly Val Phe Ala Gly Leu Asp Ala Asp Arg Tyr Asn Met Ala Val
65                  70                  75                  80

Asn Asn Xaa Ser Tyr Thr Lys Glu Arg Ala Glu Lys Tyr Leu Tyr Ala
                85                  90                  95

Ala Pro Ile Ala Gln Asn Pro Asn Val Leu Val Val Lys Lys Xaa Asp
                100                 105                 110

Ser Ser Ile Lys Ser Leu Asp Asp Ile Gly Gly Lys Ser Thr Glu Val
                115                 120                 125

Val Gln Ala Thr Thr Ser Ala Lys Gln Leu Glu Ala Tyr Asn Ala Glu
    130                 135                 140

His Thr Asp Asn Pro Thr Ile Leu Asn Tyr Thr Lys Ala Asp Xaa Gln
145                 150                 155                 160

Gln Ile Met Val Arg Leu Ser Asp Gly Gln Phe Asp Tyr Lys Ile Phe
                165                 170                 175

Asp Lys Ile Gly Val Glu Thr Val Ile Lys Asn Gln Gly Leu Asp Xaa
                180                 185                 190

Leu Lys Val Ile Glu Leu Xaa Ser Asp Gln Gln Pro Tyr Val Tyr Pro
                195                 200                 205

Leu Leu Ala Gln Gly Gln Asp Glu Leu Lys Ser Phe Val Asp Lys Arg
                210                 215                 220

Ile Lys Glu Leu Tyr Lys Asp Gly Thr Leu Glu Lys Leu Ser Lys Gln
225                 230                 235                 240

Phe Phe Gly Asp Thr Tyr Leu Pro Ala Glu Ala Asp Ile Lys Glu
                245                 250                 255

<210> SEQ ID NO 4
<211> LENGTH: 277
<212> TYPE: PRT
<213> ORGANISM: Streptococcus pneumonia
<220> FEATURE:
<223> OTHER INFORMATION: SP0148 consensus including signal sequence
<220> FEATURE:
<221> NAME/KEY: MOD_RES
<222> LOCATION: (14)..(14)
<223> OTHER INFORMATION: Ala or Gly
<220> FEATURE:
<221> NAME/KEY: MOD_RES
<222> LOCATION: (20)..(20)
<223> OTHER INFORMATION: Val or Leu
<220> FEATURE:
<221> NAME/KEY: MOD_RES
<222> LOCATION: (33)..(33)
<223> OTHER INFORMATION: Glu or Gln
<220> FEATURE:
<221> NAME/KEY: MOD_RES
<222> LOCATION: (46)..(46)
<223> OTHER INFORMATION: Gly or Ser
<220> FEATURE:
<221> NAME/KEY: MOD_RES
<222> LOCATION: (49)..(49)
<223> OTHER INFORMATION: Lys or Arg
<220> FEATURE:
<221> NAME/KEY: MOD_RES
```

```
<222> LOCATION: (52)..(52)
<223> OTHER INFORMATION: Ile or Asn
<220> FEATURE:
<221> NAME/KEY: MOD_RES
<222> LOCATION: (78)..(78)
<223> OTHER INFORMATION: Asp or Asn
<220> FEATURE:
<221> NAME/KEY: MOD_RES
<222> LOCATION: (80)..(80)
<223> OTHER INFORMATION: Lys or any amino acid
<220> FEATURE:
<221> NAME/KEY: MOD_RES
<222> LOCATION: (105)..(105)
<223> OTHER INFORMATION: Leu or Ile
<220> FEATURE:
<221> NAME/KEY: MOD_RES
<222> LOCATION: (133)..(133)
<223> OTHER INFORMATION: Asp or Glu
<220> FEATURE:
<221> NAME/KEY: MOD_RES
<222> LOCATION: (181)..(181)
<223> OTHER INFORMATION: Leu or Phe
<220> FEATURE:
<221> NAME/KEY: MOD_RES
<222> LOCATION: (214)..(214)
<223> OTHER INFORMATION: Asn or Tyr
<220> FEATURE:
<221> NAME/KEY: MOD_RES
<222> LOCATION: (221)..(221)
<223> OTHER INFORMATION: Pro or Ser
<220> FEATURE:
<221> NAME/KEY: MOD_RES
<222> LOCATION: (277)..(277)
<223> OTHER INFORMATION: May or may not be present

<400> SEQUENCE: 4

Met Lys Lys Ile Val Lys Tyr Ser Ser Leu Ala Ala Leu Xaa Leu Val
1               5                   10                  15

Ala Ala Gly Xaa Leu Ala Ala Cys Ser Gly Gly Ala Lys Lys Glu Gly
            20                  25                  30

Xaa Ala Ala Ser Lys Lys Glu Ile Ile Val Ala Thr Asn Xaa Ser Pro
        35                  40                  45

Xaa Pro Phe Xaa Tyr Glu Glu Asn Gly Glu Leu Thr Gly Tyr Glu Ile
    50                  55                  60

Glu Val Val Arg Ala Ile Phe Lys Asp Ser Asp Lys Tyr Xaa Val Xaa
65                  70                  75                  80

Phe Glu Lys Thr Glu Trp Ser Gly Val Phe Ala Gly Leu Asp Ala Asp
                85                  90                  95

Arg Tyr Asn Met Ala Val Asn Xaa Ser Tyr Thr Lys Glu Arg Ala
                100                 105                 110

Glu Lys Tyr Leu Tyr Ala Ala Pro Ile Ala Gln Asn Pro Asn Val Leu
            115                 120                 125

Val Val Lys Lys Xaa Asp Ser Ser Ile Lys Ser Leu Asp Asp Ile Gly
        130                 135                 140

Gly Lys Ser Thr Glu Val Val Gln Ala Thr Thr Ser Ala Lys Gln Leu
145                 150                 155                 160

Glu Ala Tyr Asn Ala Glu His Thr Asp Asn Pro Thr Ile Leu Asn Tyr
                165                 170                 175

Thr Lys Ala Asp Xaa Gln Gln Ile Met Val Arg Leu Ser Asp Gly Gln
            180                 185                 190

Phe Asp Tyr Lys Ile Phe Asp Lys Ile Gly Val Glu Thr Val Ile Lys
        195                 200                 205

Asn Gln Gly Leu Asp Xaa Leu Lys Val Ile Glu Leu Xaa Ser Asp Gln
    210                 215                 220
```

```
Gln Pro Tyr Val Tyr Pro Leu Leu Ala Gln Gly Gln Asp Glu Leu Lys
225                 230                 235                 240

Ser Phe Val Asp Lys Arg Ile Lys Glu Leu Tyr Lys Asp Gly Thr Leu
                245                 250                 255

Glu Lys Leu Ser Lys Gln Phe Phe Gly Asp Thr Tyr Leu Pro Ala Glu
            260                 265                 270

Ala Asp Ile Lys Glu
        275

<210> SEQ ID NO 5
<211> LENGTH: 400
<212> TYPE: PRT
<213> ORGANISM: Streptococcus pneumonia
<220> FEATURE:
<223> OTHER INFORMATION: SP2108 lacking signal sequence

<400> SEQUENCE: 5

Met Cys Gly Ser Lys Thr Ala Asp Lys Pro Ala Asp Ser Gly Ser Ser
1               5                   10                  15

Glu Val Lys Glu Leu Thr Val Tyr Val Asp Gly Tyr Lys Ser Tyr
            20                  25                  30

Ile Glu Glu Val Ala Lys Ala Tyr Glu Lys Glu Ala Gly Val Lys Val
                35                  40                  45

Thr Leu Lys Thr Gly Asp Ala Leu Gly Leu Asp Lys Leu Ser Leu
    50                  55                  60

Asp Asn Gln Ser Gly Asn Val Pro Asp Val Met Met Ala Pro Tyr Asp
65                  70                  75                  80

Arg Val Gly Ser Leu Gly Ser Asp Gly Gln Leu Ser Glu Val Lys Leu
                85                  90                  95

Ser Asp Gly Ala Lys Thr Asp Asp Thr Thr Lys Ser Leu Val Thr Ala
            100                 105                 110

Ala Asn Gly Lys Val Tyr Gly Ala Pro Ala Val Ile Glu Ser Leu Val
        115                 120                 125

Met Tyr Tyr Asn Lys Asp Leu Val Lys Asp Ala Pro Lys Thr Phe Ala
    130                 135                 140

Asp Leu Glu Asn Leu Ala Lys Asp Ser Lys Tyr Ala Phe Ala Gly Glu
145                 150                 155                 160

Asp Gly Lys Thr Thr Ala Phe Leu Ala Asp Trp Thr Asn Phe Tyr Tyr
                165                 170                 175

Thr Tyr Gly Leu Leu Ala Gly Asn Gly Ala Tyr Val Phe Gly Gln Asn
            180                 185                 190

Gly Lys Asp Ala Lys Asp Ile Gly Leu Ala Asn Asp Gly Ser Ile Val
        195                 200                 205

Gly Ile Asn Tyr Ala Lys Ser Trp Tyr Glu Lys Trp Pro Lys Gly Met
    210                 215                 220

Gln Asp Thr Glu Gly Ala Gly Asn Leu Ile Gln Thr Gln Phe Gln Glu
225                 230                 235                 240

Gly Lys Thr Ala Ala Ile Ile Asp Gly Pro Trp Lys Ala Gln Ala Phe
                245                 250                 255

Lys Asp Ala Lys Val Asn Tyr Gly Val Ala Thr Ile Pro Thr Leu Pro
            260                 265                 270

Asn Gly Lys Glu Tyr Ala Ala Phe Gly Gly Gly Lys Ala Trp Val Ile
        275                 280                 285

Pro Gln Ala Val Lys Asn Leu Glu Ala Ser Gln Lys Phe Val Asp Phe
    290                 295                 300
```

```
Leu Val Ala Thr Glu Gln Gln Lys Val Leu Tyr Asp Lys Thr Asn Glu
305                 310                 315                 320

Ile Pro Ala Asn Thr Glu Ala Arg Ser Tyr Ala Glu Gly Lys Asn Asp
                325                 330                 335

Glu Leu Thr Thr Ala Val Ile Lys Gln Phe Lys Asn Thr Gln Pro Leu
            340                 345                 350

Pro Asn Ile Ser Gln Met Ser Ala Val Trp Asp Pro Ala Lys Asn Met
        355                 360                 365

Leu Phe Asp Ala Val Ser Gly Gln Lys Asp Ala Lys Thr Ala Ala Asn
370                 375                 380

Asp Ala Val Thr Leu Ile Lys Glu Thr Ile Lys Gln Lys Phe Gly Glu
385                 390                 395                 400

<210> SEQ ID NO 6
<211> LENGTH: 423
<212> TYPE: PRT
<213> ORGANISM: Streptococcus pneumonia
<220> FEATURE:
<223> OTHER INFORMATION: SP2108 including signal
      sequence/maltose/maltodextrin ABC transporter,
      maltose/maltodextrin-binding protein (Streptococcus pneumoniae
      TIGR4)
<300> PUBLICATION INFORMATION:
<308> DATABASE ACCESSION NUMBER: 14973620
<300> PUBLICATION INFORMATION:
<308> DATABASE ACCESSION NUMBER: AAK76167.1

<400> SEQUENCE: 6

Met Ser Ser Lys Phe Met Lys Ser Ala Ala Val Leu Gly Thr Ala Thr
1               5                   10                  15

Leu Ala Ser Leu Leu Val Ala Cys Gly Ser Lys Thr Ala Asp Lys
                20                  25                  30

Pro Ala Asp Ser Gly Ser Ser Glu Val Lys Glu Leu Thr Val Tyr Val
            35                  40                  45

Asp Glu Gly Tyr Lys Ser Tyr Ile Glu Glu Val Ala Lys Ala Tyr Glu
    50                  55                  60

Lys Glu Ala Gly Val Lys Val Thr Leu Lys Thr Gly Asp Ala Leu Gly
65                  70                  75                  80

Gly Leu Asp Lys Leu Ser Leu Asp Asn Gln Ser Gly Asn Val Pro Asp
                85                  90                  95

Val Met Met Ala Pro Tyr Asp Arg Val Gly Ser Leu Gly Ser Asp Gly
            100                 105                 110

Gln Leu Ser Glu Val Lys Leu Ser Asp Gly Ala Lys Thr Asp Asp Thr
        115                 120                 125

Thr Lys Ser Leu Val Thr Ala Ala Asn Gly Lys Val Tyr Gly Ala Pro
130                 135                 140

Ala Val Ile Glu Ser Leu Val Met Tyr Tyr Asn Lys Asp Leu Val Lys
145                 150                 155                 160

Asp Ala Pro Lys Thr Phe Ala Asp Leu Glu Asn Leu Ala Lys Asp Ser
                165                 170                 175

Lys Tyr Ala Phe Ala Gly Glu Asp Gly Lys Thr Thr Ala Phe Leu Ala
            180                 185                 190

Asp Trp Thr Asn Phe Tyr Tyr Thr Tyr Gly Leu Leu Ala Gly Asn Gly
        195                 200                 205

Ala Tyr Val Phe Gly Gln Asn Gly Lys Asp Ala Lys Asp Ile Gly Leu
    210                 215                 220

Ala Asn Asp Gly Ser Ile Val Gly Ile Asn Tyr Ala Lys Ser Trp Tyr
225                 230                 235                 240
```

```
Glu Lys Trp Pro Lys Gly Met Gln Asp Thr Glu Gly Ala Gly Asn Leu
                245                 250                 255

Ile Gln Thr Gln Phe Gln Gly Lys Thr Ala Ala Ile Ile Asp Gly
    260                 265                 270

Pro Trp Lys Ala Gln Ala Phe Lys Asp Ala Lys Val Asn Tyr Gly Val
        275                 280                 285

Ala Thr Ile Pro Thr Leu Pro Asn Gly Lys Glu Tyr Ala Ala Phe Gly
        290                 295                 300

Gly Gly Lys Ala Trp Val Ile Pro Gln Ala Val Lys Asn Leu Glu Ala
305                 310                 315                 320

Ser Gln Lys Phe Val Asp Phe Leu Val Ala Thr Glu Gln Gln Lys Val
                325                 330                 335

Leu Tyr Asp Lys Thr Asn Glu Ile Pro Ala Asn Thr Glu Ala Arg Ser
                340                 345                 350

Tyr Ala Glu Gly Lys Asn Asp Glu Leu Thr Thr Ala Val Ile Lys Gln
                355                 360                 365

Phe Lys Asn Thr Gln Pro Leu Pro Asn Ile Ser Gln Met Ser Ala Val
        370                 375                 380

Trp Asp Pro Ala Lys Asn Met Leu Phe Asp Ala Val Ser Gly Gln Lys
385                 390                 395                 400

Asp Ala Lys Thr Ala Ala Asn Asp Ala Val Thr Leu Ile Lys Glu Thr
                405                 410                 415

Ile Lys Gln Lys Phe Gly Glu
                420

<210> SEQ ID NO 7
<211> LENGTH: 400
<212> TYPE: PRT
<213> ORGANISM: Streptococcus pneumonia
<220> FEATURE:
<223> OTHER INFORMATION: SP2108 consensus lacking signal sequence
<220> FEATURE:
<221> NAME/KEY: MOD_RES
<222> LOCATION: (18)..(18)
<223> OTHER INFORMATION: Val or Ala
<220> FEATURE:
<221> NAME/KEY: MOD_RES
<222> LOCATION: (48)..(48)
<223> OTHER INFORMATION: Val or Ile
<220> FEATURE:
<221> NAME/KEY: MOD_RES
<222> LOCATION: (74)..(74)
<223> OTHER INFORMATION: Val or Ile
<220> FEATURE:
<221> NAME/KEY: MOD_RES
<222> LOCATION: (83)..(83)
<223> OTHER INFORMATION: Gly or any amino acid
<220> FEATURE:
<221> NAME/KEY: MOD_RES
<222> LOCATION: (100)..(100)
<223> OTHER INFORMATION: Ala or Thr
<220> FEATURE:
<221> NAME/KEY: MOD_RES
<222> LOCATION: (177)..(177)
<223> OTHER INFORMATION: Thr or Ala
<220> FEATURE:
<221> NAME/KEY: MOD_RES
<222> LOCATION: (186)..(186)
<223> OTHER INFORMATION: Ala or Gly
<220> FEATURE:
<221> NAME/KEY: MOD_RES
<222> LOCATION: (196)..(196)
<223> OTHER INFORMATION: Ala or Pro
<220> FEATURE:
<221> NAME/KEY: MOD_RES
<222> LOCATION: (208)..(208)
```

-continued

```
<223> OTHER INFORMATION: Val or Ala
<220> FEATURE:
<221> NAME/KEY: MOD_RES
<222> LOCATION: (214)..(214)
<223> OTHER INFORMATION: Lys or any amino acid
<220> FEATURE:
<221> NAME/KEY: MOD_RES
<222> LOCATION: (237)..(237)
<223> OTHER INFORMATION: Gln or His
<220> FEATURE:
<221> NAME/KEY: MOD_RES
<222> LOCATION: (298)..(298)
<223> OTHER INFORMATION: Ser or Ala
<220> FEATURE:
<221> NAME/KEY: MOD_RES
<222> LOCATION: (307)..(307)
<223> OTHER INFORMATION: Ala or Ser
<220> FEATURE:
<221> NAME/KEY: MOD_RES
<222> LOCATION: (313)..(313)
<223> OTHER INFORMATION: Val or Ala
<220> FEATURE:
<221> NAME/KEY: MOD_RES
<222> LOCATION: (348)..(348)
<223> OTHER INFORMATION: Asn or Ser

<400> SEQUENCE: 7

Met Cys Gly Ser Lys Thr Ala Asp Lys Pro Ala Asp Ser Gly Ser Ser
1               5                   10                  15

Glu Xaa Lys Glu Leu Thr Val Tyr Val Asp Glu Gly Tyr Lys Ser Tyr
            20                  25                  30

Ile Glu Glu Val Ala Lys Ala Tyr Glu Lys Glu Ala Gly Val Lys Xaa
        35                  40                  45

Thr Leu Lys Thr Gly Asp Ala Leu Gly Gly Leu Asp Lys Leu Ser Leu
50                  55                  60

Asp Asn Gln Ser Gly Asn Val Pro Asp Xaa Met Met Ala Pro Tyr Asp
65                  70                  75                  80

Arg Val Xaa Ser Leu Gly Ser Asp Gly Gln Leu Ser Glu Val Lys Leu
                85                  90                  95

Ser Asp Gly Xaa Lys Thr Asp Asp Thr Thr Lys Ser Leu Val Thr Ala
            100                 105                 110

Ala Asn Gly Lys Val Tyr Gly Ala Pro Ala Val Ile Glu Ser Leu Val
        115                 120                 125

Met Tyr Tyr Asn Lys Asp Leu Val Lys Asp Ala Pro Lys Thr Phe Ala
130                 135                 140

Asp Leu Glu Asn Leu Ala Lys Asp Ser Lys Tyr Ala Phe Ala Gly Glu
145                 150                 155                 160

Asp Gly Lys Thr Thr Ala Phe Leu Ala Asp Trp Thr Asn Phe Tyr Tyr
                165                 170                 175

Xaa Tyr Gly Leu Leu Ala Gly Asn Gly Xaa Tyr Val Phe Gly Gln Asn
            180                 185                 190

Gly Lys Asp Xaa Lys Asp Ile Gly Leu Ala Asn Asp Gly Ser Ile Xaa
        195                 200                 205

Gly Ile Asn Tyr Ala Xaa Ser Trp Tyr Glu Lys Trp Pro Lys Gly Met
    210                 215                 220

Gln Asp Thr Glu Gly Ala Gly Asn Leu Ile Gln Thr Xaa Phe Gln Glu
225                 230                 235                 240

Gly Lys Thr Ala Ala Ile Ile Asp Gly Pro Trp Lys Ala Gln Ala Phe
                245                 250                 255

Lys Asp Ala Lys Val Asn Tyr Gly Val Ala Thr Ile Pro Thr Leu Pro
            260                 265                 270
```

-continued

```
Asn Gly Lys Glu Tyr Ala Ala Phe Gly Gly Lys Ala Trp Val Ile
        275                 280                 285

Pro Gln Ala Val Lys Asn Leu Glu Ala Xaa Gln Lys Phe Val Asp Phe
290                 295                 300

Leu Val Xaa Thr Glu Gln Gln Lys Xaa Leu Tyr Asp Lys Thr Asn Glu
305                 310                 315                 320

Ile Pro Ala Asn Thr Glu Ala Arg Ser Tyr Ala Glu Gly Lys Asn Asp
                325                 330                 335

Glu Leu Thr Thr Ala Val Ile Lys Gln Phe Lys Xaa Thr Gln Pro Leu
                340                 345                 350

Pro Asn Ile Ser Gln Met Ser Ala Val Trp Asp Pro Ala Lys Asn Met
        355                 360                 365

Leu Phe Asp Ala Val Ser Gly Gln Lys Asp Ala Lys Thr Ala Ala Asn
370                 375                 380

Asp Ala Val Thr Leu Ile Lys Glu Thr Ile Lys Gln Lys Phe Gly Glu
385                 390                 395                 400
```

<210> SEQ ID NO 8
<211> LENGTH: 423
<212> TYPE: PRT
<213> ORGANISM: Streptococcus pneumonia
<220> FEATURE:
<223> OTHER INFORMATION: SP2108 consensus including signal sequence
<220> FEATURE:
<221> NAME/KEY: MOD_RES
<222> LOCATION: (6)..(6)
<223> OTHER INFORMATION: Met or Thr
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (15)..(15)
<223> OTHER INFORMATION: Ala or Val
<220> FEATURE:
<221> NAME/KEY: MOD_RES
<222> LOCATION: (41)..(41)
<223> OTHER INFORMATION: Val or Ala
<220> FEATURE:
<221> NAME/KEY: MOD_RES
<222> LOCATION: (71)..(71)
<223> OTHER INFORMATION: Val or Ile
<220> FEATURE:
<221> NAME/KEY: MOD_RES
<222> LOCATION: (97)..(97)
<223> OTHER INFORMATION: Val or Ile
<220> FEATURE:
<221> NAME/KEY: MOD_RES
<222> LOCATION: (106)..(106)
<223> OTHER INFORMATION: Gly or any amino acid
<220> FEATURE:
<221> NAME/KEY: MOD_RES
<222> LOCATION: (123)..(123)
<223> OTHER INFORMATION: Ala or Thr
<220> FEATURE:
<221> NAME/KEY: MOD_RES
<222> LOCATION: (200)..(200)
<223> OTHER INFORMATION: Thr or Ala
<220> FEATURE:
<221> NAME/KEY: MOD_RES
<222> LOCATION: (209)..(209)
<223> OTHER INFORMATION: Ala or Gly
<220> FEATURE:
<221> NAME/KEY: MOD_RES
<222> LOCATION: (219)..(219)
<223> OTHER INFORMATION: Ala or Pro
<220> FEATURE:
<221> NAME/KEY: MOD_RES
<222> LOCATION: (231)..(231)
<223> OTHER INFORMATION: Val or Ala

```
<220> FEATURE:
<221> NAME/KEY: MOD_RES
<222> LOCATION: (237)..(237)
<223> OTHER INFORMATION: Lys or any amino acid
<220> FEATURE:
<221> NAME/KEY: MOD_RES
<222> LOCATION: (260)..(260)
<223> OTHER INFORMATION: Gln or His
<220> FEATURE:
<221> NAME/KEY: MOD_RES
<222> LOCATION: (321)..(321)
<223> OTHER INFORMATION: Ser or Ala
<220> FEATURE:
<221> NAME/KEY: MOD_RES
<222> LOCATION: (330)..(330)
<223> OTHER INFORMATION: Ala or Ser
<220> FEATURE:
<221> NAME/KEY: MOD_RES
<222> LOCATION: (336)..(336)
<223> OTHER INFORMATION: Val or Ala
<220> FEATURE:
<221> NAME/KEY: MOD_RES
<222> LOCATION: (371)..(371)
<223> OTHER INFORMATION: Asn or Ser

<400> SEQUENCE: 8

Met Ser Ser Lys Phe Xaa Lys Ser Xaa Ala Val Leu Gly Thr Xaa Thr
1               5                   10                  15

Leu Ala Ser Leu Leu Val Ala Cys Gly Ser Lys Thr Ala Asp Lys
            20                  25                  30

Pro Ala Asp Ser Gly Ser Ser Glu Xaa Lys Glu Leu Thr Val Tyr Val
                35                  40                  45

Asp Glu Gly Tyr Lys Ser Tyr Ile Glu Glu Val Ala Lys Ala Tyr Glu
50                  55                  60

Lys Glu Ala Gly Val Lys Xaa Thr Leu Lys Thr Gly Asp Ala Leu Gly
65                  70                  75                  80

Gly Leu Asp Lys Leu Ser Leu Asp Asn Gln Ser Gly Asn Val Pro Asp
                85                  90                  95

Xaa Met Met Ala Pro Tyr Asp Arg Val Xaa Ser Leu Gly Ser Asp Gly
            100                 105                 110

Gln Leu Ser Glu Val Lys Leu Ser Asp Gly Xaa Lys Thr Asp Asp Thr
        115                 120                 125

Thr Lys Ser Leu Val Thr Ala Ala Asn Gly Lys Val Tyr Gly Ala Pro
130                 135                 140

Ala Val Ile Glu Ser Leu Val Met Tyr Tyr Asn Lys Asp Leu Val Lys
145                 150                 155                 160

Asp Ala Pro Lys Thr Phe Ala Asp Leu Glu Asn Leu Ala Lys Asp Ser
                165                 170                 175

Lys Tyr Ala Phe Ala Gly Glu Asp Gly Lys Thr Thr Ala Phe Leu Ala
            180                 185                 190

Asp Trp Thr Asn Phe Tyr Tyr Xaa Tyr Gly Leu Leu Ala Gly Asn Gly
        195                 200                 205

Xaa Tyr Val Phe Gly Gln Asn Gly Lys Asp Xaa Lys Asp Ile Gly Leu
    210                 215                 220

Ala Asn Asp Gly Ser Ile Xaa Gly Ile Asn Tyr Ala Xaa Ser Trp Tyr
225                 230                 235                 240

Glu Lys Trp Pro Lys Gly Met Gln Asp Thr Glu Gly Ala Gly Asn Leu
                245                 250                 255

Ile Gln Thr Xaa Phe Gln Glu Gly Lys Thr Ala Ala Ile Ile Asp Gly
            260                 265                 270

Pro Trp Lys Ala Gln Ala Phe Lys Asp Ala Lys Val Asn Tyr Gly Val
```

```
                275                 280                 285
Ala Thr Ile Pro Thr Leu Pro Asn Gly Lys Glu Tyr Ala Ala Phe Gly
            290                 295                 300
Gly Gly Lys Ala Trp Val Ile Pro Gln Ala Val Lys Asn Leu Glu Ala
305                 310                 315                 320
Xaa Gln Lys Phe Val Asp Phe Leu Val Xaa Thr Glu Gln Gln Lys Xaa
                325                 330                 335
Leu Tyr Asp Lys Thr Asn Glu Ile Pro Ala Asn Thr Glu Ala Arg Ser
            340                 345                 350
Tyr Ala Glu Gly Lys Asn Asp Glu Leu Thr Thr Ala Val Ile Lys Gln
            355                 360                 365
Phe Lys Xaa Thr Gln Pro Leu Pro Asn Ile Ser Gln Met Ser Ala Val
        370                 375                 380
Trp Asp Pro Ala Lys Asn Met Leu Phe Asp Ala Val Ser Gly Gln Lys
385                 390                 395                 400
Asp Ala Lys Thr Ala Ala Asn Asp Ala Val Thr Leu Ile Lys Glu Thr
                405                 410                 415
Ile Lys Gln Lys Phe Gly Glu
            420

<210> SEQ ID NO 9
<211> LENGTH: 99
<212> TYPE: PRT
<213> ORGANISM: Streptococcus pneumonia
<220> FEATURE:
<223> OTHER INFORMATION: SP1912

<400> SEQUENCE: 9

Met Asn Gly Met Lys Ala Lys Lys Met Trp Met Ala Gly Leu Ala Leu
1               5                   10                  15

Leu Gly Ile Gly Ser Leu Ala Leu Ala Thr Lys Lys Val Ala Asp Asp
            20                  25                  30

Arg Lys Leu Met Lys Thr Gln Glu Glu Leu Thr Glu Ile Val Arg Asp
        35                  40                  45

His Phe Ser Asp Met Gly Glu Ile Ala Thr Leu Tyr Val Gln Val Tyr
    50                  55                  60

Glu Ser Ser Leu Glu Ser Leu Val Gly Gly Val Ile Phe Glu Asp Gly
65                  70                  75                  80

Arg His Tyr Thr Phe Val Tyr Glu Asn Glu Asp Leu Val Tyr Glu Glu
                85                  90                  95

Glu Val Leu

<210> SEQ ID NO 10
<211> LENGTH: 92
<212> TYPE: PRT
<213> ORGANISM: Streptococcus pneumonia
<220> FEATURE:
<223> OTHER INFORMATION: SP1912L

<400> SEQUENCE: 10

Met Arg Tyr Leu Ala Thr Leu Leu Ser Leu Ala Val Leu Ile Thr
1               5                   10                  15

Ala Gly Cys Lys Lys Val Ala Asp Asp Arg Lys Leu Met Lys Thr Gln
            20                  25                  30

Glu Glu Leu Thr Glu Ile Val Arg Asp His Phe Ser Asp Met Gly Glu
        35                  40                  45

Ile Ala Thr Leu Tyr Val Gln Val Tyr Glu Ser Ser Leu Glu Ser Leu
```

```
                50                  55                  60
Val Gly Gly Val Ile Phe Glu Asp Gly Arg His Tyr Thr Phe Val Tyr
 65                  70                  75                  80

Glu Asn Glu Asp Leu Val Tyr Glu Glu Val Leu
                 85                  90

<210> SEQ ID NO 11
<211> LENGTH: 99
<212> TYPE: PRT
<213> ORGANISM: Streptococcus pneumonia
<220> FEATURE:
<223> OTHER INFORMATION: SP1912 consensus
<220> FEATURE:
<221> NAME/KEY: MOD_RES
<222> LOCATION: (33)..(33)
<223> OTHER INFORMATION: Arg or His
<220> FEATURE:
<221> NAME/KEY: MOD_RES
<222> LOCATION: (44)..(44)
<223> OTHER INFORMATION: Glu or Ala
<220> FEATURE:
<221> NAME/KEY: MOD_RES
<222> LOCATION: (49)..(49)
<223> OTHER INFORMATION: His or Leu
<220> FEATURE:
<221> NAME/KEY: MOD_RES
<222> LOCATION: (61)..(61)
<223> OTHER INFORMATION: Val or Ile
<220> FEATURE:
<221> NAME/KEY: MOD_RES
<222> LOCATION: (72)..(72)
<223> OTHER INFORMATION: Val or Leu
<220> FEATURE:
<221> NAME/KEY: MOD_RES
<222> LOCATION: (74)..(74)
<223> OTHER INFORMATION: Gly or ser
<220> FEATURE:
<221> NAME/KEY: MOD_RES
<222> LOCATION: (86)..(86)
<223> OTHER INFORMATION: Val or Ile

<400> SEQUENCE: 11

Met Asn Gly Met Lys Ala Lys Lys Met Trp Met Ala Gly Leu Ala Leu
 1               5                  10                  15

Leu Gly Ile Gly Ser Leu Ala Leu Ala Thr Lys Lys Val Ala Asp Asp
                 20                  25                  30

Xaa Lys Leu Met Lys Thr Gln Glu Glu Leu Thr Xaa Ile Val Arg Asp
         35                  40                  45

Xaa Phe Ser Asp Met Gly Glu Ile Ala Thr Leu Tyr Xaa Gln Val Tyr
     50                  55                  60

Glu Ser Ser Leu Glu Ser Leu Xaa Gly Xaa Val Ile Phe Glu Asp Gly
 65                  70                  75                  80

Arg His Tyr Thr Phe Xaa Tyr Glu Asn Glu Asp Leu Val Tyr Glu Glu
                 85                  90                  95

Glu Val Leu

<210> SEQ ID NO 12
<211> LENGTH: 2140
<212> TYPE: PRT
<213> ORGANISM: Streptococcus pneumoniae
<220> FEATURE:
<223> OTHER INFORMATION: SP0641/serine protease, subtilase family
      [Streptococcus pneumoniae TIGR4]
<300> PUBLICATION INFORMATION:
<308> DATABASE ACCESSION NUMBER: 14972117
<300> PUBLICATION INFORMATION:
<308> DATABASE ACCESSION NUMBER: AAK74791.1
```

```
<400> SEQUENCE: 12

Met Lys Lys Ser Thr Val Leu Ser Leu Thr Ala Ala Val Ile Leu
1               5                   10                  15

Ala Ala Tyr Ala Pro Asn Glu Val Val Leu Ala Asp Thr Ser Ser
            20                  25                  30

Glu Asp Ala Leu Asn Ile Ser Asp Lys Glu Lys Val Ala Glu Asn Lys
            35                  40                  45

Glu Lys His Glu Asn Ile His Ser Ala Met Glu Thr Ser Gln Asp Phe
        50                  55                  60

Lys Glu Lys Lys Thr Ala Val Ile Lys Glu Lys Glu Val Val Ser Lys
65                  70                  75                  80

Asn Pro Val Ile Asp Asn Asn Thr Ser Asn Glu Glu Ala Lys Ile Lys
                85                  90                  95

Glu Glu Asn Ser Asn Lys Ser Gln Gly Asp Tyr Thr Asp Ser Phe Val
            100                 105                 110

Asn Lys Asn Thr Glu Asn Pro Lys Lys Glu Asp Lys Val Val Tyr Ile
            115                 120                 125

Ala Glu Phe Lys Asp Lys Glu Ser Gly Glu Lys Ala Ile Lys Glu Leu
        130                 135                 140

Ser Ser Leu Lys Asn Thr Lys Val Leu Tyr Thr Tyr Asp Arg Ile Phe
145                 150                 155                 160

Asn Gly Ser Ala Ile Glu Thr Thr Pro Asp Asn Leu Asp Lys Ile Lys
                165                 170                 175

Gln Ile Glu Gly Ile Ser Ser Val Glu Arg Ala Gln Lys Val Gln Pro
            180                 185                 190

Met Met Asn His Ala Arg Lys Glu Ile Gly Val Glu Glu Ala Ile Asp
        195                 200                 205

Tyr Leu Lys Ser Ile Asn Ala Pro Phe Gly Lys Asn Phe Asp Gly Arg
210                 215                 220

Gly Met Val Ile Ser Asn Ile Asp Thr Gly Thr Asp Tyr Arg His Lys
225                 230                 235                 240

Ala Met Arg Ile Asp Asp Asp Ala Lys Ala Ser Met Arg Phe Lys Lys
                245                 250                 255

Glu Asp Leu Lys Gly Thr Asp Lys Asn Tyr Trp Leu Ser Asp Lys Ile
            260                 265                 270

Pro His Ala Phe Asn Tyr Tyr Asn Gly Gly Lys Ile Thr Val Glu Lys
        275                 280                 285

Tyr Asp Asp Gly Arg Asp Tyr Phe Asp Pro His Gly Met His Ile Ala
290                 295                 300

Gly Ile Leu Ala Gly Asn Asp Thr Glu Gln Asp Ile Lys Asn Phe Asn
305                 310                 315                 320

Gly Ile Asp Gly Ile Ala Pro Asn Ala Gln Ile Phe Ser Tyr Lys Met
                325                 330                 335

Tyr Ser Asp Ala Gly Ser Gly Phe Ala Gly Asp Glu Thr Met Phe His
            340                 345                 350

Ala Ile Glu Asp Ser Ile Lys His Asn Val Asp Val Val Ser Val Ser
        355                 360                 365

Ser Gly Phe Thr Gly Thr Gly Leu Val Gly Glu Lys Tyr Trp Gln Ala
370                 375                 380

Ile Arg Ala Leu Arg Lys Ala Gly Ile Pro Met Val Val Ala Thr Gly
385                 390                 395                 400

Asn Tyr Ala Thr Ser Ala Ser Ser Ser Trp Asp Leu Val Ala Asn
                405                 410                 415
```

```
Asn His Leu Lys Met Thr Asp Thr Gly Asn Val Thr Arg Thr Ala Ala
            420                 425                 430

His Glu Asp Ala Ile Ala Val Ala Ser Ala Lys Asn Gln Thr Val Glu
            435                 440                 445

Phe Asp Lys Val Asn Ile Gly Gly Glu Ser Phe Lys Tyr Arg Asn Ile
            450                 455                 460

Gly Ala Phe Phe Asp Lys Ser Lys Ile Thr Thr Asn Glu Asp Gly Thr
465                 470                 475                 480

Lys Ala Pro Ser Lys Leu Lys Phe Val Tyr Ile Gly Lys Gly Gln Asp
                485                 490                 495

Gln Asp Leu Ile Gly Leu Asp Leu Arg Gly Lys Ile Ala Val Met Asp
            500                 505                 510

Arg Ile Tyr Thr Lys Asp Leu Lys Asn Ala Phe Lys Lys Ala Met Asp
            515                 520                 525

Lys Gly Ala Arg Ala Ile Met Val Val Asn Thr Val Asn Tyr Tyr Asn
530                 535                 540

Arg Asp Asn Trp Thr Glu Leu Pro Ala Met Gly Tyr Glu Ala Asp Glu
545                 550                 555                 560

Gly Thr Lys Ser Gln Val Phe Ser Ile Ser Gly Asp Asp Gly Val Lys
                565                 570                 575

Leu Trp Asn Met Ile Asn Pro Asp Lys Lys Thr Glu Val Lys Arg Asn
            580                 585                 590

Asn Lys Glu Asp Phe Lys Asp Lys Leu Glu Gln Tyr Tyr Pro Ile Asp
                595                 600                 605

Met Glu Ser Phe Asn Ser Asn Lys Pro Asn Val Gly Asp Glu Lys Glu
            610                 615                 620

Ile Asp Phe Lys Phe Ala Pro Asp Thr Asp Lys Glu Leu Tyr Lys Glu
625                 630                 635                 640

Asp Ile Ile Val Pro Ala Gly Ser Thr Ser Trp Gly Pro Arg Ile Asp
                645                 650                 655

Leu Leu Leu Lys Pro Asp Val Ser Ala Pro Gly Lys Asn Ile Lys Ser
            660                 665                 670

Thr Leu Asn Val Ile Asn Gly Lys Ser Thr Tyr Gly Tyr Met Ser Gly
            675                 680                 685

Thr Ser Met Ala Thr Pro Ile Val Ala Ala Ser Thr Val Leu Ile Arg
690                 695                 700

Pro Lys Leu Lys Glu Met Leu Glu Arg Pro Val Leu Lys Asn Leu Lys
705                 710                 715                 720

Gly Asp Asp Lys Ile Asp Leu Thr Ser Leu Thr Lys Ile Ala Leu Gln
                725                 730                 735

Asn Thr Ala Arg Pro Met Met Asp Ala Thr Ser Trp Lys Glu Lys Ser
            740                 745                 750

Gln Tyr Phe Ala Ser Pro Arg Gln Gln Gly Ala Gly Leu Ile Asn Val
            755                 760                 765

Ala Asn Ala Leu Arg Asn Glu Val Val Ala Thr Phe Lys Asn Thr Asp
            770                 775                 780

Ser Lys Gly Leu Val Asn Ser Tyr Gly Ser Ile Ser Leu Lys Glu Ile
785                 790                 795                 800

Lys Gly Asp Lys Lys Tyr Phe Thr Ile Lys Leu His Asn Thr Ser Asn
                805                 810                 815

Arg Pro Leu Thr Phe Lys Val Ser Ala Ser Ala Ile Thr Thr Asp Ser
            820                 825                 830
```

```
Leu Thr Asp Arg Leu Lys Leu Asp Glu Thr Tyr Lys Asp Glu Lys Ser
        835                 840                 845

Pro Asp Gly Lys Gln Ile Val Pro Glu Ile His Pro Glu Lys Val Lys
    850                 855                 860

Gly Ala Asn Ile Thr Phe Glu His Asp Thr Phe Thr Ile Gly Ala Asn
865                 870                 875                 880

Ser Ser Phe Asp Leu Asn Ala Val Ile Asn Val Gly Glu Ala Lys Asn
                885                 890                 895

Lys Asn Lys Phe Val Glu Ser Phe Ile His Phe Glu Ser Val Glu Glu
            900                 905                 910

Met Glu Ala Leu Asn Ser Asn Gly Lys Lys Ile Asn Phe Gln Pro Ser
        915                 920                 925

Leu Ser Met Pro Leu Met Gly Phe Ala Gly Asn Trp Asn His Glu Pro
    930                 935                 940

Ile Leu Asp Lys Trp Ala Trp Glu Glu Gly Ser Arg Ser Lys Thr Leu
945                 950                 955                 960

Gly Gly Tyr Asp Asp Gly Lys Pro Lys Ile Pro Gly Thr Leu Asn
                965                 970                 975

Lys Gly Ile Gly Gly Glu His Gly Ile Asp Lys Phe Asn Pro Ala Gly
            980                 985                 990

Val Ile Gln Asn Arg Lys Asp Lys Asn Thr Thr Ser Leu Asp Gln Asn
        995                 1000                1005

Pro Glu Leu Phe Ala Phe Asn Asn Glu Gly Ile Asn Ala Pro Ser
    1010                1015                1020

Ser Ser Gly Ser Lys Ile Ala Asn Ile Tyr Pro Leu Asp Ser Asn
    1025                1030                1035

Gly Asn Pro Gln Asp Ala Gln Leu Glu Arg Gly Leu Thr Pro Ser
    1040                1045                1050

Pro Leu Val Leu Arg Ser Ala Glu Glu Gly Leu Ile Ser Ile Val
    1055                1060                1065

Asn Thr Asn Lys Glu Gly Glu Asn Gln Arg Asp Leu Lys Val Ile
    1070                1075                1080

Ser Arg Glu His Phe Ile Arg Gly Ile Leu Asn Ser Lys Ser Asn
    1085                1090                1095

Asp Ala Lys Gly Ile Lys Ser Ser Lys Leu Lys Val Trp Gly Asp
    1100                1105                1110

Leu Lys Trp Asp Gly Leu Ile Tyr Asn Pro Arg Gly Arg Glu Glu
    1115                1120                1125

Asn Ala Pro Glu Ser Lys Asp Asn Gln Asp Pro Ala Thr Lys Ile
    1130                1135                1140

Arg Gly Gln Phe Glu Pro Ile Ala Glu Gly Gln Tyr Phe Tyr Lys
    1145                1150                1155

Phe Lys Tyr Arg Leu Thr Lys Asp Tyr Pro Trp Gln Val Ser Tyr
    1160                1165                1170

Ile Pro Val Lys Ile Asp Asn Thr Ala Pro Lys Ile Val Ser Val
    1175                1180                1185

Asp Phe Ser Asn Pro Glu Lys Ile Lys Leu Ile Thr Lys Asp Thr
    1190                1195                1200

Tyr His Lys Val Lys Asp Gln Tyr Lys Asn Glu Thr Leu Phe Ala
    1205                1210                1215

Arg Asp Gln Lys Glu His Pro Glu Lys Phe Asp Glu Ile Ala Asn
    1220                1225                1230

Glu Val Trp Tyr Ala Gly Ala Ala Leu Val Asn Glu Asp Gly Glu
```

-continued

```
            1235                1240                1245
Val Glu Lys Asn Leu Glu Val Thr Tyr Ala Gly Glu Gly Gln Gly
            1250                1255                1260
Arg Asn Arg Lys Leu Asp Lys Asp Gly Asn Thr Ile Tyr Glu Ile
            1265                1270                1275
Lys Gly Ala Gly Asp Leu Arg Gly Lys Ile Ile Glu Val Ile Ala
            1280                1285                1290
Leu Asp Gly Ser Ser Asn Phe Thr Lys Ile His Arg Ile Lys Phe
            1295                1300                1305
Ala Asn Gln Ala Asp Glu Lys Gly Met Ile Ser Tyr Tyr Leu Val
            1310                1315                1320
Asp Pro Asp Gln Asp Ser Ser Lys Tyr Gln Lys Leu Gly Glu Ile
            1325                1330                1335
Ala Glu Ser Lys Phe Lys Asn Leu Gly Asn Gly Lys Glu Gly Ser
            1340                1345                1350
Leu Lys Lys Asp Thr Thr Gly Val Glu His His His Gln Glu Asn
            1355                1360                1365
Glu Glu Ser Ile Lys Glu Lys Ser Ser Phe Thr Ile Asp Arg Asn
            1370                1375                1380
Ile Ser Thr Ile Arg Asp Phe Glu Asn Lys Asp Leu Lys Lys Leu
            1385                1390                1395
Ile Lys Lys Lys Phe Arg Glu Val Asp Asp Phe Thr Ser Glu Thr
            1400                1405                1410
Gly Lys Arg Met Glu Glu Tyr Asp Tyr Lys Tyr Asp Asp Lys Gly
            1415                1420                1425
Asn Ile Ile Ala Tyr Asp Asp Gly Thr Asp Leu Glu Tyr Glu Thr
            1430                1435                1440
Glu Lys Leu Asp Glu Ile Lys Ser Lys Ile Tyr Gly Val Leu Ser
            1445                1450                1455
Pro Ser Lys Asp Gly His Phe Glu Ile Leu Gly Lys Ile Ser Asn
            1460                1465                1470
Val Ser Lys Asn Ala Lys Val Tyr Tyr Gly Asn Asn Tyr Lys Ser
            1475                1480                1485
Ile Glu Ile Lys Ala Thr Lys Tyr Asp Phe His Ser Lys Thr Met
            1490                1495                1500
Thr Phe Asp Leu Tyr Ala Asn Ile Asn Asp Ile Val Asp Gly Leu
            1505                1510                1515
Ala Phe Ala Gly Asp Met Arg Leu Phe Val Lys Asp Asn Asp Gln
            1520                1525                1530
Lys Lys Ala Glu Ile Lys Ile Arg Met Pro Glu Lys Ile Lys Glu
            1535                1540                1545
Thr Lys Ser Glu Tyr Pro Tyr Val Ser Ser Tyr Gly Asn Val Ile
            1550                1555                1560
Glu Leu Gly Glu Gly Asp Leu Ser Lys Asn Lys Pro Asp Asn Leu
            1565                1570                1575
Thr Lys Met Glu Ser Gly Lys Ile Tyr Ser Asp Ser Glu Lys Gln
            1580                1585                1590
Gln Tyr Leu Leu Lys Asp Asn Ile Ile Leu Arg Lys Gly Tyr Ala
            1595                1600                1605
Leu Lys Val Thr Thr Tyr Asn Pro Gly Lys Thr Asp Met Leu Glu
            1610                1615                1620
Gly Asn Gly Val Tyr Ser Lys Glu Asp Ile Ala Lys Ile Gln Lys
            1625                1630                1635
```

Ala Asn Pro Asn Leu Arg Ala Leu Ser Glu Thr Thr Ile Tyr Ala
1640                1645                1650

Asp Ser Arg Asn Val Glu Asp Gly Arg Ser Thr Gln Ser Val Leu
1655                1660                1665

Met Ser Ala Leu Asp Gly Phe Asn Ile Ile Arg Tyr Gln Val Phe
1670                1675                1680

Thr Phe Lys Met Asn Asp Lys Gly Glu Ala Ile Asp Lys Asp Gly
1685                1690                1695

Asn Leu Val Thr Asp Ser Ser Lys Leu Val Leu Phe Gly Lys Asp
1700                1705                1710

Asp Lys Glu Tyr Thr Gly Glu Asp Lys Phe Asn Val Glu Ala Ile
1715                1720                1725

Lys Glu Asp Gly Ser Met Leu Phe Ile Asp Thr Lys Pro Val Asn
1730                1735                1740

Leu Ser Met Asp Lys Asn Tyr Phe Asn Pro Ser Lys Ser Asn Lys
1745                1750                1755

Ile Tyr Val Arg Asn Pro Glu Phe Tyr Leu Arg Gly Lys Ile Ser
1760                1765                1770

Asp Lys Gly Gly Phe Asn Trp Glu Leu Arg Val Asn Glu Ser Val
1775                1780                1785

Val Asp Asn Tyr Leu Ile Tyr Gly Asp Leu His Ile Asp Asn Thr
1790                1795                1800

Arg Asp Phe Asn Ile Lys Leu Asn Val Lys Asp Gly Asp Ile Met
1805                1810                1815

Asp Trp Gly Met Lys Asp Tyr Lys Ala Asn Gly Phe Pro Asp Lys
1820                1825                1830

Val Thr Asp Met Asp Gly Asn Val Tyr Leu Gln Thr Gly Tyr Ser
1835                1840                1845

Asp Leu Asn Ala Lys Ala Val Gly Val His Tyr Gln Phe Leu Tyr
1850                1855                1860

Asp Asn Val Lys Pro Glu Val Asn Ile Asp Pro Lys Gly Asn Thr
1865                1870                1875

Ser Ile Glu Tyr Ala Asp Gly Lys Ser Val Phe Asn Ile Asn
1880                1885                1890

Asp Lys Arg Asn Asn Gly Phe Asp Gly Glu Ile Gln Glu Gln His
1895                1900                1905

Ile Tyr Ile Asn Gly Lys Glu Tyr Thr Ser Phe Asn Asp Ile Lys
1910                1915                1920

Gln Ile Ile Asp Lys Thr Leu Asn Ile Lys Ile Val Val Lys Asp
1925                1930                1935

Phe Ala Arg Asn Thr Thr Val Lys Glu Phe Ile Leu Asn Lys Asp
1940                1945                1950

Thr Gly Glu Val Ser Glu Leu Lys Pro His Arg Val Thr Val Thr
1955                1960                1965

Ile Gln Asn Gly Lys Glu Met Ser Ser Thr Ile Val Ser Glu Glu
1970                1975                1980

Asp Phe Ile Leu Pro Val Tyr Lys Gly Glu Leu Glu Lys Gly Tyr
1985                1990                1995

Gln Phe Asp Gly Trp Glu Ile Ser Gly Phe Glu Gly Lys Lys Asp
2000                2005                2010

Ala Gly Tyr Val Ile Asn Leu Ser Lys Asp Thr Phe Ile Lys Pro
2015                2020                2025

-continued

Val Phe Lys Lys Ile Glu Glu Lys Leu Glu Glu Asn Lys Pro
2030            2035            2040

Thr Phe Asp Val Ser Lys Lys Asp Asn Pro Gln Val Asn His
2045            2050            2055

Ser Gln Leu Asn Glu Ser His Arg Lys Glu Asp Leu Gln Arg Glu
2060            2065            2070

Glu His Ser Gln Lys Ser Asp Ser Thr Lys Asp Val Thr Ala Thr
2075            2080            2085

Val Leu Asp Lys Asn Asn Ile Ser Ser Lys Ser Thr Thr Asn Asn
2090            2095            2100

Pro Asn Lys Leu Pro Lys Thr Gly Thr Ala Ser Gly Ala Gln Thr
2105            2110            2115

Leu Leu Ala Ala Gly Ile Met Phe Ile Val Gly Ile Phe Leu Gly
2120            2125            2130

Leu Lys Lys Lys Asn Gln Asp
2135            2140

<210> SEQ ID NO 13
<211> LENGTH: 662
<212> TYPE: PRT
<213> ORGANISM: Streptococcus pneumonia
<220> FEATURE:
<223> OTHER INFORMATION: SP0641N

<400> SEQUENCE: 13

Met Val Val Leu Ala Asp Thr Ser Ser Glu Asp Ala Leu Asn Ile
1               5               10              15

Ser Asp Lys Glu Lys Val Ala Glu Asn Lys Lys His Glu Asn Ile
                20              25              30

His Ser Ala Met Glu Thr Ser Gln Asp Phe Lys Glu Lys Lys Thr Ala
            35              40              45

Val Ile Lys Glu Lys Glu Val Val Ser Lys Asn Pro Val Ile Asp Asn
50              55              60

Asn Thr Ser Asn Glu Glu Ala Lys Ile Lys Glu Glu Asn Ser Asn Lys
65              70              75              80

Ser Gln Gly Asp Tyr Thr Asp Ser Phe Val Asn Lys Asn Thr Glu Asn
                85              90              95

Pro Lys Lys Glu Asp Lys Val Val Tyr Ile Ala Glu Phe Lys Asp Lys
                100             105             110

Glu Ser Gly Glu Lys Ala Ile Lys Glu Leu Ser Ser Leu Lys Asn Thr
            115             120             125

Lys Val Leu Tyr Thr Tyr Asp Arg Ile Phe Asn Gly Ser Ala Ile Glu
            130             135             140

Thr Thr Pro Asp Asn Leu Asp Lys Ile Lys Gln Ile Glu Gly Ile Ser
145             150             155             160

Ser Val Glu Arg Ala Gln Lys Val Gln Pro Met Met Asn His Ala Arg
                165             170             175

Lys Glu Ile Gly Val Glu Ala Ile Asp Tyr Leu Lys Ser Ile Asn
            180             185             190

Ala Pro Phe Gly Lys Asn Phe Asp Gly Arg Gly Met Val Ile Ser Asn
            195             200             205

Ile Asp Thr Gly Thr Asp Tyr Arg His Lys Ala Met Arg Ile Asp Asp
            210             215             220

Asp Ala Lys Ala Ser Met Arg Phe Lys Lys Glu Asp Leu Lys Gly Thr
225             230             235             240

```
Asp Lys Asn Tyr Trp Leu Ser Asp Lys Ile Pro His Ala Phe Asn Tyr
                245                 250                 255
Tyr Asn Gly Gly Lys Ile Thr Val Glu Lys Tyr Asp Asp Gly Arg Asp
            260                 265                 270
Tyr Phe Asp Pro His Gly Met His Ile Ala Gly Ile Leu Ala Gly Asn
        275                 280                 285
Asp Thr Glu Gln Asp Ile Lys Asn Phe Asn Gly Ile Asp Gly Ile Ala
    290                 295                 300
Pro Asn Ala Gln Ile Phe Ser Tyr Lys Met Tyr Ser Asp Ala Gly Ser
305                 310                 315                 320
Gly Phe Ala Gly Asp Glu Thr Met Phe His Ala Ile Glu Asp Ser Ile
                325                 330                 335
Lys His Asn Val Asp Val Val Ser Val Ser Ser Gly Phe Thr Gly Thr
            340                 345                 350
Gly Leu Val Gly Glu Lys Tyr Trp Gln Ala Ile Arg Ala Leu Arg Lys
        355                 360                 365
Ala Gly Ile Pro Met Val Val Ala Thr Gly Asn Tyr Ala Thr Ser Ala
    370                 375                 380
Ser Ser Ser Ser Trp Asp Leu Val Ala Asn Asn His Leu Lys Met Thr
385                 390                 395                 400
Asp Thr Gly Asn Val Thr Arg Thr Ala Ala His Glu Asp Ala Ile Ala
                405                 410                 415
Val Ala Ser Ala Lys Asn Gln Thr Val Glu Phe Asp Lys Val Asn Ile
            420                 425                 430
Gly Gly Glu Ser Phe Lys Tyr Arg Asn Ile Gly Ala Phe Phe Asp Lys
        435                 440                 445
Ser Lys Ile Thr Thr Asn Glu Asp Gly Thr Lys Ala Pro Ser Lys Leu
    450                 455                 460
Lys Phe Val Tyr Ile Gly Lys Gly Gln Asp Gln Asp Leu Ile Gly Leu
465                 470                 475                 480
Asp Leu Arg Gly Lys Ile Ala Val Met Asp Arg Ile Tyr Thr Lys Asp
                485                 490                 495
Leu Lys Asn Ala Phe Lys Lys Ala Met Asp Lys Gly Ala Arg Ala Ile
            500                 505                 510
Met Val Val Asn Thr Val Asn Tyr Tyr Asn Arg Asp Asn Trp Thr Glu
        515                 520                 525
Leu Pro Ala Met Gly Tyr Glu Ala Asp Glu Gly Thr Lys Ser Gln Val
    530                 535                 540
Phe Ser Ile Ser Gly Asp Asp Gly Val Lys Leu Trp Asn Met Ile Asn
545                 550                 555                 560
Pro Asp Lys Lys Thr Glu Val Lys Arg Asn Asn Lys Glu Asp Phe Lys
                565                 570                 575
Asp Lys Leu Glu Gln Tyr Tyr Pro Ile Asp Met Glu Ser Phe Asn Ser
            580                 585                 590
Asn Lys Pro Asn Val Gly Asp Glu Lys Glu Ile Asp Phe Lys Phe Ala
        595                 600                 605
Pro Asp Thr Asp Lys Glu Leu Tyr Lys Glu Asp Ile Ile Val Pro Ala
    610                 615                 620
Gly Ser Thr Ser Trp Gly Pro Arg Ile Asp Leu Leu Lys Pro Asp
625                 630                 635                 640
Val Ser Ala Pro Gly Lys Asn Ile Lys Ser Thr Leu Asn Val Ile Asn
            645                 650                 655
Gly Lys Ser Thr Tyr Gly
```

<210> SEQ ID NO 14
<211> LENGTH: 648
<212> TYPE: PRT
<213> ORGANISM: Streptococcus pneumonia
<220> FEATURE:
<223> OTHER INFORMATION: SP0641M

<400> SEQUENCE: 14

```
Met Ser Gly Thr Ser Met Ala Thr Pro Ile Val Ala Ser Thr Val
1               5                   10                  15

Leu Ile Arg Pro Lys Leu Lys Glu Met Leu Glu Arg Pro Val Leu Lys
            20                  25                  30

Asn Leu Lys Gly Asp Asp Lys Ile Asp Leu Thr Ser Leu Thr Lys Ile
            35                  40                  45

Ala Leu Gln Asn Thr Ala Arg Pro Met Met Asp Ala Thr Ser Trp Lys
        50                  55                  60

Glu Lys Ser Gln Tyr Phe Ala Ser Pro Arg Gln Gln Gly Ala Gly Leu
65                  70                  75                  80

Ile Asn Val Ala Asn Ala Leu Arg Asn Glu Val Val Ala Thr Phe Lys
                85                  90                  95

Asn Thr Asp Ser Lys Gly Leu Val Asn Ser Tyr Gly Ser Ile Ser Leu
            100                 105                 110

Lys Glu Ile Lys Gly Asp Lys Lys Tyr Phe Thr Ile Lys Leu His Asn
        115                 120                 125

Thr Ser Asn Arg Pro Leu Thr Phe Lys Val Ser Ala Ser Ala Ile Thr
130                 135                 140

Thr Asp Ser Leu Thr Asp Arg Leu Lys Leu Asp Glu Thr Tyr Lys Asp
145                 150                 155                 160

Glu Lys Ser Pro Asp Gly Lys Gln Ile Val Pro Glu Ile His Pro Glu
                165                 170                 175

Lys Val Lys Gly Ala Asn Ile Thr Phe Glu His Asp Thr Phe Thr Ile
            180                 185                 190

Gly Ala Asn Ser Ser Phe Asp Leu Asn Ala Val Ile Asn Val Gly Glu
        195                 200                 205

Ala Lys Asn Lys Asn Lys Phe Val Glu Ser Phe Ile His Phe Glu Ser
    210                 215                 220

Val Glu Glu Met Glu Ala Leu Asn Ser Asn Gly Lys Lys Ile Asn Phe
225                 230                 235                 240

Gln Pro Ser Leu Ser Met Pro Leu Met Gly Phe Ala Gly Asn Trp Asn
                245                 250                 255

His Glu Pro Ile Leu Asp Lys Trp Ala Trp Glu Glu Gly Ser Arg Ser
            260                 265                 270

Lys Thr Leu Gly Gly Tyr Asp Asp Gly Lys Pro Lys Ile Pro Gly
        275                 280                 285

Thr Leu Asn Lys Gly Ile Gly Gly Glu His Gly Ile Asp Lys Phe Asn
    290                 295                 300

Pro Ala Gly Val Ile Gln Asn Arg Lys Asp Lys Asn Thr Thr Ser Leu
305                 310                 315                 320

Asp Gln Asn Pro Glu Leu Phe Ala Phe Asn Asn Glu Gly Ile Asn Ala
                325                 330                 335

Pro Ser Ser Ser Gly Ser Lys Ile Ala Asn Ile Tyr Pro Leu Asp Ser
            340                 345                 350

Asn Gly Asn Pro Gln Asp Ala Gln Leu Glu Arg Gly Leu Thr Pro Ser
```

```
                  355                 360                 365
Pro Leu Val Leu Arg Ser Ala Glu Glu Gly Leu Ile Ser Ile Val Asn
370                 375                 380

Thr Asn Lys Glu Gly Glu Asn Gln Arg Asp Leu Lys Val Ile Ser Arg
385                 390                 395                 400

Glu His Phe Ile Arg Gly Ile Leu Asn Ser Lys Ser Asn Asp Ala Lys
                405                 410                 415

Gly Ile Lys Ser Ser Lys Leu Lys Val Trp Gly Asp Leu Lys Trp Asp
                420                 425                 430

Gly Leu Ile Tyr Asn Pro Arg Gly Arg Glu Glu Asn Ala Pro Glu Ser
                435                 440                 445

Lys Asp Asn Gln Asp Pro Ala Thr Lys Ile Arg Gly Gln Phe Glu Pro
450                 455                 460

Ile Ala Glu Gly Gln Tyr Phe Tyr Lys Phe Lys Tyr Arg Leu Thr Lys
465                 470                 475                 480

Asp Tyr Pro Trp Gln Val Ser Tyr Ile Pro Val Lys Ile Asp Asn Thr
                485                 490                 495

Ala Pro Lys Ile Val Ser Val Asp Phe Ser Asn Pro Glu Lys Ile Lys
                500                 505                 510

Leu Ile Thr Lys Asp Thr Tyr His Lys Val Lys Asp Gln Tyr Lys Asn
                515                 520                 525

Glu Thr Leu Phe Ala Arg Asp Gln Lys Glu His Pro Gly Lys Phe Asp
530                 535                 540

Glu Ile Ala Asn Glu Val Trp Tyr Ala Gly Ala Ala Leu Val Asn Glu
545                 550                 555                 560

Asp Gly Glu Val Glu Lys Asn Leu Glu Val Thr Tyr Ala Gly Glu Gly
                565                 570                 575

Gln Gly Arg Asn Arg Lys Leu Asp Lys Asp Gly Asn Thr Ile Tyr Glu
                580                 585                 590

Ile Lys Gly Ala Gly Asp Leu Arg Gly Lys Ile Ile Glu Val Ile Ala
                595                 600                 605

Leu Asp Gly Ser Ser Asn Phe Thr Lys Ile His Arg Ile Lys Phe Ala
610                 615                 620

Asn Gln Ala Asp Glu Lys Gly Met Ile Ser Tyr Tyr Leu Val Asp Pro
625                 630                 635                 640

Asp Gln Asp Ser Ser Lys Tyr Gln
                645
```

<210> SEQ ID NO 15
<211> LENGTH: 667
<212> TYPE: PRT
<213> ORGANISM: Streptococcus pneumonia
<220> FEATURE:
<223> OTHER INFORMATION: SP641N consensus
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (9)..(9)
<223> OTHER INFORMATION: Ser or Asn
<220> FEATURE:
<221> NAME/KEY: MOD_RES
<222> LOCATION: (15)..(15)
<223> OTHER INFORMATION: Asn or Ser
<220> FEATURE:
<221> NAME/KEY: MOD_RES
<222> LOCATION: (23)..(23)
<223> OTHER INFORMATION: Ala or Val -continued

```
<220> FEATURE:
<221> NAME/KEY: MOD_RES
<222> LOCATION: (24)..(24)
<223> OTHER INFORMATION: Val or Leu or not present
<220> FEATURE:
<221> NAME/KEY: MOD_RES
<222> LOCATION: (25)..(28)
<223> OTHER INFORMATION: May or may not be present
<220> FEATURE:
<221> NAME/KEY: MOD_RES
<222> LOCATION: (35)..(35)
<223> OTHER INFORMATION: Glu or Lys
<220> FEATURE:
<221> NAME/KEY: MOD_RES
<222> LOCATION: (36)..(36)
<223> OTHER INFORMATION: Asn or Asp
<220> FEATURE:
<221> NAME/KEY: MOD_RES
<222> LOCATION: (39)..(39)
<223> OTHER INFORMATION: Ser or Asn
<220> FEATURE:
<221> NAME/KEY: MOD_RES
<222> LOCATION: (41)..(41)
<223> OTHER INFORMATION: Met or Ile
<220> FEATURE:
<221> NAME/KEY: MOD_RES
<222> LOCATION: (45)..(45)
<223> OTHER INFORMATION: Gln or Lys
<220> FEATURE:
<221> NAME/KEY: MOD_RES
<222> LOCATION: (47)..(47)
<223> OTHER INFORMATION: Phe or Thr
<220> FEATURE:
<221> NAME/KEY: MOD_RES
<222> LOCATION: (48)..(48)
<223> OTHER INFORMATION: Lys or Glu
<220> FEATURE:
<221> NAME/KEY: MOD_RES
<222> LOCATION: (53)..(53)
<223> OTHER INFORMATION: Ala or Thr
<220> FEATURE:
<221> NAME/KEY: MOD_RES
<222> LOCATION: (54)..(54)
<223> OTHER INFORMATION: Val or Ile
<220> FEATURE:
<221> NAME/KEY: MOD_RES
<222> LOCATION: (56)..(56)
<223> OTHER INFORMATION: Lys or Glu
<220> FEATURE:
<221> NAME/KEY: MOD_RES
<222> LOCATION: (57)..(57)
<223> OTHER INFORMATION: Glu or Gly
<220> FEATURE:
<221> NAME/KEY: MOD_RES
<222> LOCATION: (59)..(59)
<223> OTHER INFORMATION: Glu or Ala
<220> FEATURE:
<221> NAME/KEY: MOD_RES
<222> LOCATION: (67)..(67)
<223> OTHER INFORMATION: Ile or Thr
<220> FEATURE:
<221> NAME/KEY: MOD_RES
<222> LOCATION: (69)..(69)
<223> OTHER INFORMATION: Asn or Thr
<220> FEATURE:
<221> NAME/KEY: MOD_RES
<222> LOCATION: (70)..(70)
<223> OTHER INFORMATION: Asn or Lys
<220> FEATURE:
<221> NAME/KEY: MOD_RES
<222> LOCATION: (77)..(77)
<223> OTHER INFORMATION: Lys or Arg
<220> FEATURE:
<221> NAME/KEY: MOD_RES
<222> LOCATION: (81)..(81)
<223> OTHER INFORMATION: Glu or Asp
<220> FEATURE:
<221> NAME/KEY: MOD_RES
<222> LOCATION: (82)..(82)
```

```
<223> OTHER INFORMATION: May or may not be present
<220> FEATURE:
<221> NAME/KEY: MOD_RES
<222> LOCATION: (85)..(85)
<223> OTHER INFORMATION: Lys or Gln
<220> FEATURE:
<221> NAME/KEY: MOD_RES
<222> LOCATION: (90)..(90)
<223> OTHER INFORMATION: Tyr, His or Asn
<220> FEATURE:
<221> NAME/KEY: MOD_RES
<222> LOCATION: (91)..(91)
<223> OTHER INFORMATION: Thr or Ala
<220> FEATURE:
<221> NAME/KEY: MOD_RES
<222> LOCATION: (92)..(92)
<223> OTHER INFORMATION: Asp or His
<220> FEATURE:
<221> NAME/KEY: MOD_RES
<222> LOCATION: (94)..(94)
<223> OTHER INFORMATION: Phe or Ser
<220> FEATURE:
<221> NAME/KEY: MOD_RES
<222> LOCATION: (95)..(95)
<223> OTHER INFORMATION: Val or Ala
<220> FEATURE:
<221> NAME/KEY: MOD_RES
<222> LOCATION: (98)..(98)
<223> OTHER INFORMATION: Asn or Gly
<220> FEATURE:
<221> NAME/KEY: MOD_RES
<222> LOCATION: (105)..(105)
<223> OTHER INFORMATION: Glu or Gln
<220> FEATURE:
<221> NAME/KEY: MOD_RES
<222> LOCATION: (107)..(107)
<223> OTHER INFORMATION: Lys or Arg
<220> FEATURE:
<221> NAME/KEY: MOD_RES
<222> LOCATION: (108)..(108)
<223> OTHER INFORMATION: Val or Leu
<220> FEATURE:
<221> NAME/KEY: MOD_RES
<222> LOCATION: (121)..(121)
<223> OTHER INFORMATION: Glu or Ser
<220> FEATURE:
<221> NAME/KEY: MOD_RES
<222> LOCATION: (126)..(126)
<223> OTHER INFORMATION: Glu, Gln or Gly
<220> FEATURE:
<221> NAME/KEY: MOD_RES
<222> LOCATION: (129)..(129)
<223> OTHER INFORMATION: Ser or Asn
<220> FEATURE:
<221> NAME/KEY: MOD_RES
<222> LOCATION: (146)..(146)
<223> OTHER INFORMATION: Ser or Gly
<220> FEATURE:
<221> NAME/KEY: MOD_RES
<222> LOCATION: (152)..(152)
<223> OTHER INFORMATION: Pro or Gln
<220> FEATURE:
<221> NAME/KEY: MOD_RES
<222> LOCATION: (165)..(165)
<223> OTHER INFORMATION: Ser or Thr
<220> FEATURE:
<221> NAME/KEY: MOD_RES
<222> LOCATION: (167)..(167)
<223> OTHER INFORMATION: Val or Ile
<220> FEATURE:
<221> NAME/KEY: MOD_RES
<222> LOCATION: (440)..(440)
<223> OTHER INFORMATION: Glu or Gln
<220> FEATURE:
<221> NAME/KEY: MOD_RES
<222> LOCATION: (454)..(454)
<223> OTHER INFORMATION: Ser or Asn
<220> FEATURE:
<221> NAME/KEY: MOD_RES
```

<222> LOCATION: (567)..(567)
<223> OTHER INFORMATION: Asp or Asn

<400> SEQUENCE: 15

```
Met Val Val Leu Ala Asp Thr Ser Xaa Ser Glu Asp Ala Leu Xaa Ile
1               5                   10                  15

Ser Asp Lys Glu Lys Val Xaa Xaa Asp Lys Glu Thr Glu Asn Lys Glu
            20                  25                  30

Lys His Xaa Xaa Ile His Xaa Ala Xaa Glu Thr Ser Xaa Asp Xaa Xaa
        35                  40                  45

Glu Lys Lys Thr Xaa Xaa Ile Xaa Xaa Lys Xaa Val Val Ser Lys Asn
50                  55                  60

Pro Val Xaa Asp Xaa Xaa Thr Ser Asn Glu Glu Ala Xaa Ile Lys Glu
65                  70                  75                  80

Xaa Asn Ser Asn Xaa Ser Gln Gly Asp Xaa Xaa Xaa Ser Xaa Xaa Asn
                85                  90                  95

Lys Xaa Thr Glu Asn Pro Lys Lys Xaa Asp Xaa Xaa Val Tyr Ile Ala
        100                 105                 110

Glu Phe Lys Asp Lys Glu Ser Gly Xaa Lys Ala Ile Lys Xaa Leu Ser
        115                 120                 125

Xaa Leu Lys Asn Thr Lys Val Leu Tyr Thr Tyr Asp Arg Ile Phe Asn
130                 135                 140

Gly Xaa Ala Ile Glu Thr Thr Xaa Asp Asn Leu Asp Lys Ile Lys Gln
145                 150                 155                 160

Ile Glu Gly Ile Xaa Ser Xaa Glu Arg Ala Gln Lys Val Gln Pro Met
                165                 170                 175

Met Asn His Ala Arg Lys Glu Ile Gly Val Glu Glu Ala Ile Asp Tyr
            180                 185                 190

Leu Lys Ser Ile Asn Ala Pro Phe Gly Lys Asn Phe Asp Gly Arg Gly
        195                 200                 205

Met Val Ile Ser Asn Ile Asp Thr Gly Thr Asp Tyr Arg His Lys Ala
210                 215                 220

Met Arg Ile Asp Asp Asp Ala Lys Ala Ser Met Arg Phe Lys Lys Glu
225                 230                 235                 240

Asp Leu Lys Gly Thr Asp Lys Asn Tyr Trp Leu Ser Asp Lys Ile Pro
                245                 250                 255

His Ala Phe Asn Tyr Tyr Asn Gly Gly Lys Ile Thr Val Glu Lys Tyr
            260                 265                 270

Asp Asp Gly Arg Asp Tyr Phe Asp Pro His Gly Met His Ile Ala Gly
        275                 280                 285

Ile Leu Ala Gly Asn Asp Thr Glu Gln Asp Ile Lys Asn Phe Asn Gly
290                 295                 300

Ile Asp Gly Ile Ala Pro Asn Ala Gln Ile Phe Ser Tyr Lys Met Tyr
305                 310                 315                 320

Ser Asp Ala Gly Ser Gly Phe Ala Gly Asp Glu Thr Met Phe His Ala
                325                 330                 335

Ile Glu Asp Ser Ile Lys His Asn Val Asp Val Ser Val Ser Ser
            340                 345                 350

Gly Phe Thr Gly Thr Gly Leu Val Gly Glu Lys Tyr Trp Gln Ala Ile
        355                 360                 365

Arg Ala Leu Arg Lys Ala Gly Ile Pro Met Val Val Ala Thr Gly Asn
370                 375                 380

Tyr Ala Thr Ser Ala Ser Ser Ser Ser Trp Asp Leu Val Ala Asn Asn
385                 390                 395                 400
```

```
His Leu Lys Met Thr Asp Thr Gly Asn Val Thr Arg Thr Ala Ala His
                405                 410                 415
Glu Asp Ala Ile Ala Val Ala Ser Ala Lys Asn Gln Thr Val Glu Phe
            420                 425                 430
Asp Lys Val Asn Ile Gly Gly Xaa Ser Phe Lys Tyr Arg Asn Ile Gly
        435                 440                 445
Ala Phe Phe Asp Lys Xaa Lys Ile Thr Thr Asn Glu Asp Gly Thr Lys
    450                 455                 460
Ala Pro Ser Lys Leu Lys Phe Val Tyr Ile Gly Lys Gly Gln Asp Gln
465                 470                 475                 480
Asp Leu Ile Gly Leu Asp Leu Arg Gly Lys Ile Ala Val Met Asp Arg
                485                 490                 495
Ile Tyr Thr Lys Asp Leu Lys Asn Ala Phe Lys Lys Ala Met Asp Lys
            500                 505                 510
Gly Ala Arg Ala Ile Met Val Val Asn Thr Val Asn Tyr Tyr Asn Arg
        515                 520                 525
Asp Asn Trp Thr Glu Leu Pro Ala Met Gly Tyr Glu Ala Asp Glu Gly
    530                 535                 540
Thr Lys Ser Gln Val Phe Ser Ile Ser Gly Asp Asp Gly Val Lys Leu
545                 550                 555                 560
Trp Asn Met Ile Asn Pro Xaa Lys Lys Thr Glu Val Lys Arg Asn Asn
                565                 570                 575
Lys Glu Asp Phe Lys Asp Lys Leu Glu Gln Tyr Tyr Pro Ile Asp Met
            580                 585                 590
Glu Ser Phe Asn Ser Asn Lys Pro Asn Val Gly Asp Glu Lys Glu Ile
        595                 600                 605
Asp Phe Lys Phe Ala Pro Asp Thr Asp Lys Glu Leu Tyr Lys Glu Asp
    610                 615                 620
Ile Ile Val Pro Ala Gly Ser Thr Ser Trp Gly Pro Arg Ile Asp Leu
625                 630                 635                 640
Leu Leu Lys Pro Asp Val Ser Ala Pro Gly Lys Asn Ile Lys Ser Thr
                645                 650                 655
Leu Asn Val Ile Asn Gly Lys Ser Thr Tyr Gly
                660                 665

<210> SEQ ID NO 16
<211> LENGTH: 648
<212> TYPE: PRT
<213> ORGANISM: Streptococcus pneumonia
<220> FEATURE:
<223> OTHER INFORMATION: SP641M consensus
<220> FEATURE:
<221> NAME/KEY: MOD_RES
<222> LOCATION: (28)..(28)
<223> OTHER INFORMATION: Arg or Lys
<220> FEATURE:
<221> NAME/KEY: MOD_RES
<222> LOCATION: (35)..(35)
<223> OTHER INFORMATION: Lys or Thr
<220> FEATURE:
<221> NAME/KEY: MOD_RES
<222> LOCATION: (143)..(143)
<223> OTHER INFORMATION: Ile or Val
<220> FEATURE:
<221> NAME/KEY: MOD_RES
<222> LOCATION: (165)..(165)
<223> OTHER INFORMATION: Asp or Tyr
<220> FEATURE:
<221> NAME/KEY: MOD_RES
<222> LOCATION: (210)..(210)
<223> OTHER INFORMATION: Lys or Arg
```

-continued

```
<220> FEATURE:
<221> NAME/KEY: MOD_RES
<222> LOCATION: (227)..(227)
<223> OTHER INFORMATION: Glu or Ala
<220> FEATURE:
<221> NAME/KEY: MOD_RES
<222> LOCATION: (232)..(232)
<223> OTHER INFORMATION: Asn or Ser
<220> FEATURE:
<221> NAME/KEY: MOD_RES
<222> LOCATION: (238)..(238)
<223> OTHER INFORMATION: Ile or Thr
<220> FEATURE:
<221> NAME/KEY: MOD_RES
<222> LOCATION: (239)..(239)
<223> OTHER INFORMATION: Asn or Asp
<220> FEATURE:
<221> NAME/KEY: MOD_RES
<222> LOCATION: (271)..(271)
<223> OTHER INFORMATION: Arg or Lys
<220> FEATURE:
<221> NAME/KEY: MOD_RES
<222> LOCATION: (275)..(275)
<223> OTHER INFORMATION: Leu or Met
<220> FEATURE:
<221> NAME/KEY: MOD_RES
<222> LOCATION: (276)..(276)
<223> OTHER INFORMATION: Gly or Glu
<220> FEATURE:
<221> NAME/KEY: MOD_RES
<222> LOCATION: (317)..(317)
<223> OTHER INFORMATION: Thr or Arg
<220> FEATURE:
<221> NAME/KEY: MOD_RES
<222> LOCATION: (323)..(323)
<223> OTHER INFORMATION: Asn or Asp
<220> FEATURE:
<221> NAME/KEY: MOD_RES
<222> LOCATION: (325)..(325)
<223> OTHER INFORMATION: Glu or Asp
<220> FEATURE:
<221> NAME/KEY: MOD_RES
<222> LOCATION: (332)..(332)
<223> OTHER INFORMATION: Glu or Gln
<220> FEATURE:
<221> NAME/KEY: MOD_RES
<222> LOCATION: (334)..(334)
<223> OTHER INFORMATION: Ile or Val
<220> FEATURE:
<221> NAME/KEY: MOD_RES
<222> LOCATION: (335)..(335)
<223> OTHER INFORMATION: Asn or His
<220> FEATURE:
<221> NAME/KEY: MOD_RES
<222> LOCATION: (337)..(337)
<223> OTHER INFORMATION: Pro or Glu
<220> FEATURE:
<221> NAME/KEY: MOD_RES
<222> LOCATION: (339)..(339)
<223> OTHER INFORMATION: Ser or Thr
<220> FEATURE:
<221> NAME/KEY: MOD_RES
<222> LOCATION: (393)..(393)
<223> OTHER INFORMATION: Arg or Lys
<220> FEATURE:
<221> NAME/KEY: MOD_RES
<222> LOCATION: (398)..(398)
<223> OTHER INFORMATION: Ile or Val
<220> FEATURE:
<221> NAME/KEY: MOD_RES
<222> LOCATION: (412)..(412)
<223> OTHER INFORMATION: Ser or Gly
<220> FEATURE:
<221> NAME/KEY: MOD_RES
<222> LOCATION: (594)..(594)
<223> OTHER INFORMATION: Lys or Ser
<220> FEATURE:
<221> NAME/KEY: MOD_RES
<222> LOCATION: (612)..(612)
```

```
<223> OTHER INFORMATION: Ser or Ala
<220> FEATURE:
<221> NAME/KEY: MOD_RES
<222> LOCATION: (625)..(625)
<223> OTHER INFORMATION: Asn or Asp
<220> FEATURE:
<221> NAME/KEY: MOD_RES
<222> LOCATION: (626)..(626)
<223> OTHER INFORMATION: Gln or His
<220> FEATURE:
<221> NAME/KEY: MOD_RES
<222> LOCATION: (642)..(642)
<223> OTHER INFORMATION: Gln or Lys
<220> FEATURE:
<221> NAME/KEY: MOD_RES
<222> LOCATION: (644)..(644)
<223> OTHER INFORMATION: Ser or Ala
<220> FEATURE:
<221> NAME/KEY: MOD_RES
<222> LOCATION: (648)..(648)
<223> OTHER INFORMATION: Gln or Glu

<400> SEQUENCE: 16
```

Met Ser Gly Thr Ser Met Ala Thr Pro Ile Val Ala Ala Ser Thr Val
1               5                   10                  15

Leu Ile Arg Pro Lys Leu Lys Glu Met Leu Glu Xaa Pro Val Leu Lys
            20                  25                  30

Asn Leu Xaa Gly Asp Asp Lys Ile Asp Leu Thr Ser Leu Thr Lys Ile
        35                  40                  45

Ala Leu Gln Asn Thr Ala Arg Pro Met Met Asp Ala Thr Ser Trp Lys
    50                  55                  60

Glu Lys Ser Gln Tyr Phe Ala Ser Pro Arg Gln Gln Gly Ala Gly Leu
65                  70                  75                  80

Ile Asn Val Ala Asn Ala Leu Arg Asn Glu Val Val Ala Thr Phe Lys
                85                  90                  95

Asn Thr Asp Ser Lys Gly Leu Val Asn Ser Tyr Gly Ser Ile Ser Leu
            100                 105                 110

Lys Glu Ile Lys Gly Asp Lys Lys Tyr Phe Thr Ile Lys Leu His Asn
        115                 120                 125

Thr Ser Asn Arg Pro Leu Thr Phe Lys Val Ser Ala Ser Ala Xaa Thr
    130                 135                 140

Thr Asp Ser Leu Thr Asp Arg Leu Lys Leu Asp Glu Thr Tyr Lys Asp
145                 150                 155                 160

Glu Lys Ser Pro Xaa Gly Lys Gln Ile Val Pro Glu Ile His Pro Glu
                165                 170                 175

Lys Val Lys Gly Ala Asn Ile Thr Phe Glu His Asp Thr Phe Thr Ile
            180                 185                 190

Gly Ala Asn Ser Ser Phe Asp Leu Asn Ala Val Ile Asn Val Gly Glu
        195                 200                 205

Ala Xaa Asn Lys Asn Lys Phe Val Glu Ser Phe Ile His Phe Glu Ser
    210                 215                 220

Val Glu Xaa Met Glu Ala Leu Xaa Ser Asn Gly Lys Lys Xaa Xaa Phe
225                 230                 235                 240

Gln Pro Ser Leu Ser Met Pro Leu Met Gly Phe Ala Gly Asn Trp Asn
                245                 250                 255

His Glu Pro Ile Leu Asp Lys Trp Ala Trp Glu Glu Gly Ser Xaa Ser
            260                 265                 270

Lys Thr Xaa Xaa Gly Tyr Asp Asp Asp Gly Lys Pro Lys Ile Pro Gly
        275                 280                 285

Thr Leu Asn Lys Gly Ile Gly Gly Glu His Gly Ile Asp Lys Phe Asn

```
              290                 295                 300
Pro Ala Gly Val Ile Gln Asn Arg Lys Asp Lys Asn Xaa Thr Ser Leu
305                 310                 315                 320

Asp Gln Xaa Pro Xaa Leu Phe Ala Phe Asn Asn Xaa Gly Xaa Xaa Ala
                325                 330                 335

Xaa Ser Xaa Ser Gly Ser Lys Ile Ala Asn Ile Tyr Pro Leu Asp Ser
            340                 345                 350

Asn Gly Asn Pro Gln Asp Ala Gln Leu Glu Arg Gly Leu Thr Pro Ser
                355                 360                 365

Pro Leu Val Leu Arg Ser Ala Glu Glu Gly Leu Ile Ser Ile Val Asn
            370                 375                 380

Thr Asn Lys Glu Gly Glu Asn Gln Xaa Asp Leu Lys Val Xaa Ser Arg
385                 390                 395                 400

Glu His Phe Ile Arg Gly Ile Leu Asn Ser Lys Xaa Asn Asp Ala Lys
                405                 410                 415

Gly Ile Lys Ser Ser Lys Leu Lys Val Trp Gly Asp Leu Lys Trp Asp
            420                 425                 430

Gly Leu Ile Tyr Asn Pro Arg Gly Arg Glu Glu Asn Ala Pro Glu Ser
            435                 440                 445

Lys Asp Asn Gln Asp Pro Ala Thr Lys Ile Arg Gly Gln Phe Glu Pro
450                 455                 460

Ile Ala Glu Gly Gln Tyr Phe Tyr Lys Phe Lys Tyr Arg Leu Thr Lys
465                 470                 475                 480

Asp Tyr Pro Trp Gln Val Ser Tyr Ile Pro Val Lys Ile Asp Asn Thr
                485                 490                 495

Ala Pro Lys Ile Val Ser Val Asp Phe Ser Asn Pro Glu Lys Ile Lys
            500                 505                 510

Leu Ile Thr Lys Asp Thr Tyr His Lys Val Lys Asp Gln Tyr Lys Asn
            515                 520                 525

Glu Thr Leu Phe Ala Arg Asp Gln Lys Glu His Pro Glu Lys Phe Asp
530                 535                 540

Glu Ile Ala Asn Glu Val Trp Tyr Ala Gly Ala Ala Leu Val Asn Glu
545                 550                 555                 560

Asp Gly Glu Val Glu Lys Asn Leu Glu Val Thr Tyr Ala Gly Glu Gly
                565                 570                 575

Gln Gly Arg Asn Arg Lys Leu Asp Lys Asp Gly Asn Thr Ile Tyr Glu
            580                 585                 590

Ile Xaa Gly Ala Gly Asp Leu Arg Gly Lys Ile Ile Glu Val Ile Ala
            595                 600                 605

Leu Asp Gly Xaa Ser Asn Phe Thr Lys Ile His Arg Ile Lys Phe Ala
610                 615                 620

Xaa Xaa Ala Asp Glu Lys Gly Met Ile Ser Tyr Tyr Leu Val Asp Pro
625                 630                 635                 640

Asp Xaa Asp Xaa Ser Lys Tyr Xaa
                645
```

<210> SEQ ID NO 17
<211> LENGTH: 274
<212> TYPE: PRT
<213> ORGANISM: Streptococcus pneumonia
<220> FEATURE:
<223> OTHER INFORMATION: SP0882/conserved hypothetical protein
      (Streptococcus pneumoniae TIGR4)
<300> PUBLICATION INFORMATION:
<308> DATABASE ACCESSION NUMBER: 14972356
<300> PUBLICATION INFORMATION:

<308> DATABASE ACCESSION NUMBER: AAK75009.1

<400> SEQUENCE: 17

```
Met Asn Gln Ser Tyr Phe Tyr Leu Lys Met Lys Glu His Lys Leu Lys
1               5                   10                  15

Val Pro Tyr Thr Gly Lys Glu Arg Arg Val Arg Ile Leu Leu Pro Lys
            20                  25                  30

Asp Tyr Glu Lys Asp Thr Asp Arg Ser Tyr Pro Val Val Tyr Phe His
        35                  40                  45

Asp Gly Gln Asn Val Phe Asn Ser Lys Glu Ser Phe Ile Gly His Ser
    50                  55                  60

Trp Lys Ile Ile Pro Ala Ile Lys Arg Asn Pro Asp Ile Ser Arg Met
65                  70                  75                  80

Ile Val Val Ala Ile Asp Asn Asp Gly Met Gly Arg Met Asn Glu Tyr
                85                  90                  95

Ala Ala Trp Lys Phe Gln Glu Ser Pro Ile Pro Gly Gln Gln Phe Gly
            100                 105                 110

Gly Lys Gly Val Glu Tyr Ala Glu Phe Val Met Glu Val Lys Pro
        115                 120                 125

Phe Ile Asp Glu Thr Tyr Arg Thr Lys Ala Asp Cys Gln His Thr Ala
    130                 135                 140

Met Ile Gly Ser Ser Leu Gly Gly Asn Ile Thr Gln Phe Ile Gly Leu
145                 150                 155                 160

Glu Tyr Gln Asp Gln Ile Gly Cys Leu Gly Val Phe Ser Ser Ala Asn
                165                 170                 175

Trp Leu His Gln Glu Ala Phe Asn Arg Tyr Phe Glu Cys Gln Lys Leu
            180                 185                 190

Ser Pro Asp Gln Arg Ile Phe Ile Tyr Val Gly Thr Glu Glu Ala Asp
        195                 200                 205

Asp Thr Asp Lys Thr Leu Met Asp Gly Asn Ile Lys Gln Ala Tyr Ile
    210                 215                 220

Asp Ser Ser Leu Cys Tyr Tyr His Asp Leu Ile Ala Gly Gly Val His
225                 230                 235                 240

Leu Asp Asn Leu Val Leu Lys Val Gln Ser Gly Ala Ile His Ser Glu
                245                 250                 255

Ile Pro Trp Ser Glu Asn Leu Pro Asp Cys Leu Arg Phe Phe Ala Glu
            260                 265                 270

Lys Trp
```

<210> SEQ ID NO 18
<211> LENGTH: 130
<212> TYPE: PRT
<213> ORGANISM: Streptococcus pneumonia
<220> FEATURE:
<223> OTHER INFORMATION: SP0882N

<400> SEQUENCE: 18

```
Met Asn Gln Ser Tyr Phe Tyr Leu Lys Met Lys Glu His Lys Leu Lys
1               5                   10                  15

Val Pro Tyr Thr Gly Lys Glu Arg Arg Val Arg Ile Leu Leu Pro Lys
            20                  25                  30

Asp Tyr Glu Lys Asp Thr Asp Arg Ser Tyr Pro Val Val Tyr Phe His
        35                  40                  45

Asp Gly Gln Asn Val Phe Asn Ser Lys Glu Ser Phe Ile Gly His Ser
    50                  55                  60
```

```
Trp Lys Ile Ile Pro Ala Ile Lys Arg Asn Pro Asp Ile Ser Arg Met
 65                  70                  75                  80

Ile Val Val Ala Ile Asp Asn Asp Gly Met Gly Arg Met Asn Glu Tyr
                 85                  90                  95

Ala Ala Trp Lys Phe Gln Glu Ser Pro Ile Pro Gly Gln Gln Phe Gly
            100                 105                 110

Gly Lys Gly Val Glu Tyr Ala Glu Phe Val Met Glu Val Val Lys Pro
        115                 120                 125

Phe Ile
    130

<210> SEQ ID NO 19
<211> LENGTH: 299
<212> TYPE: PRT
<213> ORGANISM: Streptococcus pneumonia
<220> FEATURE:
<223> OTHER INFORMATION: SP0882 with exogenous signal sequence

<400> SEQUENCE: 19

Met Ser Ser Lys Phe Met Lys Ser Ala Ala Val Leu Gly Thr Ala Thr
 1               5                  10                  15

Leu Ala Ser Leu Leu Val Ala Cys Met Asn Gln Ser Tyr Phe Tyr
             20                  25                  30

Leu Lys Met Lys Glu His Lys Leu Lys Val Pro Tyr Thr Gly Lys Glu
             35                  40                  45

Arg Arg Val Arg Ile Leu Leu Pro Lys Asp Tyr Glu Lys Asp Thr Asp
         50                  55                  60

Arg Ser Tyr Pro Val Val Tyr Phe His Asp Gly Gln Asn Val Phe Asn
 65                  70                  75                  80

Ser Lys Glu Ser Phe Ile Gly His Ser Trp Lys Ile Ile Pro Ala Ile
                 85                  90                  95

Lys Arg Asn Pro Asp Ile Ser Arg Met Ile Val Val Ala Ile Asp Asn
            100                 105                 110

Asp Gly Met Gly Arg Met Asn Glu Tyr Ala Ala Trp Lys Phe Gln Glu
        115                 120                 125

Ser Pro Ile Pro Gly Gln Gln Phe Gly Gly Lys Gly Val Glu Tyr Ala
    130                 135                 140

Glu Phe Val Met Glu Val Val Lys Pro Phe Ile Asp Glu Thr Tyr Arg
145                 150                 155                 160

Thr Lys Ala Asp Cys Gln His Thr Ala Met Ile Gly Ser Ser Leu Gly
                165                 170                 175

Gly Asn Ile Thr Gln Phe Ile Gly Leu Glu Tyr Gln Asp Gln Ile Gly
            180                 185                 190

Cys Leu Gly Val Phe Ser Ser Ala Asn Trp Leu His Gln Glu Ala Phe
        195                 200                 205

Asn Arg Tyr Phe Glu Cys Gln Lys Leu Ser Pro Asp Gln Arg Ile Phe
    210                 215                 220

Ile Tyr Val Gly Thr Glu Glu Ala Asp Asp Thr Asp Lys Thr Leu Met
225                 230                 235                 240

Asp Gly Asn Ile Lys Gln Ala Tyr Ile Asp Ser Ser Leu Cys Tyr Tyr
                245                 250                 255

His Asp Leu Ile Ala Gly Gly Val His Leu Asp Asn Leu Val Leu Lys
            260                 265                 270

Val Gln Ser Gly Ala Ile His Ser Glu Ile Pro Trp Ser Glu Asn Leu
        275                 280                 285
```

```
Pro Asp Cys Leu Arg Phe Phe Ala Glu Lys Trp
    290                 295

<210> SEQ ID NO 20
<211> LENGTH: 155
<212> TYPE: PRT
<213> ORGANISM: Streptococcus pneumonia
<220> FEATURE:
<223> OTHER INFORMATION: SP0882N with exogenous signal sequence

<400> SEQUENCE: 20

Met Ser Ser Lys Phe Met Lys Ser Ala Ala Val Leu Gly Thr Ala Thr
1               5                   10                  15

Leu Ala Ser Leu Leu Val Ala Cys Met Asn Gln Ser Tyr Phe Tyr
            20                  25                  30

Leu Lys Met Lys Glu His Lys Leu Lys Val Pro Tyr Thr Gly Lys Glu
        35                  40                  45

Arg Arg Val Arg Ile Leu Leu Pro Lys Asp Tyr Glu Lys Asp Thr Asp
    50                  55                  60

Arg Ser Tyr Pro Val Val Tyr Phe His Asp Gly Gln Asn Val Phe Asn
65                  70                  75                  80

Ser Lys Glu Ser Phe Ile Gly His Ser Trp Lys Ile Ile Pro Ala Ile
                85                  90                  95

Lys Arg Asn Pro Asp Ile Ser Arg Met Ile Val Val Ala Ile Asp Asn
            100                 105                 110

Asp Gly Met Gly Arg Met Asn Glu Tyr Ala Ala Trp Lys Phe Gln Glu
        115                 120                 125

Ser Pro Ile Pro Gly Gln Gln Phe Gly Gly Lys Gly Val Glu Tyr Ala
    130                 135                 140

Glu Phe Val Met Glu Val Val Lys Pro Phe Ile
145                 150                 155

<210> SEQ ID NO 21
<211> LENGTH: 274
<212> TYPE: PRT
<213> ORGANISM: Streptococcus pneumonia
<220> FEATURE:
<223> OTHER INFORMATION: SP0882 consensus
<220> FEATURE:
<221> NAME/KEY: MOD_RES
<222> LOCATION: (1)..(1)
<223> OTHER INFORMATION: Met or Ile
<220> FEATURE:
<221> NAME/KEY: MOD_RES
<222> LOCATION: (55)..(55)
<223> OTHER INFORMATION: Asn or Tyr
<220> FEATURE:
<221> NAME/KEY: MOD_RES
<222> LOCATION: (63)..(63)
<223> OTHER INFORMATION: His or Tyr
<220> FEATURE:
<221> NAME/KEY: MOD_RES
<222> LOCATION: (79)..(79)
<223> OTHER INFORMATION: Arg or His
<220> FEATURE:
<221> NAME/KEY: MOD_RES
<222> LOCATION: (97)..(97)
<223> OTHER INFORMATION: Ala or Glu
<220> FEATURE:
<221> NAME/KEY: MOD_RES
<222> LOCATION: (108)..(108)
<223> OTHER INFORMATION: Gly or Glu
<220> FEATURE:
<221> NAME/KEY: MOD_RES
<222> LOCATION: (164)..(164)
<223> OTHER INFORMATION: Asp or Glu
<220> FEATURE:
```

```
<221> NAME/KEY: MOD_RES
<222> LOCATION: (165)..(165)
<223> OTHER INFORMATION: Gln or Lys
<220> FEATURE:
<221> NAME/KEY: MOD_RES
<222> LOCATION: (187)..(187)
<223> OTHER INFORMATION: Phe or Ile
<220> FEATURE:
<221> NAME/KEY: MOD_RES
<222> LOCATION: (197)..(197)
<223> OTHER INFORMATION: Arg or His
<220> FEATURE:
<221> NAME/KEY: MOD_RES
<222> LOCATION: (238)..(238)
<223> OTHER INFORMATION: Gly or Arg

<400> SEQUENCE: 21

Xaa Asn Gln Ser Tyr Phe Tyr Leu Lys Met Lys Glu His Lys Leu Lys
 1               5                  10                  15

Val Pro Tyr Thr Gly Lys Glu Arg Arg Val Arg Ile Leu Leu Pro Lys
                20                  25                  30

Asp Tyr Glu Lys Asp Thr Asp Arg Ser Tyr Pro Val Val Tyr Phe His
            35                  40                  45

Asp Gly Gln Asn Val Phe Xaa Ser Lys Glu Ser Phe Ile Gly Xaa Ser
 50                  55                  60

Trp Lys Ile Ile Pro Ala Ile Lys Arg Asn Pro Asp Ile Ser Xaa Met
 65                  70                  75                  80

Ile Val Val Ala Ile Asp Asn Asp Gly Met Gly Arg Met Asn Glu Tyr
                85                  90                  95

Xaa Ala Trp Lys Phe Gln Glu Ser Pro Ile Pro Xaa Gln Gln Phe Gly
               100                 105                 110

Gly Lys Gly Val Glu Tyr Ala Glu Phe Val Met Glu Val Val Lys Pro
            115                 120                 125

Phe Ile Asp Glu Thr Tyr Arg Thr Lys Ala Asp Cys Gln His Thr Ala
130                 135                 140

Met Ile Gly Ser Ser Leu Gly Gly Asn Ile Thr Gln Phe Ile Gly Leu
145                 150                 155                 160

Glu Tyr Gln Xaa Xaa Ile Gly Cys Leu Gly Val Phe Ser Ser Ala Asn
               165                 170                 175

Trp Leu His Gln Glu Ala Phe Asn Arg Tyr Xaa Glu Cys Gln Lys Leu
            180                 185                 190

Ser Pro Asp Gln Xaa Ile Phe Ile Tyr Val Gly Thr Glu Glu Ala Asp
        195                 200                 205

Asp Thr Asp Lys Thr Leu Met Asp Gly Asn Ile Lys Gln Ala Tyr Ile
210                 215                 220

Asp Ser Ser Leu Cys Tyr Tyr His Asp Leu Ile Ala Gly Xaa Val His
225                 230                 235                 240

Leu Asp Asn Leu Val Leu Lys Val Gln Ser Gly Ala Ile His Ser Glu
                245                 250                 255

Ile Pro Trp Ser Glu Asn Leu Pro Asp Cys Leu Arg Phe Phe Ala Glu
            260                 265                 270

Lys Trp

<210> SEQ ID NO 22
<211> LENGTH: 130
<212> TYPE: PRT
<213> ORGANISM: Streptococcus pneumonia
<220> FEATURE:
<223> OTHER INFORMATION: SP0882N consensus
<220> FEATURE:
```

-continued

```
<221> NAME/KEY: MOD_RES
<222> LOCATION: (1)..(1)
<223> OTHER INFORMATION: Met or Ile
<220> FEATURE:
<221> NAME/KEY: MOD_RES
<222> LOCATION: (55)..(55)
<223> OTHER INFORMATION: Asn or Tyr
<220> FEATURE:
<221> NAME/KEY: MOD_RES
<222> LOCATION: (63)..(63)
<223> OTHER INFORMATION: His or Tyr
<220> FEATURE:
<221> NAME/KEY: MOD_RES
<222> LOCATION: (79)..(79)
<223> OTHER INFORMATION: Arg or His
<220> FEATURE:
<221> NAME/KEY: MOD_RES
<222> LOCATION: (97)..(97)
<223> OTHER INFORMATION: Ala or Glu
<220> FEATURE:
<221> NAME/KEY: MOD_RES
<222> LOCATION: (108)..(108)
<223> OTHER INFORMATION: Gly or Glu

<400> SEQUENCE: 22

Xaa Asn Gln Ser Tyr Phe Tyr Leu Lys Met Lys Glu His Lys Leu Lys
 1               5                  10                  15

Val Pro Tyr Thr Gly Lys Glu Arg Arg Val Arg Ile Leu Leu Pro Lys
                20                  25                  30

Asp Tyr Glu Lys Asp Thr Asp Arg Ser Tyr Pro Val Val Tyr Phe His
            35                  40                  45

Asp Gly Gln Asn Val Phe Xaa Ser Lys Glu Ser Phe Ile Gly Xaa Ser
        50                  55                  60

Trp Lys Ile Ile Pro Ala Ile Lys Arg Asn Pro Asp Ile Ser Xaa Met
65                  70                  75                  80

Ile Val Val Ala Ile Asp Asn Asp Gly Met Gly Arg Met Asn Glu Tyr
                85                  90                  95

Xaa Ala Trp Lys Phe Gln Glu Ser Pro Ile Pro Xaa Gln Gln Phe Gly
            100                 105                 110

Gly Lys Gly Val Glu Tyr Ala Glu Phe Val Met Glu Val Val Lys Pro
        115                 120                 125

Phe Ile
    130

<210> SEQ ID NO 23
<211> LENGTH: 299
<212> TYPE: PRT
<213> ORGANISM: Streptococcus pneumonia
<220> FEATURE:
<223> OTHER INFORMATION: SP0882 consensus with exogenous signal sequence
<220> FEATURE:
<221> NAME/KEY: MOD_RES
<222> LOCATION: (6)..(6)
<223> OTHER INFORMATION: Met or Thr
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (15)..(15)
<223> OTHER INFORMATION: Ala or Val
<220> FEATURE:
<221> NAME/KEY: MOD_RES
<222> LOCATION: (26)..(26)
<223> OTHER INFORMATION: Met or Ile
<220> FEATURE:
<221> NAME/KEY: MOD_RES
<222> LOCATION: (80)..(80)
```

```
<223> OTHER INFORMATION: Asn or Tyr
<220> FEATURE:
<221> NAME/KEY: MOD_RES
<222> LOCATION: (88)..(88)
<223> OTHER INFORMATION: His or Tyr
<220> FEATURE:
<221> NAME/KEY: MOD_RES
<222> LOCATION: (104)..(104)
<223> OTHER INFORMATION: Arg or His
<220> FEATURE:
<221> NAME/KEY: MOD_RES
<222> LOCATION: (122)..(122)
<223> OTHER INFORMATION: Ala or Glu
<220> FEATURE:
<221> NAME/KEY: MOD_RES
<222> LOCATION: (133)..(133)
<223> OTHER INFORMATION: Gly or Glu
<220> FEATURE:
<221> NAME/KEY: MOD_RES
<222> LOCATION: (189)..(189)
<223> OTHER INFORMATION: Asp or Glu
<220> FEATURE:
<221> NAME/KEY: MOD_RES
<222> LOCATION: (190)..(190)
<223> OTHER INFORMATION: Gln or Lys
<220> FEATURE:
<221> NAME/KEY: MOD_RES
<222> LOCATION: (212)..(212)
<223> OTHER INFORMATION: Phe or Ile
<220> FEATURE:
<221> NAME/KEY: MOD_RES
<222> LOCATION: (222)..(222)
<223> OTHER INFORMATION: Arg or His
<220> FEATURE:
<221> NAME/KEY: MOD_RES
<222> LOCATION: (263)..(263)
<223> OTHER INFORMATION: Gly or Arg

<400> SEQUENCE: 23

Met Ser Ser Lys Phe Xaa Lys Ser Xaa Ala Val Leu Gly Thr Xaa Thr
1               5                   10                  15

Leu Ala Ser Leu Leu Leu Val Ala Cys Xaa Asn Gln Ser Tyr Phe Tyr
                20                  25                  30

Leu Lys Met Lys Glu His Lys Leu Lys Val Pro Tyr Thr Gly Lys Glu
            35                  40                  45

Arg Arg Val Arg Ile Leu Leu Pro Lys Asp Tyr Glu Lys Asp Thr Asp
50                  55                  60

Arg Ser Tyr Pro Val Val Tyr Phe His Asp Gly Gln Asn Val Phe Xaa
65                  70                  75                  80

Ser Lys Glu Ser Phe Ile Gly Xaa Ser Trp Lys Ile Ile Pro Ala Ile
                85                  90                  95

Lys Arg Asn Pro Asp Ile Ser Xaa Met Ile Val Val Ala Ile Asp Asn
            100                 105                 110

Asp Gly Met Gly Arg Met Asn Glu Tyr Xaa Ala Trp Lys Phe Gln Glu
        115                 120                 125

Ser Pro Ile Pro Xaa Gln Gln Phe Gly Gly Lys Gly Val Glu Tyr Ala
    130                 135                 140

Glu Phe Val Met Glu Val Val Lys Pro Phe Ile Asp Glu Thr Tyr Arg
145                 150                 155                 160

Thr Lys Ala Asp Cys Gln His Thr Ala Met Ile Gly Ser Ser Leu Gly
                165                 170                 175

Gly Asn Ile Thr Gln Phe Ile Gly Leu Glu Tyr Gln Xaa Xaa Ile Gly
            180                 185                 190

Cys Leu Gly Val Phe Ser Ser Ala Asn Trp Leu His Gln Glu Ala Phe
        195                 200                 205
```

```
Asn Arg Tyr Xaa Glu Cys Gln Lys Leu Ser Pro Asp Gln Xaa Ile Phe
    210             215                 220

Ile Tyr Val Gly Thr Glu Glu Ala Asp Thr Asp Lys Thr Leu Met
225             230                 235                 240

Asp Gly Asn Ile Lys Gln Ala Tyr Ile Asp Ser Ser Leu Cys Tyr Tyr
                245                 250                 255

His Asp Leu Ile Ala Gly Xaa Val His Leu Asp Asn Leu Val Leu Lys
            260                 265                 270

Val Gln Ser Gly Ala Ile His Ser Glu Ile Pro Trp Ser Glu Asn Leu
        275                 280                 285

Pro Asp Cys Leu Arg Phe Phe Ala Glu Lys Trp
    290                 295

<210> SEQ ID NO 24
<211> LENGTH: 155
<212> TYPE: PRT
<213> ORGANISM: Streptococcus pneumonia
<220> FEATURE:
<223> OTHER INFORMATION: SP0882N consensus with exogenous signal
      sequence
<220> FEATURE:
<221> NAME/KEY: MOD_RES
<222> LOCATION: (6)..(6)
<223> OTHER INFORMATION: Met or Thr
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (15)..(15)
<223> OTHER INFORMATION: Ala or Val
<220> FEATURE:
<221> NAME/KEY: MOD_RES
<222> LOCATION: (26)..(26)
<223> OTHER INFORMATION: Met or Ile
<220> FEATURE:
<221> NAME/KEY: MOD_RES
<222> LOCATION: (80)..(80)
<223> OTHER INFORMATION: Asn or Tyr
<220> FEATURE:
<221> NAME/KEY: MOD_RES
<222> LOCATION: (88)..(88)
<223> OTHER INFORMATION: His or Tyr
<220> FEATURE:
<221> NAME/KEY: MOD_RES
<222> LOCATION: (104)..(104)
<223> OTHER INFORMATION: Arg or His
<220> FEATURE:
<221> NAME/KEY: MOD_RES
<222> LOCATION: (122)..(122)
<223> OTHER INFORMATION: Ala or Glu
<220> FEATURE:
<221> NAME/KEY: MOD_RES
<222> LOCATION: (133)..(133)
<223> OTHER INFORMATION: Gly or Glu

<400> SEQUENCE: 24

Met Ser Ser Lys Phe Xaa Lys Ser Xaa Ala Val Leu Gly Thr Xaa Thr
1               5                   10                  15

Leu Ala Ser Leu Leu Leu Val Ala Cys Xaa Asn Gln Ser Tyr Phe Tyr
            20                  25                  30

Leu Lys Met Lys Glu His Lys Leu Lys Val Pro Tyr Thr Gly Lys Glu
        35                  40                  45

Arg Arg Val Arg Ile Leu Leu Pro Lys Asp Tyr Glu Lys Asp Thr Asp
    50                  55                  60

Arg Ser Tyr Pro Val Val Tyr Phe His Asp Gly Gln Asn Val Phe Xaa
65                  70                  75                  80
```

```
Ser Lys Glu Ser Phe Ile Gly Xaa Ser Trp Lys Ile Ile Pro Ala Ile
                85                  90                  95

Lys Arg Asn Pro Asp Ile Ser Xaa Met Ile Val Val Ala Ile Asp Asn
            100                 105                 110

Asp Gly Met Gly Arg Met Asn Glu Tyr Xaa Ala Trp Lys Phe Gln Glu
        115                 120                 125

Ser Pro Ile Pro Xaa Gln Gln Phe Gly Gly Lys Gly Val Glu Tyr Ala
    130                 135                 140

Glu Phe Val Met Glu Val Val Lys Pro Phe Ile
145                 150                 155
```

<210> SEQ ID NO 25
<211> LENGTH: 357
<212> TYPE: PRT
<213> ORGANISM: Streptococcus pneumonia
<220> FEATURE:
<223> OTHER INFORMATION: SP1634/hypothetical protein SP_1634
      Streptococcus pneumoniae TIGR4
<300> PUBLICATION INFORMATION:
<308> DATABASE ACCESSION NUMBER: 14973124
<300> PUBLICATION INFORMATION:
<308> DATABASE ACCESSION NUMBER: AAK75714.1

<400> SEQUENCE: 25

```
Met Ala Asn Ile Phe Asp Tyr Leu Lys Asp Val Ala Tyr Asp Ser Tyr
1               5                   10                  15

Tyr Asp Leu Pro Leu Asn Glu Leu Asp Ile Leu Thr Leu Ile Glu Ile
            20                  25                  30

Thr Tyr Leu Ser Phe Asp Asn Leu Val Ser Thr Leu Pro Gln Arg Leu
        35                  40                  45

Leu Asp Leu Ala Pro Gln Val Pro Arg Asp Pro Thr Met Leu Thr Ser
    50                  55                  60

Lys Asn Arg Leu Gln Leu Leu Asp Glu Leu Ala Gln His Lys Arg Phe
65                  70                  75                  80

Lys Asn Cys Lys Leu Ser His Phe Ile Asn Asp Ile Asp Pro Glu Leu
                85                  90                  95

Gln Lys Gln Phe Ala Ala Met Thr Tyr Arg Val Ser Leu Asp Thr Tyr
            100                 105                 110

Leu Ile Val Phe Arg Gly Thr Asp Asp Ser Ile Ile Gly Trp Lys Glu
        115                 120                 125

Asp Phe His Leu Thr Tyr Met Lys Glu Ile Pro Ala Gln Lys His Ala
    130                 135                 140

Leu Arg Tyr Leu Lys Asn Phe Phe Ala His His Pro Lys Gln Lys Val
145                 150                 155                 160

Ile Leu Ala Gly His Ser Lys Gly Gly Asn Leu Ala Ile Tyr Ala Ala
                165                 170                 175

Ser Gln Ile Glu Gln Ser Leu Gln Asn Gln Ile Thr Ala Val Tyr Thr
            180                 185                 190

Phe Asp Ala Pro Gly Leu His Gln Glu Leu Thr Gln Thr Ala Gly Tyr
        195                 200                 205

Gln Arg Ile Met Asp Arg Ser Lys Ile Phe Ile Pro Gln Gly Ser Ile
    210                 215                 220

Ile Gly Met Met Leu Glu Ile Pro Ala His Gln Ile Ile Val Gln Ser
225                 230                 235                 240

Thr Ala Leu Gly Gly Ile Ala Gln His Asp Thr Phe Ser Trp Gln Ile
                245                 250                 255
```

```
Glu Asp Lys His Phe Val Gln Leu Asp Lys Thr Asn Ser Asp Ser Gln
            260                 265                 270

Gln Val Asp Thr Thr Phe Lys Glu Trp Val Ala Thr Val Pro Asp Glu
        275                 280                 285

Glu Leu Gln Leu Tyr Phe Asp Leu Phe Phe Gly Thr Ile Leu Asp Ala
    290                 295                 300

Gly Ile Ser Ser Ile Asn Asp Leu Ala Ser Leu Lys Ala Leu Glu Tyr
305                 310                 315                 320

Ile His His Leu Phe Val Gln Ala Gln Ser Leu Thr Pro Glu Glu Arg
            325                 330                 335

Glu Thr Leu Gly Arg Leu Thr Gln Leu Leu Ile Asp Thr Arg Tyr Gln
        340                 345                 350

Ala Trp Lys Asn Arg
        355

<210> SEQ ID NO 26
<211> LENGTH: 1066
<212> TYPE: PRT
<213> ORGANISM: Streptococcus pneumonia
<220> FEATURE:
<223> OTHER INFORMATION: SP0314/hyaluronidase Streptococcus pneumonia
      TIGR4
<300> PUBLICATION INFORMATION:
<308> DATABASE ACCESSION NUMBER: 14971788
<300> PUBLICATION INFORMATION:
<308> DATABASE ACCESSION NUMBER: AAK74491.1

<400> SEQUENCE: 26

Met Gln Thr Lys Thr Lys Lys Leu Ile Val Ser Leu Ser Ser Leu Val
1               5                   10                  15

Leu Ser Gly Phe Leu Leu Asn His Tyr Met Thr Ile Gly Ala Glu Glu
            20                  25                  30

Thr Thr Thr Asn Thr Ile Gln Gln Ser Gln Lys Glu Val Gln Tyr Gln
        35                  40                  45

Gln Arg Asp Thr Lys Asn Leu Val Glu Asn Gly Asp Phe Gly Gln Thr
    50                  55                  60

Glu Asp Gly Ser Ser Pro Trp Thr Gly Ser Lys Ala Gln Gly Trp Ser
65                  70                  75                  80

Ala Trp Val Asp Gln Lys Asn Ser Ala Asp Ala Ser Thr Arg Val Ile
            85                  90                  95

Glu Ala Lys Asp Gly Ala Ile Thr Ile Ser Ser His Glu Lys Leu Arg
            100                 105                 110

Ala Ala Leu His Arg Met Val Pro Ile Glu Ala Lys Lys Lys Tyr Lys
        115                 120                 125

Leu Arg Phe Lys Ile Lys Thr Asp Asn Lys Ile Gly Ile Ala Lys Val
    130                 135                 140

Arg Ile Ile Glu Glu Ser Gly Lys Asp Lys Arg Leu Trp Asn Ser Ala
145                 150                 155                 160

Thr Thr Ser Gly Thr Lys Asp Trp Gln Thr Ile Glu Ala Asp Tyr Ser
            165                 170                 175

Pro Thr Leu Asp Val Asp Lys Ile Lys Leu Glu Leu Phe Tyr Glu Thr
        180                 185                 190

Gly Thr Gly Thr Val Ser Phe Lys Asp Ile Glu Leu Glu Val Ala
    195                 200                 205

Asp Gln Leu Ser Glu Asp Ser Gln Thr Asp Lys Gln Leu Glu Glu Lys
    210                 215                 220

Ile Asp Leu Pro Ile Gly Lys Lys His Val Phe Ser Leu Ala Asp Tyr
```

-continued

```
                225                 230                 235                 240
            Thr Tyr Lys Val Glu Asn Pro Asp Val Ala Ser Val Lys Asn Gly Ile
                            245                 250                 255
            Leu Glu Pro Leu Lys Glu Gly Thr Thr Asn Val Ile Val Ser Lys Asp
                            260                 265                 270
            Gly Lys Glu Val Lys Lys Ile Pro Leu Lys Ile Leu Ala Ser Val Lys
                            275                 280                 285
            Asp Ala Tyr Thr Asp Arg Leu Asp Asp Trp Asn Gly Ile Ile Ala Gly
                290                 295                 300
            Asn Gln Tyr Tyr Asp Ser Lys Asn Glu Gln Met Ala Lys Leu Asn Gln
            305                 310                 315                 320
            Glu Leu Glu Gly Lys Val Ala Asp Ser Leu Ser Ser Ile Ser Ser Gln
                            325                 330                 335
            Ala Asp Arg Thr Tyr Leu Trp Glu Lys Phe Ser Asn Tyr Lys Thr Ser
                            340                 345                 350
            Ala Asn Leu Thr Ala Thr Tyr Arg Lys Leu Glu Glu Met Ala Lys Gln
                            355                 360                 365
            Val Thr Asn Pro Ser Ser Arg Tyr Tyr Gln Asp Glu Thr Val Val Arg
                370                 375                 380
            Thr Val Arg Asp Ser Met Glu Trp Met His Lys His Val Tyr Asn Ser
            385                 390                 395                 400
            Glu Lys Ser Ile Val Gly Asn Trp Trp Asp Tyr Glu Ile Gly Thr Pro
                            405                 410                 415
            Arg Ala Ile Asn Asn Thr Leu Ser Leu Met Lys Glu Tyr Phe Ser Asp
                            420                 425                 430
            Glu Glu Ile Lys Lys Tyr Thr Asp Val Ile Glu Lys Phe Val Pro Asp
                            435                 440                 445
            Pro Glu His Phe Arg Lys Thr Thr Asp Asn Pro Phe Lys Ala Leu Gly
                            450                 455                 460
            Gly Asn Leu Val Asp Met Gly Arg Val Lys Val Ile Ala Gly Leu Leu
            465                 470                 475                 480
            Arg Lys Asp Asp Gln Glu Ile Ser Ser Thr Ile Arg Ser Ile Glu Gln
                            485                 490                 495
            Val Phe Lys Leu Val Asp Gln Gly Glu Gly Phe Tyr Gln Asp Gly Ser
                            500                 505                 510
            Tyr Ile Asp His Thr Asn Val Ala Tyr Thr Gly Ala Tyr Gly Asn Val
                            515                 520                 525
            Leu Ile Asp Gly Leu Ser Gln Leu Leu Pro Val Ile Gln Lys Thr Lys
                530                 535                 540
            Asn Pro Ile Asp Lys Asp Lys Met Gln Thr Met Tyr His Trp Ile Asp
            545                 550                 555                 560
            Lys Ser Phe Ala Pro Leu Leu Val Asn Gly Glu Leu Met Asp Met Ser
                            565                 570                 575
            Arg Gly Arg Ser Ile Ser Arg Ala Asn Ser Glu Gly His Val Ala Ala
                            580                 585                 590
            Val Glu Val Leu Arg Gly Ile His Arg Ile Ala Asp Met Ser Glu Gly
                            595                 600                 605
            Glu Thr Lys Gln Cys Leu Gln Ser Leu Val Lys Thr Ile Val Gln Ser
                            610                 615                 620
            Asp Ser Tyr Tyr Asp Val Phe Lys Asn Leu Lys Thr Tyr Lys Asp Ile
            625                 630                 635                 640
            Ser Leu Met Gln Ser Leu Leu Ser Asp Ala Gly Val Ala Ser Val Pro
                            645                 650                 655
```

```
Arg Pro Ser Tyr Leu Ser Ala Phe Asn Lys Met Asp Lys Thr Ala Met
            660                 665                 670

Tyr Asn Ala Glu Lys Gly Phe Gly Phe Gly Leu Ser Leu Phe Ser Ser
            675                 680                 685

Arg Thr Leu Asn Tyr Glu His Met Asn Lys Glu Asn Lys Arg Gly Trp
690                 695                 700

Tyr Thr Ser Asp Gly Met Phe Tyr Leu Tyr Asn Gly Asp Leu Ser His
705                 710                 715                 720

Tyr Ser Asp Gly Tyr Trp Pro Thr Val Asn Pro Tyr Lys Met Pro Gly
                725                 730                 735

Thr Thr Glu Thr Asp Ala Lys Arg Ala Asp Ser Asp Thr Gly Lys Val
            740                 745                 750

Leu Pro Ser Ala Phe Val Gly Thr Ser Lys Leu Asp Asp Ala Asn Ala
            755                 760                 765

Thr Ala Thr Met Asp Phe Thr Asn Trp Asn Gln Thr Leu Thr Ala His
            770                 775                 780

Lys Ser Trp Phe Met Leu Lys Asp Lys Ile Ala Phe Leu Gly Ser Asn
785                 790                 795                 800

Ile Gln Asn Thr Ser Thr Asp Thr Ala Ala Thr Thr Ile Asp Gln Arg
                805                 810                 815

Lys Leu Glu Ser Gly Asn Pro Tyr Lys Val Tyr Val Asn Asp Lys Glu
            820                 825                 830

Ala Ser Leu Thr Glu Gln Glu Lys Asp Tyr Pro Glu Thr Gln Ser Val
            835                 840                 845

Phe Leu Glu Ser Phe Asp Ser Lys Lys Asn Ile Gly Tyr Phe Phe Phe
850                 855                 860

Lys Lys Ser Ser Ile Ser Met Ser Lys Ala Leu Gln Lys Gly Ala Trp
865                 870                 875                 880

Lys Asp Ile Asn Glu Gly Gln Ser Asp Lys Glu Val Glu Asn Glu Phe
                885                 890                 895

Leu Thr Ile Ser Gln Ala His Lys Gln Asn Arg Asp Ser Tyr Gly Tyr
                900                 905                 910

Met Leu Ile Pro Asn Val Asp Arg Ala Thr Phe Asn Gln Met Ile Lys
            915                 920                 925

Glu Leu Glu Ser Ser Leu Ile Glu Asn Asn Glu Thr Leu Gln Ser Val
            930                 935                 940

Tyr Asp Ala Lys Gln Gly Val Trp Gly Ile Val Lys Tyr Asp Asp Ser
945                 950                 955                 960

Val Ser Thr Ile Ser Asn Gln Phe Gln Val Leu Lys Arg Gly Val Tyr
                965                 970                 975

Thr Ile Arg Lys Glu Gly Asp Gly Tyr Lys Ile Ala Tyr Tyr Asn Pro
            980                 985                 990

Glu Thr Gln Glu Ser Ala Pro Asp Gln Glu Val Phe Lys Lys Leu Glu
            995                 1000                1005

Gln Ala Ala Gln Pro Gln Val Gln Asn Ser Lys Glu Lys Glu Lys
        1010                1015                1020

Ser Glu Glu Glu Lys Asn His Ser Asp Gln Lys Asn Leu Pro Gln
        1025                1030                1035

Thr Gly Glu Gly Gln Ser Ile Leu Ala Ser Leu Gly Phe Leu Leu
        1040                1045                1050

Leu Gly Ala Phe Tyr Leu Phe Arg Arg Gly Lys Asn Asn
        1055                1060                1065
```

<210> SEQ ID NO 27
<211> LENGTH: 653
<212> TYPE: PRT
<213> ORGANISM: Streptococcus pneumonia
<220> FEATURE:
<223> OTHER INFORMATION: PspA

<400> SEQUENCE: 27

```
Met Asn Lys Lys Met Ile Leu Thr Ser Leu Ala Ser Val Ala Ile
1               5                   10                  15

Leu Gly Ala Gly Phe Val Ala Ser Ser Pro Thr Phe Val Arg Ala Glu
                20                  25                  30

Glu Ala Pro Val Ala Asn Gln Ser Lys Ala Glu Lys Asp Tyr Asp Ala
            35                  40                  45

Ala Val Lys Lys Ser Glu Ala Ala Lys Lys Asp Tyr Glu Thr Ala Lys
        50                  55                  60

Lys Lys Ala Glu Asp Ala Gln Lys Lys Tyr Asp Glu Asp Gln Lys Lys
65                  70                  75                  80

Thr Glu Ala Lys Ala Glu Lys Glu Arg Lys Ala Ser Glu Lys Ile Ala
                85                  90                  95

Glu Ala Thr Lys Glu Val Gln Gln Ala Tyr Leu Ala Tyr Leu Gln Ala
            100                 105                 110

Ser Asn Glu Ser Gln Arg Lys Glu Ala Asp Lys Lys Ile Lys Glu Ala
        115                 120                 125

Thr Gln Arg Lys Asp Glu Ala Glu Ala Ala Phe Ala Thr Ile Arg Thr
    130                 135                 140

Thr Ile Val Val Pro Glu Pro Ser Glu Leu Ala Glu Thr Lys Lys Lys
145                 150                 155                 160

Ala Glu Glu Ala Thr Lys Glu Ala Glu Val Ala Lys Lys Lys Ser Glu
                165                 170                 175

Glu Ala Ala Lys Glu Val Glu Val Glu Lys Asn Lys Ile Leu Glu Gln
            180                 185                 190

Asp Ala Glu Asn Glu Lys Lys Ile Asp Val Leu Gln Asn Lys Val Ala
        195                 200                 205

Asp Leu Glu Lys Gly Ile Ala Pro Tyr Gln Asn Glu Val Ala Glu Leu
    210                 215                 220

Asn Lys Glu Ile Ala Arg Leu Gln Ser Asp Leu Lys Asp Ala Glu Glu
225                 230                 235                 240

Asn Asn Val Glu Asp Tyr Ile Lys Glu Gly Leu Glu Gln Ala Ile Thr
                245                 250                 255

Asn Lys Lys Ala Glu Leu Ala Thr Thr Gln Gln Asn Ile Asp Lys Thr
            260                 265                 270

Gln Lys Asp Leu Glu Asp Ala Glu Leu Glu Leu Glu Lys Val Leu Ala
        275                 280                 285

Thr Leu Asp Pro Glu Gly Lys Thr Gln Asp Glu Leu Asp Lys Glu Ala
    290                 295                 300

Ala Glu Ala Glu Leu Asn Glu Lys Val Glu Ala Leu Gln Asn Gln Val
305                 310                 315                 320

Ala Glu Leu Glu Glu Leu Ser Lys Leu Glu Asp Asn Leu Lys Asp
                325                 330                 335

Ala Glu Thr Asn Asn Val Glu Asp Tyr Ile Lys Glu Gly Leu Glu Glu
            340                 345                 350

Ala Ile Ala Thr Lys Lys Ala Glu Leu Glu Lys Thr Gln Lys Glu Leu
        355                 360                 365
```

```
Asp Ala Ala Leu Asn Glu Leu Gly Pro Asp Gly Asp Glu Glu Thr
        370                 375                 380

Pro Ala Pro Ala Pro Gln Pro Glu Lys Pro Ala Glu Glu Pro Glu Asn
385                 390                 395                 400

Pro Ala Pro Ala Pro Lys Pro Glu Lys Ser Ala Asp Gln Gln Ala Glu
                405                 410                 415

Glu Asp Tyr Ala Arg Arg Ser Glu Glu Glu Tyr Asn Arg Leu Thr Gln
            420                 425                 430

Gln Gln Pro Pro Lys Ala Glu Lys Pro Ala Pro Ala Pro Gln Pro Glu
        435                 440                 445

Gln Pro Ala Pro Ala Pro Lys Ile Gly Trp Lys Gln Glu Asn Gly Met
450                 455                 460

Trp Tyr Phe Tyr Asn Thr Asp Gly Ser Met Ala Thr Gly Trp Leu Gln
465                 470                 475                 480

Asn Asn Gly Ser Trp Tyr Tyr Leu Asn Ser Asn Gly Ala Met Ala Thr
                485                 490                 495

Gly Trp Leu Gln Tyr Asn Gly Ser Trp Tyr Tyr Leu Asn Ala Asn Gly
            500                 505                 510

Ala Met Ala Thr Gly Trp Leu Gln Tyr Asn Gly Ser Trp Tyr Tyr Leu
        515                 520                 525

Asn Ala Asn Gly Ala Met Ala Thr Gly Trp Leu Gln Tyr Asn Gly Ser
530                 535                 540

Trp Tyr Tyr Leu Asn Ala Asn Gly Asp Met Ala Thr Gly Trp Leu Gln
545                 550                 555                 560

Tyr Asn Gly Ser Trp Tyr Tyr Leu Asn Ala Asn Gly Asp Met Ala Thr
                565                 570                 575

Gly Trp Ala Lys Val His Gly Ser Trp Tyr Tyr Leu Asn Ala Asn Gly
            580                 585                 590

Ser Met Ala Thr Gly Trp Val Lys Asp Gly Glu Thr Trp Tyr Tyr Leu
        595                 600                 605

Glu Ala Ser Gly Ser Met Lys Ala Asn Gln Trp Phe Gln Val Ser Asp
610                 615                 620

Lys Trp Tyr Tyr Val Asn Gly Leu Gly Ser Leu Ser Val Asn Thr Thr
625                 630                 635                 640

Val Asp Gly Tyr Lys Val Asn Ala Asn Gly Glu Trp Val
                645                 650

<210> SEQ ID NO 28
<211> LENGTH: 283
<212> TYPE: PRT
<213> ORGANISM: Streptococcus pneumonia
<220> FEATURE:
<223> OTHER INFORMATION: Immunogenic PspA/PspC polypeptides including
      the coiled-coil structure (PR + NPB)

<400> SEQUENCE: 28

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80
```

```
Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
        115                 120                 125

Arg Gly Ser Gly Met Lys Glu Thr Ala Ala Lys Phe Glu Arg Gln
    130                 135                 140

His Met Asp Ser Pro Asp Leu Gly Thr Asp Asp Asp Lys Ala Met
145                 150                 155                 160

Ala Asp Leu Lys Lys Ala Val Asn Glu Pro Glu Lys Pro Ala Glu Glu
                165                 170                 175

Pro Glu Asn Pro Ala Pro Ala Pro Lys Pro Ala Pro Ala Pro Gln Pro
            180                 185                 190

Glu Lys Pro Ala Pro Ala Pro Ala Pro Lys Pro Glu Lys Ser Ala Asp
        195                 200                 205

Gln Gln Ala Glu Glu Asp Tyr Ala Arg Arg Ser Glu Glu Tyr Asn
    210                 215                 220

Arg Leu Thr Gln Gln Pro Lys Ala Glu Lys Pro Ala Pro Ala
225                 230                 235                 240

Pro Val Pro Lys Pro Glu Gln Pro Ala Pro Ala Pro Lys Thr Gly Trp
                245                 250                 255

Gly Gln Glu Asn Gly Met Trp Cys Arg Gln Ala Cys Gly Arg Thr Arg
            260                 265                 270

Ala Pro Pro Pro Pro Leu Arg Ser Gly Cys
        275                 280

<210> SEQ ID NO 29
<211> LENGTH: 103
<212> TYPE: PRT
<213> ORGANISM: Streptococcus pneumonia
<220> FEATURE:
<223> OTHER INFORMATION: Immunogenic PspA/PspC polypeptide CD2

<400> SEQUENCE: 29

Ala Asp Leu Lys Lys Ala Val Asn Glu Pro Glu Lys Pro Ala Glu Glu
1               5                   10                  15

Pro Glu Asn Pro Ala Pro Ala Pro Lys Pro Ala Pro Ala Pro Gln Pro
            20                  25                  30

Glu Lys Pro Ala Pro Ala Pro Ala Pro Lys Pro Glu Lys Ser Ala Asp
        35                  40                  45

Gln Gln Ala Glu Glu Asp Tyr Ala Arg Arg Ser Glu Glu Tyr Asn
    50                  55                  60

Arg Leu Thr Gln Gln Pro Pro Lys Ala Glu Lys Pro Ala Pro Ala
65                  70                  75                  80

Pro Val Pro Lys Pro Glu Gln Pro Ala Pro Ala Pro Lys Thr Gly Trp
                85                  90                  95

Gly Gln Glu Asn Gly Met Trp
            100

<210> SEQ ID NO 30
<211> LENGTH: 58
<212> TYPE: PRT
<213> ORGANISM: Streptococcus pneumonia
<220> FEATURE:
<223> OTHER INFORMATION: Immunogenic PspA/PspC polypeptides lacking the
      coiled-coil structure (PR + NPB)
```

```
<400> SEQUENCE: 30

Met Ala Lys Lys Ala Glu Leu Glu Lys Thr Pro Glu Lys Pro Ala Glu
1               5                   10                  15

Glu Pro Glu Asn Pro Ala Pro Ala Pro Gln Pro Glu Lys Ser Ala Asp
            20                  25                  30

Gln Gln Ala Glu Glu Asp Tyr Ala Arg Arg Ser Glu Glu Glu Tyr Asn
        35                  40                  45

Arg Leu Thr Gln Gln Gln Pro Pro Lys Ala
        50                  55

<210> SEQ ID NO 31
<211> LENGTH: 286
<212> TYPE: PRT
<213> ORGANISM: Streptococcus pneumonia
<220> FEATURE:
<223> OTHER INFORMATION: Immunogenic PspA/PspC polypeptides including
      the coiled-coil structure (PR only)

<400> SEQUENCE: 31

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65              70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Ala Met
145                 150                 155                 160

Ala Asp Leu Lys Lys Ala Val Asn Glu Pro Glu Thr Pro Ala Pro Ala
                165                 170                 175

Pro Ala Pro Ala Pro Ala Pro Ala Pro Thr Pro Glu Ala Pro Ala Pro
            180                 185                 190

Ala Pro Ala Pro Ala Pro Lys Pro Ala Pro Ala Pro Lys Pro Ala Pro
        195                 200                 205

Ala Pro Lys Pro Ala Pro Ala Pro Lys Pro Ala Pro Ala Pro Lys Pro
    210                 215                 220

Ala Pro Ala Pro Lys Pro Ala Pro Ala Pro Ala Pro Ala Pro Lys Pro
225                 230                 235                 240

Glu Lys Pro Ala Glu Lys Pro Ala Pro Ala Pro Lys Pro Glu Thr Pro
                245                 250                 255

Lys Thr Gly Trp Lys Gln Glu Asn Gly Met Trp Cys Arg Gln Ala Cys
            260                 265                 270

Gly Arg Thr Arg Ala Pro Pro Pro Pro Leu Arg Ser Gly
        275                 280                 285
```

```
<210> SEQ ID NO 32
<211> LENGTH: 106
<212> TYPE: PRT
<213> ORGANISM: Streptococcus pneumonia
<220> FEATURE:
<223> OTHER INFORMATION: Immunogenic PspA/PspC polypeptides lacking the
      coiled-coil structure (PR only)

<400> SEQUENCE: 32
```

Asp Leu Lys Lys Ala Val Asn Glu Pro Glu Thr Pro Ala Pro Ala Pro
1               5                   10                  15

Ala Pro Ala Pro Ala Pro Ala Pro Thr Pro Glu Ala Pro Ala Pro Ala
            20                  25                  30

Pro Ala Pro Ala Pro Lys Pro Ala Pro Ala Pro Lys Pro Ala Pro Ala
        35                  40                  45

Pro Lys Pro Ala Pro Ala Pro Lys Pro Ala Pro Ala Pro Lys Pro Ala
    50                  55                  60

Pro Ala Pro Lys Pro Ala Pro Ala Pro Ala Pro Lys Pro Ala Pro Glu
65                  70                  75                  80

Lys Pro Ala Glu Lys Pro Ala Pro Ala Pro Lys Pro Glu Thr Pro Lys
                85                  90                  95

Thr Gly Trp Lys Gln Glu Asn Gly Met Trp
            100                 105

```
<210> SEQ ID NO 33
<211> LENGTH: 121
<212> TYPE: PRT
<213> ORGANISM: Streptococcus pneumonia
<220> FEATURE:
<223> OTHER INFORMATION: Immunogenic PspA/PspC polypeptide H70 (aa
      290-410 of PspA)

<400> SEQUENCE: 33
```

Tyr Phe Lys Glu Gly Leu Glu Lys Thr Ile Ala Ala Lys Lys Ala Glu
1               5                   10                  15

Leu Glu Lys Thr Glu Ala Asp Leu Lys Lys Ala Val Asn Glu Pro Glu
            20                  25                  30

Lys Pro Ala Pro Ala Pro Glu Thr Pro Ala Pro Glu Ala Pro Ala Glu
        35                  40                  45

Gln Pro Lys Pro Ala Pro Ala Pro Gln Pro Ala Pro Ala Pro Lys Pro
    50                  55                  60

Glu Lys Pro Ala Glu Gln Pro Lys Pro Glu Lys Thr Asp Asp Gln Gln
65                  70                  75                  80

Ala Glu Glu Asp Tyr Ala Arg Arg Ser Glu Glu Tyr Asn Arg Leu
                85                  90                  95

Thr Gln Gln Gln Pro Pro Lys Ala Glu Lys Pro Ala Pro Ala Pro Lys
            100                 105                 110

Thr Gly Trp Lys Gln Glu Asn Gly Met
        115                 120

```
<210> SEQ ID NO 34
<211> LENGTH: 27
<212> TYPE: PRT
<213> ORGANISM: Streptococcus pneumonia
<220> FEATURE:
<223> OTHER INFORMATION: Non-proline Block (NPB)

<400> SEQUENCE: 34
```

Glu Lys Ser Ala Asp Gln Gln Ala Glu Glu Asp Tyr Ala Arg Arg Ser

```
                1               5                  10                 15
Glu Glu Glu Tyr Asn Arg Leu Thr Gln Gln Gln
            20                  25

<210> SEQ ID NO 35
<211> LENGTH: 23
<212> TYPE: PRT
<213> ORGANISM: Streptococcus pneumonia
<220> FEATURE:
<223> OTHER INFORMATION: Non-proline Block (NPB)

<400> SEQUENCE: 35

Asp Gln Gln Ala Glu Glu Asp Tyr Ala Arg Arg Ser Glu Glu Glu Tyr
1               5                  10                  15
Asn Arg Leu Thr Gln Gln Gln
            20

<210> SEQ ID NO 36
<211> LENGTH: 28
<212> TYPE: PRT
<213> ORGANISM: Streptococcus pneumonia
<220> FEATURE:
<223> OTHER INFORMATION: Non-proline Block (NPB)

<400> SEQUENCE: 36

Met Glu Lys Ser Ala Asp Gln Gln Ala Glu Glu Asp Tyr Ala Arg Arg
1               5                  10                  15
Ser Glu Glu Glu Tyr Asn Arg Leu Thr Gln Gln Gln
            20                  25

<210> SEQ ID NO 37
<211> LENGTH: 768
<212> TYPE: DNA
<213> ORGANISM: Streptococcus pneumonia
<220> FEATURE:
<223> OTHER INFORMATION: SP0148 lacking signal sequence (nucleotides)

<400> SEQUENCE: 37
atgtgctcag ggggtgctaa gaaagaagga gaagcagcta gcaagaaaga aatcatcgtt      60
gcaaccaatg gatcaccaaa gccatttatc tatgaagaaa atggcgaatt gactggttac    120
gagattgaag tcgttcgcgc tatctttaaa gattctgaca aatatgatgt caagtttgaa    180
aagacagaat ggtcaggtgt cttgctggt cttgacgctg atcgttacaa tatggctgtc     240
aacaatctta gctacactaa agaacgtgcg gagaaatacc tctatgccgc accaattgcc    300
caaaatccta atgtccttgt cgtgaagaaa gatgactcta gtatcaagtc tctcgatgat    360
atcggtggaa aatcgacgga agtcgttcaa gccactacat cagctaagca gttagaagca    420
tacaatgctg aacacacgga caaccccaact atccttaact atactaaggc agacttccaa    480
caaatcatgg tacgtttgag cgatggacaa tttgactata agattttttga taaaatcggt   540
gttgaaacag tgatcaagaa ccaaggtttg gacaacttga agttatcga acttccaagc     600
gaccaacaac cgtacgttta cccacttctt gctcagggtc aagatgagtt gaaatcgttt    660
gtagacaaac gcatcaaaga actttataaa gatggaactc ttgaaaaatt gtctaaacaa    720
ttcttcggag acacttatct accggcagaa gctgatatta aagagtaa                 768

<210> SEQ ID NO 38
<211> LENGTH: 834
<212> TYPE: DNA
<213> ORGANISM: Streptococcus pneumonia
<220> FEATURE:
```

<223> OTHER INFORMATION: SP0148 including signal sequence (nucleotides)

<400> SEQUENCE: 38

```
atgaaaaaaa tcgttaaata ctcatctctt gcagcccttg ctcttgttgc tgcaggtgtg      60
cttgcggctt gctcaggggg tgctaagaaa gaaggagaag cagctagcaa gaaagaaatc     120
atcgttgcaa ccaatggatc accaaagcca tttatctatg aagaaatgg cgaattgact      180
ggttacgaga ttgaagtcgt tcgcgctatc tttaaagatt ctgacaaata tgatgtcaag     240
tttgaaaaga cagaatggtc aggtgtcttt gctggtcttg acgctgatcg ttacaatatg     300
gctgtcaaca atcttagcta cactaaagaa cgtgcggaga atacctcta tgccgcacca     360
attgcccaaa atcctaatgt ccttgtcgtg aagaaagatg actctagtat caagtctctc     420
gatgatatcg gtggaaaatc gacggaagtc gttcaagcca ctacatcagc taagcagtta     480
gaagcataca atgctgaaca cacggacaac ccaactatcc ttaactatac taaggcagac     540
ttccaacaaa tcatggtacg tttgagcgat ggacaatttg actataagat ttttgataaa     600
atcggtgttg aaacagtgat caagaaccaa ggttttggaca acttgaaagt tatcgaactt     660
ccaagcgacc aacaaccgta cgtttaccca cttcttgctc agggtcaaga tgagttgaaa     720
tcgtttgtag acaaacgcat caaagaactt tataaagatg aactcttga aaaattgtct      780
aaacaattct tcggagacac ttatctaccg gcagaagctg atattaaaga gtaa           834
```

<210> SEQ ID NO 39
<211> LENGTH: 1203
<212> TYPE: DNA
<213> ORGANISM: Streptococcus pneumonia
<220> FEATURE:
<223> OTHER INFORMATION: SP2108 lacking signal sequence (nucleotides)

<400> SEQUENCE: 39

```
atgtgcggaa gcaaaactgc tgataagcct gctgattctg gttcatctga agtcaaagaa      60
ctcactgtat atgtagacga gggatataag agctatattg aagaggttgc taaagcttat     120
gaaaagaag ctggagtaaa agtcactctt aaaactggtg atgctctagg aggtcttgat      180
aaactttctc ttgacaacca atctggtaat gtccctgatg ttatgatggc tccatacgac     240
cgtgtaggta gccttggttc tgacggacaa cttttcagaag tgaaattgag cgatggtgct     300
aaaacagacg cacaactaa atctcttgta acagctgcta atggtaaagt ttacggtgct     360
cctgccgtta tcgagtcact tgttatgtac tacaacaaag acttggtgaa agatgctcca     420
aaaacatttg ctgacttgga aaaccttgct aaagatagca atacgcatt cgctggtgaa      480
gatggtaaaa ctactgcctt cctagctgac tggacaaact tctactatac atatggactt     540
cttgccggta acggtgctta cgtctttggc caaaacggta agacgctaa agacatcggt     600
cttgcaaacg acggttctat cgtaggtatc aactacgcta atcttggta cgaaaaatgg      660
cctaaaggta tgcaagatac agaaggtgct ggaaacttaa tccaaactca attccaagaa     720
ggtaaaacag ctgctatcat cgacggacct tggaaagctc aagcctttaa agatgctaaa     780
gtaaactacg gagttgcaac tatcccaact cttccaaatg gaaagaata tgctgcattc     840
ggtggtggta agcttgggt cattcctcaa gccgttaaga accttgaagc ttctcaaaaa     900
tttgtagact tccttgttgc aactgaacaa caaaaagtat tatatgataa gactaacgaa     960
atcccagcta atactgaggc tcgttcatac gctgaaggta aaaacgatga gttgacaaca    1020
gctgttatca aacagttcaa gaacactcaa ccactgccaa acatctctca aatgtctgca    1080
gtttgggatc cagcgaaaaa tatgctcttt gatgctgtaa gtggtcaaaa agatgctaaa    1140
```

-continued

```
acagctgcta acgatgctgt aacattgatc aaagaaacaa tcaaacaaaa atttggtgaa   1200
taa                                                                  1203

<210> SEQ ID NO 40
<211> LENGTH: 300
<212> TYPE: DNA
<213> ORGANISM: Streptococcus pneumonia
<220> FEATURE:
<223> OTHER INFORMATION: SP1912 (nucleotides)

<400> SEQUENCE: 40
atgaatggta tgaaagctaa aaaaatgtgg atggcaggct tggctctgct aggtatcgga     60
agccttgctc ttgctacgaa aaaagttgca gatgaccgta agctcatgaa gactcaggaa    120
gagttgacag agattgtgcg agaccatttt tccgacatgg gggaaattgc gacccttttat   180 gttcaagttt acgaaagcag tctggagagc ttggttggtg gcgtcatttt tgaggatggc    240
cgtcattata cctttgtcta tgaaaatgaa gacctagtct atgaggagga agtcttatga    300

<210> SEQ ID NO 41
<211> LENGTH: 279
<212> TYPE: DNA
<213> ORGANISM: Streptococcus pneumonia
<220> FEATURE:
<223> OTHER INFORMATION: SP1912L (nucleotides)

<400> SEQUENCE: 41
atgagatacc tggcaacatt gttgttatct ctggcggtgt taatcaccgc cgggtgcaaa     60
aaagttgcag atgaccgtaa gctcatgaag actcaggaag agttgacaga gattgtgcga    120
gaccattttt ccgacatggg ggaaattgcg acccttatg ttcaagttta cgaaagcagt     180
ctggagagct tggttggtgg cgtcattttt gaggatggcc gtcattatac ctttgtctat    240
gaaaatgaag acctagtcta tgaggaggaa gtcttatga                           279

<210> SEQ ID NO 42
<211> LENGTH: 1986
<212> TYPE: DNA
<213> ORGANISM: Streptococcus pneumonia
<220> FEATURE:
<223> OTHER INFORMATION: SP0641N (nucleotides)

<400> SEQUENCE: 42
atggtagtct tagcagacac atctagctct gaagatgctt taaacatctc tgataaagaa     60
aaagtagcag aaaataaaga gaaacatgaa aatatccata gtgctatgga aacttcacag    120
gattttaaag agaagaaaac agcagtcatt aaggaaaaag aagttgttag taaaaatcct    180
gtgatagaca ataacactag caatgaagaa gcaaaaatca agaagaaaa ttccaataaa      240 tcccaaggag attatacgga ctcatttgtg aataaaaaca cagaaaatcc caaaaagaa      300 gataaagttg tctatattgc tgaatttaaa gataaagaat ctggagaaaa agcaatcaag    360
gaactatcca gtcttaagaa tacaaaagtt ttatatactt atgatagaat ttttaacggt    420
agtgccatag aaacaactcc agataacttg gacaaaatta acaaataga aggtatttca     480 tcggttgaaa gggcacaaaa agtccaaccc atgatgaatc atgccagaaa ggaaattgga    540
gttgaggaag ctattgatta cctaaagtct atcaatgctc cgtttgggaa aaattttgat    600
ggtagaggta tggtcatttc aaatatcgat actggaacag attatagaca taaggctatg    660
agaatcgatg atgatgccaa agcctcaatg agatttaaaa aagaagactt aaaaggcact    720
```

```
gataaaaatt attggttgag tgataaaatc cctcatgcgt tcaattatta taatggtggc    780
aaaatcactg tagaaaaata tgatgatgga agggattatt ttgacccaca tgggatgcat    840
attgcaggga ttcttgctgg aaatgatact gaacaagaca tcaaaaactt taacggcata   900
gatggaattg cacctaatgc acaaattttc tcttacaaaa tgtattctga cgcaggatct   960
gggtttgcgg gtgatgaaac aatgtttcat gctattgaag attctatcaa acacaacgtt  1020
gatgttgttt cggtatcatc tggttttaca ggaacaggtc ttgtaggtga aaatattgg   1080 caagctattc gggcattaag aaaagcaggc attccaatgg ttgtcgctac gggtaactat  1140
gcgacttctg cttcaagttc ttcatgggat ttagtagcaa ataatcatct gaaaatgacc  1200
gacactggaa atgtaacacg aactgcagca catgaagatg cgatagcggt cgcttctgct  1260
aaaaatcaaa cagttgagtt tgataaagtt aacataggtg gagaaagttt taaatacaga  1320 aatataggg  cctttttcga taagagtaaa atcacaacaa atgaagatgg aacaaaagct  1380
cctagtaaat taaaatttgt atatataggc aaggggcaag accagatttt gataggtttg  1440
gatcttaggg gcaaaattgc agtaatggat agaatttata caaaggattt aaaaaatgct  1500
tttaaaaaag ctatggataa gggtgcacgc gccattatgg ttgtaaatac tgtaaattac  1560
tacaatagag ataattggac agagcttcca gctatgggat atgaagcgga tgaaggtact  1620
aaaagtcaag tgttttcaat ttcaggagat gatggtgtaa agctatggaa catgattaat  1680
cctgataaaa aaactgaagt caaaagaaat aataaagaag attttaaaga taaattggag  1740
caatactatc caattgatat ggaaagtttt aattccaaca aaccgaatgt aggtgacgaa  1800
aaagagattg actttaagtt tgcacctgac acagacaaag aactctataa agaagatatc  1860
atcgttccag caggatctac atcttgggg  ccaagaatag atttactttt aaaacccgat  1920
gtttcagcac ctggtaaaaa tattaaatcc acgcttaatg ttattaatgg caaatcaact  1980
tatggc                                                             1986
```

<210> SEQ ID NO 43
<211> LENGTH: 390
<212> TYPE: DNA
<213> ORGANISM: Streptococcus pneumonia
<220> FEATURE:
<223> OTHER INFORMATION: SP0882N DNA

<400> SEQUENCE: 43

```
atgaatcaat cctactttta tctaaaaatg aaagaacaca aactcaaggt tccttataca    60
ggtaaggagc gccgtgtacg tattcttctt cctaaagatt atgagaaaga tacagaccgt   120
tcctatcctg ttgtatactt tcatgacggg caaaatgttt taatagcaa  agagtctttc   180 attggacatt catggaagat tatcccagct atcaaacgaa atccggatat cagtcgcatg   240
attgtcgttg ctattgacaa tgatggtatg gggcggatga atgagtatgc ggcttggaag   300
ttccaagaat ctcctatccc agggcagcag tttggtggta agggtgtgga gtatgctgag   360
tttgtcatgg aggtggtcaa gccttttatc                                   390
```

<210> SEQ ID NO 44
<211> LENGTH: 900
<212> TYPE: DNA
<213> ORGANISM: Streptococcus pneumonia
<220> FEATURE:
<223> OTHER INFORMATION: SP0882 with exogenous signal sequence
      (nucleotides)

<400> SEQUENCE: 44

```
atgtcatcta aatttatgaa gagcgctgcg gtgcttggaa ctgctacact tgctagcttg    60
cttttggtag cttgcatgaa tcaatcctac ttttatctaa aaatgaaaga acacaaactc   120
aaggttcctt atacaggtaa ggagcgccgt gtacgtattc ttcttcctaa agattatgag   180
aaagatacag accgttccta tcctgttgta tactttcatg acgggcaaaa tgttttaat   240 agcaaagagt ctttcattgg acattcatgg aagattatcc cagctatcaa acgaaatccg   300
gatatcagtc gcatgattgt cgttgctatt gacaatgatg gtatggggcg gatgaatgag   360
tatgcggctt ggaagttcca agaatctcct atcccagggc agcagtttgg tggtaagggt   420
gtggagtatg ctgagtttgt catggaggtg gtcaagcctt ttatcgatga gacctatcgt   480
acaaaagcag actgccagca tacggctatg attggttcct cactaggagg caatattacc   540
cagtttatcg gtttggaata ccaagaccaa attggttgct tgggcgtttt ttcatctgca   600
aactggctcc accaagaagc ctttaaccgc tatttcgagt gccagaaact atcgcctgac   660
cagcgcatct tcatctatgt aggaacagaa gaagcagatg atacagacaa gaccttgatg   720
gatggcaata tcaaacaagc ctatatcgac tcgtcgcttt gctattacca tgatttgata   780 gcaggggag tacatctgga taatcttgtg ctaaaagttc agtctggtgc catccatagt   840
gaaatccctt ggtcagaaaa tctaccagat tgtctgagat tttttgcaga aaaatggtaa   900
```

<210> SEQ ID NO 45
<211> LENGTH: 465
<212> TYPE: DNA
<213> ORGANISM: Streptococcus pneumonia
<220> FEATURE:
<223> OTHER INFORMATION: SP0882N with exogenous signal sequence
      (nucleotides)

<400> SEQUENCE: 45

```
atgtcatcta aatttatgaa gagcgctgcg gtgcttggaa ctgctacact tgctagcttg    60
cttttggtag cttgcatgaa tcaatcctac ttttatctaa aaatgaaaga acacaaactc   120
aaggttcctt atacaggtaa ggagcgccgt gtacgtattc ttcttcctaa agattatgag   180
aaagatacag accgttccta tcctgttgta tactttcatg acgggcaaaa tgttttaat   240 agcaaagagt ctttcattgg acattcatgg aagattatcc cagctatcaa acgaaatccg   300
gatatcagtc gcatgattgt cgttgctatt gacaatgatg gtatggggcg gatgaatgag   360
tatgcggctt ggaagttcca agaatctcct atcccagggc agcagtttgg tggtaagggt   420
gtggagtatg ctgagtttgt catggaggtg gtcaagcctt ttatc                   465
```

<210> SEQ ID NO 46
<211> LENGTH: 2046
<212> TYPE: DNA
<213> ORGANISM: Streptococcus pneumonia
<220> FEATURE:
<223> OTHER INFORMATION: PSPA (nucleotides)

<400> SEQUENCE: 46

```
ttgacaaata tttacggagg aggcttatgc ttaatataag tataggctaa aaatgattat    60
cagaaaagag gtaaatttag atgaataaga aaaaaatgat tttaacaagc ctagccagcg   120
tcgctatctt aggggctggt tttgttgcgt cttcgcctac ttttgtaaga gcagaagaag   180
ctcctgtagc taaccagtct aaagctgaga agactatga tgcagcagtg aaaaaatctg   240
aagctgctaa gaaagattac gaaacggcta aaagaaagc agaagacgct cagaagaaat   300
atgatgagga tcagaagaaa actgaggcaa agcggaaaa agaaagaaaa gcttctgaaa   360
```

```
agatagctga ggcaacaaaa gaagttcaac aagcgtacct agcttatcta caagctagca    420
acgaaagtca gagaaaagag gcagataaga agataaaaga agctacgcaa cgcaaagatg    480
aggcggaagc tgcatttgct actattcgaa caacaattgt agttcctgaa ccaagtgagt    540
tagctgagac taagaaaaaa gcagaagagg caacaaaaga agcagaagta gctaagaaaa    600
aatctgaaga ggcagctaaa gaggtagaag tagagaaaaa taaaatactt gaacaagatg    660
ctgaaaacga aaagaaaatt gacgtacttc aaaacaaagt cgctgattta gaaaaaggaa    720
ttgctcctta tcaaaacgaa gtcgctgaat taaataaaga aattgctaga cttcaaagcg    780
atttaaaaga tgctgaagaa ataatgtag aagactacat aaagaaggt ttagagcaag     840 ctatcactaa taaaaaagct gaattagcta caactcaaca aaacatagat aaaactcaaa    900
aagatttaga ggatgctgaa ttagaacttg aaaaagtatt agctacatta gaccctgaag    960
gtaaaactca agatgaatta gataaagaag ctgctgaagc tgagttgaat gaaaaagttg   1020
aagctcttca aaaccaagtt gctgaattag aagaagaact ttcaaaactt gaagataatc   1080
ttaaagatgc tgaaacaaac aacgttgaag actacattaa agaaggttta gaagaagcta   1140
tcgcgactaa aaaagctgaa ttggaaaaaa ctcaaaaaga attagatgca gctcttaatg   1200
agttaggccc tgatggagat gaagaagaga ctccagcgcc ggctcctcaa ccagaaaaac   1260
cagctgaaga gcctgagaat ccagctccag caccaaaacc agagaagtca gcagatcaac   1320
aagctgaaga agactatgct cgtagatcag aagaagaata taatcgcttg acccaacagc   1380
aaccgccaaa agcagaaaaa ccagctcctg caccacaacc agagcaacca gctcctgcac   1440
caaaaatagg ttgaaacaa gaaaacggta tgtggtactt ctacaatact gatggttcaa   1500
tggcgacagg ttggctacaa acaacggtt catggtacta cctcaacagc aatggcgcta   1560
tggctacagg ttggctccaa tacaatggtt catggtatta cctaaacgct aacggcgcta   1620
tggcgacagg ctggctccaa tacaatggct catggtacta cctcaacgct aacggcgcta   1680
tggcgacagg ctggctccaa tacaatggct catggtacta cctcaacgct aatggtgata   1740
tggcgacagg atggctccaa tacaacggtt catggtatta cctcaacgct aatggtgata   1800
tggctacagg ttgggctaaa gtccacggtt catggtacta cctcaacgct aacggttcaa   1860
tggcaacagg ttgggtgaaa gatggagaaa cctggtacta tcttgaagca tcaggttcta   1920
tgaaagcaaa ccaatggttc caagtatcag ataaatggta ctatgtcaat ggtttaggtt   1980 cccttttcagt caacacaact gtagatggct ataaagtcaa tgccaatggt gaatgggttt   2040
aagccg                                                              2046
```

<210> SEQ ID NO 47
<211> LENGTH: 675
<212> TYPE: PRT
<213> ORGANISM: Artificial Sequence
<220> FEATURE:
<223> OTHER INFORMATION: Description of Artificial Sequence: Synthetic
      Streptococcus pneumonia fusion protein
<220> FEATURE:
<223> OTHER INFORMATION: SP2108/SP0148 fusion protein (675 amino acids)

<400> SEQUENCE: 47

```
Met Ser Ser Lys Phe Met Lys Ser Ala Ala Val Leu Gly Thr Ala Thr
1               5                   10                  15

Leu Ala Ser Leu Leu Leu Val Ala Cys Gly Ser Lys Thr Ala Asp Lys
                20                  25                  30

Pro Ala Asp Ser Gly Ser Ser Glu Val Lys Glu Leu Thr Val Tyr Val
            35                  40                  45
```

```
Asp Glu Gly Tyr Lys Ser Tyr Ile Glu Val Ala Lys Ala Tyr Glu
 50                  55                  60

Lys Glu Ala Gly Val Lys Val Thr Leu Lys Thr Gly Asp Ala Leu Gly
 65                  70                  75                  80

Gly Leu Asp Lys Leu Ser Leu Asp Asn Gln Ser Gly Asn Val Pro Asp
                     85                  90                  95

Val Met Met Ala Pro Tyr Asp Arg Val Gly Ser Leu Gly Ser Asp Gly
                 100                 105                 110

Gln Leu Ser Glu Val Lys Leu Ser Asp Gly Ala Lys Thr Asp Asp Thr
             115                 120                 125

Thr Lys Ser Leu Val Thr Ala Ala Asn Gly Lys Val Tyr Gly Ala Pro
     130                 135                 140

Ala Val Ile Glu Ser Leu Val Met Tyr Tyr Asn Lys Asp Leu Val Lys
145                 150                 155                 160

Asp Ala Pro Lys Thr Phe Ala Asp Leu Glu Asn Leu Ala Lys Asp Ser
                 165                 170                 175

Lys Tyr Ala Phe Ala Gly Glu Asp Gly Lys Thr Thr Ala Phe Leu Ala
             180                 185                 190

Asp Trp Thr Asn Phe Tyr Tyr Thr Tyr Gly Leu Leu Ala Gly Asn Gly
         195                 200                 205

Ala Tyr Val Phe Gly Gln Asn Gly Lys Asp Ala Lys Asp Ile Gly Leu
     210                 215                 220

Ala Asn Asp Gly Ser Ile Val Gly Ile Asn Tyr Ala Lys Ser Trp Tyr
225                 230                 235                 240

Glu Lys Trp Pro Lys Gly Met Gln Asp Thr Glu Gly Ala Gly Asn Leu
                 245                 250                 255

Ile Gln Thr Gln Phe Gln Glu Gly Lys Thr Ala Ala Ile Ile Asp Gly
             260                 265                 270

Pro Trp Lys Ala Gln Ala Phe Lys Asp Ala Lys Val Asn Tyr Gly Val
     275                 280                 285

Ala Thr Ile Pro Thr Leu Pro Asn Gly Lys Glu Tyr Ala Ala Phe Gly
     290                 295                 300

Gly Gly Lys Ala Trp Val Ile Pro Gln Ala Val Lys Asn Leu Glu Ala
305                 310                 315                 320

Ser Gln Lys Phe Val Asp Phe Leu Val Ala Thr Glu Gln Gln Lys Val
                 325                 330                 335

Leu Tyr Asp Lys Thr Asn Glu Ile Pro Ala Asn Thr Glu Ala Arg Ser
             340                 345                 350

Tyr Ala Glu Gly Lys Asn Asp Glu Leu Thr Thr Ala Val Ile Lys Gln
     355                 360                 365

Phe Lys Asn Thr Gln Pro Leu Pro Asn Ile Ser Gln Met Ser Ala Val
     370                 375                 380

Trp Asp Pro Ala Lys Asn Met Leu Phe Asp Ala Val Ser Gly Gln Lys
385                 390                 395                 400

Asp Ala Lys Thr Ala Ala Asn Asp Ala Val Thr Leu Ile Lys Glu Thr
                 405                 410                 415

Ile Lys Gln Lys Phe Gly Glu Ser Gly Gly Ala Lys Lys Glu Gly Glu
             420                 425                 430

Ala Ala Ser Lys Lys Glu Ile Ile Val Ala Thr Asn Gly Ser Pro Lys
     435                 440                 445

Pro Phe Ile Tyr Glu Glu Asn Gly Glu Leu Thr Gly Tyr Glu Ile Glu
     450                 455                 460
```

```
Val Val Arg Ala Ile Phe Lys Asp Ser Asp Lys Tyr Asp Val Lys Phe
465                 470                 475                 480

Glu Lys Thr Glu Trp Ser Gly Val Phe Ala Gly Leu Asp Ala Asp Arg
                485                 490                 495

Tyr Asn Met Ala Val Asn Asn Leu Ser Tyr Thr Lys Glu Arg Ala Glu
            500                 505                 510

Lys Tyr Leu Tyr Ala Ala Pro Ile Ala Gln Asn Pro Asn Val Leu Val
        515                 520                 525

Val Lys Lys Asp Asp Ser Ser Ile Lys Ser Leu Asp Asp Ile Gly Gly
    530                 535                 540

Lys Ser Thr Glu Val Val Gln Ala Thr Thr Ser Ala Lys Gln Leu Glu
545                 550                 555                 560

Ala Tyr Asn Ala Glu His Thr Asp Asn Pro Thr Ile Leu Asn Tyr Thr
                565                 570                 575

Lys Ala Asp Phe Gln Gln Ile Met Val Arg Leu Ser Asp Gly Gln Phe
            580                 585                 590

Asp Tyr Lys Ile Phe Asp Lys Ile Gly Val Glu Thr Val Ile Lys Asn
        595                 600                 605

Gln Gly Leu Asp Asn Leu Lys Val Ile Glu Leu Pro Ser Asp Gln Gln
610                 615                 620

Pro Tyr Val Tyr Pro Leu Leu Ala Gln Gly Gln Asp Glu Leu Lys Ser
625                 630                 635                 640

Phe Val Asp Lys Arg Ile Lys Glu Leu Tyr Lys Asp Gly Thr Leu Glu
                645                 650                 655

Lys Leu Ser Lys Gln Phe Phe Gly Asp Thr Tyr Leu Pro Ala Glu Ala
            660                 665                 670

Asp Ile Lys
        675

<210> SEQ ID NO 48
<211> LENGTH: 674
<212> TYPE: PRT
<213> ORGANISM: Artificial Sequence
<220> FEATURE:
<223> OTHER INFORMATION: Description of Artificial Sequence: Synthetic
      Streptococcus pneumonia fusion protein
<220> FEATURE:
<223> OTHER INFORMATION: SP0148/SP2108 fusion protein (674 amino acids)

<400> SEQUENCE: 48

Met Lys Lys Ile Val Lys Tyr Ser Ser Leu Ala Ala Leu Ala Leu Val
1               5                   10                  15

Ala Ala Gly Val Leu Ala Ala Cys Ser Gly Gly Ala Lys Lys Glu Gly
                20                  25                  30

Glu Ala Ala Ser Lys Lys Glu Ile Ile Val Ala Thr Asn Gly Ser Pro
            35                  40                  45

Lys Pro Phe Ile Tyr Glu Glu Asn Gly Glu Leu Thr Gly Tyr Glu Ile
        50                  55                  60

Glu Val Val Arg Ala Ile Phe Lys Asp Ser Asp Lys Tyr Asp Val Lys
65                  70                  75                  80

Phe Glu Lys Thr Glu Trp Ser Gly Val Phe Ala Gly Leu Asp Ala Asp
                85                  90                  95

Arg Tyr Asn Met Ala Val Asn Asn Leu Ser Tyr Thr Lys Glu Arg Ala
            100                 105                 110

Glu Lys Tyr Leu Tyr Ala Ala Pro Ile Ala Gln Asn Pro Asn Val Leu
        115                 120                 125
```

-continued

Val Val Lys Lys Asp Asp Ser Ser Ile Lys Ser Leu Asp Asp Ile Gly
130                     135                 140

Gly Lys Ser Thr Glu Val Val Gln Ala Thr Thr Ser Ala Lys Gln Leu
145                 150                 155                 160

Glu Ala Tyr Asn Ala Glu His Thr Asp Asn Pro Thr Ile Leu Asn Tyr
                165                 170                 175

Thr Lys Ala Asp Phe Gln Gln Ile Met Val Arg Leu Ser Asp Gly Gln
            180                 185                 190

Phe Asp Tyr Lys Ile Phe Asp Lys Ile Gly Val Glu Thr Val Ile Lys
        195                 200                 205

Asn Gln Gly Leu Asp Asn Leu Lys Val Ile Glu Leu Pro Ser Asp Gln
210                 215                 220

Gln Pro Tyr Val Tyr Pro Leu Ala Gln Gly Gln Asp Glu Leu Lys
225                 230                 235                 240

Ser Phe Val Asp Lys Arg Ile Lys Glu Leu Tyr Lys Asp Gly Thr Leu
                245                 250                 255

Glu Lys Leu Ser Lys Gln Phe Phe Gly Asp Thr Tyr Leu Pro Ala Glu
            260                 265                 270

Ala Asp Ile Lys Gly Ser Lys Thr Ala Asp Lys Pro Ala Asp Ser Gly
        275                 280                 285

Ser Ser Glu Val Lys Glu Leu Thr Val Tyr Val Asp Glu Gly Tyr Lys
290                 295                 300

Ser Tyr Ile Glu Glu Val Ala Lys Ala Tyr Glu Lys Glu Ala Gly Val
305                 310                 315                 320

Lys Val Thr Leu Lys Thr Gly Asp Ala Leu Gly Gly Leu Asp Lys Leu
                325                 330                 335

Ser Leu Asp Asn Gln Ser Gly Asn Val Pro Asp Val Met Met Ala Pro
            340                 345                 350

Tyr Asp Arg Val Gly Ser Leu Gly Ser Asp Gly Gln Leu Ser Glu Val
        355                 360                 365

Lys Leu Ser Asp Gly Ala Lys Thr Asp Asp Thr Thr Lys Ser Leu Val
370                 375                 380

Thr Ala Ala Asn Gly Lys Val Tyr Gly Ala Pro Ala Val Ile Glu Ser
385                 390                 395                 400

Leu Val Met Tyr Tyr Asn Lys Asp Leu Val Lys Asp Ala Pro Lys Thr
                405                 410                 415

Phe Ala Asp Leu Glu Asn Leu Ala Lys Asp Ser Lys Tyr Ala Phe Ala
            420                 425                 430

Gly Glu Asp Gly Lys Thr Thr Ala Phe Leu Ala Asp Trp Thr Asn Phe
        435                 440                 445

Tyr Tyr Thr Tyr Gly Leu Leu Ala Gly Asn Gly Ala Tyr Val Phe Gly
450                 455                 460

Gln Asn Gly Lys Asp Ala Lys Asp Ile Gly Leu Ala Asn Asp Gly Ser
465                 470                 475                 480

Ile Val Gly Ile Asn Tyr Ala Lys Ser Trp Tyr Glu Lys Trp Pro Lys
                485                 490                 495

Gly Met Gln Asp Thr Glu Gly Ala Gly Asn Leu Ile Gln Thr Gln Phe
            500                 505                 510

Gln Glu Gly Lys Thr Ala Ala Ile Ile Asp Gly Pro Trp Lys Ala Gln
        515                 520                 525

Ala Phe Lys Asp Ala Lys Val Asn Tyr Gly Val Ala Thr Ile Pro Thr
530                 535                 540

Leu Pro Asn Gly Lys Glu Tyr Ala Ala Phe Gly Gly Gly Lys Ala Trp

```
            545                 550                 555                 560
Val Ile Pro Gln Ala Val Lys Asn Leu Glu Ala Ser Gln Lys Phe Val
                565                 570                 575

Asp Phe Leu Val Ala Thr Glu Gln Gln Lys Val Leu Tyr Asp Lys Thr
                580                 585                 590

Asn Glu Ile Pro Ala Asn Thr Glu Ala Arg Ser Tyr Ala Glu Gly Lys
                595                 600                 605

Asn Asp Glu Leu Thr Thr Ala Val Ile Lys Gln Phe Lys Asn Thr Gln
                610                 615                 620

Pro Leu Pro Asn Ile Ser Gln Met Ser Ala Val Trp Asp Pro Ala Lys
625                 630                 635                 640

Asn Met Leu Phe Asp Ala Val Ser Gly Gln Lys Asp Ala Lys Thr Ala
                645                 650                 655

Ala Asn Asp Ala Val Thr Leu Ile Lys Glu Thr Ile Lys Gln Lys Phe
                660                 665                 670

Gly Glu

<210> SEQ ID NO 49
<211> LENGTH: 521
<212> TYPE: PRT
<213> ORGANISM: Artificial Sequence
<220> FEATURE:
<223> OTHER INFORMATION: Description of Artificial Sequence: Synthetic
      Streptococcus pneumonia fusion protein
<220> FEATURE:
<223> OTHER INFORMATION: SP2108/SP1912 fusion protein (521 amino acids)

<400> SEQUENCE: 49

Met Ser Ser Lys Phe Met Lys Ser Ala Ala Val Leu Gly Thr Ala Thr
1               5                   10                  15

Leu Ala Ser Leu Leu Val Ala Cys Gly Ser Lys Thr Ala Asp Lys
                20                  25                  30

Pro Ala Asp Ser Gly Ser Ser Glu Val Lys Glu Leu Thr Val Tyr Val
                35                  40                  45

Asp Glu Gly Tyr Lys Ser Tyr Ile Glu Glu Val Ala Lys Ala Tyr Glu
    50                  55                  60

Lys Glu Ala Gly Val Lys Val Thr Leu Lys Thr Gly Asp Ala Leu Gly
65                  70                  75                  80

Gly Leu Asp Lys Leu Ser Leu Asp Asn Gln Ser Gly Asn Val Pro Asp
                85                  90                  95

Val Met Met Ala Pro Tyr Asp Arg Val Gly Ser Leu Gly Ser Asp Gly
                100                 105                 110

Gln Leu Ser Glu Val Lys Leu Ser Asp Gly Ala Lys Thr Asp Asp Thr
                115                 120                 125

Thr Lys Ser Leu Val Thr Ala Ala Asn Gly Lys Val Tyr Gly Ala Pro
    130                 135                 140

Ala Val Ile Glu Ser Leu Val Met Tyr Tyr Asn Lys Asp Leu Val Lys
145                 150                 155                 160

Asp Ala Pro Lys Thr Phe Ala Asp Leu Glu Asn Leu Ala Lys Asp Ser
                165                 170                 175

Lys Tyr Ala Phe Ala Gly Glu Asp Gly Lys Thr Thr Ala Phe Leu Ala
                180                 185                 190

Asp Trp Thr Asn Phe Tyr Tyr Thr Tyr Gly Leu Leu Ala Gly Asn Gly
                195                 200                 205

Ala Tyr Val Phe Gly Gln Asn Gly Lys Asp Ala Lys Asp Ile Gly Leu
    210                 215                 220
```

```
Ala Asn Asp Gly Ser Ile Val Gly Ile Asn Tyr Ala Lys Ser Trp Tyr
225                 230                 235                 240

Glu Lys Trp Pro Lys Gly Met Gln Asp Thr Glu Gly Ala Gly Asn Leu
            245                 250                 255

Ile Gln Thr Gln Phe Gln Glu Gly Lys Thr Ala Ala Ile Ile Asp Gly
            260                 265                 270

Pro Trp Lys Ala Gln Ala Phe Lys Asp Ala Lys Val Asn Tyr Gly Val
            275                 280                 285

Ala Thr Ile Pro Thr Leu Pro Asn Gly Lys Glu Tyr Ala Ala Phe Gly
            290                 295                 300

Gly Gly Lys Ala Trp Val Ile Pro Gln Ala Val Lys Asn Leu Glu Ala
305                 310                 315                 320

Ser Gln Lys Phe Val Asp Phe Leu Val Ala Thr Glu Gln Gln Lys Val
            325                 330                 335

Leu Tyr Asp Lys Thr Asn Glu Ile Pro Ala Asn Thr Glu Ala Arg Ser
            340                 345                 350

Tyr Ala Glu Gly Lys Asn Asp Glu Leu Thr Thr Ala Val Ile Lys Gln
            355                 360                 365

Phe Lys Asn Thr Gln Pro Leu Pro Asn Ile Ser Gln Met Ser Ala Val
370                 375                 380

Trp Asp Pro Ala Lys Asn Met Leu Phe Asp Ala Val Ser Gly Gln Lys
385                 390                 395                 400

Asp Ala Lys Thr Ala Ala Asn Asp Ala Val Thr Leu Ile Lys Glu Thr
            405                 410                 415

Ile Lys Gln Lys Phe Gly Glu Asn Gly Met Lys Ala Lys Lys Met Trp
            420                 425                 430

Met Ala Gly Leu Ala Leu Leu Gly Ile Gly Ser Leu Ala Leu Ala Thr
            435                 440                 445

Lys Lys Val Ala Asp Asp Arg Lys Leu Met Lys Thr Gln Glu Glu Leu
            450                 455                 460

Thr Glu Ile Val Arg Asp His Phe Ser Asp Met Gly Glu Ile Ala Thr
465                 470                 475                 480

Leu Tyr Val Gln Val Tyr Glu Ser Ser Leu Glu Ser Leu Val Gly Gly
            485                 490                 495

Val Ile Phe Glu Asp Gly Arg His Tyr Thr Phe Val Tyr Glu Asn Glu
            500                 505                 510

Asp Leu Val Tyr Glu Glu Val Leu
            515                 520

<210> SEQ ID NO 50
<211> LENGTH: 374
<212> TYPE: PRT
<213> ORGANISM: Artificial Sequence
<220> FEATURE:
<223> OTHER INFORMATION: Description of Artificial Sequence: Synthetic
      Streptococcus pneumonia fusion protein
<220> FEATURE:
<223> OTHER INFORMATION: SP0148/SP1912 fusion protein (

```
Lys Pro Phe Ile Tyr Glu Glu Asn Gly Glu Leu Thr Gly Tyr Glu Ile
     50                  55                  60

Glu Val Val Arg Ala Ile Phe Lys Asp Ser Asp Lys Tyr Asp Val Lys
 65                  70                  75                  80

Phe Glu Lys Thr Glu Trp Ser Gly Val Phe Ala Gly Leu Asp Ala Asp
                 85                  90                  95

Arg Tyr Asn Met Ala Val Asn Asn Leu Ser Tyr Thr Lys Glu Arg Ala
                100                 105                 110

Glu Lys Tyr Leu Tyr Ala Ala Pro Ile Ala Gln Asn Pro Asn Val Leu
            115                 120                 125

Val Val Lys Lys Asp Asp Ser Ser Ile Lys Ser Leu Asp Ile Gly
130                 135                 140

Gly Lys Ser Thr Glu Val Val Gln Ala Thr Thr Ser Ala Lys Gln Leu
145                 150                 155                 160

Glu Ala Tyr Asn Ala Glu His Thr Asp Asn Pro Thr Ile Leu Asn Tyr
                165                 170                 175

Thr Lys Ala Asp Phe Gln Gln Ile Met Val Arg Leu Ser Asp Gly Gln
            180                 185                 190

Phe Asp Tyr Lys Ile Phe Asp Lys Ile Gly Val Glu Thr Val Ile Lys
            195                 200                 205

Asn Gln Gly Leu Asp Asn Leu Lys Val Ile Glu Leu Pro Ser Asp Gln
210                 215                 220

Gln Pro Tyr Val Tyr Pro Leu Leu Ala Gln Gly Gln Asp Glu Leu Lys
225                 230                 235                 240

Ser Phe Val Asp Lys Arg Ile Lys Glu Leu Tyr Lys Asp Gly Thr Leu
                245                 250                 255

Glu Lys Leu Ser Lys Gln Phe Phe Gly Asp Thr Tyr Leu Pro Ala Glu
            260                 265                 270

Ala Asp Ile Lys Asn Gly Met Lys Ala Lys Lys Met Trp Met Ala Gly
            275                 280                 285

Leu Ala Leu Leu Gly Ile Gly Ser Leu Ala Leu Ala Thr Lys Lys Val
290                 295                 300

Ala Asp Asp Arg Lys Leu Met Lys Thr Gln Glu Glu Leu Thr Glu Ile
305                 310                 315                 320

Val Arg Asp His Phe Ser Asp Met Gly Glu Ile Ala Thr Leu Tyr Val
                325                 330                 335

Gln Val Tyr Glu Ser Ser Leu Glu Ser Leu Val Gly Gly Val Ile Phe
            340                 345                 350

Glu Asp Gly Arg His Tyr Thr Phe Val Tyr Glu Asn Glu Asp Leu Val
            355                 360                 365

Tyr Glu Glu Glu Val Leu
    370
```

<210> SEQ ID NO 51
<211> LENGTH: 773
<212> TYPE: PRT
<213> ORGANISM: Artificial Sequence
<220> FEATURE:
<223> OTHER INFORMATION: Description of Artificial Sequence: Synthetic
      Streptococcus pneumonia fusion protein
<220> FEATURE:
<223> OTHER INFORMATION: SP2108/SP1912/SP0148 fusion protein (773 amino
      acids)

<400> SEQUENCE: 51

Met Ser Ser Lys Phe Met Lys Ser Ala Ala Val Leu Gly Thr Ala Thr

```
  1               5                   10                  15
Leu Ala Ser Leu Leu Val Ala Cys Gly Ser Lys Thr Ala Asp Lys
            20                  25                  30

Pro Ala Asp Ser Gly Ser Ser Glu Val Lys Glu Leu Thr Val Tyr Val
            35                  40                  45

Asp Glu Gly Tyr Lys Ser Tyr Ile Glu Glu Val Ala Lys Ala Tyr Glu
    50                  55                  60

Lys Glu Ala Gly Val Lys Val Thr Leu Lys Thr Gly Asp Ala Leu Gly
65                  70                  75                  80

Gly Leu Asp Lys Leu Ser Leu Asp Asn Gln Ser Gly Asn Val Pro Asp
                85                  90                  95

Val Met Met Ala Pro Tyr Asp Arg Val Gly Ser Leu Gly Ser Asp Gly
                100                 105                 110

Gln Leu Ser Glu Val Lys Leu Ser Asp Gly Ala Lys Thr Asp Asp Thr
            115                 120                 125

Thr Lys Ser Leu Val Thr Ala Ala Asn Gly Lys Val Tyr Gly Ala Pro
130                 135                 140

Ala Val Ile Glu Ser Leu Val Met Tyr Tyr Asn Lys Asp Leu Val Lys
145                 150                 155                 160

Asp Ala Pro Lys Thr Phe Ala Asp Leu Glu Asn Leu Ala Lys Asp Ser
                165                 170                 175

Lys Tyr Ala Phe Ala Gly Glu Asp Gly Lys Thr Thr Ala Phe Leu Ala
                180                 185                 190

Asp Trp Thr Asn Phe Tyr Tyr Thr Tyr Gly Leu Leu Ala Gly Asn Gly
                195                 200                 205

Ala Tyr Val Phe Gly Gln Asn Gly Lys Asp Ala Lys Asp Ile Gly Leu
    210                 215                 220

Ala Asn Asp Gly Ser Ile Val Gly Ile Asn Tyr Ala Lys Ser Trp Tyr
225                 230                 235                 240

Glu Lys Trp Pro Lys Gly Met Gln Asp Thr Glu Gly Ala Gly Asn Leu
                245                 250                 255

Ile Gln Thr Gln Phe Gln Glu Gly Lys Thr Ala Ala Ile Ile Asp Gly
                260                 265                 270

Pro Trp Lys Ala Gln Ala Phe Lys Asp Ala Lys Val Asn Tyr Gly Val
                275                 280                 285

Ala Thr Ile Pro Thr Leu Pro Asn Gly Lys Glu Tyr Ala Ala Phe Gly
                290                 295                 300

Gly Gly Lys Ala Trp Val Ile Pro Gln Ala Val Lys Asn Leu Glu Ala
305                 310                 315                 320

Ser Gln Lys Phe Val Asp Phe Leu Val Ala Thr Glu Gln Gln Lys Val
                325                 330                 335

Leu Tyr Asp Lys Thr Asn Glu Ile Pro Ala Asn Thr Glu Ala Arg Ser
                340                 345                 350

Tyr Ala Glu Gly Lys Asn Asp Glu Leu Thr Thr Ala Val Ile Lys Gln
                355                 360                 365

Phe Lys Asn Thr Gln Pro Leu Pro Asn Ile Ser Gln Met Ser Ala Val
                370                 375                 380

Trp Asp Pro Ala Lys Asn Met Leu Phe Asp Ala Val Ser Gly Gln Lys
385                 390                 395                 400

Asp Ala Lys Thr Ala Ala Asn Asp Ala Val Thr Leu Ile Lys Glu Thr
                405                 410                 415

Ile Lys Gln Lys Phe Gly Glu Asn Gly Met Lys Ala Lys Lys Met Trp
                420                 425                 430
```

```
Met Ala Gly Leu Ala Leu Leu Gly Ile Gly Ser Leu Ala Leu Ala Thr
        435                 440                 445

Lys Lys Val Ala Asp Asp Arg Lys Leu Met Lys Thr Gln Glu Glu Leu
    450                 455                 460

Thr Glu Ile Val Arg Asp His Phe Ser Asp Met Gly Glu Ile Ala Thr
465                 470                 475                 480

Leu Tyr Val Gln Val Tyr Glu Ser Ser Leu Glu Ser Leu Val Gly Gly
                485                 490                 495

Val Ile Phe Glu Asp Gly Arg His Tyr Thr Phe Val Tyr Glu Asn Glu
            500                 505                 510

Asp Leu Val Tyr Glu Glu Val Leu Ser Gly Gly Ala Lys Lys Glu
        515                 520                 525

Gly Glu Ala Ala Ser Lys Lys Glu Ile Ile Val Ala Thr Asn Gly Ser
    530                 535                 540

Pro Lys Pro Phe Ile Tyr Glu Glu Asn Gly Glu Leu Thr Gly Tyr Glu
545                 550                 555                 560

Ile Glu Val Val Arg Ala Ile Phe Lys Asp Ser Asp Lys Tyr Asp Val
                565                 570                 575

Lys Phe Glu Lys Thr Glu Trp Ser Gly Val Phe Ala Gly Leu Asp Ala
            580                 585                 590

Asp Arg Tyr Asn Met Ala Val Asn Asn Leu Ser Tyr Thr Lys Glu Arg
        595                 600                 605

Ala Glu Lys Tyr Leu Tyr Ala Ala Pro Ile Ala Gln Asn Pro Asn Val
    610                 615                 620

Leu Val Val Lys Lys Asp Asp Ser Ser Ile Lys Ser Leu Asp Asp Ile
625                 630                 635                 640

Gly Gly Lys Ser Thr Glu Val Val Gln Ala Thr Thr Ser Ala Lys Gln
                645                 650                 655

Leu Glu Ala Tyr Asn Ala Glu His Thr Asp Asn Pro Thr Ile Leu Asn
            660                 665                 670

Tyr Thr Lys Ala Asp Phe Gln Gln Ile Met Val Arg Leu Ser Asp Gly
        675                 680                 685

Gln Phe Asp Tyr Lys Ile Phe Asp Lys Ile Gly Val Glu Thr Val Ile
    690                 695                 700

Lys Asn Gln Gly Leu Asp Asn Leu Lys Val Ile Glu Leu Pro Ser Asp
705                 710                 715                 720

Gln Gln Pro Tyr Val Tyr Pro Leu Leu Ala Gln Gly Gln Asp Glu Leu
                725                 730                 735

Lys Ser Phe Val Asp Lys Arg Ile Lys Glu Leu Tyr Lys Asp Gly Thr
            740                 745                 750

Leu Glu Lys Leu Ser Lys Gln Phe Phe Gly Asp Thr Tyr Leu Pro Ala
        755                 760                 765

Glu Ala Asp Ile Lys
    770

<210> SEQ ID NO 52
<211> LENGTH: 772
<212> TYPE: PRT
<213> ORGANISM: Artificial Sequence
<220> FEATURE:
<223> OTHER INFORMATION: Description of Artificial Sequence: Synthetic
      Streptococcus pneumonia fusion protein
<220> FEATURE:
<223> OTHER INFORMATION: SP0148/SP1912/SP2108 fusion protein (772 amino
      acids)
```

```
<400> SEQUENCE: 52

Met Lys Lys Ile Val Lys Tyr Ser Ser Leu Ala Ala Leu Ala Leu Val
1               5                   10                  15

Ala Ala Gly Val Leu Ala Ala Cys Ser Gly Gly Ala Lys Lys Glu Gly
            20                  25                  30

Glu Ala Ala Ser Lys Lys Glu Ile Ile Val Ala Thr Asn Gly Ser Pro
        35                  40                  45

Lys Pro Phe Ile Tyr Glu Glu Asn Gly Glu Leu Thr Gly Tyr Glu Ile
    50                  55                  60

Glu Val Val Arg Ala Ile Phe Lys Asp Ser Asp Lys Tyr Asp Val Lys
65                  70                  75                  80

Phe Glu Lys Thr Glu Trp Ser Gly Val Phe Ala Gly Leu Asp Ala Asp
                85                  90                  95

Arg Tyr Asn Met Ala Val Asn Asn Leu Ser Tyr Thr Lys Glu Arg Ala
            100                 105                 110

Glu Lys Tyr Leu Tyr Ala Ala Pro Ile Ala Gln Asn Pro Asn Val Leu
        115                 120                 125

Val Val Lys Lys Asp Asp Ser Ile Lys Ser Leu Asp Asp Ile Gly
    130                 135                 140

Gly Lys Ser Thr Glu Val Val Gln Ala Thr Thr Ser Ala Lys Gln Leu
145                 150                 155                 160

Glu Ala Tyr Asn Ala Glu His Thr Asp Asn Pro Thr Ile Leu Asn Tyr
                165                 170                 175

Thr Lys Ala Asp Phe Gln Gln Ile Met Val Arg Leu Ser Asp Gly Gln
            180                 185                 190

Phe Asp Tyr Lys Ile Phe Asp Lys Ile Gly Val Glu Thr Val Ile Lys
        195                 200                 205

Asn Gln Gly Leu Asp Asn Leu Lys Val Ile Glu Leu Pro Ser Asp Gln
    210                 215                 220

Gln Pro Tyr Val Tyr Pro Leu Leu Ala Gln Gly Gln Asp Glu Leu Lys
225                 230                 235                 240

Ser Phe Val Asp Lys Arg Ile Lys Glu Leu Tyr Lys Asp Gly Thr Leu
                245                 250                 255

Glu Lys Leu Ser Lys Gln Phe Phe Gly Asp Thr Tyr Leu Pro Ala Glu
            260                 265                 270

Ala Asp Ile Lys Asn Gly Met Lys Ala Lys Met Trp Met Ala Gly
        275                 280                 285

Leu Ala Leu Leu Gly Ile Gly Ser Leu Ala Leu Ala Thr Lys Lys Val
    290                 295                 300

Ala Asp Asp Arg Lys Leu Met Lys Thr Gln Glu Leu Thr Glu Ile
305                 310                 315                 320

Val Arg Asp His Phe Ser Asp Met Gly Glu Ile Ala Thr Leu Tyr Val
                325                 330                 335

Gln Val Tyr Glu Ser Ser Leu Glu Ser Leu Val Gly Val Ile Phe
            340                 345                 350

Glu Asp Gly Arg His Tyr Thr Phe Val Tyr Glu Asn Glu Asp Leu Val
        355                 360                 365

Tyr Glu Glu Glu Val Leu Gly Ser Lys Thr Ala Asp Lys Pro Ala Asp
    370                 375                 380

Ser Gly Ser Ser Glu Val Lys Glu Leu Thr Val Tyr Val Asp Glu Gly
385                 390                 395                 400

Tyr Lys Ser Tyr Ile Glu Glu Val Ala Lys Ala Tyr Glu Lys Glu Ala
                405                 410                 415
```

Gly Val Lys Val Thr Leu Lys Thr Gly Asp Ala Leu Gly Gly Leu Asp
            420                 425                 430

Lys Leu Ser Leu Asp Asn Gln Ser Gly Asn Val Pro Asp Val Met Met
            435                 440                 445

Ala Pro Tyr Asp Arg Val Gly Ser Leu Gly Ser Asp Gly Gln Leu Ser
450                 455                 460

Glu Val Lys Leu Ser Asp Gly Ala Lys Thr Asp Asp Thr Thr Lys Ser
465                 470                 475                 480

Leu Val Thr Ala Ala Asn Gly Lys Val Tyr Gly Ala Pro Ala Val Ile
            485                 490                 495

Glu Ser Leu Val Met Tyr Tyr Asn Lys Asp Leu Val Lys Asp Ala Pro
            500                 505                 510

Lys Thr Phe Ala Asp Leu Glu Asn Leu Ala Lys Asp Ser Lys Tyr Ala
            515                 520                 525

Phe Ala Gly Glu Asp Gly Lys Thr Thr Ala Phe Leu Ala Asp Trp Thr
530                 535                 540

Asn Phe Tyr Tyr Thr Tyr Gly Leu Leu Ala Gly Asn Gly Ala Tyr Val
545                 550                 555                 560

Phe Gly Gln Asn Gly Lys Asp Ala Lys Asp Ile Gly Leu Ala Asn Asp
            565                 570                 575

Gly Ser Ile Val Gly Ile Asn Tyr Ala Lys Ser Trp Tyr Glu Lys Trp
            580                 585                 590

Pro Lys Gly Met Gln Asp Thr Glu Gly Ala Gly Asn Leu Ile Gln Thr
            595                 600                 605

Gln Phe Gln Glu Gly Lys Thr Ala Ala Ile Ile Asp Gly Pro Trp Lys
            610                 615                 620

Ala Gln Ala Phe Lys Asp Ala Lys Val Asn Tyr Gly Val Ala Thr Ile
625                 630                 635                 640

Pro Thr Leu Pro Asn Gly Lys Glu Tyr Ala Ala Phe Gly Gly Gly Lys
            645                 650                 655

Ala Trp Val Ile Pro Gln Ala Val Lys Asn Leu Glu Ala Ser Gln Lys
            660                 665                 670

Phe Val Asp Phe Leu Val Ala Thr Glu Gln Lys Val Leu Tyr Asp
            675                 680                 685

Lys Thr Asn Glu Ile Pro Ala Asn Thr Glu Ala Arg Ser Tyr Ala Glu
            690                 695                 700

Gly Lys Asn Asp Glu Leu Thr Thr Ala Val Ile Lys Gln Phe Lys Asn
705                 710                 715                 720

Thr Gln Pro Leu Pro Asn Ile Ser Gln Met Ser Ala Val Trp Asp Pro
            725                 730                 735

Ala Lys Asn Met Leu Phe Asp Val Ser Gly Gln Lys Asp Ala Lys
            740                 745                 750

Thr Ala Ala Asn Asp Ala Val Thr Leu Ile Lys Glu Thr Ile Lys Gln
            755                 760                 765

Lys Phe Gly Glu
    770

<210> SEQ ID NO 53
<211> LENGTH: 773
<212> TYPE: PRT
<213> ORGANISM: Artificial Sequence
<220> FEATURE:
<223> OTHER INFORMATION: Description of Artificial Sequence: Synthetic
      Streptococcus pneumonia fusion protein
<220> FEATURE:

<223> OTHER INFORMATION: SP2108/SP0148/SP1912 fusion protein (773 amino acids)

<400> SEQUENCE: 53

```
Met Ser Ser Lys Phe Met Lys Ser Ala Ala Val Leu Gly Thr Ala Thr
1               5                   10                  15

Leu Ala Ser Leu Leu Val Ala Cys Gly Ser Lys Thr Ala Asp Lys
                20                  25                  30

Pro Ala Asp Ser Gly Ser Ser Glu Val Lys Glu Leu Thr Val Tyr Val
                35                  40                  45

Asp Glu Gly Tyr Lys Ser Tyr Ile Glu Val Ala Lys Ala Tyr Glu
50                  55                  60

Lys Glu Ala Gly Val Lys Val Thr Leu Lys Thr Gly Asp Ala Leu Gly
65                  70                  75                  80

Gly Leu Asp Lys Leu Ser Leu Asp Asn Gln Ser Gly Asn Val Pro Asp
                85                  90                  95

Val Met Met Ala Pro Tyr Asp Arg Val Gly Ser Leu Gly Ser Asp Gly
                100                 105                 110

Gln Leu Ser Glu Val Lys Leu Ser Asp Gly Ala Lys Thr Asp Asp Thr
            115                 120                 125

Thr Lys Ser Leu Val Thr Ala Ala Asn Gly Lys Val Tyr Gly Ala Pro
130                 135                 140

Ala Val Ile Glu Ser Leu Val Met Tyr Tyr Asn Lys Asp Leu Val Lys
145                 150                 155                 160

Asp Ala Pro Lys Thr Phe Ala Asp Leu Glu Asn Leu Ala Lys Asp Ser
                165                 170                 175

Lys Tyr Ala Phe Ala Gly Glu Asp Gly Lys Thr Thr Ala Phe Leu Ala
            180                 185                 190

Asp Trp Thr Asn Phe Tyr Tyr Thr Tyr Gly Leu Leu Ala Gly Asn Gly
                195                 200                 205

Ala Tyr Val Phe Gly Gln Asn Gly Lys Asp Ala Lys Asp Ile Gly Leu
            210                 215                 220

Ala Asn Asp Gly Ser Ile Val Gly Ile Asn Tyr Ala Lys Ser Trp Tyr
225                 230                 235                 240

Glu Lys Trp Pro Lys Gly Met Gln Asp Thr Glu Gly Ala Gly Asn Leu
                245                 250                 255

Ile Gln Thr Gln Phe Gln Glu Gly Lys Thr Ala Ile Ile Asp Gly
            260                 265                 270

Pro Trp Lys Ala Gln Ala Phe Lys Asp Ala Lys Val Asn Tyr Gly Val
            275                 280                 285

Ala Thr Ile Pro Thr Leu Pro Asn Gly Lys Glu Tyr Ala Ala Phe Gly
290                 295                 300

Gly Gly Lys Ala Trp Val Ile Pro Gln Ala Val Lys Asn Leu Glu Ala
305                 310                 315                 320

Ser Gln Lys Phe Val Asp Phe Leu Val Ala Thr Glu Gln Lys Val
                325                 330                 335

Leu Tyr Asp Lys Thr Asn Glu Ile Pro Ala Asn Thr Glu Ala Arg Ser
                340                 345                 350

Tyr Ala Glu Gly Lys Asn Asp Glu Leu Thr Thr Ala Val Ile Lys Gln
            355                 360                 365

Phe Lys Asn Thr Gln Pro Leu Pro Asn Ile Ser Gln Met Ser Ala Val
            370                 375                 380

Trp Asp Pro Ala Lys Asn Met Leu Phe Asp Ala Val Ser Gly Gln Lys
385                 390                 395                 400
```

-continued

```
Asp Ala Lys Thr Ala Ala Asn Asp Ala Val Thr Leu Ile Lys Glu Thr
                405                 410                 415
Ile Lys Gln Lys Phe Gly Glu Ser Gly Ala Lys Lys Glu Gly Glu
            420                 425                 430
Ala Ala Ser Lys Lys Glu Ile Ile Val Ala Thr Asn Gly Ser Pro Lys
            435                 440                 445
Pro Phe Ile Tyr Glu Glu Asn Gly Glu Leu Thr Gly Tyr Glu Ile Glu
    450                 455                 460
Val Val Arg Ala Ile Phe Lys Asp Ser Asp Lys Tyr Asp Val Lys Phe
465                 470                 475                 480
Glu Lys Thr Glu Trp Ser Gly Val Phe Ala Gly Leu Asp Ala Asp Arg
                485                 490                 495
Tyr Asn Met Ala Val Asn Asn Leu Ser Tyr Thr Lys Glu Arg Ala Glu
            500                 505                 510
Lys Tyr Leu Tyr Ala Ala Pro Ile Ala Gln Asn Pro Asn Val Leu Val
        515                 520                 525
Val Lys Lys Asp Asp Ser Ser Ile Lys Ser Leu Asp Asp Ile Gly Gly
    530                 535                 540
Lys Ser Thr Glu Val Val Gln Ala Thr Thr Ser Ala Lys Gln Leu Glu
545                 550                 555                 560
Ala Tyr Asn Ala Glu His Thr Asp Asn Pro Thr Ile Leu Asn Tyr Thr
                565                 570                 575
Lys Ala Asp Phe Gln Gln Ile Met Val Arg Leu Ser Asp Gly Gln Phe
            580                 585                 590
Asp Tyr Lys Ile Phe Asp Lys Ile Gly Val Glu Thr Val Ile Lys Asn
        595                 600                 605
Gln Gly Leu Asp Asn Leu Lys Val Ile Glu Leu Pro Ser Asp Gln Gln
    610                 615                 620
Pro Tyr Val Tyr Pro Leu Leu Ala Gln Gly Gln Asp Glu Leu Lys Ser
625                 630                 635                 640
Phe Val Asp Lys Arg Ile Lys Glu Leu Tyr Lys Asp Gly Thr Leu Glu
                645                 650                 655
Lys Leu Ser Lys Gln Phe Phe Gly Asp Thr Tyr Leu Pro Ala Glu Ala
            660                 665                 670
Asp Ile Lys Asn Gly Met Lys Ala Lys Lys Met Trp Met Ala Gly Leu
        675                 680                 685
Ala Leu Leu Gly Ile Gly Ser Leu Ala Leu Ala Thr Lys Lys Val Ala
    690                 695                 700
Asp Asp Arg Lys Leu Met Lys Thr Gln Glu Glu Leu Thr Glu Ile Val
705                 710                 715                 720
Arg Asp His Phe Ser Asp Met Gly Glu Ile Ala Thr Leu Tyr Val Gln
                725                 730                 735
Val Tyr Glu Ser Ser Leu Glu Ser Leu Val Gly Gly Val Ile Phe Glu
            740                 745                 750
Asp Gly Arg His Tyr Thr Phe Val Tyr Glu Asn Glu Asp Leu Val Tyr
        755                 760                 765
Glu Glu Glu Val Leu
    770
```

<210> SEQ ID NO 54
<211> LENGTH: 772
<212> TYPE: PRT
<213> ORGANISM: Artificial Sequence
<220> FEATURE:

<223> OTHER INFORMATION: Description of Artificial Sequence: Synthetic
Streptococcus pneumonia fusion protein
<220> FEATURE:
<223> OTHER INFORMATION: SP0148/SP2108/SP1912 fusion protein (772 amino
acids)

<400> SEQUENCE: 54

```
Met Lys Lys Ile Val Lys Tyr Ser Ser Leu Ala Ala Leu Ala Leu Val
1               5                   10                  15

Ala Ala Gly Val Leu Ala Ala Cys Ser Gly Gly Ala Lys Lys Glu Gly
            20                  25                  30

Glu Ala Ala Ser Lys Lys Glu Ile Ile Val Ala Thr Asn Gly Ser Pro
        35                  40                  45

Lys Pro Phe Ile Tyr Glu Glu Asn Gly Glu Leu Thr Gly Tyr Glu Ile
50                  55                  60

Glu Val Val Arg Ala Ile Phe Lys Asp Ser Asp Lys Tyr Asp Val Lys
65                  70                  75                  80

Phe Glu Lys Thr Glu Trp Ser Gly Val Phe Ala Gly Leu Asp Ala Asp
                85                  90                  95

Arg Tyr Asn Met Ala Val Asn Asn Leu Ser Tyr Thr Lys Glu Arg Ala
            100                 105                 110

Glu Lys Tyr Leu Tyr Ala Ala Pro Ile Ala Gln Asn Pro Asn Val Leu
        115                 120                 125

Val Val Lys Lys Asp Asp Ser Ser Ile Lys Ser Leu Asp Asp Ile Gly
130                 135                 140

Gly Lys Ser Thr Glu Val Val Gln Ala Thr Thr Ser Ala Lys Gln Leu
145                 150                 155                 160

Glu Ala Tyr Asn Ala Glu His Thr Asp Asn Pro Thr Ile Leu Asn Tyr
                165                 170                 175

Thr Lys Ala Asp Phe Gln Gln Ile Met Val Arg Leu Ser Asp Gly Gln
            180                 185                 190

Phe Asp Tyr Lys Ile Phe Asp Lys Ile Gly Val Glu Thr Val Ile Lys
        195                 200                 205

Asn Gln Gly Leu Asp Asn Leu Lys Val Ile Glu Leu Pro Ser Asp Gln
210                 215                 220

Gln Pro Tyr Val Tyr Pro Leu Leu Ala Gln Gly Gln Asp Glu Leu Lys
225                 230                 235                 240

Ser Phe Val Asp Lys Arg Ile Lys Glu Leu Tyr Lys Asp Gly Thr Leu
                245                 250                 255

Glu Lys Leu Ser Lys Gln Phe Phe Gly Asp Thr Tyr Leu Pro Ala Glu
            260                 265                 270

Ala Asp Ile Lys Gly Ser Lys Thr Ala Asp Lys Pro Ala Asp Ser Gly
        275                 280                 285

Ser Ser Glu Val Lys Glu Leu Thr Val Tyr Val Asp Glu Gly Tyr Lys
290                 295                 300

Ser Tyr Ile Glu Glu Val Ala Lys Ala Tyr Glu Lys Glu Ala Gly Val
305                 310                 315                 320

Lys Val Thr Leu Lys Thr Gly Asp Ala Leu Gly Gly Leu Asp Lys Leu
                325                 330                 335

Ser Leu Asp Asn Gln Ser Gly Asn Val Pro Asp Val Met Met Ala Pro
            340                 345                 350

Tyr Asp Arg Val Gly Ser Leu Gly Ser Asp Gly Gln Leu Ser Glu Val
        355                 360                 365

Lys Leu Ser Asp Gly Ala Lys Thr Asp Asp Thr Thr Lys Ser Leu Val
370                 375                 380
```

```
Thr Ala Ala Asn Gly Lys Val Tyr Gly Ala Pro Ala Val Ile Glu Ser
385                 390                 395                 400

Leu Val Met Tyr Tyr Asn Lys Asp Leu Val Lys Asp Ala Pro Lys Thr
            405                 410                 415

Phe Ala Asp Leu Glu Asn Leu Ala Lys Asp Ser Lys Tyr Ala Phe Ala
        420                 425                 430

Gly Glu Asp Gly Lys Thr Thr Ala Phe Leu Ala Asp Trp Thr Asn Phe
            435                 440                 445

Tyr Tyr Thr Tyr Gly Leu Leu Ala Gly Asn Gly Ala Tyr Val Phe Gly
            450                 455                 460

Gln Asn Gly Lys Asp Ala Lys Asp Ile Gly Leu Ala Asn Asp Gly Ser
465                 470                 475                 480

Ile Val Gly Ile Asn Tyr Ala Lys Ser Trp Tyr Glu Lys Trp Pro Lys
            485                 490                 495

Gly Met Gln Asp Thr Glu Gly Ala Gly Asn Leu Ile Gln Thr Gln Phe
            500                 505                 510

Gln Glu Gly Lys Thr Ala Ala Ile Ile Asp Gly Pro Trp Lys Ala Gln
            515                 520                 525

Ala Phe Lys Asp Ala Lys Val Asn Tyr Gly Val Ala Thr Ile Pro Thr
530                 535                 540

Leu Pro Asn Gly Lys Glu Tyr Ala Ala Phe Gly Gly Lys Ala Trp
545                 550                 555                 560

Val Ile Pro Gln Ala Val Lys Asn Leu Glu Ala Ser Gln Lys Phe Val
            565                 570                 575

Asp Phe Leu Val Ala Thr Glu Gln Gln Lys Val Leu Tyr Asp Lys Thr
            580                 585                 590

Asn Glu Ile Pro Ala Asn Thr Glu Ala Arg Ser Tyr Ala Glu Gly Lys
            595                 600                 605

Asn Asp Glu Leu Thr Thr Ala Val Ile Lys Gln Phe Lys Asn Thr Gln
            610                 615                 620

Pro Leu Pro Asn Ile Ser Gln Met Ser Ala Val Trp Asp Pro Ala Lys
625                 630                 635                 640

Asn Met Leu Phe Asp Ala Val Ser Gly Gln Lys Asp Ala Lys Thr Ala
                645                 650                 655

Ala Asn Asp Ala Val Thr Leu Ile Lys Glu Thr Ile Lys Gln Lys Phe
            660                 665                 670

Gly Glu Asn Gly Met Lys Ala Lys Met Trp Met Ala Gly Leu Ala
            675                 680                 685

Leu Leu Gly Ile Gly Ser Leu Ala Leu Ala Thr Lys Lys Val Ala Asp
            690                 695                 700

Asp Arg Lys Leu Met Lys Thr Gln Glu Glu Leu Thr Glu Ile Val Arg
705                 710                 715                 720

Asp His Phe Ser Asp Met Gly Glu Ile Ala Thr Leu Tyr Val Gln Val
                725                 730                 735

Tyr Glu Ser Ser Leu Glu Ser Leu Val Gly Gly Val Ile Phe Glu Asp
            740                 745                 750

Gly Arg His Tyr Thr Phe Val Tyr Glu Asn Glu Asp Leu Val Tyr Glu
            755                 760                 765

Glu Glu Val Leu
    770

<210> SEQ ID NO 55
<211> LENGTH: 471
```

```
<212> TYPE: PRT
<213> ORGANISM: Streptococcus pneumonia
<220> FEATURE:
<223> OTHER INFORMATION: L460D (471 amino acids)

<400> SEQUENCE: 55
```

| | | | | | | | | | | | | | | |
|---|---|---|---|---|---|---|---|---|---|---|---|---|---|---|
| Met | Ala | Asn | Lys | Ala | Val | Asn | Asp | Phe | Ile | Leu | Ala | Met | Asn | Tyr | Asp |
| 1 | | | | 5 | | | | | 10 | | | | | 15 | |

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
                115                 120                 125

Asp Leu Leu Ala Lys Trp His Gln Asp Tyr Gly Gln Val Asn Asn Val
            130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
                260                 265                 270

Ala Pro Gln Thr Glu Trp Lys Gln Ile Leu Asp Asn Thr Glu Val Lys
                275                 280                 285

Ala Val Ile Leu Gly Gly Asp Pro Ser Ser Gly Ala Arg Val Val Thr
            290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asp Glu Leu Ser Tyr
370                 375                 380

| Asp His Gln Gly Lys Glu Val Leu Thr Pro Lys Ala Trp Asp Arg Asn |
| 385 390 395 400 |

Gly Gln Asp Leu Thr Ala His Phe Thr Thr Ser Ile Pro Leu Lys Gly
            405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Asp Tyr Pro Gln Val
    450                 455                 460

Glu Asp Lys Val Glu Asn Asp
465                 470

<210> SEQ ID NO 56
<211> LENGTH: 2025
<212> TYPE: DNA
<213> ORGANISM: Artificial Sequence
<220> FEATURE:
<223> OTHER INFORMATION: Description of Artificial Sequence: Synthetic
      Streptococcus pneumonia fusion sequence
<220> FEATURE:
<223> OTHER INFORMATION: SP2108/SP0148 fusion (nucleotides)

<400> SEQUENCE: 56

```
atgtcatcta aatttatgaa gagcgctgcg gtgcttggaa ctgctacact tgctagcttg      60
cttttggtag cttgcggaag caaaactgct gataagcctg ctgattctgg ttcatctgaa     120
gtcaaagaac tcactgtata tgtagacgag ggatataaga gctatattga agaggttgct     180
aaagcttatg aaaagaagc tggagtaaaa gtcactctta aaactggtga tgctctagga     240
ggtcttgata actttctct tgacaaccaa tctggtaatg tccctgatgt tatgatggct     300 ccatcgacc gtgtaggtag ccttggttct gacggacaac tttcagaagt gaaattgagc     360
gatggtgcta aaacagacga cacaactaaa tctcttgtaa cagctgctaa tggtaaagtt     420
tacggtgctc ctgccgttat cgagtcactt gttatgtact acaacaaaga cttggtgaaa     480
gatgctccaa aaacatttgc tgacttggaa aaccttgcta agatagcaa atacgcattc     540 gctggtgaag atggtaaaac tactgccttc ctagctgact ggacaaactt ctactataca     600
tatggacttc ttgccggtaa cggtgcttac gtctttggcc aaaacggtaa agacgctaaa     660
gacatcggtc ttgcaaacga cggttctatc gtaggtatca actacgctaa atcttggtac     720
gaaaaatggc ctaaaggtat gcaagataca gaaggtgctg aaacttaat ccaaactcaa     780 ttccaagaag gtaaaacagc tgctatcatc gacggacctt ggaaagctca agcctttaaa     840
gatgctaaag taaactacgg agttgcaact atcccaactc ttccaaatgg aaaagaatat     900
gctgcattcg gtggtggtaa agcttgggtc attcctcaag ccgttaagaa ccttgaagct     960
tctcaaaaat ttgtagactt ccttgttgca actgaacaac aaaaagtatt atatgataag    1020
actaacgaaa tcccagctaa tactgaggct cgttcatacg ctgaaggtaa aaacgatgag    1080
ttgacaacag ctgttatcaa acagttcaag aacactcaac cactgccaaa catctctcaa    1140
atgtctgcag tttgggatcc agcgaaaaat atgctctttg atgctgtaag tggtcaaaaa    1200
gatgctaaaa cagctgctaa cgatgctgta acattgatca agaaacaat caaacaaaaa    1260 tttggtgaat caggggggtgc taagaaagaa ggagaagcag ctagcaagaa agaaatcatc    1320
gttgcaacca atggatcacc aaagccattt atctatgaag aaaatggcga attgactggt    1380
tacgagattg aagtcgttcg cgctatcttt aaagattctg acaaatatga tgtcaagttt    1440
```

| | |
|---|---:|
| gaaaagacag aatggtcagg tgtctttgct ggtcttgacg ctgatcgtta caatatggct | 1500 |
| gtcaacaatc ttagctacac taaagaacgt gcggagaaat acctctatgc cgcaccaatt | 1560 |
| gcccaaaatc ctaatgtcct tgtcgtgaag aaagatgact ctagtatcaa gtctctcgat | 1620 |
| gatatcggtg gaaaatcgac ggaagtcgtt caagccacta catcagctaa gcagttagaa | 1680 |
| gcatacaatg ctgaacacac ggacaaccca actatcctta actatactaa ggcagacttc | 1740 |
| caacaaatca tggtacgttt gagcgatgga caatttgact ataagatttt tgataaaatc | 1800 |
| ggtgttgaaa cagtgatcaa gaaccaaggt ttggacaact tgaaagttat cgaacttcca | 1860 |
| agcgaccaac aaccgtacgt ttacccactt cttgctcagg gtcaagatga gttgaaatcg | 1920 |
| tttgtagaca aacgcatcaa agaactttat aaagatggaa ctcttgaaaa attgtctaaa | 1980 |
| caattcttcg gagacactta tctaccggca gaagctgata ttaaa | 2025 |

<210> SEQ ID NO 57
<211> LENGTH: 2022
<212> TYPE: DNA
<213> ORGANISM: Artificial Sequence
<220> FEATURE:
<223> OTHER INFORMATION: Description of Artificial Sequence: Synthetic
Streptococcus pneumonia fusion sequence
<220> FEATURE:
<223> OTHER INFORMATION: SP0148/SP2108 fusion (nucleotides)

<400> SEQUENCE: 57

| | |
|---|---:|
| atgaaaaaaa tcgttaaata ctcatctctt gcagcccttg ctcttgttgc tgcaggtgtg | 60 |
| cttgcggctt gctcagggg tgctaagaaa gaaggagaag cagctagcaa gaaagaaatc | 120 |
| atcgttgcaa ccaatggatc accaaagcca tttatctatg aagaaatgg cgaattgact | 180 |
| ggttacgaga ttgaagtcgt tcgcgctatc tttaaagatt ctgacaaata tgatgtcaag | 240 |
| tttgaaaaga cagaatggtc aggtgtcttt gctggtcttg acgctgatcg ttacaatatg | 300 |
| gctgtcaaca atcttagcta cactaaagaa cgtgcggaga atacctcta tgccgcacca | 360 |
| attgcccaaa atcctaatgt ccttgtcgtg aagaaagatg actctagtat caagtctctc | 420 |
| gatgatatcg gtggaaaatc gacggaagtc gttcaagcca ctacatcagc taagcagtta | 480 |
| gaagcataca atgctgaaca cacggacaac ccaactatcc ttaactatac taaggcagac | 540 |
| ttcaacaaa tcatggtacg tttgagcgat ggacaatttg actataagat ttttgataaa | 600 |
| atcggtgttg aaacagtgat caagaaccaa ggtttggaca acttgaaagt tatcgaactt | 660 |
| ccaagcgacc aacaaccgta cgtttacca cttcttgctc agggtcaaga tgagttgaaa | 720 |
| tcgtttgtag acaaacgcat caaagaactt tataaagatg gaactcttga aaaattgtct | 780 |
| aaacaattct tcggagacac ttatctaccg gcagaagctg atattaaagg aagcaaaact | 840 |
| gctgataagc ctgctgattc tggttcatct gaagtcaaag aactcactgt atatgtagac | 900 |
| gagggatata agagctatat tgaagaggtt gctaaagctt atgaaaaaga agctggagta | 960 |
| aaagtcactc ttaaaactgg tgatgctcta ggaggtcttg ataaactttc tcttgacaac | 1020 |
| caatctggta atgtccctga tgttatgatg gctccatacg accgtgtagg tagccttggt | 1080 |
| tctgacggac aactttcaga agtgaaattg agcgatggtg ctaaaacaga cgacacaact | 1140 |
| aaatctcttg taacagctgc taatggtaaa gtttacggtg ctcctgccgt tatcgagtca | 1200 |
| cttgttatgt actacaacaa agacttggtg aaagatgctc caaaaacatt tgctgacttg | 1260 |
| gaaaaccttg ctaagataag caaatacgca ttcgctggtg aagatggtaa aactactgcc | 1320 |
| ttcctagctg actggacaaa cttctactat acatatggac ttcttgccgg taacggtgct | 1380 |

```
tacgtctttg gccaaaacgg taaagacgct aaagacatcg gtcttgcaaa cgacggttct   1440
atcgtaggta tcaactacgc taaatcttgg tacgaaaaat ggcctaaagg tatgcaagat   1500
acagaaggtg ctggaaactt aatccaaact caattccaag aaggtaaaac agctgctatc   1560
atcgacggac cttggaaagc tcaagccttt aaagatgcta agtaaacta cggagttgca    1620 actatcccaa ctcttccaaa tggaaaagaa tatgctgcat tcggtggtgg taaagcttgg   1680
gtcattcctc aagccgttaa gaaccttgaa gcttctcaaa aatttgtaga cttccttgtt   1740
gcaactgaac aacaaaaagt attatatgat aagactaacg aaatcccagc taatactgag   1800
gctcgttcat acgctgaagg taaaaacgat gagttgacaa cagctgttat caaacagttc   1860
aagaacactc aaccactgcc aaacatctct caaatgtctg cagtttggga tccagcgaaa   1920
aatatgctct tgatgctgt aagtggtcaa aaagatgcta aaacagctgc taacgatgct    1980
gtaacattga tcaaagaaac aatcaaacaa aaatttggtg aa                      2022

<210> SEQ ID NO 58
<211> LENGTH: 1563
<212> TYPE: DNA
<213> ORGANISM: Artificial Sequence
<220> FEATURE:
<223> OTHER INFORMATION: Description of Artificial Sequence: Synthetic
      Streptococcus pneumonia fusion sequence
<220> FEATURE:
<223> OTHER INFORMATION: SP2108/SP1912 fusion (nucleotides)

<400> SEQUENCE: 58
atgtcatcta aatttatgaa gagcgctgcg gtgcttggaa ctgctacact tgctagcttg     60
cttttggtag cttgcggaag caaaactgct gataagcctg ctgattctgg ttcatctgaa   120
gtcaaagaac tcactgtata tgtagacgag ggatataaga gctatattga agaggttgct   180
aaagcttatg aaaaagaagc tggagtaaaa gtcactctta aaactggtga tgctctagga   240
ggtcttgata actttctct tgacaaccaa tctggtaatg tccctgatgt tatgatggct   300 ccatcgacc gtgtaggtag ccttggttct gacggacaac tttcagaagt gaaattgagc   360
gatggtgcta aaacagacga cacaactaaa tctcttgtaa cagctgctaa tggtaaagtt   420
tacggtgctc ctgccgttat cgagtcactt gttatgtact acaacaaaga cttggtgaaa   480
gatgctccaa aacatttgc tgacttggaa aaccttgcta agatagcaa atacgcattc     540 gctggtgaag atggtaaaac tactgccttc ctagctgact ggacaaactt ctactataca   600
tatggacttc ttgccggtaa cggtgcttac gtctttggcc aaaacggtaa agacgctaaa   660
gacatcggtc ttgcaaacga cggttctatc gtaggtatca actacgctaa atcttggtac   720
gaaaaatggc ctaaaggtat gcaagataca gaaggtgctg gaaacttaat ccaaactcaa   780
ttccaagaag gtaaaacagc tgctatcatc gacggacctt ggaaagctca agcctttaaa   840
gatgctaaag taaactacgg agttgcaact atcccaactc ttccaaatgg aaaagaatat   900
gctgcattcg gtggtggtaa agcttgggtc attcctcaag ccgttaagaa ccttgaagct   960
tctcaaaaat ttgtagactt ccttgttgca actgaacaac aaaaagtatt atatgataag  1020
actaacgaaa tcccagctaa tactgaggct cgttcatacg ctgaaggtaa aaacgatgag  1080
ttgacaacag ctgttatcaa acagttcaag aacactcaac cactgccaaa catctctcaa  1140
atgtctgcag tttgggatcc agcgaaaaat atgctctttg atgctgtaag tggtcaaaaa  1200
gatgctaaaa cagctgctaa cgatgctgta acattgatca aagaacaat caaacaaaaa   1260 tttggtgaaa atggtatgaa agctaaaaaa atgtggatgg caggcttggc tctgctaggt  1320
```

| | |
|---|---|
| atcggaagcc ttgctcttgc tacgaaaaaa gttgcagatg accgtaagct catgaagact | 1380 |
| caggaagagt tgacagagat tgtgcgagac cattttccg acatggggga aattgcgacc | 1440 |
| ctttatgttc aagtttacga aagcagtctg gagagcttgg ttggtggcgt cattttgag | 1500 |
| gatggccgtc attataccTT tgtctatgaa aatgaagacc tagtctatga ggaggaagtc | 1560 |
| tta | 1563 |

<210> SEQ ID NO 59
<211> LENGTH: 1122
<212> TYPE: DNA
<213> ORGANISM: Artificial Sequence
<220> FEATURE:
<223> OTHER INFORMATION: Description of Artificial Sequence: Synthetic
    Streptococcus pneumonia fusion sequence
<220> FEATURE:
<223> OTHER INFORMATION: SP0148/SP1912 fusion (nucleotides)

<400> SEQUENCE: 59

| | |
|---|---|
| atgaaaaaaa tcgttaaata ctcatctctt gcagcccttg ctcttgttgc tgcaggtgtg | 60 |
| cttgcggctt gctcagggg tgctaagaaa gaaggagaag cagctagcaa gaaagaaatc | 120 |
| atcgttgcaa ccaatggatc accaaagcca tttatctatg aagaaaatgg cgaattgact | 180 |
| ggttacgaga ttgaagtcgt tcgcgctatc tttaaagatt ctgacaaata tgatgtcaag | 240 |
| tttgaaaaga cagaatggtc aggtgtcttt gctggtcttg acgctgatcg ttacaatatg | 300 |
| gctgtcaaca atcttagcta cactaaagaa cgtgcggaga atacctcta tgccgcacca | 360 |
| attgcccaaa atcctaatgt ccttgtcgtg aagaaagatg actctagtat caagtctctc | 420 |
| gatgatatcg gtggaaaatc gacggaagtc gttcaagcca ctacatcagc taagcagtta | 480 |
| gaagcataca atgctgaaca cacggacaac ccaactatcc ttaactatac taaggcagac | 540 |
| ttccaacaaa tcatggtacg tttgagcgat ggacaatttg actataagat ttttgataaa | 600 |
| atcggtgttg aaacagtgat caagaaccaa ggtttggaca acttgaaagt tatcgaactt | 660 |
| ccaagcgacc aacaaccgta cgtttaccca cttcttgctc agggtcaaga tgagttgaaa | 720 |
| tcgtttgtag acaaacgcat caaagaactt tataaagatg gaactcttga aaaattgtct | 780 |
| aaacaattct tcggagacac ttatctaccg gcagaagcta tattaaaaa tggtatgaaa | 840 |
| gctaaaaaaa tgtggatggc aggcttggct ctgctaggta tcggaagcct tgctcttgct | 900 |
| acgaaaaaag ttgcagatga ccgtaagctc atgaagactc aggaagagtt gacagagatt | 960 |
| gtgcgagacc attttccga catgggggaa attgcgaccc tttatgttca agtttacgaa | 1020 |
| agcagtctgg agagcttggt tggtggcgt attttgagg atggccgtca ttatacctTT | 1080 |
| gtctatgaaa atgaagacct agtctatgag gaggaagtct ta | 1122 |

<210> SEQ ID NO 60
<211> LENGTH: 2322
<212> TYPE: DNA
<213> ORGANISM: Artificial Sequence
<220> FEATURE:
<223> OTHER INFORMATION: Description of Artificial Sequence: Synthetic
    Streptococcus pneumonia fusion sequence
<220> FEATURE:
<223> OTHER INFORMATION: SP2108/SP1912/SP0148 fusion (nucleotides)

<400> SEQUENCE: 60

| | |
|---|---|
| atgtcatcta aatttatgaa gagcgctgcg gtgcttggaa ctgctacact tgctagcttg | 60 |
| cttttggtag cttgcggaag caaaactgct gataagcctg ctgattctgg ttcatctgaa | 120 |
| gtcaaagaac tcactgtata tgtagacgag ggatataaga gctatattga agaggttgct | 180 |

```
aaagcttatg aaaaagaagc tggagtaaaa gtcactctta aaactggtga tgctctagga      240
ggtcttgata aactttctct tgacaaccaa tctggtaatg tccctgatgt tatgatggct      300
ccatacgacc gtgtaggtag ccttggttct gacggacaac tttcagaagt gaaattgagc      360
gatggtgcta aaacagacga cacaactaaa tctcttgtaa cagctgctaa tggtaaagtt      420
tacggtgctc ctgccgttat cgagtcactt gttatgtact acaacaaaga cttggtgaaa      480
gatgctccaa aaacatttgc tgacttggaa accttgcta aagatagcaa atacgcattc       540
gctggtgaag atggtaaaac tactgccttc ctagctgact ggacaaactt ctactataca      600
tatgacttc ttgccggtaa cggtgcttac gtctttggcc aaaacggtaa agacgctaaa       660
gacatcggtc ttgcaaacga cggttctatc gtaggtatca actacgctaa atcttggtac      720
gaaaaatggc ctaaaggtat gcaagataca gaaggtgctg aaacttaat ccaaactcaa       780
ttccaagaag gtaaaacagc tgctatcatc gacggacctt ggaaagctca agcctttaaa      840
gatgctaaag taaactacgg agttgcaact atcccaactc ttccaaatgg aaaagaatat      900
gctgcattcg gtggtggtaa agcttgggtc attcctcaag ccgttaagaa ccttgaagct      960
tctcaaaaat ttgtagactt ccttgttgca actgaacaac aaaaagtatt atatgataag     1020
actaacgaaa tcccagctaa tactgaggct cgttcatacg ctgaaggtaa aaacgatgag     1080
ttgacaacga ctgttatcaa acagttcaag aacactcaac cactgccaaa catctctcaa     1140
atgtctgcag tttgggatcc agcgaaaaat atgctctttg atgctgtaag tggtcaaaaa     1200
gatgctaaaa cagctgctaa cgatgctgta acattgatca agaaacaat caaacaaaaa      1260
tttggtgaaa atggtatgaa agctaaaaaa atgtggatgg caggcttggc tctgctaggt     1320
atcggaagcc ttgctcttgc tacgaaaaaa gttgcagatg accgtaagct catgaagact     1380
caggaagagt tgacagagat tgtgcgagac cattttccg acatggggga aattgcgacc      1440
ctttatgttc aagtttacga aagcagtctg gagagcttgg ttggtggcgt cattttgag     1500
gatggccgtc attataccct tgtctatgaa atgaagacc tagtctatga ggaggaagtc      1560
ttatgctcag ggggtgctaa gaaagaagga gaagcagcta gcaagaaaga aatcatcgtt     1620
gcaaccaatg gatcaccaaa gccatttatc tatgaagaaa atggcgaatt gactggttac     1680
gagattgaag tcgttcgcgc tatctttaaa gattctgaca aatatgatgt caagtttgaa     1740
aagacagaat ggtcaggtgt cttttgctggt cttgacgctg atcgttacaa tatggctgtc     1800
aacaatctta gctacactaa agaacgtgcg gagaaatacc tctatgccgc accaattgcc     1860
caaaatccta atgtccttgt cgtgaagaaa gatgactcta gtatcaagtc tctcgatgat     1920
atcggtggaa aatcgacgga agtcgttcaa gccactacat cagctaagca gttagaagca     1980
tacaatgctg aacacacgga caacccaact atccttaact atactaaggc agacttccaa     2040
caaatcatgg tacgtttgag cgatggacaa tttgactata agattttga taaaatcggt     2100
gttgaaacag tgatcaagaa ccaaggtttg gacaacttga aagttatcga acttccaagc     2160
gaccaacaac cgtacgttta cccacttctt gctcagggtc aagatgagtt gaaatcgttt     2220
gtagacaaac gcatcaaaga actttataaa gatggaactc ttgaaaaatt gtctaaacaa     2280
ttcttcggag acacttatct accggcagaa gctgatatta aa                        2322
```

<210> SEQ ID NO 61  
<211> LENGTH: 2337  
<212> TYPE: DNA  
<213> ORGANISM: Artificial Sequence  
<220> FEATURE:

<223> OTHER INFORMATION: Description of Artificial Sequence: Synthetic
     Streptococcus pneumonia fusion sequence
<220> FEATURE:
<223> OTHER INFORMATION: SP0148/SP1912/SP2108 fusion (nucleotides)

<400> SEQUENCE: 61

```
atgaaaaaaa tcgttaaata ctcatctctt gcagcccttg ctcttgttgc tgcaggtgtg     60
cttgcggctt gctcaggggg tgctaagaaa gaaggagaag cagctagcaa gaaagaaatc    120
atcgttgcaa ccaatggatc accaaagcca tttatctatg aagaaaatgg cgaattgact    180
ggttacgaga ttgaagtcgt tcgcgctatc tttaaagatt ctgacaaata tgatgtcaag    240
tttgaaaaga cagaatggtc aggtgtcttt gctggtcttg acgctgatcg ttacaatatg    300
gctgtcaaca atcttagcta cactaaagaa cgtgcggaga aatacctcta tgccgcacca    360
attgcccaaa atcctaatgt ccttgtcgtg aagaaagatg actctagtat caagtctctc    420
gatgatatcg gtggaaaatc gacggaagtc gttcaagcca ctacatcagc taagcagtta    480
gaagcataca atgctgaaca cacggacaac ccaactatcc ttaactatac taaggcagac    540
ttccaacaaa tcatggtacg tttgagcgat ggacaatttg actataagat tttgataaa     600 atcggtgttg aaacagtgat caagaaccaa ggtttggaca acttgaaagt tatcgaactt    660
ccaagcgacc aacaaccgta cgtttaccca cttcttgctc agggtcaaga tgagttgaaa    720
tcgtttgtag acaaacgcat caaagaactt tataaagatg gaactcttga aaaattgtct    780
aaacaattct tcggagacac ttatctaccg gcagaagctg atattaaaaa tggtatgaaa    840
gctaaaaaaa tgtggatggc aggcttggct ctgctaggta tcggaagcct tgctcttgct    900
acgaaaaaag ttgcagatga ccgtaagctc atgaagactc aggaagagtt gacagagatt    960
gtgcgagacc atttttccga catgggggaa attgcgaccc tttatgttca agtttacgaa   1020
agcagtctgg agagcttggt tggtggcgtc atttttgagg atggccgtca ttataccttt   1080
gtctatgaaa atgaagacct agtctatgag gaggaagtct taggaagcaa aactgctgat   1140
aagcctgctg attctggttc atctgaagtc aaagaactca ctgtatatgt agacgaggga   1200
tataagagct atattgaaga ggttgctaaa gcttatgaaa aagaagctgg agtaaaagtc   1260
actcttaaaa ctggtgatgc tctaggaggt cttgataaac tttctcttga caaccaatct   1320
ggtaatgtcc ctgatgttat gatggctcca tacgaccgtg taggtagcct tggttctgac   1380
ggacaacttt cagaagtgaa attgagcgat ggtgctaaaa cagacgacac aactaaatct   1440
cttgtaacag ctgctaatgg taaagtttac ggtgctcctg ccgttatcga gtcacttgtt   1500
atgtactaca acaaagactt ggtgaaagat gctccaaaaa catttgctga cttggaaaac   1560
cttgctaaag atagcaaata cgcattcgct ggtgaagatg gtaaaactac tgccttccta   1620
gctgactgga caaacttcta ctatacatat ggacttcttg ccggtaacgg tgcttacgtc   1680
tttggccaaa acggtaaaga cgctaaagac atcggtcttg caaacgacgg ttctatcgta   1740
ggtatcaact acgctaaatc ttggtacgaa aaatggccta aaggtatgca agatacagaa   1800
ggtgctggaa acttaatcca aactcaattc caagaaggta aaacagctgc tatcatcgac   1860
ggaccttgga aagctcaagc ctttaaagat gctaaagtaa actacggagt tgcaactatc   1920
ccaactcttc caaatggaaa agaatatgct gcattcggtg gtggtaaagc ttgggtcatt   1980
cctcaagccg ttaagaacct tgaagcttct caaaaatttg tagacttcct tgttgcaact   2040
gaacaacaaa aagtattata tgataagact aacgaaatcc cagctaatac tgaggctcgt   2100
tcatacgctg aaggtaaaaa cgatgagttg acaacagctg ttatcaaaca gttcaagaac   2160
```

| | | | |
|---|---|---|---|
| actcaaccac tgccaaacat ctctcaaatg tctgcagttt gggatccagc gaaaaatatg | | | 2220 |
| ctctttgatg ctgtaagtgg tcaaaaagat gctaaaacag ctgctaacga tgctgtaaca | | | 2280 |
| ttgatcaaag aaacaatcaa acaaaaattt ggtgaacacc accaccacca ccactga | | | 2337 |

<210> SEQ ID NO 62
<211> LENGTH: 2319
<212> TYPE: DNA
<213> ORGANISM: Artificial Sequence
<220> FEATURE:
<223> OTHER INFORMATION: Description of Artificial Sequence: Synthetic
      Streptococcus pneumonia fusion sequence
<220> FEATURE:
<223> OTHER INFORMATION: SP2108/SP0148/SP1912 fusion (nucleotides)

<400> SEQUENCE: 62

| | | | |
|---|---|---|---|
| atgtcatcta aatttatgaa gagcgctgcg gtgcttggaa ctgctacact tgctagcttg | | | 60 |
| cttttggtag cttgcggaag caaaactgct gataagcctg ctgattctgg ttcatctgaa | | | 120 |
| gtcaaagaac tcactgtata tgtagacgag ggatataaga gctatattga agaggttgct | | | 180 |
| aaagcttatg aaaaagaagc tggagtaaaa gtcactctta aaactggtga tgctctagga | | | 240 |
| ggtcttgata actttctctc tgacaaccaa tctggtaatg tccctgatgt tatgatggct | | | 300 |
| ccatcgaccc gtgtaggtag ccttggttct gacggacaac tttcagaagt gaaattgagc | | | 360 |
| gatggtgcta aaacagacga cacaactaaa tctcttgtaa cagctgctaa tggtaaagtt | | | 420 |
| tacggtgctc ctgccgttat cgagtcactt gttatgtact acaacaaaga cttggtgaaa | | | 480 |
| gatgctccaa aaacatttgc tgacttggaa aaccttgcta agatagcaa atacgcattc | | | 540 |
| gctggtgaag atggtaaaac tactgccttc ctagctgact ggacaaactt ctactataca | | | 600 |
| tatggacttc ttgccggtaa cggtgcttac gtctttggcc aaaacggtaa agacgctaaa | | | 660 |
| gacatcggtc ttgcaaacga cggttctatc gtaggtatca actacgctaa atcttggtac | | | 720 |
| gaaaaatggc ctaaaggtat gcaagataca gaaggtgctg gaaacttaat ccaaactcaa | | | 780 |
| ttccaagaag gtaaaacagc tgctatcatc gacggaccct tggaaagctca agcctttaaa | | | 840 |
| gatgctaaag taaactacgg agttgcaact atcccaactc ttccaaatgg aaaagaatat | | | 900 |
| gctgcattcg gtggtggtaa agcttgggtc attcctcaag ccgttaagaa ccttgaagct | | | 960 |
| tctcaaaaat ttgtagactt ccttgttgca actgaacaac aaaaagtatt atatgataag | | | 1020 |
| actaacgaaa tcccagctaa tactgaggct cgttcatacg ctgaaggtaa aaacgatgag | | | 1080 |
| ttgacaacag ctgttatcaa acagttcaag aacactcaac cactgccaaa catctctcaa | | | 1140 |
| atgtctgcag tttgggatcc agcgaaaaat atgctctttg atgctgtaag tggtcaaaaa | | | 1200 |
| gatgctaaaa cagctgctaa cgatgctgta acattgatca agaaacaat caaacaaaaa | | | 1260 |
| tttggtgaat caggggtgc taagaaagaa ggagaagcag ctagcaagaa agaaatcatc | | | 1320 |
| gttgcaacca atggatcacc aaagccattt atctatgaag aaaatggcga attgactggt | | | 1380 |
| tacgagattg aagtcgttcg cgctatcttt aaagattctg acaaatatga tgtcaagttt | | | 1440 |
| gaaaagacag aatggtcagg tgtctttgct ggtcttgacg ctgatcgtta caatatggct | | | 1500 |
| gtcaacaatc ttagctacac taaagaacgt gcggagaaat acctctatgc cgcaccaatt | | | 1560 |
| gcccaaaatc ctaatgtcct tgtcgtgaag aaagatgact ctagtatcaa gtctctcgat | | | 1620 |
| gatatcggtg aaatcgac ggaagtcgtt caagccacta catcagctaa gcagttagaa | | | 1680 |
| gcatacaatg ctgaacacac ggacaaccca actatcctta actatactaa ggcagacttc | | | 1740 |
| caacaaatca tggtacgttt gagcgatgga caatttgact ataagatttt tgataaaatc | | | 1800 |

| | |
|---|---:|
| ggtgttgaaa cagtgatcaa gaaccaaggt ttggacaact tgaaagttat cgaacttcca | 1860 |
| agcgaccaac aaccgtacgt ttacccactt cttgctcagg gtcaagatga gttgaaatcg | 1920 |
| tttgtagaca aacgcatcaa agaactttat aaagatggaa ctcttgaaaa attgtctaaa | 1980 |
| caattcttcg gagacactta tctaccggca gaagctgata ttaaaaatgg tatgaaagct | 2040 |
| aaaaaaatgt ggatggcagg cttggctctg ctaggtatcg gaagccttgc tcttgctacg | 2100 |
| aaaaaagttg cagatgaccg taagctcatg aagactcagg aagagttgac agagattgtg | 2160 |
| cgagaccatt tttccgacat gggggaaatt gcgacccttt atgttcaagt ttacgaaagc | 2220 |
| agtctggaga gcttggttgg tggcgtcatt tttgaggatg ccgtcatta tcctttgtc | 2280 |
| tatgaaaatg aagacctagt ctatgaggag gaagtctta | 2319 |

<210> SEQ ID NO 63
<211> LENGTH: 2316
<212> TYPE: DNA
<213> ORGANISM: Artificial Sequence
<220> FEATURE:
<223> OTHER INFORMATION: Description of Artificial Sequence: Synthetic
Streptococcus pneumonia fusion sequence
<220> FEATURE:
<223> OTHER INFORMATION: SP0148/SP2108/SP1912 fusion (nucleotides)

<400> SEQUENCE: 63

| | |
|---|---:|
| atgaaaaaaa tcgttaaata tcatctctct gcagcccttg ctcttgttgc tgcaggtgtg | 60 |
| cttgcggctt gctcaggggg tgctaagaaa gaaggagaag cagctagcaa gaaagaaatc | 120 |
| atcgttgcaa ccaatggatc accaaagcca tttatctatg aagaaaatgg cgaattgact | 180 |
| ggttacgaga ttgaagtcgt tcgcgctatc tttaaagatt ctgacaaata tgatgtcaag | 240 |
| tttgaaaaga cagaatggtc aggtgtcttt gctggtcttg acgctgatcg ttacaatatg | 300 |
| gctgtcaaca atcttagcta cactaaagaa cgtgcggaga atacctcta tgccgcacca | 360 |
| attgcccaaa atcctaatgt ccttgtcgtg aagaaagatg actctagtat caagtctctc | 420 |
| gatgatatcg gtggaaaatc gacggaagtc gttcaagcca ctacatcagc taagcagtta | 480 |
| gaagcataca atgctgaaca cacggacaac ccaactatcc ttaactatac taaggcagac | 540 |
| ttccaacaaa tcatggtacg tttgagcgat ggacaatttg actataagat ttttgataaa | 600 |
| atcggtgttg aaacagtgat caagaaccaa ggtttggaca acttgaaagt tatcgaactt | 660 |
| ccaagcgacc aacaaccgta cgtttaccca cttcttgctc agggtcaaga tgagttgaaa | 720 |
| tcgtttgtag acaaacgcat caaagaactt tataaagatg gaactcttga aaaattgtct | 780 |
| aaacaattct tcggagacac tatctaccg gcagaagctg atattaaagg aagcaaaact | 840 |
| gctgataagc ctgctgattc tggttcatct gaagtcaaag aactcactgt atatgtagac | 900 |
| gagggatata gagctatat tgaagaggtt gctaaagctt atgaaaaaga agctggagta | 960 |
| aaagtcactc ttaaaactgg tgatgctcta ggaggtcttg ataaactttc tcttgacaac | 1020 |
| caatctggta atgtccctga tgttatgatg gctccatacg accgtgtagg tagccttggt | 1080 |
| tctgacggac aactttcaga agtgaaattg agcgatggtc taaaacaga cgacacaact | 1140 |
| aaatctcttg taacagctgc taatggtaaa gttacggtg ctcctgccgt tatcgagtca | 1200 |
| cttgttatgt actacaacaa agacttggtg aaagatgctc aaaaacatt tgctgacttg | 1260 |
| gaaaaccttg ctaaagatag caaatacgca ttcgctggtg aagatggtaa aactactgcc | 1320 |
| ttcctagctg actggacaaa cttctactat acatatggac ttcttgccgg taacggtgct | 1380 |
| tacgtctttg gccaaaacgg taagacgct aaagacatcg gtcttgcaaa cgacggttct | 1440 |

```
atcgtaggta tcaactacgc taaatcttgg tacgaaaaat ggcctaaagg tatgcaagat   1500
acagaaggtg ctggaaactt aatccaaact caattccaag aaggtaaaac agctgctatc   1560
atcgacggac cttggaaagc tcaagccttt aaagatgcta agtaaactac ggagttgca    1620 actatcccaa ctcttccaaa tggaaaagaa tatgctgcat tcggtggtgg taaagcttgg   1680
gtcattcctc aagccgttaa gaaccttgaa gcttctcaaa aatttgtaga cttccttgtt   1740
gcaactgaac aacaaaaagt attatatgat aagactaacg aaatcccagc taatactgag   1800
gctcgttcat acgctgaagg taaaaacgat gagttgacaa cagctgttat caaacagttc   1860
aagaacactc aaccactgcc aaacatctct caaatgtctg cagtttggga tccagcgaaa   1920
aatatgctct ttgatgctgt aagtggtcaa aaagatgcta aacagctgc taacgatgct    1980 gtaacattga tcaaagaaac aatcaaacaa aaatttggtg aaaatggtat gaaagctaaa   2040
aaaatgtgga tggcaggctt ggctctgcta ggtatcggaa gccttgctct tgctacgaaa   2100
aaagttgcag atgaccgtaa gctcatgaag actcaggaag agttgacaga gattgtgcga   2160 gaccatttt ccgacatggg ggaaattgcg acccttatg ttcaagttta cgaaagcagt     2220
ctggagagct tggttggtgg cgtcattttt gaggatggcc gtcattatac ctttgtctat   2280
gaaaatgaag acctagtcta tgaggaggaa gtctta                             2316
```

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 64

His His His His His His
1               5

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      Histidine tag

<400> SEQUENCE: 65

Met Ser Tyr Tyr His His His His His His
1               5                   10

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      Canonical lipobox motif
<220> FEATURE:
<221> NAME/KEY: MOD_RES
<222> LOCATION: (1)..(1)
<223> OTHER INFORMATION: Leu, Ile, Val, Met, Phe, Glu, Ser, Thr, Ala,
      Gly, Pro or Cys
<220> FEATURE:
<221> NAME/KEY: MOD_RES
<222> LOCATION: (2)..(2)
<223> OTHER INFORMATION: Leu, Val, Ile, Ala, Met, Phe, Thr or Gly
<220> FEATURE:
<221> NAME/KEY: MOD_RES
<222> LOCATION: (3)..(3)
<223> OTHER INFORMATION: Ile, Val, Met, Ser, Thr, Ala, Gly, Cys or Pro

```
<220> FEATURE:
<221> NAME/KEY: MOD_RES
<222> LOCATION: (4)..(4)
<223> OTHER INFORMATION: Ala, Gly or Ser

<400> SEQUENCE: 66

Xaa Xaa Xaa Xaa Cys
1               5

<210> SEQ ID NO 67
<211> LENGTH: 25
<212> TYPE: PRT
<213> ORGANISM: Streptococcus pneumonia
<220> FEATURE:
<223> OTHER INFORMATION: SP2108 signal sequence

<400> SEQUENCE: 67

Met Ser Ser Lys Phe Met Lys Ser Ala Ala Val Leu Gly Thr Ala Thr
1               5                   10                  15

Leu Ala Ser Leu Leu Leu Val Ala Cys
            20                  25

<210> SEQ ID NO 68
<211> LENGTH: 19
<212> TYPE: PRT
<213> ORGANISM: Escherichia coli
<220> FEATURE:
<223> OTHER INFORMATION: RlpB signal sequence
<220> FEATURE:
<221> NAME/KEY: MOD_RES
<222> LOCATION: (19)..(19)
<223> OTHER INFORMATION: May or may not be present

<400> SEQUENCE: 68

Met Arg Tyr Leu Ala Thr Leu Leu Leu Ser Leu Ala Val Leu Ile Thr
1               5                   10                  15

Ala Gly Cys

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      Fusion protein linker sequence (19-mer)

<400> SEQUENCE: 69

Leu Gly Gly Gly Gly Ser Gly Gly Gly Ser Gly Gly Gly Gly Ser
1               5                   10                  15

Ala Ala Ala

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      Fusion protein LR linker sequence (20-mer)

<400> SEQUENCE: 70

Leu Ala Glu Ala Thr Ala Lys Glu Ala Thr Ala Lys Glu Ala Thr Ala
1               5                   10                  15

Lys Ala Thr Ala
            20
```

```
<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      Fusion protein LC linker sequence (14-mer)

<400> SEQUENCE: 71

Gly Pro Lys Pro His Arg Ile Gln Ser Thr Pro Lys Gly Ser
1               5                   10

<210> SEQ ID NO 72
<211> LENGTH: 8
<212> TYPE: PRT
<213> ORGANISM: Streptococcus pneumonia
<220> FEATURE:
<223> OTHER INFORMATION: Amino-terminal boundary to the PR-region

<400> SEQUENCE: 72

Asp Leu Lys Lys Ala Val Asn Glu
1               5

<210> SEQ ID NO 73
<211> LENGTH: 11
<212> TYPE: PRT
<213> ORGANISM: Streptococcus pneumonia
<220> FEATURE:
<223> OTHER INFORMATION: Carboxy-terminal boundary to the PR-region
<220> FEATURE:
<221> NAME/KEY: MOD_RES
<222> LOCATION: (1)..(1)
<223> OTHER INFORMATION: Lys or Gly
<220> FEATURE:
<221> NAME/KEY: MOD_RES
<222> LOCATION: (5)..(5)
<223> OTHER INFORMATION: Lys or Gly

<400> SEQUENCE: 73

Xaa Thr Gly Trp Xaa Gln Glu Asn Gly Met Trp
1               5                   10

<210> SEQ ID NO 74
<211> LENGTH: 9
<212> TYPE: PRT
<213> ORGANISM: Streptococcus pneumonia

<400> SEQUENCE: 74

Ala Leu Gly Leu Val Ala Ala Gly Val
1               5

<210> SEQ ID NO 75
<211> LENGTH: 9
<212> TYPE: PRT
<213> ORGANISM: Streptococcus pneumonia

<400> SEQUENCE: 75

Glu Leu Thr Gly Tyr Glu Ile Glu Val
1               5

<210> SEQ ID NO 76
<211> LENGTH: 9
<212> TYPE: PRT
<213> ORGANISM: Streptococcus pneumonia

<400> SEQUENCE: 76

Ala Val Asn Asn Leu Ser Tyr Thr Lys
1               5
```

<210> SEQ ID NO 77
<211> LENGTH: 9
<212> TYPE: PRT
<213> ORGANISM: Streptococcus pneumonia

<400> SEQUENCE: 77

Thr Tyr Leu Pro Ala Glu Ala Asp Ile
1               5

<210> SEQ ID NO 78
<211> LENGTH: 9
<212> TYPE: PRT
<213> ORGANISM: Streptococcus pneumonia

<400> SEQUENCE: 78

Arg Tyr Asn Met Ala Val Asn Asn Leu
1               5

<210> SEQ ID NO 79
<211> LENGTH: 9
<212> TYPE: PRT
<213> ORGANISM: Streptococcus pneumonia

<400> SEQUENCE: 79

Asp Phe Gln Gln Ile Met Val Arg Leu
1               5

<210> SEQ ID NO 80
<211> LENGTH: 9
<212> TYPE: PRT
<213> ORGANISM: Streptococcus pneumonia

<400> SEQUENCE: 80

Glu His Thr Asp Asn Pro Thr Ile Leu
1               5

<210> SEQ ID NO 81
<211> LENGTH: 9
<212> TYPE: PRT
<213> ORGANISM: Streptococcus pneumonia

<400> SEQUENCE: 81

Ala Pro Ile Ala Gln Asn Pro Asn Val
1               5

<210> SEQ ID NO 82
<211> LENGTH: 9
<212> TYPE: PRT
<213> ORGANISM: Streptococcus pneumonia

<400> SEQUENCE: 82

Leu Pro Ser Asp Gln Gln Pro Tyr Val
1               5

<210> SEQ ID NO 83
<211> LENGTH: 9
<212> TYPE: PRT
<213> ORGANISM: Streptococcus pneumonia

<400> SEQUENCE: 83

Tyr Val Tyr Pro Leu Leu Ala Gln Gly
1               5

<210> SEQ ID NO 84
<211> LENGTH: 9
<212> TYPE: PRT
<213> ORGANISM: Streptococcus pneumonia

<400> SEQUENCE: 84

Gln Gly Leu Asp Asn Leu Lys Val Ile
1               5

<210> SEQ ID NO 85
<211> LENGTH: 8
<212> TYPE: PRT
<213> ORGANISM: Streptococcus pneumonia

<400> SEQUENCE: 85

Lys Tyr Leu Tyr Ala Ala Pro Ile
1               5

<210> SEQ ID NO 86
<211> LENGTH: 8
<212> TYPE: PRT
<213> ORGANISM: Streptococcus pneumonia

<400> SEQUENCE: 86

Gly Glu Leu Thr Gly Tyr Glu Ile
1               5

<210> SEQ ID NO 87
<211> LENGTH: 9
<212> TYPE: PRT
<213> ORGANISM: Streptococcus pneumonia

<400> SEQUENCE: 87

Asn Pro Asn Val Leu Val Val Lys Lys
1               5

<210> SEQ ID NO 88
<211> LENGTH: 9
<212> TYPE: PRT
<213> ORGANISM: Streptococcus pneumonia

<400> SEQUENCE: 88

Lys Leu Ser Lys Gln Phe Phe Gly Asp
1               5

<210> SEQ ID NO 89
<211> LENGTH: 9
<212> TYPE: PRT
<213> ORGANISM: Streptococcus pneumonia

<400> SEQUENCE: 89

Gly Ser Pro Arg Pro Phe Ile Tyr Glu
1               5

<210> SEQ ID NO 90
<211> LENGTH: 9
<212> TYPE: PRT
<213> ORGANISM: Streptococcus pneumonia

<400> SEQUENCE: 90

Ala Val Asn Asn Leu Ser Tyr Thr Lys
1               5

<210> SEQ ID NO 91
<211> LENGTH: 9

```
<212> TYPE: PRT
<213> ORGANISM: Streptococcus pneumonia

<400> SEQUENCE: 91

Lys Ile Phe Asp Lys Ile Gly Val Glu
1               5

<210> SEQ ID NO 92
<211> LENGTH: 9
<212> TYPE: PRT
<213> ORGANISM: Streptococcus pneumonia

<400> SEQUENCE: 92

Met Val Arg Leu Ser Asp Gly Gln Phe
1               5

<210> SEQ ID NO 93
<211> LENGTH: 9
<212> TYPE: PRT
<213> ORGANISM: Streptococcus pneumonia

<400> SEQUENCE: 93

Tyr Val Tyr Pro Leu Leu Ala Gln Gly
1               5

<210> SEQ ID NO 94
<211> LENGTH: 9
<212> TYPE: PRT
<213> ORGANISM: Streptococcus pneumonia

<400> SEQUENCE: 94

Val Val Gln Ala Thr Thr Ser Ala Lys
1               5

<210> SEQ ID NO 95
<211> LENGTH: 9
<212> TYPE: PRT
<213> ORGANISM: Streptococcus pneumonia

<400> SEQUENCE: 95

Thr Leu Glu Lys Leu Ser Lys Gln Phe
1               5

<210> SEQ ID NO 96
<211> LENGTH: 9
<212> TYPE: PRT
<213> ORGANISM: Streptococcus pneumonia

<400> SEQUENCE: 96

Val Ala Ala Gly Val Leu Ala Ala Cys
1               5

<210> SEQ ID NO 97
<211> LENGTH: 9
<212> TYPE: PRT
<213> ORGANISM: Streptococcus pneumonia

<400> SEQUENCE: 97

Leu Asp Asn Leu Lys Val Ile Glu Leu
1               5

<210> SEQ ID NO 98
<211> LENGTH: 9
<212> TYPE: PRT
<213> ORGANISM: Streptococcus pneumonia
```

<400> SEQUENCE: 98

Asn Met Ala Val Asn Asn Leu Ser Tyr
1               5

<210> SEQ ID NO 99
<211> LENGTH: 9
<212> TYPE: PRT
<213> ORGANISM: Streptococcus pneumonia

<400> SEQUENCE: 99

Ala Ile Ile Asp Gly Pro Trp Lys Ala
1               5

<210> SEQ ID NO 100
<211> LENGTH: 9
<212> TYPE: PRT
<213> ORGANISM: Streptococcus pneumonia

<400> SEQUENCE: 100

Val Met Met Ala Pro Tyr Asp Arg Val
1               5

<210> SEQ ID NO 101
<211> LENGTH: 9
<212> TYPE: PRT
<213> ORGANISM: Streptococcus pneumonia

<400> SEQUENCE: 101

Ser Ile Ala Gly Ile Asn Tyr Ala Lys
1               5

<210> SEQ ID NO 102
<211> LENGTH: 9
<212> TYPE: PRT
<213> ORGANISM: Streptococcus pneumonia

<400> SEQUENCE: 102

Val Trp Asp Pro Ala Lys Asn Met Leu
1               5

<210> SEQ ID NO 103
<211> LENGTH: 9
<212> TYPE: PRT
<213> ORGANISM: Streptococcus pneumonia

<400> SEQUENCE: 103

Gln Pro Leu Pro Asn Ile Ser Gln Met
1               5

<210> SEQ ID NO 104
<211> LENGTH: 9
<212> TYPE: PRT
<213> ORGANISM: Streptococcus pneumonia

<400> SEQUENCE: 104

Ala Pro Tyr Asp Arg Val Gly Ser Leu
1               5

<210> SEQ ID NO 105
<211> LENGTH: 9
<212> TYPE: PRT
<213> ORGANISM: Streptococcus pneumonia

<400> SEQUENCE: 105

```
Ala Pro Ala Val Ile Glu Ser Leu Val
1               5

<210> SEQ ID NO 106
<211> LENGTH: 9
<212> TYPE: PRT
<213> ORGANISM: Streptococcus pneumonia

<400> SEQUENCE: 106

Phe Tyr Tyr Thr Tyr Gly Leu Leu Ala
1               5

<210> SEQ ID NO 107
<211> LENGTH: 8
<212> TYPE: PRT
<213> ORGANISM: Streptococcus pneumonia

<400> SEQUENCE: 107

Ser Lys Tyr Ala Phe Ala Gly Glu
1               5

<210> SEQ ID NO 108
<211> LENGTH: 8
<212> TYPE: PRT
<213> ORGANISM: Streptococcus pneumonia

<400> SEQUENCE: 108

Thr Glu Gly Ala Gly Asn Leu Ile
1               5

<210> SEQ ID NO 109
<211> LENGTH: 9
<212> TYPE: PRT
<213> ORGANISM: Streptococcus pneumonia

<400> SEQUENCE: 109

Leu Ala Asp Trp Thr Asn Phe Tyr Tyr
1               5

<210> SEQ ID NO 110
<211> LENGTH: 9
<212> TYPE: PRT
<213> ORGANISM: Streptococcus pneumonia

<400> SEQUENCE: 110

Ser Leu Val Met Tyr Tyr Asn Lys Asp
1               5

<210> SEQ ID NO 111
<211> LENGTH: 9
<212> TYPE: PRT
<213> ORGANISM: Streptococcus pneumonia

<400> SEQUENCE: 111

Lys Glu Ala Gly Val Lys Val Thr Leu
1               5

<210> SEQ ID NO 112
<211> LENGTH: 9
<212> TYPE: PRT
<213> ORGANISM: Streptococcus pneumonia

<400> SEQUENCE: 112

Lys Ser Thr Ala Val Leu Gly Thr Val
```

```
<210> SEQ ID NO 113
<211> LENGTH: 9
<212> TYPE: PRT
<213> ORGANISM: Streptococcus pneumonia

<400> SEQUENCE: 113

Gly Ala Lys Thr Asp Asp Thr Thr Lys
1               5

<210> SEQ ID NO 114
<211> LENGTH: 9
<212> TYPE: PRT
<213> ORGANISM: Streptococcus pneumonia

<400> SEQUENCE: 114

Ser Gln Lys Phe Val Asp Phe Leu Val
1               5

<210> SEQ ID NO 115
<211> LENGTH: 9
<212> TYPE: PRT
<213> ORGANISM: Streptococcus pneumonia

<400> SEQUENCE: 115

Gln Ala Phe Lys Asp Ala Lys Val Asn
1               5

<210> SEQ ID NO 116
<211> LENGTH: 9
<212> TYPE: PRT
<213> ORGANISM: Streptococcus pneumonia

<400> SEQUENCE: 116

Ala Val Ile Glu Ser Leu Val Met Tyr
1               5

<210> SEQ ID NO 117
<211> LENGTH: 9
<212> TYPE: PRT
<213> ORGANISM: Streptococcus pneumonia

<400> SEQUENCE: 117

Asp Ala Lys Thr Ala Ala Asn Asp Ala
1               5

<210> SEQ ID NO 118
<211> LENGTH: 9
<212> TYPE: PRT
<213> ORGANISM: Streptococcus pneumonia

<400> SEQUENCE: 118

Tyr Gly Val Ala Thr Ile Pro Thr Leu
1               5

<210> SEQ ID NO 119
<211> LENGTH: 9
<212> TYPE: PRT
<213> ORGANISM: Streptococcus pneumonia

<400> SEQUENCE: 119

Lys Thr Ala Ala Ile Ile Asp Gly Pro
1               5
```

<210> SEQ ID NO 120
<211> LENGTH: 9
<212> TYPE: PRT
<213> ORGANISM: Streptococcus pneumonia

<400> SEQUENCE: 120

Lys Ala Tyr Glu Lys Glu Ala Gly Val
1               5

<210> SEQ ID NO 121
<211> LENGTH: 9
<212> TYPE: PRT
<213> ORGANISM: Streptococcus pneumonia

<400> SEQUENCE: 121

Ala Gly Asn Gly Ala Tyr Val Phe Gly
1               5

<210> SEQ ID NO 122
<211> LENGTH: 9
<212> TYPE: PRT
<213> ORGANISM: Streptococcus pneumonia

<400> SEQUENCE: 122

Ala Trp Val Ile Pro Gln Ala Val Lys
1               5

<210> SEQ ID NO 123
<211> LENGTH: 15
<212> TYPE: PRT
<213> ORGANISM: Streptococcus pneumonia

<400> SEQUENCE: 123

Lys Met Trp Met Ala Gly Leu Ala Leu Leu Gly Ile Gly Ser Leu
1               5                   10                  15

<210> SEQ ID NO 124
<211> LENGTH: 15
<212> TYPE: PRT
<213> ORGANISM: Streptococcus pneumonia

<400> SEQUENCE: 124

Leu Leu Gly Ile Gly Ser Leu Ala Leu Ala Thr Lys Lys Val Ala
1               5                   10                  15

<210> SEQ ID NO 125
<211> LENGTH: 15
<212> TYPE: PRT
<213> ORGANISM: Streptococcus pneumonia

<400> SEQUENCE: 125

Met Ala Gly Leu Ala Leu Leu Gly Ile Gly Ser Leu Ala Leu Ala
1               5                   10                  15

<210> SEQ ID NO 126
<211> LENGTH: 15
<212> TYPE: PRT
<213> ORGANISM: Streptococcus pneumonia

<400> SEQUENCE: 126

Trp Met Ala Gly Leu Ala Leu Leu Gly Ile Gly Ser Leu Ala Leu
1               5                   10                  15

<210> SEQ ID NO 127

```
<211> LENGTH: 15
<212> TYPE: PRT
<213> ORGANISM: Streptococcus pneumonia

<400> SEQUENCE: 127

Gly Leu Ala Leu Leu Gly Ile Gly Ser Leu Ala Leu Ala Thr Lys
1               5                   10                  15

<210> SEQ ID NO 128
<211> LENGTH: 15
<212> TYPE: PRT
<213> ORGANISM: Streptococcus pneumonia

<400> SEQUENCE: 128

Leu Ala Leu Leu Gly Ile Gly Ser Leu Ala Leu Ala Thr Lys Lys
1               5                   10                  15

<210> SEQ ID NO 129
<211> LENGTH: 15
<212> TYPE: PRT
<213> ORGANISM: Streptococcus pneumonia

<400> SEQUENCE: 129

Phe Ser Asp Met Gly Glu Ile Ala Thr Leu Tyr Val Gln Val Tyr
1               5                   10                  15

<210> SEQ ID NO 130
<211> LENGTH: 15
<212> TYPE: PRT
<213> ORGANISM: Streptococcus pneumonia

<400> SEQUENCE: 130

Lys Ala Lys Lys Met Trp Met Ala Gly Leu Ala Leu Leu Gly Ile
1               5                   10                  15

<210> SEQ ID NO 131
<211> LENGTH: 30
<212> TYPE: PRT
<213> ORGANISM: Streptococcus pneumonia

<400> SEQUENCE: 131

Ala Leu Leu Gly Ile Gly Ser Leu Ala Leu Ala Thr Lys Lys Val Ala
1               5                   10                  15

Lys Lys Met Trp Met Ala Gly Leu Ala Leu Leu Gly Ile Gly
            20                  25                  30

<210> SEQ ID NO 132
<211> LENGTH: 15
<212> TYPE: PRT
<213> ORGANISM: Streptococcus pneumonia

<400> SEQUENCE: 132

Ser Asp Met Gly Glu Ile Ala Thr Leu Tyr Val Gln Val Tyr Glu
1               5                   10                  15

<210> SEQ ID NO 133
<211> LENGTH: 15
<212> TYPE: PRT
<213> ORGANISM: Streptococcus pneumonia

<400> SEQUENCE: 133

Asp Met Gly Glu Ile Ala Thr Leu Tyr Val Gln Val Tyr Glu Ser
1               5                   10                  15
```

<210> SEQ ID NO 134
<211> LENGTH: 15
<212> TYPE: PRT
<213> ORGANISM: Streptococcus pneumonia

<400> SEQUENCE: 134

Ala Gly Leu Ala Leu Leu Gly Ile Gly Ser Leu Ala Leu Ala Thr
1               5                   10                  15

<210> SEQ ID NO 135
<211> LENGTH: 15
<212> TYPE: PRT
<213> ORGANISM: Streptococcus pneumonia

<400> SEQUENCE: 135

Met Gly Glu Ile Ala Thr Leu Tyr Val Gln Val Tyr Glu Ser Ser
1               5                   10                  15

<210> SEQ ID NO 136
<211> LENGTH: 15
<212> TYPE: PRT
<213> ORGANISM: Streptococcus pneumonia

<400> SEQUENCE: 136

Lys Lys Met Trp Met Ala Gly Leu Ala Leu Leu Gly Ile Gly Ser
1               5                   10                  15

<210> SEQ ID NO 137
<211> LENGTH: 15
<212> TYPE: PRT
<213> ORGANISM: Streptococcus pneumonia

<400> SEQUENCE: 137

Gly Met Lys Ala Lys Lys Met Trp Met Ala Gly Leu Ala Leu Leu
1               5                   10                  15

<210> SEQ ID NO 138
<211> LENGTH: 15
<212> TYPE: PRT
<213> ORGANISM: Streptococcus pneumonia

<400> SEQUENCE: 138

Met Lys Ala Lys Lys Met Trp Met Ala Gly Leu Ala Leu Leu Gly
1               5                   10                  15

<210> SEQ ID NO 139
<211> LENGTH: 15
<212> TYPE: PRT
<213> ORGANISM: Streptococcus pneumonia

<400> SEQUENCE: 139

His Phe Ser Asp Met Gly Glu Ile Ala Thr Leu Tyr Val Gln Val
1               5                   10                  15

<210> SEQ ID NO 140
<211> LENGTH: 15
<212> TYPE: PRT
<213> ORGANISM: Streptococcus pneumonia

<400> SEQUENCE: 140

Met Asn Gly Met Lys Ala Lys Lys Met Trp Met Ala Gly Leu Ala
1               5                   10                  15

<210> SEQ ID NO 141
<211> LENGTH: 15

```
<212> TYPE: PRT
<213> ORGANISM: Streptococcus pneumonia

<400> SEQUENCE: 141

Met Trp Met Ala Gly Leu Ala Leu Leu Gly Ile Gly Ser Leu Ala
1               5                   10                  15

<210> SEQ ID NO 142
<211> LENGTH: 15
<212> TYPE: PRT
<213> ORGANISM: Streptococcus pneumonia

<400> SEQUENCE: 142

Asp His Phe Ser Asp Met Gly Glu Ile Ala Thr Leu Tyr Val Gln
1               5                   10                  15

<210> SEQ ID NO 143
<211> LENGTH: 15
<212> TYPE: PRT
<213> ORGANISM: Streptococcus pneumonia

<400> SEQUENCE: 143

Arg Asp His Phe Ser Asp Met Gly Glu Ile Ala Thr Leu Tyr Val
1               5                   10                  15

<210> SEQ ID NO 144
<211> LENGTH: 15
<212> TYPE: PRT
<213> ORGANISM: Streptococcus pneumonia

<400> SEQUENCE: 144

Asn Gly Met Lys Ala Lys Lys Met Trp Met Ala Gly Leu Ala Leu
1               5                   10                  15
```

// FUSED ANTIGEN VACCINES AND COMPOSITIONS AGAINST *STREPTOCOCCUS PNEUMONIAE*

CROSS REFERENCE TO RELATED APPLICATIONS

The present application is the National Stage of International Application PCT/US2013/022309, filed Jan. 18, 2013, which claims the benefit of U.S. provisional application Ser. No. 61/589,267, filed on Jan. 20, 2012, the contents of both of which are herein incorporated by reference in their entirety.

GOVERNMENT SUPPORT

This work was made with Government support under Grant AI066013 awarded by the National Institutes of Health. Therefore, the U.S. Government has certain rights in this invention.

REFERENCE TO SEQUENCE LISTING

The specification includes a Sequence Listing in the form of an ASCII compliant text file named "Sequence_Listing", which was created on Mar. 11, 2013, and has a size of 227 kilobytes. The content of the aforementioned "Sequence_Listing" file is hereby incorporated by reference in its entirety.

I. BACKGROUND

Pneumococcal disease continues to be a leading cause of sickness and death in the United States and throughout the world. Each year, millions of cases of pneumonia, meningitis, bacteremia, and otitis media are attributed to infection with the pathogen *Streptococcus pneumoniae*. *S. pneumoniae* is a Gram-positive encapsulated coccus that colonizes the nasopharynx in about 5-10% of healthy adults and 20-40% of healthy children. Normal colonization becomes pathogenic when *S. pneumoniae* is carried into the Eustachian tubes, nasal sinuses, lungs, bloodstream, meninges, joint spaces, bones or peritoneal cavity. *S. pneumoniae* has several virulence factors that enable the organism to evade the immune system. Examples include a polysaccharide capsule that prevents phagocytosis by host immune cells, proteases that inhibit complement-mediated opsonization, and proteins that cause lysis of host cells. In the polysaccharide capsule, the presence of complex polysaccharides forms the basis for classifying pneumococci into different serotypes. To date, over 93 serotypes of *S. pneumoniae* have been identified.

Various pharmaceutical compositions have been used to harness an immune response against infection by *S. pneumoniae*. A polyvalent pneumococcal vaccine, PPV-23, was developed for preventing pneumonia and other invasive diseases due to *S. pneumoniae* in the adult and aging populations. The vaccine contains capsular polysaccharides (CPs) from 23 serotypes of *S. pneumoniae*. As T independent antigens, these CPs induce only short-lived antibody responses, necessitating repeated doses, which increases the risk of immunological tolerance. The antibodies raised against the *S. pneumoniae* capsular polysaccharides, termed anticapsular antibodies, are recognized as protective in adult and immunocompetent individuals. However, children under 2 years of age and immunocompromised individuals, including the elderly, do not respond well to T independent antigens and, therefore, are not afforded optimal protection by PPV-23. Another *S. pneumoniae* vaccine, PREVNAR, includes bacterial polysaccharides from 7 *S. pneumoniae* serovars conjugated to the diphtheria toxoid protein. This vaccine induces both B and T cell responses. However, because it only protects against 7 pneumococcal serotypes, serotype replacement can render PREVNAR ineffective against non-vaccine serotypes. Serotype replacement has already been demonstrated in several clinical trials and epidemiologic studies, necessitating development of different formulations of these vaccines. An example is the recently introduced PREVNAR 13®, directed to 13 pneumococcal serotypes. Furthermore, the two PREVNAR formulations are expensive to manufacture, greatly limiting their availability in the developing world. PPV-23, which consists of 23 purified but unconjugated polysaccharides, has broader coverage, but does not provide protection to children under the age of 2 years, a population which is at the highest risk for pneumococcal disease.

Thus, there remains a need to design more effective pharmaceutical compositions than the current strategies offer. In particular, such compositions need to incorporate novel or specific antigens that elicit an immune response against *S. pneumoniae*.

II. SUMMARY

*Streptococcus pneumoniae* is a major health concern, especially in very young, elderly, or immunocompromised patients. While DNA and protein sequence information for *S. pneumoniae* have been known for some time, and researchers have long attempted to produce vaccines against *S. pneumoniae*, a major problem was how to elicit an immune response that is both long-lived and effective in all age groups. Certain of the *S. pneumoniae* antigens used in the instant application were initially identified by screening immune cells from mice either immunized with unencapsulated killed whole *S. pneumoniae* or infected with live *S. pneumoniae*, or from healthy human donors for T cell specific immune responses. Accordingly, the present disclosure provides, inter alia, certain highly effective vaccines against *Streptococcus pneumoniae*. The vaccines may be used therapeutically or prophylactically. The present disclosure also provides specific antigens and methods for using the antigens to elicit an immune response against *S. pneumoniae*.

In some embodiments, two, three, four, or more polypeptides from Table 1 or immunogenic fragments or variants thereof are covalently bound to each other, e.g. as a fusion protein.

In some embodiments, the vaccine formulation comprises or consists of one or more fusion proteins comprising (or consisting of) one or all or fragments of SP0148, SP2108 and SP1912 or variants thereof, such as those shown in Table 2.

In certain aspects, the present disclosure provides a vaccine formulation comprising or consisting of a pharmaceutically acceptable carrier and a fusion protein comprising or consisting of two or more immunogenic polypeptides, wherein the immunogenic polypeptides have an amino acid sequence at least 70, 80 or 90% homologous to SEQ ID NO: 6, SEQ ID NO: 2 or SEQ ID NO: 9, or an immunogenic fragment thereof.

In certain embodiments, the present disclosure provides fusion proteins comprising or consisting of a first immunogenic polypeptide having an amino acid sequence at least 90% homologous to the amino acid sequence of SEQ ID NO: 6, or an immunogenic fragment thereof and a second immunogenic polypeptide having an amino acid sequence at least 90% homologous to the amino acid sequence of SEQ ID NO: 9, or an immunogenic fragment thereof. In some embodiments, the first immunogenic polypeptide consists of or comprises the amino acid sequence of SEQ ID NO: 6, or an immunogenic fragment thereof, and the second immunogenic polypeptide consists of or comprises the amino acid sequence of SEQ ID NO: 9, or an immunogenic fragment thereof. In some embodiments, the first immunogenic polypeptide is located at the amino terminus of the fusion protein and the second immunogenic polypeptide is located at the carboxyl terminus of the fusion protein.

In some embodiments, the fusion protein further comprises or consists of a third immunogenic polypeptide having an amino acid sequence at least 90% homologous to the amino acid sequence of SEQ ID NO: 2, or an immunogenic fragment thereof. In some embodiments, the third immunogenic polypeptide consists of or comprises SEQ ID NO: 2, or an immunogenic fragment thereof. In some embodiments, the third immunogenic polypeptide is located at the amino terminus of the fusion protein and the first immunogenic polypeptide is located at the carboxyl terminus of the fusion protein. In some embodiments, the first immunogenic polypeptide is located at the amino terminus of the fusion protein and the second immunogenic polypeptide is located at the carboxyl terminus of the fusion protein. In some embodiments, the third immunogenic polypeptide is located at the amino terminus of the fusion protein and the second immunogenic polypeptide is located at the carboxyl terminus of the fusion protein. In some embodiments, the first immunogenic polypeptide is located at the amino terminus of the fusion protein and the third immunogenic polypeptide is located at the carboxyl terminus of the fusion protein.

In certain embodiments, the present disclosure provides fusion proteins comprising or consisting of a first immunogenic polypeptide having an amino acid sequence at least 90% homologous to the amino acid sequence of SEQ ID NO: 2, or an immunogenic fragment thereof and a second immunogenic polypeptide having an amino acid sequence at least 90% homologous to the amino acid sequence of SEQ ID NO: 9, or an immunogenic fragment thereof. In some embodiments, the first immunogenic polypeptide consists of or comprises the amino acid sequence of SEQ ID NO: 2, or an immunogenic fragment thereof, and the second immunogenic polypeptide consists of or comprises the amino acid sequence of SEQ ID NO: 9, or an immunogenic fragment thereof. In some embodiments, the first immunogenic polypeptide is located at the amino terminus of the fusion protein and the second immunogenic polypeptide is located at the carboxyl terminus of the fusion protein.

In further embodiments, the present disclosure provides fusion proteins comprising or consisting of a first immunogenic polypeptide having an amino acid sequence at least 90% homologous to the amino acid sequence of SEQ ID NO: 2, or an immunogenic fragment thereof and a second immunogenic polypeptide having an amino acid sequence at least 90% homologous to the amino acid sequence of SEQ ID NO: 6, or an immunogenic fragment thereof. In some embodiments, the first immunogenic polypeptide consists of or comprises the amino acid sequence of SEQ ID NO: 2, or an immunogenic fragment thereof, and the second immunogenic polypeptide consists of or comprises the amino acid sequence of SEQ ID NO: 6, or an immunogenic fragment thereof. In some embodiments, the first immunogenic polypeptide is located at the amino terminus of the fusion protein and the second immunogenic polypeptide is located at the carboxyl terminus of the fusion protein. In some embodiments, the second immunogenic polypeptide is located at the amino terminus of the fusion protein and the first immunogenic polypeptide is located at the carboxyl terminus of the fusion protein.

In some embodiments, the present disclosure provides vaccine formulations comprising or consisting of one or more fusion proteins described herein and a pharmaceutically acceptable carrier.

In further embodiments, the present disclosure provides methods of treating a subject suffering from or susceptible to *S. pneumoniae* infection, comprising administering to the subject an effective amount of a vaccine formulation described herein.

III. BRIEF DESCRIPTION OF THE DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

FIG. 1 shows the concentration of IL-17A generated by blood samples from mice that were immunized with the indicated protein(s) and cholera toxin adjuvant, then stimulated with killed, unencapsulated whole cell *S. pneumoniae*, as described in Example 1. The left panel shows the data in scatter format, and the right panel shows the average and standard deviation for each sample Immunization group "All 3" represents animals immunized with a combination of SP2108, SP0148, and SP1634.

FIG. 15 shows the percent of animals protected from sepsis in six separate aspiration challenge studies, two of which are described in more detail in Examples 6 and 12.

FIGS. 19A and 19B show the mean IL-17A response generated by blood samples from mice immunized at the indicated doses with the indicated proteins and alum, or with alum alone. Blood samples were stimulated with overlapping peptides (OLP) or killed unencapsulated whole cell *S. pneumoniae* (WCA), as indicated at upper left and described in Example 16.

Figure 22A:
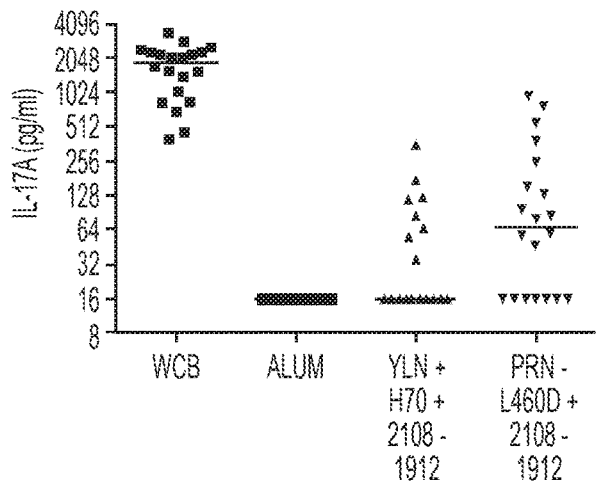
Figure 22A:
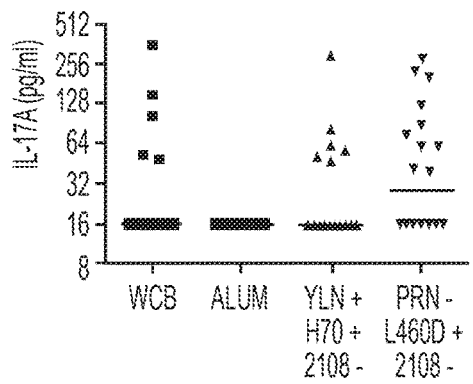
Figure 22A:
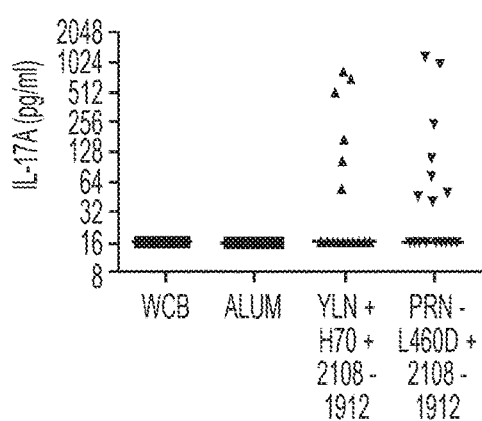
Figure 22B:
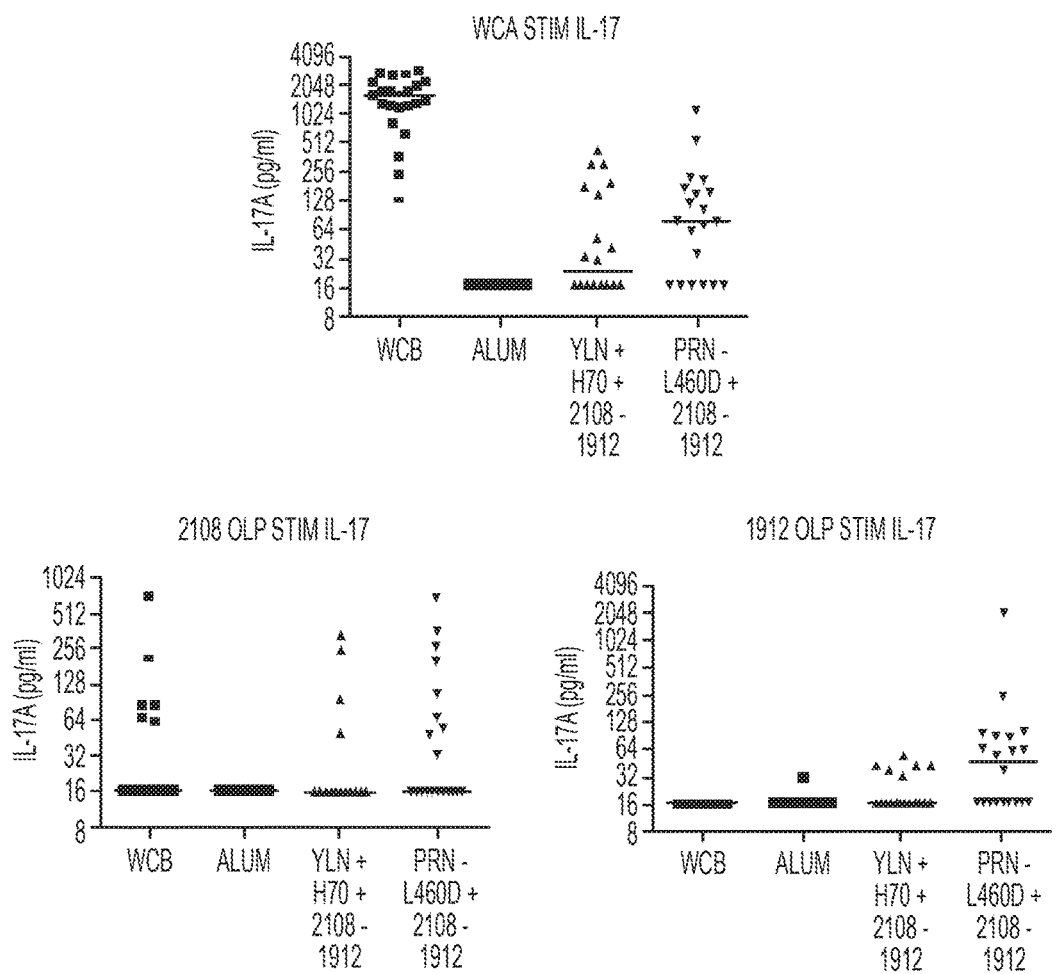

FIGS. 22A and 22B show the concentration of IL-17A generated by blood samples from mice immunized with the indicated combinations of proteins and alum, killed unencapsulated whole cell *S. pneumoniae* and alum (WCB), or alum alone. Blood samples were stimulated with overlapping peptides (OLP) or killed unencapsulated whole cell *S. pneumoniae* (WCA), as indicated above each graph and described in Example 20.

Figure 23A:
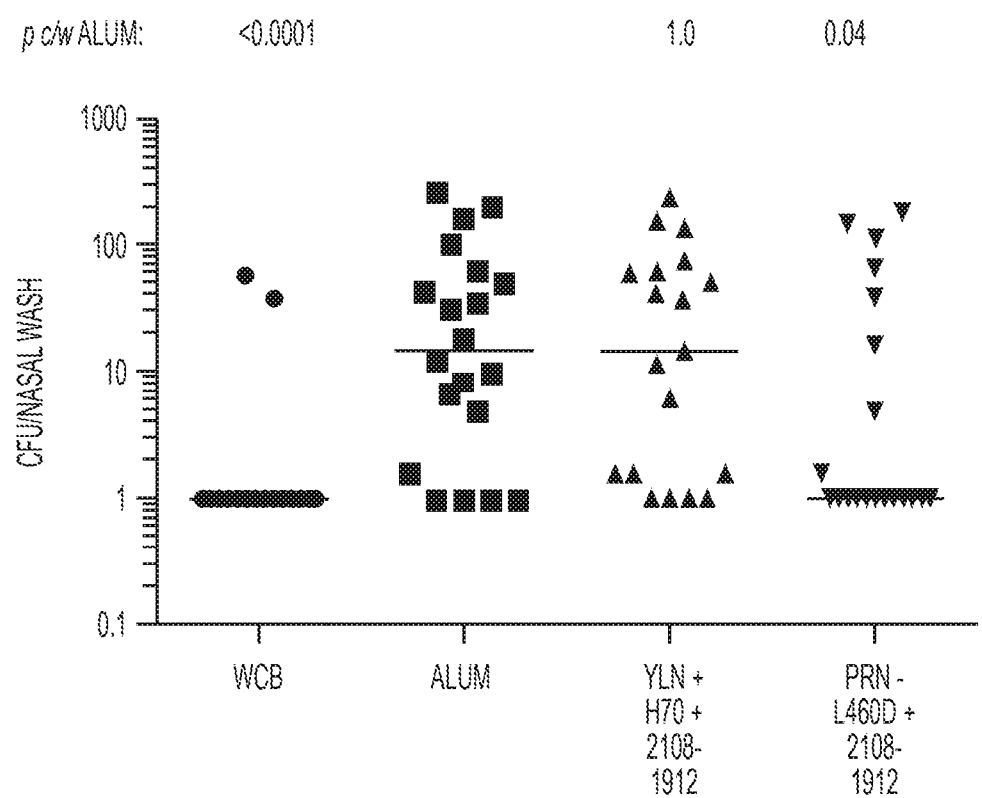
Figure 23B:
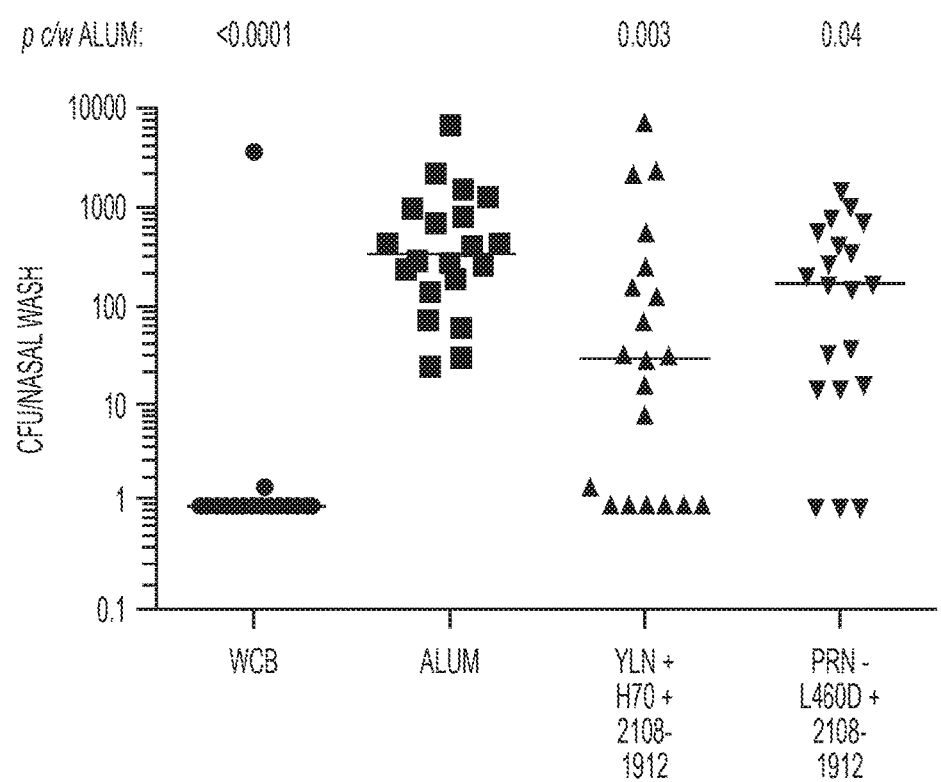

FIGS. 23A and 23B show the number of *S. pneumoniae* colonies (CFU) obtained from nasal washes of mice immunized with the indicated combinations of proteins and alum, killed unencapsulated whole cell *S. pneumoniae* and alum (WCB), or alum alone, then challenged by intranasal administration of *S. pneumoniae*, as described in Example 21.

Figure 24A:
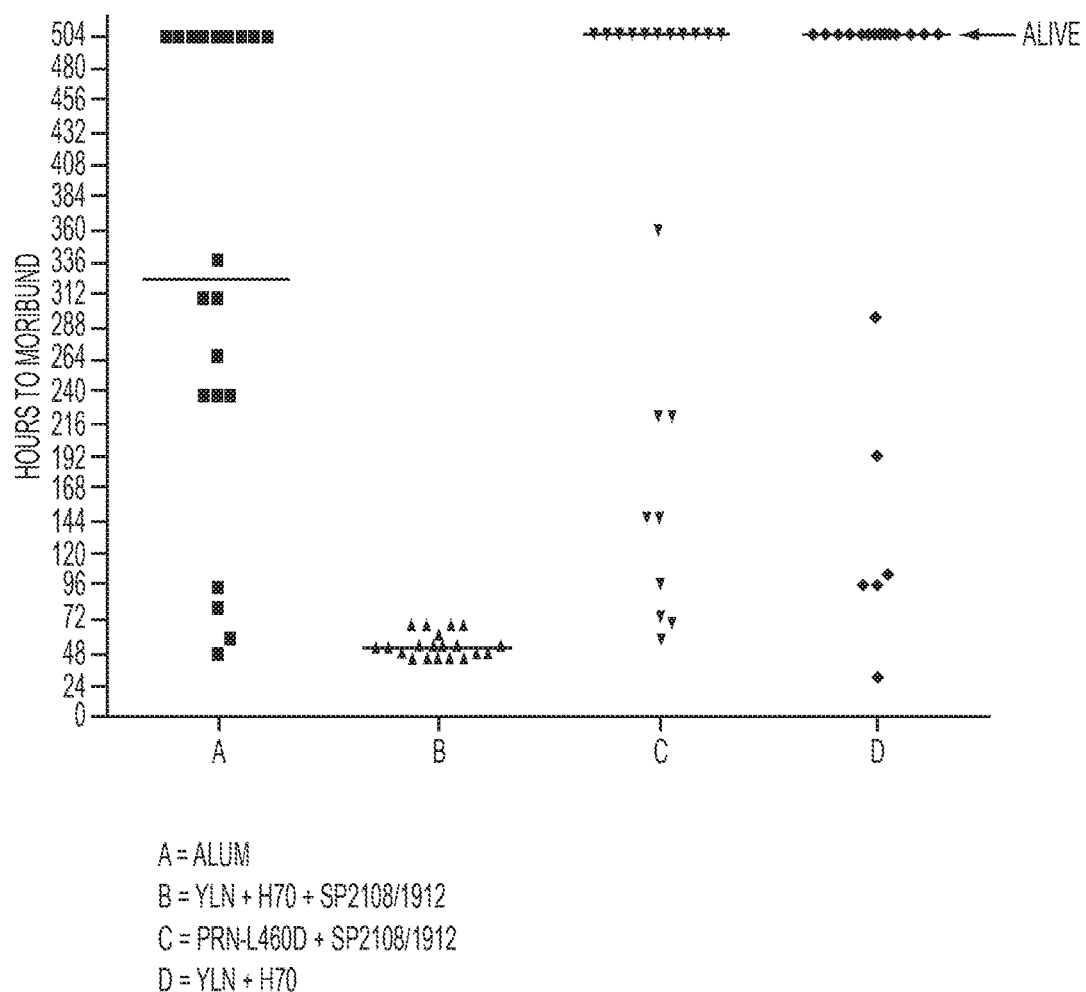
Figure 24B:
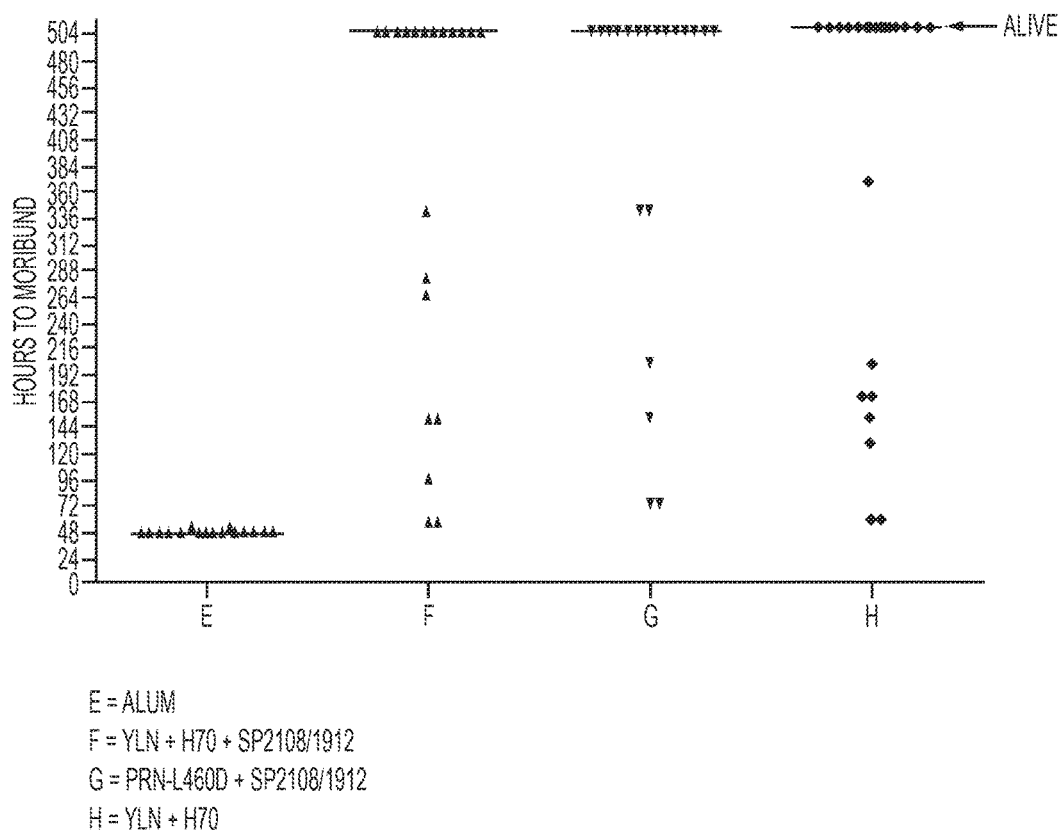

FIGS. 24A and 24B show hours to moribund for mice immunized with the indicated combinations of proteins and alum, or alum alone, then challenged by intravenous administration of *S. pneumoniae*, as described in Example 22.

IV. DETAILED DESCRIPTION

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

A. Fusion Proteins

This application describes *S. pneumoniae* fusion proteins. The fusion proteins include one, two or more polypeptides that elicit (e.g., primarily elicit) a T cell response, or that elicit both a T cell and a B cell response. In certain embodiments, the fusion protein comprises one, two or more of the polypeptides or genes listed in Table 1. In some embodiments, the fusion protein comprises two of the polypeptides or genes listed in Table 1. In some embodiments, the fusion protein comprises three of the polypeptides or genes listed in Table 1.

In some embodiments, a fusion protein comprises two or more immunogenic polypeptides having an amino acid sequence comprising SEQ ID NOs: 1-11, shown in Table 1, or immunogenic fragments thereof. In some embodiments, a fusion protein comprises two immunogenic polypeptides having an amino acid sequence comprising SEQ ID NOs: 1-11, shown in Table 1, or immunogenic fragments thereof. In some embodiments, a fusion protein comprises three immunogenic polypeptides having an amino acid sequence comprising SEQ ID NOs: 1-11, shown in Table 1, or immunogenic fragments thereof. In some embodiments, at least one immunogenic polypeptide is SP2108 (SEQ ID NO: 6). In some embodiments, at least one immunogenic polypeptide is SP0148 (SEQ ID NO: 2). In some embodiments, at least one immunogenic polypeptide is SP1912 (SEQ ID NO: 9).

In some embodiments, a fusion protein comprises one or more polypeptides homologous to the polypeptides listed in Table 1 (for example, SP1912, SP1912L, SP0148 with or without a signal sequence, SP2108 with or without a signal sequence). Individual strains of *S. pneumoniae* contain numerous mutations relative to each other, and some of these result in different protein sequences between the different strains. One of skill in the art may readily substitute an amino acid sequence, or a portion thereof, with the homologous amino acid sequence from a different *S. pneumoniae* strain. In certain aspects, this application provides immunogenic polypeptides with at least 90%, 95%, 97%, 98%, 99%, or 99.5% identity to the polypeptides listed in Table 1 or an immunogenic fragment thereof. Serotypic variation may be used to design such variants of the polypeptides listed in Table 1.

In some embodiments, fusion proteins described herein comprise two or more fragments of immunogenic peptides listed in Table 1 (for example, fragments of SP 1912, SP1912L, SP0148 with or without a signal sequence, SP2108 with or without a signal sequence). In some embodiments, fusion proteins described herein comprise truncation mutants that are close in size to the polypeptides listed in Table 1. For example, they may lack at most one, two three, four, five, ten, or twenty amino acids from one or both termini (referring to component polypeptides in a fusion protein). In certain embodiments, a fragment is a truncated fragment of any of SEQ ID NOs: 1-11 lacking 1-5, 1-10, or 1-20 amino acid residues from the N-terminus, C-terminus, or both, of any one of SEQ ID NOs: 1-11. In certain embodiments, a fragment is a truncated fragment of any of SEQ ID NOs: 1-11 lacking 1-10 amino acid residues from the N-terminus, C-terminus, or both, of any one of SEQ ID NOs: 1-11. For instance, a fragment may lack 10 amino acid residues at both the N-terminus and C-terminus of any one of SEQ ID NOs:1-11, resulting in a protein lacking 20 amino acid residues. Internal deletions, e.g., of 1-10, 11-20, 21-30, or 31-40 amino acids, are also contemplated.

TABLE 1

Immunogenic polypeptides

| Locus tag name and description | Protein SEQ ID No. | DNA SEQ ID No. | DNA GenBank Accession No. (from Mar. 30, 2010) |
|---|---|---|---|
| SP0148 lacking signal sequence | 1 | 37 | — |
| SP0148 including signal sequence | 2 | 38 | NC_003028.3|: 145,513-146,343* |
| SP0148 consensus lacking signal sequence | 3 | — | — |
| SP0148 consensus including signal sequence | 4 | — | — |
| SP2108 lacking signal sequence | 5 | 39 | — |
| SP2108 including signal sequence | 6 | — | NC_003028.3|: 2020750-2022021 |
| SP2108 consensus lacking signal sequence | 7 | — | — |
| SP2108 consensus including signal sequence | 8 | — | — |
| SP1912 | 9 | 40 | NC_003028.3|: 1824672-1824971 |
| SP1912L | 10 | 41 | — |
| SP1912 consensus | 11 | — | — |
| SP0641 | 12 | — | — |
| SP0641N | 13 | 42 | — |
| SP0641M | 14 | — | — |
| SP0641N consensus | 15 | — | — |
| SP0641M consensus | 16 | — | — |

TABLE 1-continued

Immunogenic polypeptides

| Locus tag name and description | Protein SEQ ID No. | DNA SEQ ID No. | DNA GenBank Accession No. (from Mar. 30, 2010) |
|---|---|---|---|
| SP0882 | 17 | — | NC_003028.3|: 831804-832628 |
| SP0882N | 18 | 43 | — |
| SP0882 with exogenous signal sequence | 19 | 44 | — |
| SP0882N with exogenous signal sequence | 20 | 45 | — |
| SP0882 consensus | 21 | — | — |
| SP0882N consensus | 22 | — | — |
| SP0882 consensus with exogenous leader | 23 | — | — |
| SP0882N consensus with exogenous leader | 24 | — | — |
| SP1634 | 25 | — | NC_003028.3|: 1534348-1535421 |
| SP0314 | 26 | — | NC_003028.3|: 287483-290683 |

*NB: The database sequence incorrectly lists TTG (encoding Leu) at nucleotide positions 541-543. The correct sequence, as shown in SEQ ID NO: 38, has TTC at that codon and encodes Phe. The database sequence further does not include a C-terminal Glu found in certain isolates.

Particular examples of fusion proteins are provided in Table 2.

TABLE 2

Immunogenic fusion proteins

| Locus tag names | Protein SEQ ID No. | DNA SEQ ID No. |
|---|---|---|
| SP2108/0148 | 47 | 56 |
| SP0148/2108 | 48 | 57 |
| SP2108/1912 | 49 | 58 |
| SP0148/1912 | 50 | 59 |
| SP2108/1912/0148 | 51 | 60 |
| SP0148/1912/2108 | 52 | 61 |
| SP2108/0148/1912 | 53 | 62 |
| SP0148/2108/1912 | 54 | 63 |

In some embodiments, a fusion protein comprises an N-terminal polypeptide and a C-terminal polypeptide. In some embodiments, one or both of the N-terminal polypeptide and the C-terminal polypeptide comprise an immunogenic polypeptide, for example, a polypeptide having an amino acid sequence comprising one of SEQ ID NOs: 1-11 or an immunogenic fragment or variant thereof.

In some embodiments, the N-terminal polypeptide and the C-terminal polypeptide are directly bound to each other. In some embodiments, the N-terminal polypeptide and the C-terminal polypeptide are linked via a linker peptide. The length and/or amino acids of a linker, when present, can be adjusted to obtain a more flexible or rigid linker. Exemplary peptide linkers are shown as SEQ ID NOs: 69-71. A linker can generally be from 1-40, such as 10-30 and specifically 10, 11, 12, 13, 14, 15, 16, 17, 18, 19 or 20 amino acids in length.

In some embodiments, a fusion protein comprises an immunogenic fragment of a fusion protein shown in Table 2. In some embodiments, a fusion protein is or includes an immunogenic fragment of any of SEQ ID NOs: 47-54. For example, a fusion protein may lack at most one, two three, four, five, ten, or twenty amino acids from the N-terminus, C-terminus, or both of any one of SEQ ID NOs: 47-54. In some such embodiments, the same number of residues is removed from the N-terminus and the C-terminus, while in other embodiments, a different number of residues is removed from the N-terminus compared to the C-terminus Advantageously, in some embodiments, the N-terminal polypeptide is not truncated so as not to prevent lipidation.

In certain aspects, this application provides fusion proteins with at least 90%, 95%, 97%, 98%, 99%, or 99.5% sequence identity to a fusion protein listed in Table 2. In certain embodiments, a fusion protein is or includes an amino acid sequence having at least 90%, 95%, 97%, 98%, 99%, or 99.5% identity to any one of SEQ ID NOs: 47-54.

In some embodiments, the fusion proteins include variants or fragments of the polypeptides or genes listed in Table 1. In some embodiments, a fragment included in a fusion protein described herein is close in size to a full-length polypeptide or a polypeptide listed in Table 1. For example, they may lack at most one, two, three, four, five, ten, twenty, or thirty amino acids from one or both termini. In certain embodiments, the fragment is 100-500 amino acids in length, or 150-450, or 200-400, or 250-350 amino acids in length. In some embodiments, the fragment is 100-200, 150-250, 200-300, 250-350, 300-400, 350-450, or 400-500 amino acids in length. In certain embodiments, the fragments result from processing, or partial processing, of signal sequences by an expression host, e.g. *E. coli*, an insect cell line (e.g., the baculovirus expression system), or a mammalian (e.g., human or Chinese Hamster Ovary) cell line. The fragments described above or sub-fragments thereof (e.g., fragments of 8-50, 8-30, or 8-20 amino acid residues) preferably have one of the biological activities described below, such as increasing the amount of IL-17 released by at least 1.5 fold or 2 fold or more (e.g., either as an absolute measure or relative to an immunologically inactive protein).

The DNA and protein sequence of each gene and polypeptide may be found by searching for the Locus Tag in the publicly available database, Entrez Gene (on the NCBI NIH web site on the World Wide Web, at www.ncbi.nlm.nih.gov/sites/entrez?db=gene), in the *Streptococcus pneumoniae* TIGR4 genome, and the indicated sequences are also included in this application.

Certain polypeptides of Table 1, and variants thereof, are described in greater detail below.

1. SP0148 (SEQ ID NO: 2) and Variants Thereof

The protein SP0148 is named "ABC transporter, substrate-binding protein". Proteins of this class are typically extracellular proteins that interact transiently with a transmembrane protein complex. Such complexes use energy generated by ATP hydrolysis to translocate specific substrates across a cell membrane. SP0148 is a 276 or 277 (depending on the isolate) amino acid protein that contains a conserved PBPb (periplasmic binding protein) domain, spanning amino acids 40-246, which is typical of membrane-bound transport complexes. In addition, SP0148 has a bacterial extracellular solute-binding proteins family 3 domain which is largely co-extensive with the PBPb domain and extends from amino acid 40 to 244. In some embodiments, a fusion protein comprises a truncation mutant of SP0148 comprising or lacking one or more of said domains and motifs.

In some embodiments, a fusion protein includes a polypeptide containing at least 20 consecutive amino acid residues selected from SP0148. The polypeptide may also be a variant of the at least 20 residue fragment. In certain embodiments, the polypeptide includes no more than 250, 225, 200, 175, 150, 125, or 100 consecutive amino acids from SP0148.

Endogenous SP0148 comprises a signal sequence that directs its secretion and potential lipidation. In some embodiments, the signal sequence of the polypeptide of SEQ ID NO: 2 is partially or fully processed by an expression host, e.g. *E. coli*. In some embodiments, a variant of SP0148 that lacks the signal sequence (SEQ ID NO: 1) is used. The polypeptide of SEQ ID NO: 1 is encoded by the nucleic acid of SEQ ID NO: 37, although other nucleic acid sequences (including codon-optimized sequences) may be used. SEQ ID NO: 38 encodes the full length sequence of SP0148 used in the screens herein.

Variants of the amino acid sequence and nucleotide sequence of SP0148 may be found in U.S. Patent Application Publication No. 2005/0020813, U.S. Pat. Nos. 7,378,514 and 7,504,110, and European Patent Application No. EP1572868 and EP1855717.

Consensus sequences illustrating combinations of SP0148 sequences from different *S. pneumoniae* serotypes are provided as SEQ ID NOs: 3 and 4. Accordingly, in certain embodiments, a fusion protein includes a polypeptide having an amino acid sequence comprising, or consisting of, either of SEQ ID NOs: 3-4, or an immunogenic fragment thereof (e.g., in place of a polypeptide having an amino acid sequence comprising one of SEQ ID NOs: 1 or 2).

In some embodiments a fusion protein comprises or consists of an immunogenic fragment of SP0148. Exemplary immunogenic fragments of SP0148 include ALGLVAAGV (SEQ ID NO: 74), ELTGYEIEV (SEQ ID NO: 75), AVNNLSYTK (SEQ ID NO: 76), TYLPAEADI (SEQ ID NO: 77), RYNMAVNNL (SEQ ID NO: 78), DFQQIMVRL (SEQ ID NO: 79), EHTDNPTIL (SEQ ID NO: 80), APIAQNPNV (SEQ ID NO: 81), LPSDQQPYV (SEQ ID NO: 82), YVYPLLAQG (SEQ ID NO: 83), QGLDNLKVI (SEQ ID NO: 84), KYLYAAPI (SEQ ID NO: 85), GELTGYEI (SEQ ID NO: 86), NPNVLVVKK (SEQ ID NO: 87), KLSKQFFGD (SEQ ID NO: 88), GSPRPFIYE (SEQ ID NO: 89), AVNNLSYTK (SEQ ID NO: 90), KIFD-KIGVE (SEQ ID NO: 91), MVRLSDGQF (SEQ ID NO: 92), YVYPLLAQG (SEQ ID NO: 93), VVQATTSAK (SEQ ID NO: 94), TLEKLSKQF (SEQ ID NO: 95), VAAGV-LAAC (SEQ ID NO: 96), LDNLKVIEL (SEQ ID NO: 97), and NMAVNNLSY (SEQ ID NO: 98).

2. SP2108 (SEQ ID NO: 6) and Variants Thereof

The polypeptide SP2108 is 423 amino acids in length and is alternatively known as MalX, maltose/maltodextrin ABC transporter, or maltose/maltodextrin-binding protein. Much of the protein (amino acids 3-423) is classified as a MalE (Maltose-binding periplasmic) domain. In addition, SP2108 contains a signal sequence that directs its secretion and potential lipidation. In some embodiments, the signal sequence of the polypeptide of SEQ ID NO: 6 is partially or fully processed by an expression host, e.g. *E. coli*. In some embodiments, a fusion protein comprises a truncation mutant of SP2108 comprising one or more of said domains and motifs.

In some embodiments, a fusion protein includes an SP2108 variant that lacks the signal sequence. This variant is represented by polypeptide sequence SEQ ID NO: 5 and may be encoded by, for example, a nucleic acid according to SEQ ID NO: 39, although due to degeneracy in the genetic code, other DNA sequences (including codon-optimized sequences) may be used.

In some embodiments, a fusion protein includes a polypeptide containing at least 20 consecutive amino acid residues selected from SP2108. The polypeptide may also be a variant of the at least 20 residue fragment. In certain embodiments, the polypeptide includes no more than 400, 350, 300, 250, 200, 150, or 100 consecutive amino acids from SP2108.

Consensus sequences illustrating combinations of SP2108 sequences from different serotypes are provided as SEQ ID NOs: 7 and 8. Thus, in certain embodiments, a fusion protein contains a polypeptide having an amino acid sequence comprising, or consisting of, either of SEQ ID NOs: 7-8, or an immunogenic fragment thereof (e.g., in place of a polypeptide having an amino acid sequence comprising one of SEQ ID NOs: 5 or 6).

In some embodiments a fusion protein comprises or consists of an immunogenic fragment of SP2108. Exemplary immunogenic fragments of SP2108 include AIIDGP-WKA (SEQ ID NO: 99), VMMAPYDRV (SEQ ID NO: 100), SIAGINYAK (SEQ ID NO: 101), VWDPAKNML (SEQ ID NO: 102), QPLPNISQM (SEQ ID NO: 103), APYDRVGSL (SEQ ID NO: 104), APAVIESLV (SEQ ID NO: 105), FYYTYGLLA (SEQ ID NO: 106), SKYAFAGE (SEQ ID NO: 107), TEGAGNLI (SEQ ID NO: 108), LADWTNFYY (SEQ ID NO: 109), SLVMYYNKD (SEQ ID NO: 110), KEAGVKVTL (SEQ ID NO: 111), KSTAVLGTV (SEQ ID NO: 112), GAKTDDTTK (SEQ ID NO: 113), SQKFVDFLV (SEQ ID NO: 114), QAFKDAKVN (SEQ ID NO: 115), AVIESLVMY (SEQ ID NO: 116), DAKTAANDA (SEQ ID NO: 117), YGVATIPTL (SEQ ID NO: 118), KTAAIIDGP (SEQ ID NO: 119), KAYEKEAGV (SEQ ID NO: 120), AGNGAYVFG (SEQ ID NO: 121), and AWVIPQAVK (SEQ ID NO: 122).

3. SP1912 (SEQ ID NO: 9) and Variants Thereof

SP1912 is a hypothetical protein of 99 amino acids. While the protein function is not definitively known, sequence analysis suggests it is a putative thioredoxin.

In some embodiments, a fusion protein includes a polypeptide containing at least 20 consecutive amino acid residues selected from SP1912. The polypeptide may also be a variant of the at least 20 residue fragment. In certain embodiments, the polypeptide includes no more than 90, 75, 60, 45 or 30 consecutive amino acids from SP1912.

In some embodiments, a fusion protein includes an SP1912 variant that comprises an exogenous lipidation sequence. In some embodiments, a signal sequence directs lipidation. Thus, the lipidation signal may be, e.g., the signal sequence of SP2108 (SEQ ID NO: 67) or SP0148, or an *E. coli* signal sequence. The exemplary variant SP1912L, comprising the signal sequence of the *E. coli* gene RlpB (SEQ ID NO: 68) is represented by polypeptide sequence SEQ ID NO: 10. SP1912 (SEQ ID NO: 9) and SP1912L (SEQ ID NO: 10) may be encoded, respectively, by nucleic acids according to SEQ ID NO: 40 and 41, although due to degeneracy in the genetic code, other DNA sequences (including codon-optimized sequences) may be used. In some embodiments, the lipidation sequence is provided by fusing a full-length polypeptide such as SP2108 (SEQ ID NO: 6) or SP0148 (SEQ ID NO: 2) to SP1912. Exemplary fusions are SEQ ID NOs: 49-54.

Consensus sequences illustrating combinations of SP1912 sequences from different serotypes are provided as SEQ ID NO: 11. Thus, in certain embodiments, formulation fusion protein comprises a polypeptide having an amino acid sequence comprising, or consisting of, SEQ ID NO: 11, or an immunogenic fragment thereof (e.g., in place of a polypeptide having an amino acid sequence comprising SEQ ID NO: 9).

In some embodiments a fusion protein comprises or consists of an immunogenic fragment of SP 1912. Exemplary immunogenic fragments of SP 1912 include KMWMAGLALLGIGSL (SEQ ID NO: 123), LLGIGSLALATKKVA (SEQ ID NO: 124), MAGLALLGIGSLALA (SEQ ID NO: 125), WMAGLALLGIGSLAL (SEQ ID NO: 126), GLALLGIGSLALATK (SEQ ID NO: 127), LALLGIGSLALATKK (SEQ ID NO: 128), FSDMGEIATLYVQVY (SEQ ID NO: 129), KAKKMWMAGLALLGI (SEQ ID NO: 130), ALLGIGSLALATKKVAKKM-WMAGLALLGIG (SEQ ID NO: 131), SDMGEIATLYVQVYE (SEQ ID NO: 132), DMGEIATLYVQVYES (SEQ ID NO: 133), AGLALLGIGSLALAT (SEQ ID NO: 134), MGEIATLYVQVYESS (SEQ ID NO: 135), KKM-WMAGLALLGIGS (SEQ ID NO: 136), GMKAKKM-WMAGLALL (SEQ ID NO: 137), MKAKKM-WMAGLALLG (SEQ ID NO: 138), HFSDMGEIATLYVQV (SEQ ID NO: 139), MNGMKAK-KMWMAGLA (SEQ ID NO: 140), MWMAGLALLGIG-SLA (SEQ ID NO: 141), DHFSDMGEIATLYVQ (SEQ ID NO: 142), RDHFSDMGEIATLYV (SEQ ID NO: 143), and NGMKAKKMWMAGLAL (SEQ ID NO: 144).

4. Lipidated Polypeptides

In certain embodiments, a fusion protein described herein contains at least one lipidated polypeptide. In some embodiments, the fusion protein is lipidated. In certain embodiments, the fusion protein is lipidated on the N-terminal peptide. Conjugation to the lipid moiety may be direct or indirect (e.g., via a linker). The lipid moiety may be synthetic or naturally produced. In certain embodiments, a polypeptide from Table 1 or 2 may be chemically conjugated to a lipid moiety. In certain embodiments, a construct may comprise a gene or polypeptide from Table 1, or 2, or an immunogenic fragment or variant thereof, and a lipidation sequence including a lipobox motif. A canonical lipobox motif is shown as SEQ ID NO: 66. A lipidation sequence may be N-terminal or C-terminal to the protein, and may be embedded in a signal or other sequence, or in a fusion protein. Exemplary lipidation sequences include the signal sequence of SP2108 (SEQ ID NO: 67) and the signal sequence of the *E. coli* gene RlpB (SEQ ID NO: 68). A signal sequence may be, for example, an *E. coli* or *S. pneumoniae* signal sequence. Exemplary *E. coli* signal sequences include the mlpA signal sequence (Lin, J. J. et al., "An *Escherichia coli* mutant with an amino acid alteration within the signal sequence of outer membrane prolipoprotein" Proc Natl Acad Sci USA. 1978 October; 75(10):4891-5), the lamB signal sequence (Emr, S. D. et al. "Mutations altering the cellular localization of the phage lambda receptor, an *Escherichia coli* outer membrane protein", Proc Natl Acad Sci USA. 1978 December; 75(12):5802-6), or the MBP signal sequence (Bassford, P. J., "Use of gene fusion to study secretion of maltose-binding protein into *Escherichia coli* periplasm" J Bacteriol. 1979 July; 139(1):19-31). Lpp is an exemplary *E. coli* signal sequence that directs lipidation (Cullen, P. A. et al. "Construction and evaluation of a plasmid vector for the expression of recombinant lipoproteins in *Escherichia coli*" Plasmid. 2003 January; 49(1):18-29.) *E. coli* signal sequences that direct lipidation are also described in Legrain, M. et al. ("Production of lipidated meningococcal transferrin binding protein 2 in *Escherichia coli*" Protein Expr Purif. 1995 October; 6(5): 570-8), e.g. the signal sequence of the gene RlpB (SEQ ID NO: 68). Numerous *S. pneumoniae* signal sequences are known in the art. One such signal sequence is SEQ ID NO: 67.

5. Tagged Polypeptides

In some embodiments, one or more polypeptides included in a fusion protein described herein may comprise a tag. A tag may be N-terminal or C-terminal. For instance, tags may be added to a nucleic acid or polypeptide to facilitate purification, detection, solubility, or confer other desirable characteristics on the protein or nucleic acid. For instance, a purification tag may be a peptide, oligopeptide, or polypeptide that may be used in affinity purification. Examples include His, GST, TAP, FLAG, myc, HA, MBP, VSV-G, thioredoxin, V5, avidin, streptavidin, BCCP, Calmodulin, Nus, S tags, lipoprotein D, and β galactosidase. Particular exemplary His tags include HHHHHH (SEQ ID NO:64) and MSYYHHHHHH (SEQ ID NO: 65). In other embodiments, the polypeptide is free of tags such as protein purification tags, and is purified by a method not relying on affinity for a purification tag. In some embodiments, the fused portion is short. This, in some instances, the fusion protein comprises no more than 1, 2, 3, 4, 5, 10, or 20 additional amino acids on one or both termini of the polypeptide of Table 1 or 2.

B. Nucleic Acids

In certain embodiments, this application provides nucleic acids encoding one or more of the polypeptides and/or fusion proteins described herein, such as DNA, RNA, or an analog thereof. The underlying DNA sequences for the polypeptides described above may be modified in ways that do not affect the sequence of the protein product, and such sequences are included in the invention. For instance, the DNA sequence may be codon-optimized to improve expression in a host such as E. coli, an insect cell line (e.g., using the baculovirus expression system), or a mammalian (e.g., human or Chinese Hamster Ovary) cell line.

In certain embodiments, this application provides polynucleotides (such as DNA, RNA, or an analog thereof) that are at least 70%, 80%, 90%, 95%, 97%, 98%, 99%, or 100% identical to polynucleotide sequences of Table 1 or 2, or a variant or portion of said sequence. In certain embodiments, the polynucleotide is 600-2000, 800-1800, 1000-1600, 1200-1400 nucleotides in length. In some embodiments, the polynucleotide is 600-1600, 800-1800, 1000-2000, 2000-3000, or 3000-4000 nucleotides in length. The nucleic acids may be used, for example, for recombinant production of a polypeptide of Table 1 or a fusion protein of Table 2, or immunogenic fragments thereof.

Polynucleotides encoding peptides of Tables 1 or 2 or a fragment thereof can be cloned into any of a variety of expression vectors, under the control of a variety of regulatory elements, and fusions can be created with other peptides of Tables 1 or 2 or with other sequences of interest. Methods of cloning nucleic acids are routine and conventional in the art. For general references describing methods of molecular biology which are mentioned in this application, e.g., isolating, cloning, modifying, labeling, manipulating, sequencing and otherwise treating or analyzing nucleic acids and/or proteins, see, e.g., Sambrook, J. et al. (1989). Molecular Cloning, a Laboratory Manual. Cold Harbor Laboratory Press, Cold Spring Harbor, N.Y.; Ausubel, F. M. et al. (1995). Current Protocols in Molecular Biology, N.Y., John Wiley & Sons; Davis et al. (1986), Basic Methods in Molecular Biology, Elsevir Sciences Publishing, Inc., New York; Hames et al. (1985), Nucleic Acid Hybridization, IL Press; Dracopoli, N. C. et al. Current Protocols in Human Genetics, John Wiley & Sons, Inc.; and Coligan, J. E., et al. Current Protocols in Protein Science, John Wiley & Sons, Inc.

C. Immunogenic Compositions

The present disclosure also provides immunogenic compositions (e.g., vaccine compositions) of, or including, one or more fusion proteins described herein. In some embodiments, an immunogenic composition further includes a pharmaceutically acceptable carrier. The S. pneumoniae antigens described herein were identified by screening immune cells from mice either immunized with unencapsulated killed whole S. pneumoniae or infected with live S. pneumoniae, or from healthy human donors that elicit a T cell specific immune response. The human donors have almost certainly been exposed to S. pneumoniae at some point during their lifetimes, because S. pneumoniae is a very common disease and colonizing pathogen. Thus, the present disclosure contemplates immunogenic compositions of fusion proteins including S. pneumoniae antigens that elicit a strong immune response in all age groups that is long-lived in immunized or infected mice or humans for counteracting infection by S. pneumoniae.

In certain embodiments, an immunogenic composition described herein (e.g., a vaccine composition) induces a $T_H17$ cell response at least 1.5-fold greater than that induced by a control unrelated antigen (such as the HSV-2 protein ICP47 with the gene name US12) after contacting $T_H17$ cells. In some embodiments, an immunogenic composition described herein inhibits infection by S. pneumoniae in an uninfected subject. In certain embodiments, an immunogenic composition described herein reduces occurrence or duration of S. pneumoniae nasopharyngeal colonization in an individual colonized or infected by S. pneumoniae. In some embodiments, an immunogenic composition described herein inhibits development of sepsis in an individual infected by S. pneumoniae. In some embodiments, an immunogenic composition described herein inhibits development of invasive diseases such as pneumonia, meningitis, otitis media, sinusitis or infection of other sites or organs with S. pneumoniae.

In some embodiments, an immunogenic composition described herein may also comprise portions of said Streptococcus polypeptides, including fusion proteins, for example deletion mutants, truncation mutants, oligonucleotides, and peptide fragments. In some embodiments, the portions of said polypeptides are immunogenic. The immunogenicity of a portion of a protein is readily determined using the same assays that are used to determine the immunogenicity of the full-length protein. In some embodiments, the portion of the polypeptide has substantially the same immunogenicity as the full-length proteins. In some embodiments, the immunogenicity is no more than 10%, 20%, 30%, 40%, or 50% less than that of the full-length protein (e.g., polypeptides of Tables 1, 2 and 3). The peptide fragments may be, for example, linear, circular, or branched.

Typically, polypeptides and fusion proteins described herein, and fragments and variants thereof, are immunogenic. These polypeptides may be immunogenic in mammals, for example mice, guinea pigs, or humans. An immunogenic polypeptide is typically one capable of raising a significant immune response in an assay or in a subject. The immune response may be innate, humoral, cell-mediated, or mucosal (combining elements of innate, humoral and cell-mediated immunity). For instance, an immunogenic polypeptide may increase the amount of IL-17 produced by T cells. Alternatively or additionally, an immunogenic polypeptide may (i) induce production of antibodies, e.g., neutralizing antibodies, that bind to the polypeptide and/or the whole bacteria, (ii) induce $T_H17$ immunity, (iii) activate the $CD4^+$ T cell response, for example by increasing $CD4^+$ T cells and/or increasing localization of $CD4^+$ T cells to the site of infection or reinfection, (iv) activate the $CD8^+$ CTL response, for example by increasing $CD8^+$ T cells and/or increasing localization of $CD8^+$ T cells to the site of infection or reinfection, (v) induce $T_H1$ immunity, (vi) induce anti-microbial peptides, and/or (vii) activate innate immunity. In some embodiments, an immunogenic polypeptide causes the production of a detectable amount of antibody specific to that antigen.

In certain embodiments, polypeptides described herein have less than 20%, 30%, 40%, 50%, 60% or 70% identity to human autoantigens and/or gut commensal bacteria (e.g., certain *Bacteroides, Clostridium, Fusobacterium, Eubacterium, Ruminococcus, Peptococcus, Peptostreptococcus, Bifidobacterium, Escherichia* and *Lactobacillus* species). Examples of human autoantigens include insulin, proliferating cell nuclear antigen, cytochrome P450, and myelin basic protein.

A polypeptide described herein (e.g., a polypeptide included in a fusion protein described herein) may comprise one or more immunogenic portions and one or more non-immunogenic portions. The immunogenic portions may be identified by various methods, including protein microarrays, ELISPOT/ELISA techniques, and/or specific assays on different deletion mutants (e.g., fragments) of the polypeptide in question Immunogenic portions may also be identified by computer algorithms. Some such algorithms, like EpiMatrix (produced by EpiVax), use a computational matrix approach. Other computational tools for identifying antigenic epitopes include PEPVAC (Promiscuous EPitope-based VACcine, hosted by Dana Farber Cancer Institute on the world wide web at immunax.dfci.harvard.edu/PEPVAC), MHCPred (which uses a partial least squares approach and is hosted by The Jenner Institute on the world wide web at www.jenner.ac.uk/MHCPred), and Immune Epitope Database algorithms on the world wide web at tools.immuneepitope.org. An immunogenic fragment of a polypeptide described herein comprises at least one immunogenic portion, as measured experimentally or identified by algorithm (for example, the SYFPEITHI algorithm found at www.syfpeithi.de).

D. Multi-Component Immunogenic Compositions

In certain embodiments, an immunogenic composition described herein (e.g., a vaccine composition) includes a fusion protein described herein and additionally one or more, or two or more, known *S. pneumoniae* antigens. In some instances, the known *S. pneumoniae* antigens are predominantly antibody targets shown in Table 3. In some instances, the known *S. pneumoniae* antigens are polysaccharides. In some instances, the known *S. pneumoniae* antigens protect from *S. pneumoniae* colonization, or from *S. pneumoniae*-induced sepsis, pneumonia, meningitis, otitis media, sinusitis, or infection of other sites or organs by *S. pneumoniae*.

TABLE 3

Immunogenic polypeptides for vaccine formulations

| PspA | 27 | 46 |
| PR + NRB from PspA with coiled-coil | 28 | |
| CD2 | 29 | |
| PR + NRB from PspA w/o coiled-coil | 30 | |
| PR only with coiled-coil | 31 | |
| PR only w/o coiled-coil | 32 | |
| H70 (PR + NRB from PspA aa 290-410) | 33 | |
| Non-proline Block (NPB) | 34 | |
| Non-proline Block (NPB) | 35 | |
| Non-proline Block (NPB) | 36 | |
| L460D | 55 | |

One appropriate art-recognized class of *S. pneumoniae* antigen is Pneumococcal surface protein A (PspA) (SEQ ID NO: 27) and derivatives of PspA. Derivatives of PspA include proline-rich segments with the non-proline block (PR+NPB, also referred to as PRN and further described below as well as in Daniels, C. C. et al. (2010) Infection and Immunity 78:2163-72) and related constructs comprising all or a fragment of the proline-rich region of PspA (e.g., regions containing one or more of the sequences PAPAP, PKP, PKEPEQ and PEKP and optionally including a non-proline block). In some embodiments, fragments or variants of PspA comprise proline-rich segments with the non-proline block and 10, 20 30, 40 or more additional amino acids of PspA sequence. H70 (SEQ ID NO: 33) is one exemplary sequence which includes the proline-rich region and non-proline-block encompassing amino acids 290-410 PspA. An example of the non-proline-block has the exemplary sequence EKSADQQAEEDYARRSEEEYN-RLTQQQ (SEQ ID NO: 34), which generally has no proline residues in an otherwise proline-rich area of the non-coiled region of PspA. Other embodiments of non-proline block (NPB) sequences include SEQ ID NOs: 35 and 36 and PspA and its derivatives can include genes expressing similar proline-rich structures (i.e. PKP, PKEPEQ and PEKP), with or without the NPB. The amino acids at either end of the NPB mark the boundaries of the proline-rich region. In one example, the amino-terminal boundary to the PR-region is DLKKAVNE (SEQ ID NO: 72), and the carboxy-terminal boundary is (K/G)TGW(K/G)QENGMW (SEQ ID NO: 73). Peptides containing the NPB are particularly immunogenic, suggesting that the NPB may be an important epitope. Exemplary immunogenic PspA polypeptide derivatives containing the coiled-coil structure include SEQ ID NOs: 28 and 31. Particular embodiments of the immunogenic PspA polypeptide derivatives lacking the coiled-coil structure have the amino acid sequences shown as SEQ ID NOs: 29, 30 and 32 Immunogenic PspA polypeptides SEQ ID NO: 28-30 include both PR and NPB sequences (PR+NPB) Immunogenic PspA polypeptides of SEQ ID NOs: 31 and 32 include only a PR sequence (PR only) and lack the NPB.

Another appropriate art-recognized class of *S. pneumoniae* antigen is the pneumolysoids. Pneumolysoids have homology to the *S. pneumoniae* protein pneumolysin (PLY), but have reduced toxicity compared to pneumolysin. Pneumolysoids can be naturally occurring or engineered derivatives of pneumolysin. In some embodiments, a pneumolysoid has at least 70%, 80%, 85%, 90%, 95%, 97%, 98%, or 99% identity to pneumolysin. In some embodiments, the pneumolysoid demonstrates less than ½, ⅕, ¹⁄₁₀, ¹⁄₂₀, ¹⁄₅₀, ¹⁄₁₀₀, ¹⁄₂₀₀, ¹⁄₅₀₀, or ¹⁄₁₀₀₀ the toxicity of pneumolysin in an assay for one or both of hemolytic activity towards erythrocytes and inhibition of polymorphonuclear leukocytes. Both assays are described in Saunders F. K. et al. ("Pneumolysin, the thiol-activated toxin of *Streptococcus pneumoniae*, does not require a thiol group for in vitro activity" Infect Immun 1989 August; 57(8):2547-52). Exemplary pneumolysoids include PdT (a triple mutant further described in Berry, A. M. et al. (1995) Infection and Immunity 63:1969-74); Pd-A and Pd-B (Paton J. C. et al. "Purification and immunogenicity of genetically obtained pneumolysin toxoids and their conjugation to *Streptococcus pneumoniae* type 19F polysaccharide" Infect Immun 1991 July; 59(7):2297-304); rPd2 and rPd3 (Ferreira et al. "DNA vaccines based on genetically detoxified derivatives of pneumolysin fail to protect mice against challenge with *Streptococcus pneumoniae*" FEMS Immunol Med Microbiol (2006) 46: 291-297); Ply8, Δ6PLY, L460D (see, e.g., US 2009/0285846 and L. Mitchell, Protective Immune Responses to *Streptococcus pneumoniae* Pneumolysoids, ASM2011 conference abstract, 2011); or a variant thereof.

In some embodiments, the pneumolysin has a mutation in the catalytic center, such as at amino acid 428 or 433 or the vicinity.

Other appropriate *S. pneumoniae* antigens include Choline-binding protein A (CbpA) and derivatives thereof (A D Ogunniyi et al., "Protection against *Streptococcus pneumoniae* elicited by immunization with pneumolysin and CbpA," Infect Immun. 2001 October; 69(10): 5997-6003); Pneumococcal surface adhesin A (PsaA); caseinolytic protease; sortase A (SrtA); pilus 1 RrgA adhesin; PpmA; PrtA; PavA; LytA; Stk-PR; PcsB; RrgB and derivatives thereof. CpbA derivatives include fusion proteins described in WO 2012/134975. Such fusion proteins may comprise one or more copies of the R2 domain, $R2_1$ and/or $R2_2$ subdomains of CpbA, or active variants and fragments thereof, or any combination thereof. Such fusion proteins may further comprise a pneumolysoid. The construct YLN, for example, comprises CpbA polypeptides YPT and NEEK, and pneumolysoid L460D (SEQ ID NO: 55).

In some cases, the antigen is at least 70%, 80%, 85%, 90%, 95%, 97%, 98%, or 99% identical to the corresponding wild-type *S. pneumoniae* protein. Sequences of the above-mentioned polypeptides, and nucleic acids that encode them, are known; see, for example, the *S. pneumoniae* ATCC 700669 complete genome sequence under GenBank accession number FM211187.1 and linked polypeptide sequences therein.

In some embodiments, an immunogenic composition (e.g., a vaccine composition) contains one or more fusion proteins described herein in combination with one or more, e.g., two, three, four, or more polypeptides from Table 1 or 3 or immunogenic fragments or variants thereof in a mixture. In some embodiments, the mixture contains both full-length polypeptides and fragments resulting from processing, or partial processing, of signal sequences by an expression host, e.g. *E. coli*, an insect cell line (e.g., the baculovirus expression system), or a mammalian (e.g., human or Chinese Hamster Ovary) cell line. In some embodiments, an immunogenic composition contains one or more fusion proteins of any of SEQ ID NOs: 47-54 in the absence of any other antigens. In some embodiments, an immunogenic composition contains one or more fusion proteins of any of SEQ ID NOs: 47-54 in combination with one or more additional proteins of any of SEQ ID NOs: 1-36, in the absence of other antigens.

In some embodiments, polypeptides described in Tables 1 and 3 may be used without modification in conjunction with the fusion proteins described herein. In certain embodiments, when smaller related polypeptides are used, such as fragments or the like, and their molecular weight is less than about 5000 daltons, e.g., 1500 to 5000 daltons, modification may be useful in eliciting the desired immune response. For example, the smaller polypeptides can be conjugated to an appropriate immunogenic carrier such as tetanus toxoid, keyhole limpet hemocyanin or the like.

In some embodiments, polypeptides described herein may be conjugated to *S. pneumoniae* polysaccharides. The conjugated polysaccharides may be, for example, as described in U.S. Pat. No. 5,623,057, U.S. Pat. No. 5,371,197, or PCT/US2011/023526.

Some embodiments of immunogenic compositions described herein include an immunogenic polypeptide, including fusion proteins (e.g., a polypeptide of Table 1, 2 or 3) that contains a membrane translocating sequence (MTS), to facilitate introduction of the polypeptide into the mammalian cell and subsequent stimulation of the cell-mediated immune response. Exemplary membrane translocating sequences include hydrophobic region in the signal sequence of Kaposi fibroblast growth factor, the MTS of α-synuclein, β-synuclein, or γ-synuclein, the third helix of the Antennapedia homeodomain, SN50, integrin β3 h-region, HIV Tat, pAntp, PR-39, abaecin, apidaecin, Bac5, Bac7, *P. berghei* CS protein, and those MTSs described in U.S. Pat. Nos. 6,248,558, 6,432,680 and 6,248,558.

In certain embodiments, an antigen (e.g., a polypeptide of Table 1, 2 or 3) is covalently bound to another molecule. This may, for example, increase the half-life, solubility, bioabailability, or immunogenicity of the antigen. Molecules that may be covalently bound to the antigen include a carbohydrate, biotin, poly(ethylene glycol) (PEG), polysialic acid, N-propionylated polysialic acid, nucleic acids, polysaccharides, and PLGA. There are many different types of PEG, ranging from molecular weights of below 300 g/mol to over 10,000,000 g/mol. PEG chains can be linear, branched, or with comb or star geometries. In some embodiments, the naturally produced form of a protein is covalently bound to a moeity that stimulates the immune system. An example of such a moeity is a lipid moeity. In some instances, lipid moieties are recognized by a Toll-like receptor (TLR) such as TLR-2 or TLR-4, and activate the innate immune system.

In some embodiments, a fusion protein and one or more additional components described herein are mixed together using known methods to form a multi-component immunogenic composition. In some embodiments, a fusion protein and one or more additional components described herein are nano-encapsulated using known methods. In some embodiments, a fusion protein and one or more additional components described herein are molded into nano- or microparticles using known methods. In some embodiments, a fusion protein and one or more additional components described herein are conjugated through a covalent bond using known methods to form a multi-component immunogenic composition. In some embodiments, a fusion protein and one or more additional components described herein are joined non-covalently using known methods to form a multi-component immunogenic composition. Additional methods of combining a fusion protein and one or more additional components are described in, e.g., PCT/US12/37412 and PCT/US09/44956.

E. Additional Immunogenic Composition Components

In certain embodiments, an immunogenic composition described herein (e.g, a vaccine composition) comprises one or more of the following: an adjuvant, stabilizer, buffer, surfactant, controlled release component, salt, preservative, and/or an antibody specific to a polypeptide included in an immunogenic composition.

1. Adjuvants

In some embodiments, an immunogenic composition may include an adjuvant. Adjuvants can be broadly separated into two classes, based on their principal mechanisms of action: vaccine delivery systems and immunostimulatory adjuvants (see, e.g., Singh et al., *Curr. HIV Res.* 1:309-20, 2003). In most vaccine formulations, the adjuvant provides a signal to the immune system so that it generates a response to the antigen, and the antigen is required for driving the specificity of the response to the pathogen. Vaccine delivery systems are often particulate formulations, e.g., emulsions, microparticles, immune-stimulating complexes (ISCOMs), nanoparticles, which may be, for example, particles and/or matrices, and liposomes. In contrast, immunostimulatory adjuvants are sometimes derived from pathogens and can represent pathogen associated molecular patterns (PAMP), e.g., lipopolysaccharides (LPS), monophosphoryl lipid (MPL), or CpG-containing DNA, which activate cells of the innate immune system.

Alternatively, adjuvants may be classified as organic and inorganic. Inorganic adjuvants include alum salts such as aluminum phosphate, amorphous aluminum hydroxyphosphate sulfate, and aluminum hydroxide, which are commonly used in human vaccines. Organic adjuvants comprise organic molecules including macromolecules. An example of an organic adjuvant is cholera toxin.

Adjuvants may also be classified by the response they induce. In some embodiments, the adjuvant induces the activation of $T_H1$ cells or $T_H2$ cells. In other embodiments, the adjuvant induces the activation of B cells. In yet other embodiments, the adjuvant induces the activation of antigen-presenting cells. These categories are not mutually exclusive; in some cases, an adjuvant activates more than one type of cell.

In certain embodiments, the adjuvant induces the activation of $T_H17$ cells. It may promote the CD4$^+$ or CD8$^+$ T cells to secrete IL-17. In some embodiments, an adjuvant that induces the activation of $T_H17$ cells is one that produces at least a 2-fold, and in some cases a 10-fold, experimental sample to control ratio in the following assay. In the assay, an experimenter compares the IL-17 levels secreted by two populations of cells: (1) cells from animals immunized with the adjuvant and a polypeptide known to induce $T_H17$ activation, and (2) cells from animals treated with the adjuvant and an irrelevant (control) polypeptide. An adjuvant that induces the activation of $T_H17$ cells may cause the cells of population (1) to produce more than 2-fold, or more than 10-fold more IL-17 than the cells of population (2). IL-17 may be measured, for example, by ELISA or ELISPOT. Certain toxins, such as cholera toxin and labile toxin (produced by enterotoxigenic *E. coli*, or ETEC), activate a $T_H17$ response. Thus, in some embodiments, the adjuvant is a toxin. Cholera toxin was successfully used in the mouse model to induce protective immunity in conjunction with certain polypeptides from Table 1 (see Examples 1-2). One form of labile toxin is produced by Intercell. Mutant derivates of labile toxin that are active as adjuvants but significantly less toxic can be used as well. Exemplary detoxified mutant derivatives of labile toxin include mutants lacking ADP-ribosyltransferase activity. Particular detoxified mutant derivatives of labile toxin include LTK7 (Douce et al., "Mutants of *Escherichia coli* heat-labile toxin lacking ADP-ribosyltransferase activity act as nontoxic, mucosal adjuvants" PNAS Vol. 92, pp. 1644-1648, February 1995) and LTK63 (Williams et al., "Innate Imprinting by the Modified Heat-Labile Toxin of *Escherichia coli* (LTK63) Provides Generic Protection against Lung Infectious Disease" The Journal of Immunology, 2004, 173: 7435-7443), LT-G192 (Douce et al. "Genetically detoxified mutants of heat-labile toxin from *Escherichia coli* are able to act as oral adjuvants" Infect Immun. 1999 September; 67(9):4400-6), and LTR72 ("Mucosal adjuvanticity and immunogenicity of LTR72, a novel mutant of *Escherichia coli* heat-labile enterotoxin with partial knockout of ADP-ribosyltransferase activity." J Exp Med. 1998 Apr. 6; 187(7):1123-32).

In some embodiments, the adjuvant comprises a VLP (virus-like particle). One such adjuvant platform, Alphavirus replicons, induces the activation of $T_H17$ cells using alphavirus and is produced by Alphavax. In certain embodiments of the Alphavirus replicon system, alphavirus may be engineered to express an antigen of interest, a cytokine of interest (for example, IL-17 or a cytokine that stimulates IL-17 production), or both, and may be produced in a helper cell line. More detailed information may be found in U.S. Pat. Nos. 5,643,576 and 6,783,939. In some embodiments, a vaccine formulation is administered to a patient in combination with a nucleic acid encoding a cytokine.

Certain classes of adjuvants activate toll-like receptors (TLRs) in order to activate a $T_H17$ response. TLRs are well known proteins that may be found on leukocyte membranes, and recognize foreign antigens (including microbial antigens). Administering a known TLR ligand together with an antigen of interest (for instance, as a fusion protein) can promote the development of an immune response specific to the antigen of interest. One exemplary adjuvant that activates TLRs comprises Monophosphoryl Lipid A (MPL). Traditionally, MPL has been produced as a detoxified lipopolysaccharide (LPS) endotoxin obtained from gram negative bacteria, such as *S. minnesota*. In particular, sequential acid and base hydrolysis of LPS produces an immunoactive lipid A fraction (which is MPL), and lacks the saccharide groups and all but one of the phosphates present in LPS. A number of synthetic TLR agonists (in particular, TLR-4 agonists) are disclosed in Evans J T et al. "Enhancement of antigen-specific immunity via the TLR-4 ligands MPL adjuvant and RIBI.529." Expert Rev Vaccines 2003 April; 2(2):219-29. Like MPL adjuvants, these synthetic compounds activate the innate immune system via TLR. Another type of TLR agonist is a synthetic phospholipid dimer, for example E6020 (Ishizaka S T et al. "E6020: a synthetic Toll-like receptor 4 agonist as a vaccine adjuvant" Expert Rev. Vaccines. 2007 October; 6(5):773-84.). Various TLR agonists (including TLR-4 agonists) have been produced and/or sold by, for example, the Infectious Disease Research Institute (IRDI), Corixa, Esai, Avanti Polar Lipids, Inc., and Sigma Aldrich. Another exemplary adjuvant that activates TLRs comprises a mixture of MPL, Trehalose Dicoynomycolate (TDM), and dioctadecyldimethylammonium bromide (DDA). Another TLR-activating adjuvant is R848 (resiquimod).

In some embodiments, the adjuvant is or comprises a saponin. Typically, the saponin is a triterpene glycoside, such as those isolated from the bark of the *Quillaja saponaria* tree. A saponin extract from a biological source can be further fractionated (e.g., by chromatography) to isolate the portions of the extract with the best adjuvant activity and with acceptable toxicity. Typical fractions of extract from *Quillaja saponaria* tree used as adjuvants are known as fractions A and C.

A particular form of saponins that may be used in vaccine formulations described herein is immunostimulating complexes (ISCOMs). ISCOMs are an art-recognized class of adjuvants, that generally comprise *Quillaja* saponin fractions and lipids (e.g., cholesterol and phospholipids such as phosphatidyl choline). In certain embodiments, an ISCOM is assembled together with a polypeptide or nucleic acid of interest. However, different saponin fractions may be used in different ratios. In addition, the different saponin fractions may either exist together in the same particles or have substantially only one fraction per particle (such that the indicated ratio of fractions A and C are generated by mixing together particles with the different fractions). In this context, "substantially" refers to less than 20%, 15%, 10%, 5%, 4%, 3%, 2% or even 1%. Such adjuvants may comprise fraction A and fraction C mixed into a ratio of 70-95 A:30-5 C, such as 70 A:30 C to 75 A:5 C, 75 A:5 C to 80 A:20 C, 80 A:20 C to 85 A:15 C, 85 A:15 C to 90 A:10 C, 90 A:10 C to 95 A:5 C, or 95 A:5 C to 99 A:1 C.

In certain embodiments, combinations of adjuvants are used. Three exemplary combinations of adjuvants are MPL and alum, E6020 and alum, and MPL and an ISCOM.

Adjuvants may be covalently bound to antigens. In some embodiments, the adjuvant may comprise a protein which induces inflammatory responses through activation of antigen-presenting cells (APCs). In some embodiments, one or more of these proteins can be recombinantly fused with an antigen of choice, such that the resultant fusion molecule promotes dendritic cell maturation, activates dendritic cells to produce cytokines and chemokines, and ultimately, enhances presentation of the antigen to T cells and initiation of T cell responses (see Wu et al., Cancer Res 2005; 65(11), pp 4947-4954). In certain embodiments, a polypeptide, including a fusion protein, described herein is presented in the context of the trivalent conjugate system, comprising a fusion protein of S. pneumoniae Pneumococcal surface adhesin A (PsaA) with the pneumolysoid PdT and a cell wall polysaccharide (PsaA:PdT-CPs), described in Lu et al. ("Protection against Pneumococcal colonization and fatal pneumonia by a trivalent conjugate of a fusion protein with the cell wall polysaccharide." Infect Immun. 2009 May; 77(5):2076-83). PdT carries three amino acid substitutions (W433F, D385N, and C428G) which render the molecule nontoxic but do not interfere with its TLR-4-mediated inflammatory properties. Conjugation of a polysaccharide to the fusion of a polypeptide to the TLR-4-agonist PdT enhances immunological response to the polypeptide. In some embodiments, one or more polypeptides described herein are used in place of PsaA in the trivalent conjugate. The trivalent conjugate system typically includes alum and is usually administered parenterally. Other exemplary adjuvants that may be covalently bound to antigens comprise polysaccharides, pneumolysin, synthetic peptides, lipopeptides, and nucleic acids.

Typically, the same adjuvant or mixture of adjuvants is present in each dose of a vaccine. Optionally, however, an adjuvant may be administered with the first dose of vaccine and not with subsequent doses (i.e., booster shots). Alternatively, a strong adjuvant may be administered with the first dose of vaccine and a weaker adjuvant or lower dose of the strong adjuvant may be administered with subsequent doses. The adjuvant can be administered before the administration of the antigen, concurrent with the administration of the antigen or after the administration of the antigen to a subject (sometimes within 1, 2, 6, or 12 hours, and sometimes within 1, 2, or 5 days). Certain adjuvants are appropriate for human patients, non-human animals, or both.

2. Other Components

In addition to the antigens and the adjuvants described above, a vaccine formulation or immunogenic composition may include one or more additional components.

In certain embodiments, the vaccine formulation or immunogenic composition may include one or more stabilizers such as sugars (such as sucrose, glucose, or fructose), phosphate (such as sodium phosphate dibasic, potassium phosphate monobasic, dibasic potassium phosphate, or monosodium phosphate), glutamate (such as monosodium L-glutamate), gelatin (such as processed gelatin, hydrolyzed gelatin, or porcine gelatin), amino acids (such as arginine, asparagine, histidine, L-histidine, alanine, valine, leucine, isoleucine, serine, threonine, lysine, phenylalanine, tyrosine, and the alkyl esters thereof), inosine, or sodium borate.

In certain embodiments, the vaccine formulation or immunogenic composition includes one or more buffers such as a mixture of sodium bicarbonate and ascorbic acid.

In some embodiments, the vaccine formulation may be administered in saline, such as phosphate buffered saline (PBS), or distilled water.

In certain embodiments, the vaccine formulation or immunogenic composition includes one or more surfactants such as polysorbate 80 (TWEEN® 80), TRITON™ X-100, Polyethylene glycol tert-octylphenyl ether t-Octylphenoxypolyethoxyethanol 4-(1,1,3,3-Tetramethylbutyl)phenyl-polyethylene glycol (TRITON™ X-100); Polyoxyethylene-sorbitan monolaurate, Polyethylene glycol sorbitan monolaurate (TWEEN® 20); and 4-(1,1,3,3-Tetramethylbutyl)phenol polymer with formaldehyde and oxirane (TYLOXAPOL). A surfactant can be ionic or nonionic.

In certain embodiments, the vaccine formulation or immunogenic composition includes one or more salts such as sodium chloride, ammonium chloride, calcium chloride, or potassium chloride.

In certain embodiments, a preservative is included in the vaccine or immunogenic composition. In other embodiments, no preservative is used. A preservative is most often used in multi-dose vaccine vials, and is less often needed in single-dose vaccine vials. In certain embodiments, the preservative is 2-phenoxyethanol, methyl and propyl parabens, benzyl alcohol, and/or sorbic acid.

In certain embodiments, the vaccine formulation or immunogenic composition is a controlled release formulation.

F. Use of Vaccines

The S. pneumoniae vaccines described herein may be used for prophylactic and/or therapeutic treatment of S. pneumoniae. Accordingly, this application provides a method for treating a subject suffering from or susceptible to S. pneumoniae infection, comprising administering an effective amount of any of the vaccine formulations described herein. In some aspects, the method inhibits S. pneumoniae colonization in an individual. In some aspects, the method inhibits S. pneumoniae symptoms, invasive disease or sequelae, such as sepsis, pneumonia, meningitis, otitis media, sinusitis or infection of other sites or organs with S. pneumoniae. The subject receiving the vaccination may be a male or a female, and may be a child or adult. In some embodiments, the subject being treated is a human. In other embodiments, the subject is a non-human animal.

1. Prophylactic Use

In prophylactic embodiments, the vaccine is administered to a subject to induce an immune response that can help protect against the establishment of S. pneumoniae, for example by protecting against colonization, the first and necessary step in disease. Thus, in some aspects, the method inhibits infection by S. pneumoniae in a non-colonized or uninfected subject. In another aspect, the method may reduce the duration of colonization in an individual who is already colonized.

In some embodiments, the vaccine compositions of the invention confer protective immunity, allowing a vaccinated individual to exhibit delayed onset of symptoms or sequelae, or reduced severity of symptoms or sequelae, as the result of his or her exposure to the vaccine. In certain embodiments, the reduction in severity of symptoms or sequelae is at least 25%, 40%, 50%, 60%, 70%, 80% or even 90%. In particular embodiments, vaccinated individuals may display no symptoms or sequelae upon contact with S. pneumoniae, do not become colonized by S. pneumoniae, or both. Protective immunity is typically achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Humoral immunity is typically the result of IgG antibodies and IgM antibodies in serum. Cellular immunity can be achieved through cytotoxic T lymphocytes or through delayed-type hypersensitivity that involves macrophages and T lymphocytes, as well as other mechanisms involving T cells without a requirement for antibodies. In particular, cellular immunity may be mediated by $T_H1$ or $T_H17$ cells.

Essentially any individual has a certain risk of becoming infected with S. pneumoniae. However, certain sub-populations have an increased risk of infection. In some embodiments, a vaccine formulation as described herein (e.g., a composition comprising one or more polypeptides from Table 1, 2 or 3, or nucleic acids encoding the polypeptides, or antibodies reactive with the polypeptides) is administered to patients that are immunocompromised.

An immunocompromising condition arising from a medical treatment is likely to expose the individual in question to a higher risk of infection with S. pneumoniae. It is possible to treat an infection prophylactically in an individual having the immunocompromised condition before or during treatments known to compromise immune function. By prophylactically treating with an antigenic composition (e.g., two or more antigens from Table 1 or 2, or an antigen from Table 3, or nucleic acids encoding the antigens), or with antibodies reactive to two or more antigens from Table 1 or 2, or to an antigen from Table 3, before or during a treatment known to compromise immune function, it is possible to prevent a subsequent S. pneumoniae infection or to reduce the risk of the individual contracting an infection due to the immunocompromised condition. Should the individual contract an S. pneumoniae infection e.g., following a treatment leading to an immunocompromised condition it is also possible to treat the infection by administering to the individual an antigen composition.

The following groups are at increased risk of pneumococcal disease or its complications, and therefore it is advantageous for subjects falling into one or more of these groups to receive a vaccine formulation described herein: children, especially those from 1 month to 5 years old or 2 months to 2 years old; children who are at least 2 years of age with asplenia, splenic dysfunction or sickle-cell disease; children who are at least 2 years of age with nephrotic syndrome, chronic cerebrospinal fluid leak, HIV infection or other conditions associated with immunosuppression.

In another embodiment, at least one dose of the pneumococcal antigen composition is given to adults in the following groups at increased risk of pneumococcal disease or its complications: all persons 65 years of age; adults with asplenia, splenic dysfunction or sickle-cell disease; adults with the following conditions: chronic cardiorespiratory disease, cirrhosis, alcoholism, chronic renal disease, nephrotic syndrome, diabetes mellitus, chronic cerebrospinal fluid leak, HIV infection, AIDS and other conditions associated with immunosuppression (Hodgkin's disease, lymphoma, multiple myeloma, immunosuppression for organ transplantation), individuals with cochlear implants; individuals with long-term health problems such as heart disease and lung disease, as well as individuals who are taking any drug or treatment that lowers the body's resistance to infection, such as long-term steroids, certain cancer drugs, radiation therapy; Alaskan natives and certain Native American populations.

2. Therapeutic Use

In therapeutic applications, the vaccine may be administered to a patient suffering from S. pneumoniae infection, in an amount sufficient to treat the patient. Treating the patient, in this case, refers to reducing S. pneumoniae symptoms and/or bacterial load and/or sequelae bin an infected individual. In some embodiments, treating the patient refers to reducing the duration of symptoms or sequelae, or reducing the intensity of symptoms or sequelae. In some embodiments, the vaccine reduces transmissibility of S. pneumoniae from the vaccinated patient. In certain embodiments, the reductions described above are at least 25%, 30%, 40%, 50%, 60%, 70%, 80% or even 90%.

In therapeutic embodiments, the vaccine is administered to an individual post-infection. The vaccine may be administered shortly after infection, e.g. before symptoms or sequelae manifest, or may be administered during or after manifestation of symptoms or sequelae.

A therapeutic S. pneumoniae vaccine can reduce the intensity and/or duration of the various symptoms or sequelae of S. pneumoniae infection. Symptoms or sequelae of S. pneumoniae infection can take many forms. In some cases, an infected patient develops pneumonia, acute sinusitis, otitis media (ear infection), meningitis, bacteremia, sepsis, osteomyelitis, septic arthritis, endocarditis, peritonitis, pericarditis, cellulitis, or brain abscess.

Sepsis is a rare but life-threatening complication of S. pneumoniae infection, where the bacterium invades the bloodstream and systemic inflammation results. Typically, fever is observed and white blood cell count increases. A further description of sepsis is found in Goldstein, B. et al. "International pediatric sepsis consensus conference: definitions for sepsis and organ dysfunction in pediatrics." Pediatr Crit Care Med. January 2005; 6(1):2-8.

3. Assaying Vaccination Efficacy

The efficacy of vaccination with the vaccines disclosed herein may be determined in a number of ways, in addition to the clinical outcomes described above. First, one may assay IL-17 levels (particularly IL-17A) by stimulating T cells derived from the subject after vaccination. The IL-17 levels may be compared to IL-17 levels in the same subject before vaccination. Increased IL-17 (e.g., IL-17A) levels, such as a 1.5 fold, 2-fold, 5-fold, 10-fold, 20-fold, 50-fold or 100-fold or more increase, would indicate an increased response to the vaccine. Alternatively (or in combination), one may assay neutrophils in the presence of T cells or antibodies from the patient for pneumococcal killing. Increased pneumococcal killing, such as a 1.5 fold, 2-fold, 5-fold, 10-fold, 20-fold, 50-fold or 100-fold or more increase, would indicate an increased response to the vaccine. In addition, one may measure $T_H17$ cell activation, where increased $T_H17$ cell activation, such as a 1.5 fold, 2-fold, 5-fold, 10-fold, 20-fold, 50-fold or 100-fold or more increase, correlates with an increased response to the vaccine. One may also measure levels of an antibody specific to the vaccine, where increased levels of the specific antibody, such as a 1.5 fold, 2-fold, 5-fold, 10-fold, 20-fold, 50-fold or 100-fold or more increase, are correlated with increased vaccine efficacy. In certain embodiments, two or more of these assays are used. For example, one may measure IL-17 levels and the levels of vaccine-specific antibody. Alternatively, one may follow epidemiological markers such as incidence of, severity of, or duration of pneumococcal infection in vaccinated individuals compared to unvaccinated individuals.

Vaccine efficacy may also be assayed in various model systems such as the mouse model. For instance, BALB/c or C57BL/6 strains of mice may be used. After administering the test vaccine to a subject (as a single dose or multiple doses), the experimenter administers a challenge dose of *S. pneumoniae*. In some cases, a challenge dose administered intranasally is sufficient to cause *S. pneumoniae* colonization (especially nasal colonization) in an unvaccinated animal, and in some cases a challenge dose administered via aspiration is sufficient to cause sepsis and a high rate of lethality in unvaccinated animals. One can then measure the reduction in colonization or the reduction in lethality in vaccinated animals. Examples 1-2 and 4 show the efficacy of polypeptides of Table 1 in inhibiting *S. pneumoniae* nasal colonization following intranasal challenge in the mouse model. Examples 5 and 6 show the efficacy of polypeptides of Table 1 in protecting against sepsis and death following infection with *S. pneumoniae* via aspiration in the mouse model.

G. Use of Immunogenic Compositions

1. Defense Against *S. pneumoniae* Infection

The immunogenic compositions of the present disclosure are designed to elicit an immune response against *S. pneumoniae*. Compositions described herein (e.g., ones comprising one or more polypeptides, including fusion proteins, of Table 1, 2 or 3, or nucleic acids encoding the polypeptides) may stimulate an antibody response or a cell-mediated immune response, or both, in the mammal to which it is administered. In some embodiments, the composition stimulates a $T_H1$-biased CD4$^+$ T cell response, a $T_H17$-biased CD4$^+$ T cell response and/or a CD8$^+$ T cell response. In some embodiments, the composition stimulates an antibody response. In some embodiments, the composition stimulates a $T_H1$-biased CD4$^+$ T cell response, $T_H17$-biased CD4$^+$ T cell response and/or a CD8$^+$ T cell response, and an antibody response.

In certain embodiments, the composition (e.g., one comprising one or more polypeptides of Table 1, 2 or 3, or nucleic acids encoding the polypeptides, or antibodies reactive with the peptides) includes a cytokine or nucleotide coding region encoding a cytokine such as IL-17, to provide additional stimulation to the immune system of the mammal. In certain embodiments, the composition comprises a cytokine such as IL-17.

While not wishing to be bound by theory, in some embodiments a $T_H17$ cell response is desirable in mounting an immune response to the compositions disclosed herein, e.g., ones comprising one or more polypeptides of Table 1, 2 or 3. In certain embodiments, an active $T_H17$ response is beneficial in clearing a pneumococcal infection. For instance, mice lacking the IL-17A receptor show decreased whole cell vaccine-based protection from a pneumococcal challenge (Lu et al., "Interleukin-17A mediates acquired immunity to pneumococcal colonization." PLoS Pathog. 2008 Sep. 19; 4(9)).

Thus, herein is provided a method of increasing IL-17 production by administering the compositions described herein (e.g., ones comprising one or more polypeptides of Table 1, 2 or 3) to a subject. Furthermore, this application provides a method of activating $T_H17$ cells by administering said compositions to a subject. In certain embodiments, increased IL-17A levels result in increased pneumococcal killing by neutrophils or neutrophil-like cells, for instance by inducing recruitment and activation of neutrophils of neutrophil-like cells. In certain embodiments, this pneumococcal killing is independent of antibodies and complement. However, specific antibody production and complement activation may be useful additional mechanisms that contribute to clearing of a pneumococcal infection.

Immunogenic compositions containing immunogenic polypeptides or polynucleotides encoding immunogenic polypeptides together with a pharmaceutical carrier are also provided.

In some instances, the immunogenic composition comprises one or more nucleic acids encoding one or more polypeptides of SEQ ID NOs: 1-26 and 47-54, such as one or more polypeptides selected from SEQ ID NOs: 47-54. In some embodiments these nucleic acids are expressed in the immunized individual, producing the encoded *S. pneumoniae* antigens, and the *S. pneumoniae* antigens so produced can produce an immunostimulatory effect in the immunized individual.

Such a nucleic acid-containing immunostimulatory composition may comprise, for example, an origin of replication, and a promoter that drives expression of one or more nucleic acids encoding one or more polypeptides of SEQ ID NOs: 47-54. Such a composition may also comprise a bacterial plasmid vector into which is inserted a promoter (sometimes a strong viral promoter), one or more nucleic acids encoding one or more polypeptides of SEQ ID NOs: 47-54, and a polyadenylation/transcriptional termination sequence. In some instances, the nucleic acid is DNA.

H. Doses and Routes of Administration

1. Dosage Forms, Amounts, and Timing

The amount of antigen in each vaccine or immunogenic composition dose is selected as an effective amount, which induces a prophylactic or therapeutic response, as described above, in either a single dose or over multiple doses. Preferably, the dose is without significant adverse side effects in typical vaccines. Such amount will vary depending upon which specific antigen is employed. Generally, it is expected that a dose will comprise 1-1000 μg of each protein, in some instances 2-100 μg, for instance 4-40 μg. In some aspects, the vaccine formulation comprises 1-1000 μg of the polypeptide and 1-250 μg of the adjuvant. In some embodiments, the appropriate amount of antigen to be delivered will depend on the age, weight, and health (e.g. immunocompromised status) of a subject. When present, typically an adjuvant will be present in amounts from 1 μg-250 μg per dose, for example 50-150 μg, 75-125 μg or 100 μg.

In some embodiments, only one dose of the vaccine is administered to achieve the results described above. In other embodiments, following an initial vaccination, subjects receive one or more boost vaccinations, for a total of two, three, four or five vaccinations. Advantageously, the number is three or fewer. A boost vaccination may be administered, for example, about 1 month, 2 months, 4 months, 6 months, or 12 months after the initial vaccination, such that one vaccination regimen involves administration at 0, 0.5-2 and 4-8 months. It may be advantageous to administer split doses of vaccines which may be administered by the same or different routes.

The vaccines and immunogenic compositions described herein may take on a variety of dosage forms. In certain embodiments, the composition is provided in solid or powdered (e.g., lyophilized) form; it also may be provided in solution form. In certain embodiments, a dosage form is provided as a dose of lyophilized composition and at least one separate sterile container of diluent.

In some embodiments, the composition will be administered in a dose escalation manner, such that successive administrations of the composition contain a higher concentration of composition than previous administrations. In some embodiments, the composition will be administered in a manner such that successive administrations of the composition contain a lower concentration of composition than previous administrations.

In therapeutic applications, compositions are administered to a patient suffering from a disease in an amount sufficient to treat the patient. Therapeutic applications of a composition described herein include reducing transmissibility, slowing disease progression, reducing bacterial viability or replication, or inhibiting the expression of proteins required for toxicity, such as by 90%, 80%, 70%, 60%, 50%, 40%, 30%, 20% or 10% of the levels at which they would occur in individuals who are not treated with the composition.

In prophylactic embodiments, compositions are administered to a human or other mammal to induce an immune response that can inhibit the establishment of an infectious disease or other condition. In some embodiments, a composition may partially block the bacterium from establishing an infection.

In some embodiments, the compositions are administered in combination with antibiotics. This co-administration is particularly appropriate when the pharmaceutical composition is administered to a patient who has recently been exposed (or is suspected of having been recently exposed) to *S. pneumoniae*. Many antibiotics are used to treat pneumococcal infections, including penicillin, amoxicillin, amoxicillin/clavulanate, cefuroxime, cefotaxime, ceftriaxone, and vancomycin. The appropriate antibiotic may be selected based on the type and severity of the infection, as well as any known antibiotic resistance of the infection (Jacobs M R "Drug-resistant *Streptococcus pneumoniae*: rational antibiotic choices" Am J Med. 1999 May 3; 106(5A):19S-25S).

2. Routes of Administration

The vaccine formulations and pharmaceutical compositions herein can be delivered by administration to an individual, typically by systemic administration (e.g., intravenous, intraperitoneal, intramuscular, intradermal, subcutaneous, subdermal, transdermal, intracranial, intranasal, mucosal, anal, vaginal, oral, buccal route or they can be inhaled) or they can be administered by topical application. In some embodiments, the route of administration is intramuscular. In other embodiments, the route of administration is subcutaneous. In yet other embodiments, the route of administration is mucosal. In certain embodiments, the route of administration is transdermal or intradermal.

Certain routes of administration are particularly appropriate for vaccine formulations and immunogenic compositions comprising specified adjuvants. In particular, transdermal administration is one suitable route of administration for *S. pneumoniae* vaccines comprising toxins (e.g. cholera toxin or labile toxin); in other embodiments, the administration is intranasal. Vaccines formulated with Alphavirus replicons may be administered, for example, by the intramuscular or the subcutaneous route. Vaccines comprising Monophosphory Lipid A (MPL), Trehalose Dicoynomycolate (TDM), and dioctadecyldimethylammonium bromide (DDA) are suitable (inter alia) for intramuscular and subcutaneous administration. A vaccine comprising resiquimod may be administered topically or subcutaneously, for example.

3. Formulations

The vaccine formulation or immunogenic composition may be suitable for administration to a human patient, and vaccine or immunogenic composition preparation may conform to USFDA guidelines. In some embodiments, the vaccine formulation or immunogenic composition is suitable for administration to a non-human animal. In some embodiments, the vaccine or immunogenic composition is substantially free of either endotoxins or exotoxins. Endotoxins may include pyrogens, such as lipopolysaccharide (LPS) molecules. The vaccine or immunogenic composition may also be substantially free of inactive protein fragments which may cause a fever or other side effects. In some embodiments, the composition contains less than 1%, less than 0.1%, less than 0.01%, less than 0.001%, or less than 0.0001% of endotoxins, exotoxins, and/or inactive protein fragments. In some embodiments, the vaccine or immunogenic composition has lower levels of pyrogens than industrial water, tap water, or distilled water. Other vaccine or immunogenic composition components may be purified using methods known in the art, such as ion-exchange chromatography, ultrafiltration, or distillation. In other embodiments, the pyrogens may be inactivated or destroyed prior to administration to a patient. Raw materials for vaccines, such as water, buffers, salts and other chemicals may also be screened and depyrogenated. All materials in the vaccine may be sterile, and each lot of the vaccine may be tested for sterility. Thus, in certain embodiments the endotoxin levels in the vaccine fall below the levels set by the USFDA, for example 0.2 endotoxin (EU)/kg of product for an intrathecal injectable composition; 5 EU/kg of product for a non-intrathecal injectable composition, and 0.25-0.5 EU/mL for sterile water.

In certain embodiments, the preparation comprises less than 50%, 20%, 10%, or 5% (by dry weight) contaminating protein. In certain embodiments, the desired molecule is present in the substantial absence of other biological macromolecules, such as other proteins (particularly other proteins which may substantially mask, diminish, confuse or alter the characteristics of the component proteins either as purified preparations or in their function in the subject reconstituted mixture). In certain embodiments, at least 80%, 90%, 95%, 99%, or 99.8% (by dry weight) of biological macromolecules of the same type present (but water, buffers, and other small molecules, especially molecules having a molecular weight of less than 5000, can be present). In some embodiments, the vaccine or immunogenic composition comprising purified subunit proteins contains less than 5%, 2%, 1%, 0.5%, 0.2%, 0.1% of protein from host cells in which the subunit proteins were expressed, relative to the amount of purified subunit. In some embodiments, the desired polypeptides are substantially free of nucleic acids and/or carbohydrates. For instance, in some embodiments, the vaccine or immunogenic composition contains less than 5%, less than 2%, less than 1%, less than 0.5%, less than 0.2%, or less than 0.1% host cell DNA and/or RNA. In certain embodiments, at least 80%, 90%, 95%, 99%, or 99.8% (by dry weight) of biological macromolecules of the same type are present in the preparation (but water, buffers, and other small molecules, especially molecules having a molecular weight of less than 5000, can be present).

It is preferred that the vaccine or immunogenic composition has low or no toxicity, within a reasonable risk-benefit ratio. In certain embodiments, the vaccine or immunogenic composition comprises ingredients at concentrations that are less than $LD_{50}$ measurements for the animal being vaccinated. $LD_{50}$ measurements may be obtained in mice or other experimental model systems, and extrapolated to humans and other animals. Methods for estimating the $LD_{50}$ of compounds in humans and other animals are well-known in the art. A vaccine formulation or immunogenic composition, and any component within it, might have an $LD_{50}$ value in rats of greater than 100 g/kg, greater than 50 g/kg, greater than 20 g/kg, greater than 10 g/kg, greater than 5 g/kg, greater than 2 g/kg, greater than 1 g/kg, greater than 500 mg/kg, greater than 200 mg/kg, greater than 100 mg/kg, greater than 50 mg/kg, greater than 20 mg/kg, or greater than 10 mg/kg. A vaccine formulation or immunogenic composition that comprises a toxin such as botulinum toxin (which can be used as an adjuvant) should contain significantly less than the $LD_{50}$ of botulinum toxin.

The formulations suitable for introduction of the vaccine formulations or pharmaceutical composition vary according to route of administration. Formulations suitable for parenteral administration, such as, for example, by intraarticular (in the joints), intravenous, intramuscular, intradermal, intraperitoneal, intranasal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials.

Injection solutions and suspensions can be prepared from sterile powders, granules, and tablets of the kind previously described. In the case of adoptive transfer of therapeutic T cells, the cells can be administered intravenously or parenterally.

Formulations suitable for oral administration can consist of (a) liquid solutions, such as an effective amount of the polypeptides or packaged nucleic acids suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. The pharmaceutical compositions can be encapsulated, e.g., in liposomes, or in a formulation that provides for slow release of the active ingredient.

The antigens, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like. Aerosol formulations can be delivered orally or nasally.

Suitable formulations for vaginal or rectal administration include, for example, suppositories, which consist of the polypeptides or packaged nucleic acids with a suppository base. Suitable suppository bases include natural or synthetic triglycerides or paraffin hydrocarbons. In addition, it is also possible to use gelatin rectal capsules which consist of a combination of the polypeptides or packaged nucleic acids with a base, including, for example, liquid triglycerides, polyethylene glycols, and paraffin hydrocarbons.

I. Preparation and Storage of Vaccine Formulations and Immunogenic Compositions

The *S. pneumoniae* vaccines and immunogenic compositions described herein may be produced using a variety of techniques. For example, a polypeptide may be produced using recombinant DNA technology in a suitable host cell. A suitable host cell may be bacterial, yeast, mammalian, or other type of cell. The host cell may be modified to express an exogenous copy of one of the relevant polypeptide genes. Typically, the gene is operably linked to appropriate regulatory sequences such as a strong promoter and a polyadenylation sequence. In some embodiments, the promoter is inducible or repressible. Other regulatory sequences may provide for secretion or excretion of the polypeptide of interest or retention of the polypeptide of interest in the cytoplasm or in the membrane, depending on how one wishes to purify the polypeptide. The gene may be present on an extrachromosomal plasmid, or may be integrated into the host genome. One of skill in the art will recognize that it is not necessary to use a nucleic acid 100% identical to the naturally-occurring sequence. Rather, some alterations to these sequences are tolerated and may be desirable. For instance, the nucleic acid may be altered to take advantage of the degeneracy of the genetic code such that the encoded polypeptide remains the same. In some embodiments, the gene is codon-optimized to improve expression in a particular host. The nucleic acid may be produced, for example, by PCR or by chemical synthesis.

Once a recombinant cell line has been produced, a polypeptide may be isolated from it. The isolation may be accomplished, for example, by affinity purification techniques or by physical separation techniques (e.g., a size column).

In a further aspect of the present disclosure, there is provided a method of manufacture comprising mixing one or more polypeptides or an immunogenic fragment or variant thereof with a carrier and/or an adjuvant.

In some embodiments, antigens for inclusion the vaccine formulations and immunogenic compositions may be produced in cell culture. One method comprises providing one or more expression vectors and cloning nucleotides encoding one or more polypeptides selected from polypeptides having an amino acid sequence of Table 1, 2 or 3, such as SEQ ID NO: 47-54, then expressing and isolating the polypeptides.

The immunogenic polypeptides described herein, and nucleic acid compositions that express the polypeptides, can be packaged in packs, dispenser devices, and kits for administering nucleic acid compositions to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition, such as those disclosed herein.

The disclosure is further illustrated by the following examples. The examples are provided for illustrative purposes only. They are not to be construed as limiting the scope or content of the disclosure in any way.

V. EXAMPLES

Example 1

SP2108, SP0148 and SP1634 Polypeptides

Figure 1:
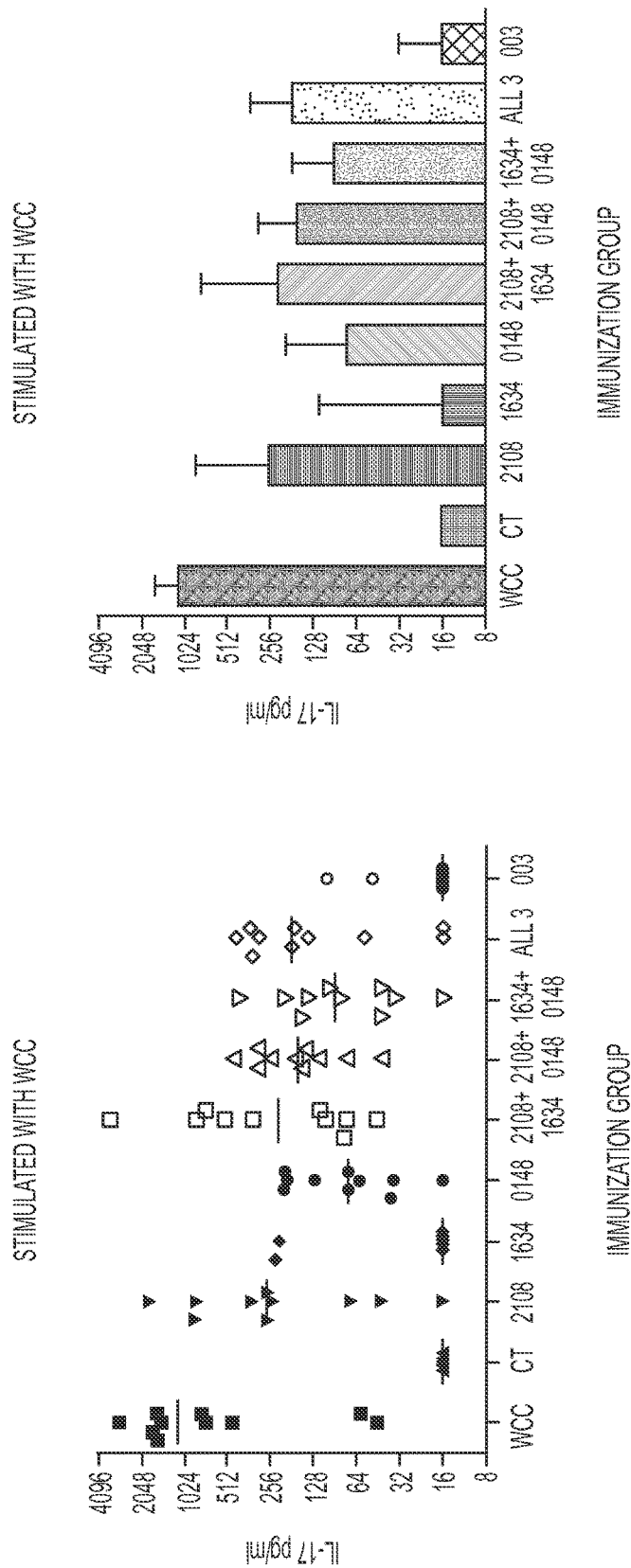
Figure 2:
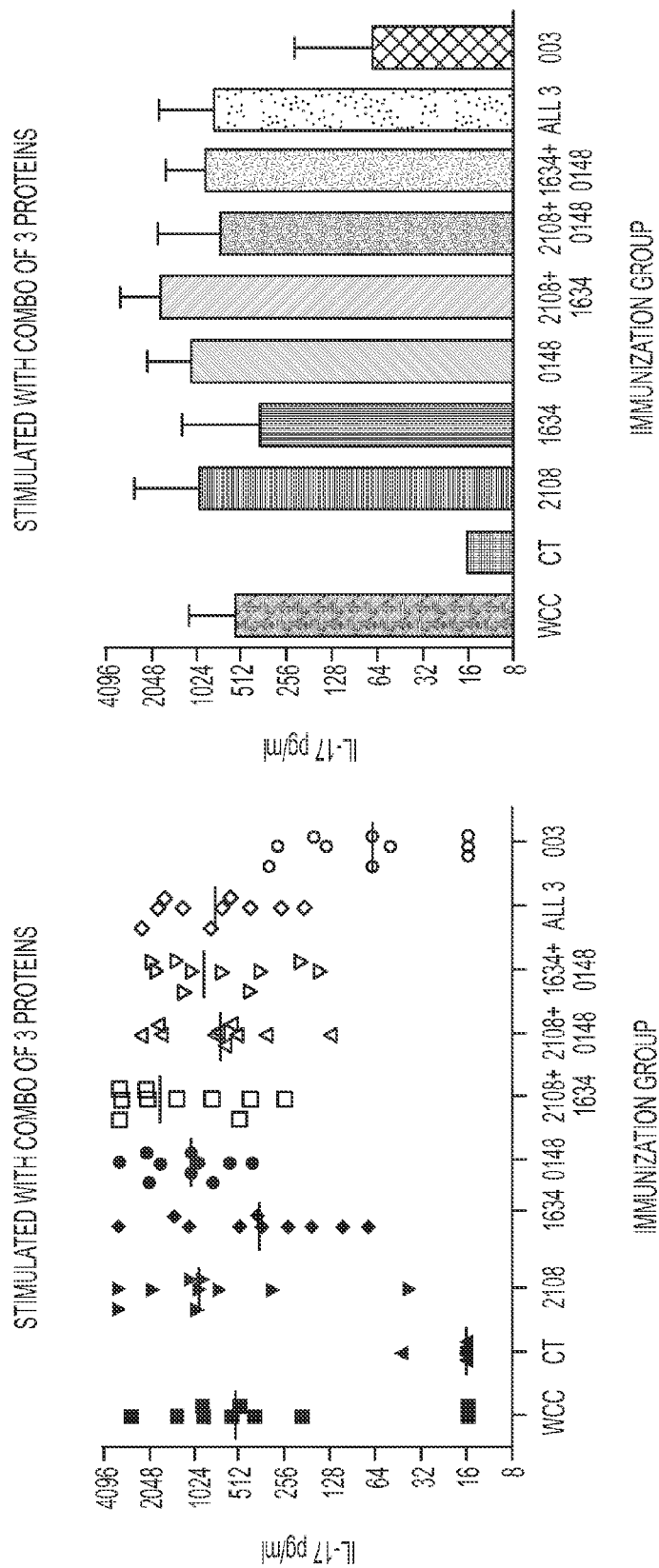
FIG. 2 shows the concentration of IL-17A generated by blood samples from mice that were immunized with the indicated protein(s) and cholera toxin adjuvant, then stimulated with a combination of three proteins (SP2108, SP0148, and SP1634), as described in Example 1.
Figure 3:
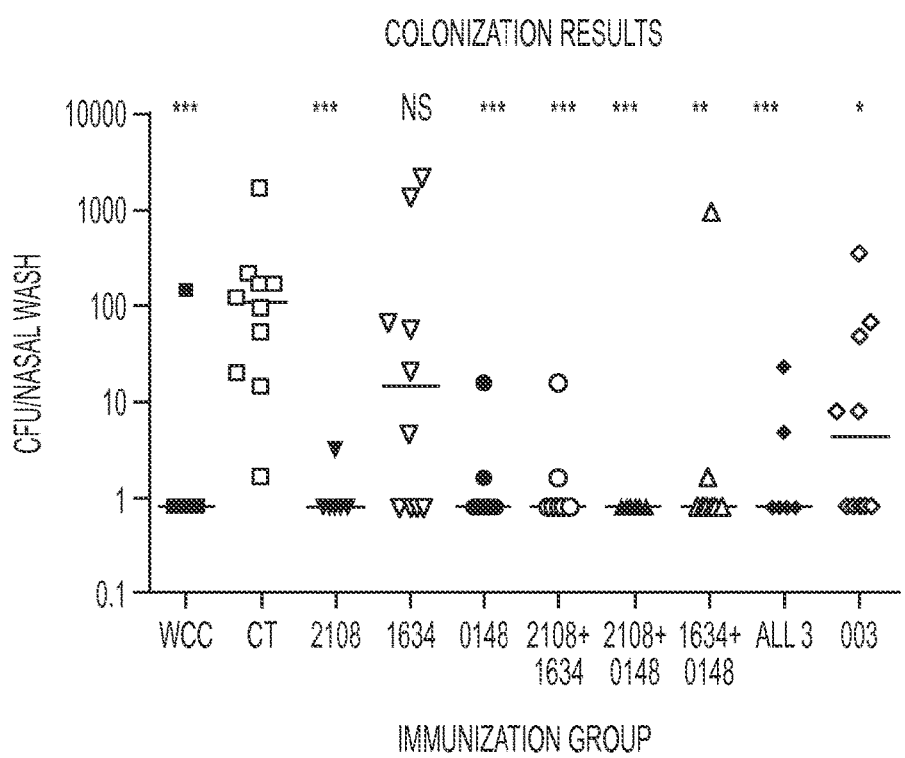
FIG. 3 shows the number of *S. pneumoniae* colonies obtained from a nasal wash in mice that were immunized with the indicated protein(s) and cholera toxin adjuvant, then challenged with intranasal administration of *S. pneumoniae*, as described in Example 1. 003 represents a control unrelated antigen.

The SP2108 polypeptide (SEQ ID NO: 6), SP0148 polypeptide (SEQ ID NO: 2) and SP1634 polypeptide (SEQ ID NO: 25) were formulated as vaccine compositions using 4

µg of the polypeptide in combination with 1 µg cholera toxin adjuvant (CT). For combinations, 4 µg of each polypeptide was used. The compositions were administered intranasally to C57BL/6 mice three times, one week apart. The subjects were then allowed to rest for 3 weeks, and bled at that time for immunogenicity. For this assay, heparinized whole blood was collected from the retrograde orbital sinus. The total PBMC were stimulated with either killed, unencapsulated whole cell S. pneumoniae (WCC) or a combination of the three polypeptides in round bottomed tubes for three days. The supernatants were then harvested and evaluated by ELISA for IL-17 levels. Cholera toxin alone (CT) or an unrelated antigen from HSV (003) were used as negative controls. Results of the IL-17 immunogenicity assay are shown in FIGS. 1 and 2, where the left panels show data in scatter format, and the right panels show data as averages with standard deviations. The subjects were allowed to rest an additional 2 weeks, at which time they were challenged with intranasal administration of live, encapsulated S. pneumoniae. The subjects were sacrificed a week later, and the number of colony-forming units (CFU) was counted from nasal washes. Results of the colonization assay are shown in FIG. 3.

Example 2

SP0148, SP0314, SP0882, and SP2108 Polypeptides Tested in the BALB/c Mouse

Figure 4:
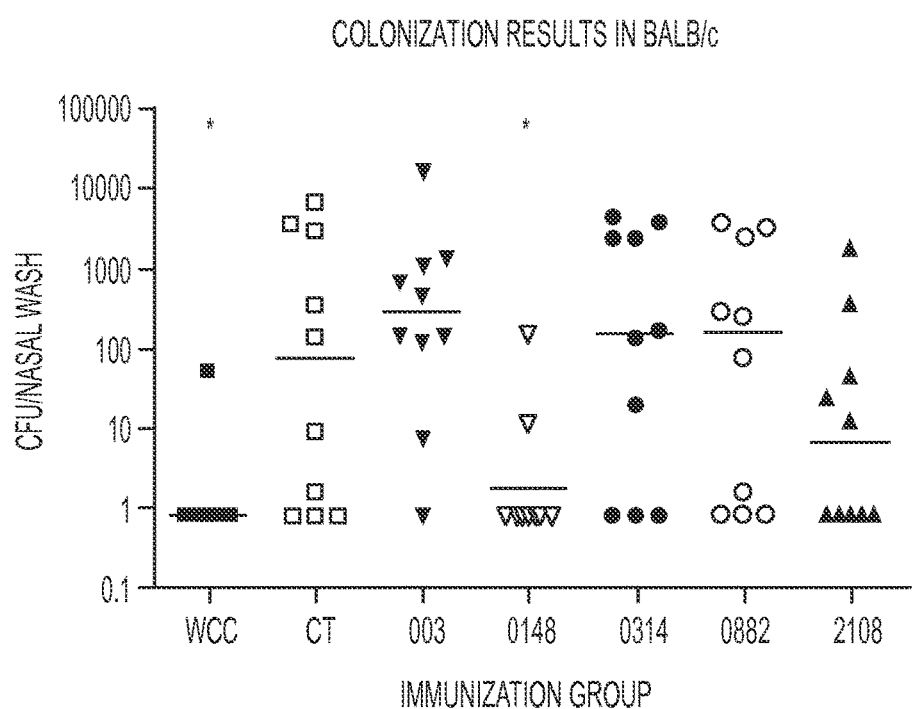
FIG. 4 shows the number of *S. pneumoniae* colonies obtained from a nasal wash in BALB/c mice that were immunized with the indicated protein(s) and cholera toxin adjuvant, then challenged with intranasal administration of *S. pneumoniae*, as described in Example 2.

To determine whether similar immune responses were seen across different mouse genotypes, vaccine compositions were administered to BALB/c mice. Vaccine compositions comprised the polypeptides SP0148 (SEQ ID NO: 2), SP0314 (SEQ ID NO: 26), SP0882 (SEQ ID NO: 17) or SP2108 (SEQ ID NO: 6), and cholera toxin adjuvant (CT). Using a protocol similar to that of Example 1, the mice were immunized, challenged intranasally with S. pneumoniae, and the number of CFU was recorded. The results of this colonization experiment are shown in FIG. 4.

Example 3

SP1912, SP2108 and SP0148 Polypeptides: IL-17A Immunogenicity Assay

Figure 5:
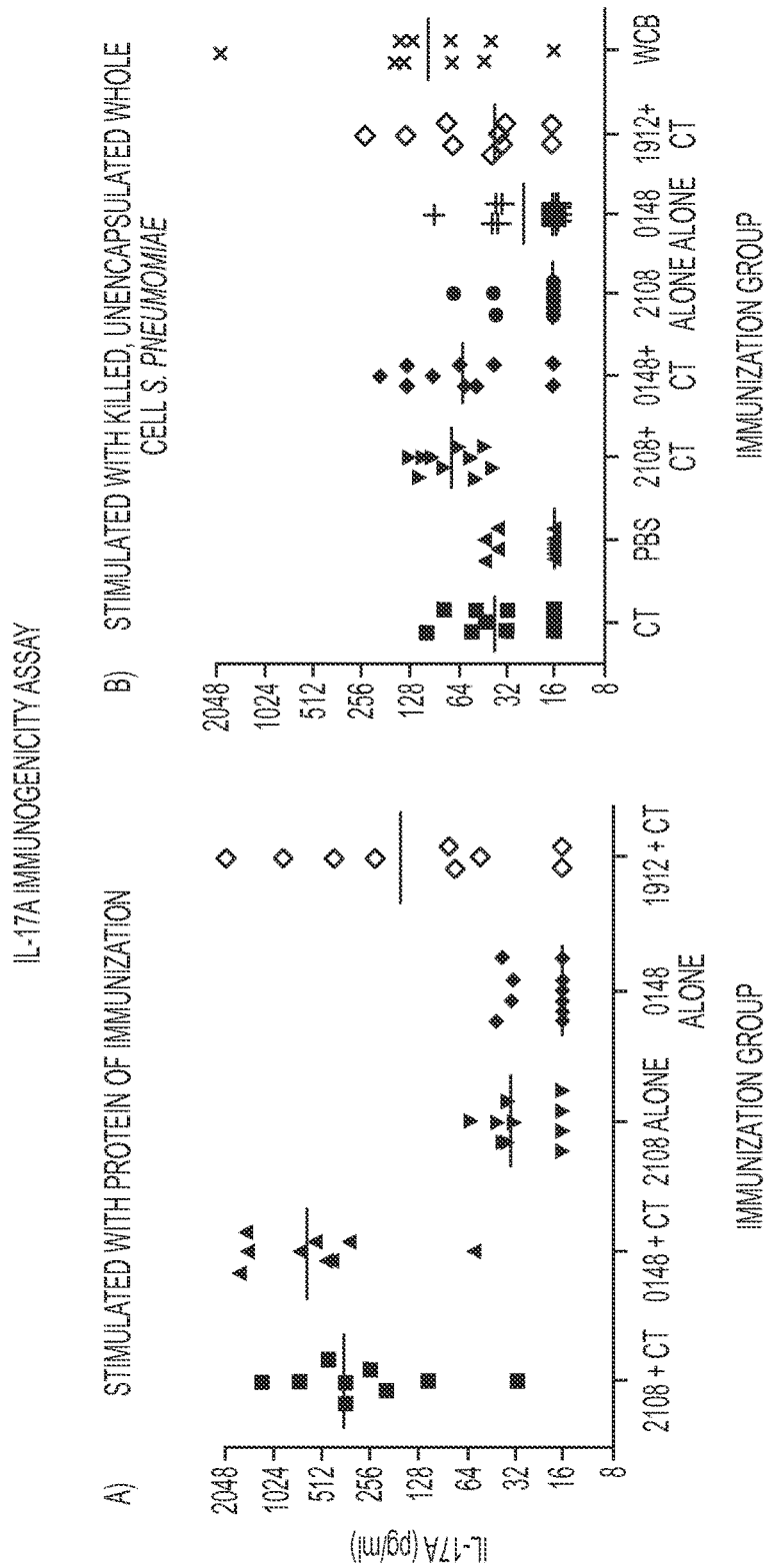
FIG. 5 shows the concentration of IL-17A generated by blood samples from mice that were immunized with the indicated proteins and cholera toxin adjuvant, then stimulated with the protein of immunization (left panel) or killed, unencapsulated whole cell *S. pneumoniae* (right panel), as described in Example 3.

The polypeptides SP1912 (SEQ ID NO: 9), SP2108 (SEQ ID NO: 6) or SP0148 (SEQ ID NO: 2) were formulated as vaccine compositions with cholera toxin adjuvant (CT). The vaccine compositions were administered to mice two times, one week apart. The positive control was killed, unencapsulated whole cell S. pneumoniae+CT (WCB), and the negative controls were CT alone or recombinant proteins without CT (with the exception of SP1912). Three weeks after the last immunization, peripheral blood was collected from the retroorbital sinus and evaluated in a whole blood assay. Briefly, the heparinized whole blood was diluted in media and then cultured in duplicate with A) the protein of immunization, or B) the whole cell vaccine for six days. The supernatants were harvested and IL-17A levels measured by ELISA. Results of the IL-17A immunogenicity assay are shown in FIG. 5. Each symbol in the graph represents responses from individual mice, and the line indicates the median response of the group.

Example 4

SP1912, SP2108 and SP0148 Polypeptides: Colonization Assay

Figure 6:
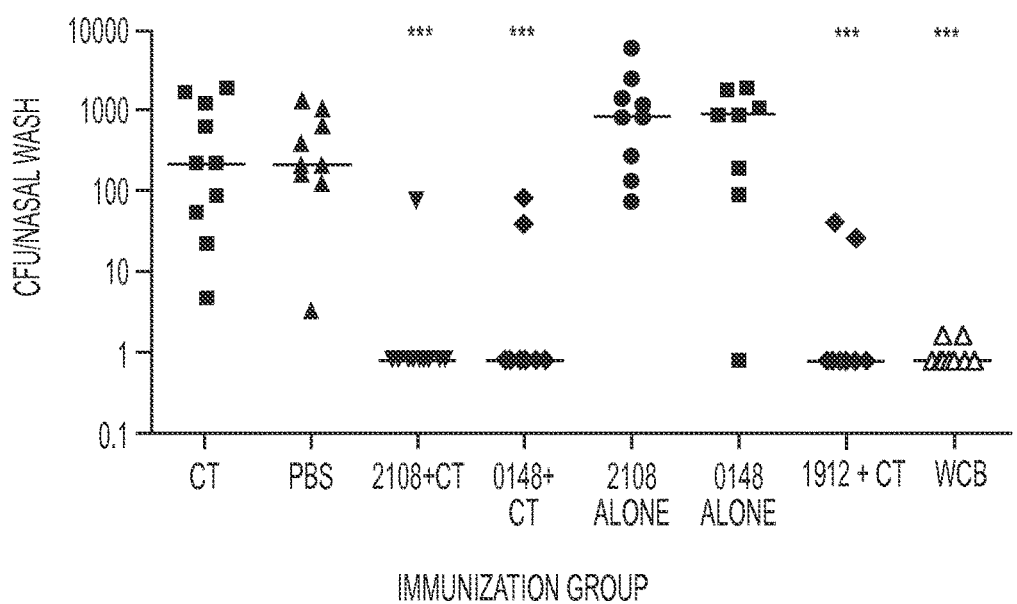
FIG. 6 shows the number of *S. pneumoniae* colonies obtained from a nasal wash in mice that were immunized with the indicated proteins and cholera toxin adjuvant, then challenged with intranasal administration of *S. pneumoniae*, as described in Example 4.

Animals were immunized with vaccine formulations comprising the polypeptides SP1912 (SEQ ID NO:9), SP2108 (SEQ ID NO: 6) or SP0148 (SEQ ID NO: 2) and cholera toxin adjuvant (CT) as described in Example 3, and then challenged intranasally with $10^7$ live type 6B S. pneumoniae four weeks after the last immunization (and one week after retroorbital blood collection). Seven days after challenge, animals were euthanized and the nasopharyngeal cavities lavaged and cultured on permissive media to evaluate the S. pneumoniae titers. Results are shown in FIG. 6 as the colony forming units of bacteria (CFU) per lavage. Each symbol represents a titer from an individual mouse response, and the horizontal line represents the median of the group. (***=p-value <0.05).

Example 5

SP1912 Polypeptide: Aspiration Challenge (Sepsis Assay)

Figure 7:
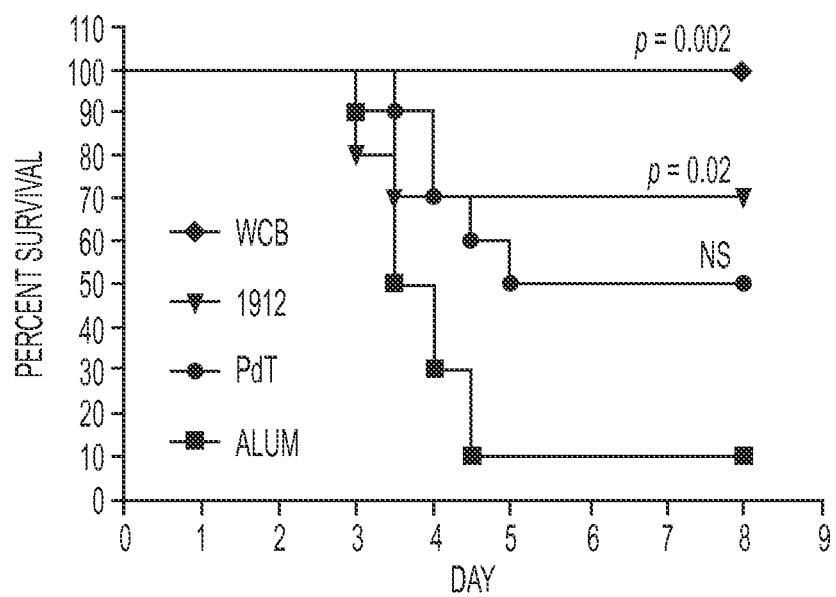
FIG. 7 shows survival of mice that were immunized with the indicated proteins and the adjuvant alum, then underwent aspiration challenge with *S. pneumoniae* as described in Example 5.

Polypeptide SP1912 was evaluated for its ability to protect mice from sepsis. Groups of ten mice were subcutaneously immunized three times, two weeks apart with vaccine compositions comprising either the SP1912 polypeptide (SEQ ID NO: 9) or pneumolysoid (PdT) adsorbed to alum. The positive control was killed, unencapsulated whole cell S. pneumoniae+alum (WCB), and the negative control was alum alone. Three weeks after the final immunization, blood was collected for evaluation of IL-17A response and antibody levels, and then one week later, the mice underwent aspiration challenge with $10^7$ live strain 0603 (type 6B) S. pneumoniae. Animals were monitored for survival for eight days. Results of the aspiration challenge are shown in FIG. 7 as survival curves for each immunized group.

Example 6

Pneumolysoid PdT, SP0148 and SP0641N Polypeptides: Aspiration Challenge (Sepsis Assay)

Figure 8:
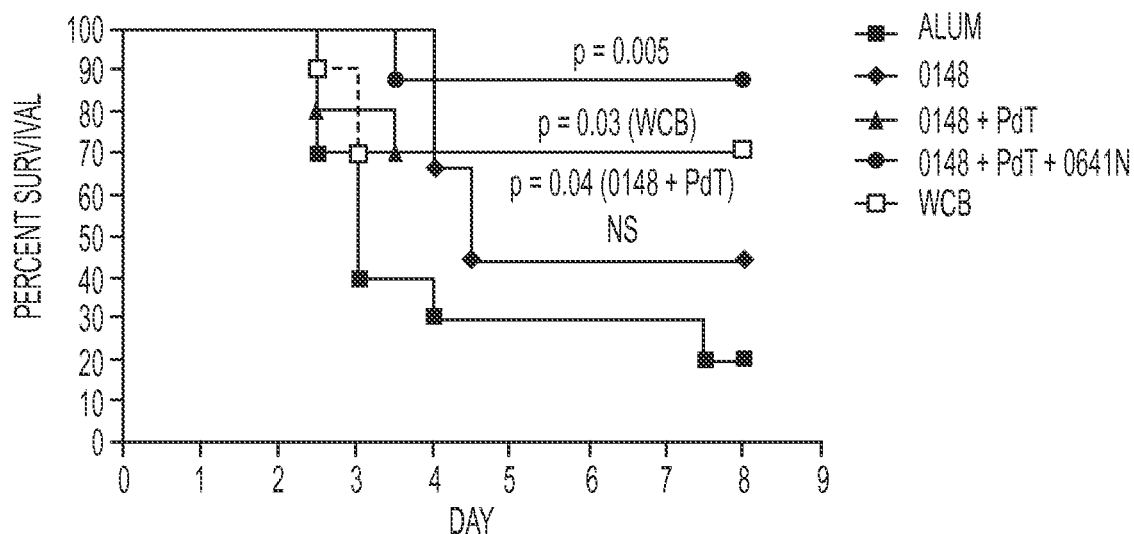
FIG. 8 shows survival of mice that were immunized with the indicated proteins and the adjuvant alum, then underwent aspiration challenge with *S. pneumoniae* as described in Example 6.

Polypeptide SP0148 was evaluated for its ability to protect mice from sepsis when immunized singly or in combination with SP0641N and/or pneumolysoid (PdT). Groups of ten mice were subcutaneously immunized three times, two weeks apart with vaccine compositions comprising polypeptide SP0148 (SEQ ID NO: 2), singly or in combination with polypeptide SP0641N (SEQ ID NO: 13) and/or PdT, adsorbed to alum. The positive control was killed, unencapsulated whole cell S. pneumoniae+alum (WCB), and the negative control was alum alone. Three weeks after the final immunization, blood was collected for evaluation of IL-17 and antibody, and then one week later, the mice underwent aspiration challenge with $10^7$ live strain 0603 (type 6B) S. pneumoniae. Animals were monitored for survival for eight days. The data are shown in FIG. 8 as survival curves for each immunized group.

Example 7

SP1912, SP2108 and SP0148 Polypeptides: Colonization Assay

Figure 9:
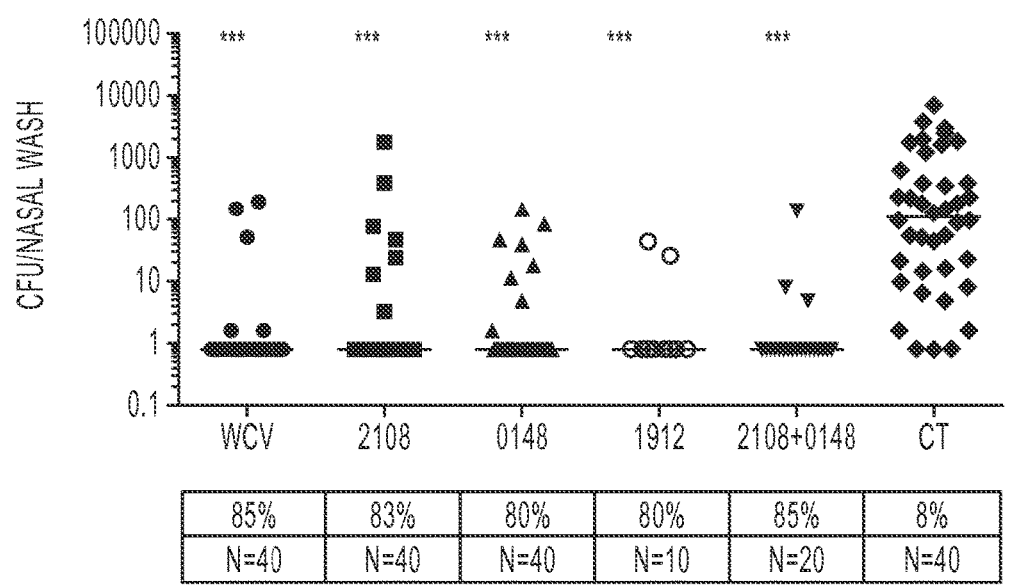
FIG. 9 shows the number of *S. pneumoniae* colonies obtained from a nasal wash in mice that were immunized with the indicated proteins and cholera toxin adjuvant, then challenged with intranasal administration of *S. pneumoniae*, as described in Example 7.

Additional studies were performed essentially as described in Example 4, for a total of four separate studies. Briefly, animals were immunized with vaccine formulations comprising the polypeptides SP1912 (SEQ ID NO: 9), SP2108 (SEQ ID NO: 6), SP0148 (SEQ ID NO: 2), or additionally SP2108 plus SP0148, and cholera toxin adjuvant (CT) as described in Example 3. Control animals were immunized with killed, unencapsulated whole cell *S. pneumoniae* plus CT (WCV), or CT alone Immunized animals were challenged intranasally with $10^7$ live type 6B *S. pneumoniae* four weeks after the last immunization. Seven days after challenge, animals were euthanized and the nasopharyngeal cavities lavaged and cultured on permissive media to evaluate the *S. pneumoniae* titers. Pooled results of four studies are shown in FIG. 9 as the colony forming units of bacteria (CFU) per lavage. Each symbol represents a titer from an individual mouse response, and the horizontal line represents the median of the group. (***=p-value <0.05). N indicates the total number of animals evaluated. Percentages refer to the number of animals protected from colonization.

Example 8

SP1912 and SP0148 Polypeptides: IL-17A Immunogenicity Assay

Figure 10:
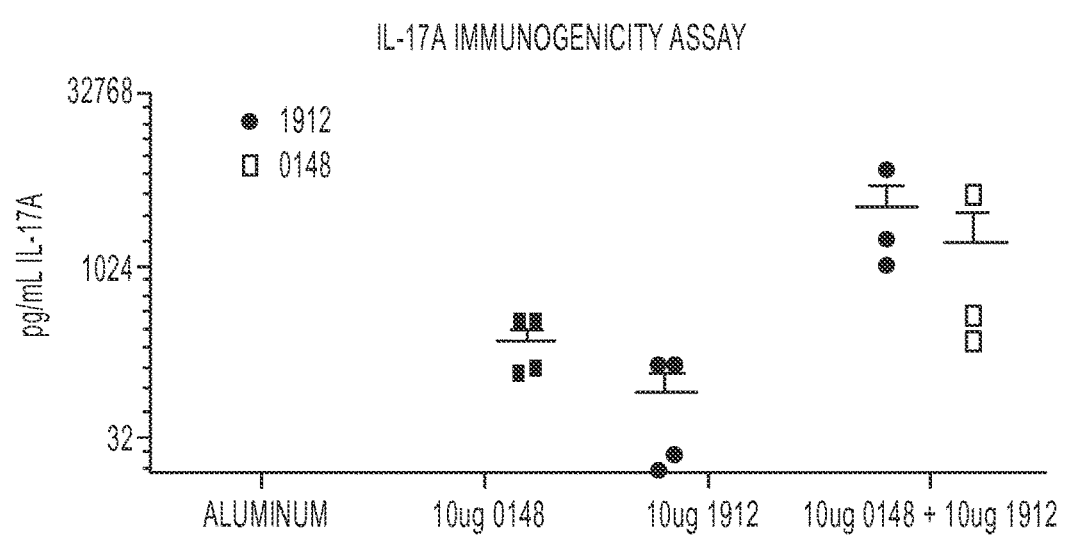
FIG. 10 shows the concentration of IL-17A generated by blood samples from mice that were immunized with the indicated proteins and alum, then stimulated with the proteins indicated at upper left, as described in Example 8.

Groups of ten mice were subcutaneously immunized twice, two weeks apart with vaccine compositions comprising either SP1912 polypeptide (SEQ ID NO: 9), SP0148 polypeptide (SEQ ID NO: 2), or both adsorbed to alum. Control animals were immunized with alum alone. Three weeks after the last immunization, heparinized blood was collected by cardiac puncture and evaluated for IL-17A levels in a whole blood assay. Briefly, the heparinized whole blood was diluted in media and then cultured for six days with the protein(s) of immunization. The supernatants were harvested and IL-17A levels measured by ELISA. Results of the IL-17A immunogenicity assay are shown in FIG. 10. Each symbol in the graph represents responses from individual mice, and the line indicates the median response of the group.

Example 9

SP1912 and SP0148 Polypeptides: Colonization Assay

Figure 11:
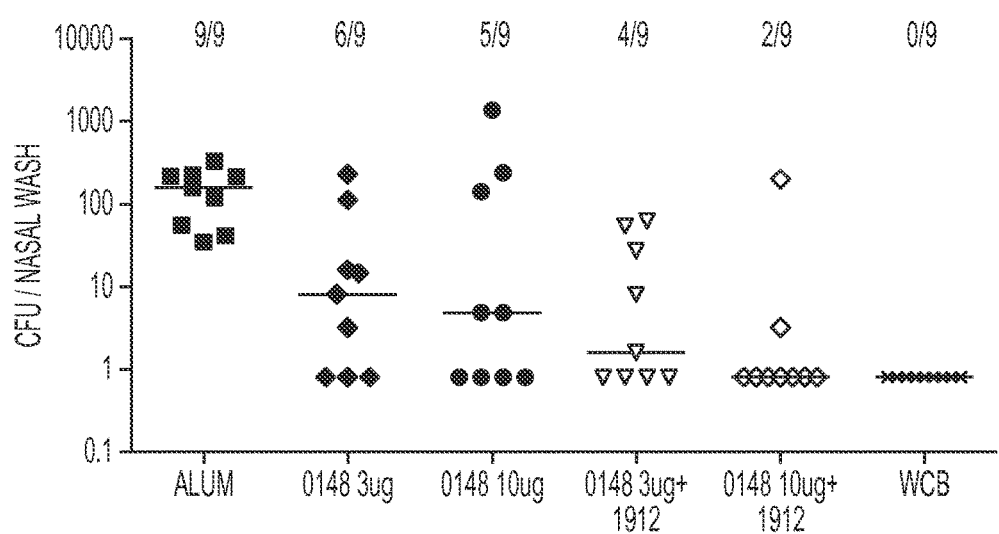
FIG. 11 shows the number of *S. pneumoniae* colonies obtained from a nasal wash in mice that were immunized with the indicated proteins and alum or with killed, unencapsulated whole cell *S. pneumoniae* plus alum (WCV), then challenged with intranasal administration of *S. pneumoniae*, as described in Example 9.

Animals were subcutaneously immunized three times, two weeks apart with vaccine formulations comprising the polypeptides SP0148 (SEQ ID NO: 2) at different doses plus and minus SP1912 (SEQ ID NO: 9), adsorbed to alum. Control animals were immunized with killed, unencapsulated whole cell *S. pneumoniae* plus alum (WCV), or alum alone. Immunized animals were challenged intranasally with $10^7$ live type 6B *S. pneumoniae* four weeks after the last immunization. Seven days after challenge, animals were euthanized and the nasopharyngeal cavities lavaged and cultured on permissive media to evaluate the *S. pneumoniae* titers. Results are shown in FIG. 11 as the colony forming units of bacteria (CFU) per lavage. Each symbol represents a titer from an individual mouse response, and the horizontal line represents the median of the group. The number of animals protected from colonization out of the number of animals in the group is indicated at the top of the figure.

Example 10

SP1912, SP0148, and SP2108 Polypeptides: Colonization Assay

Figure 12:
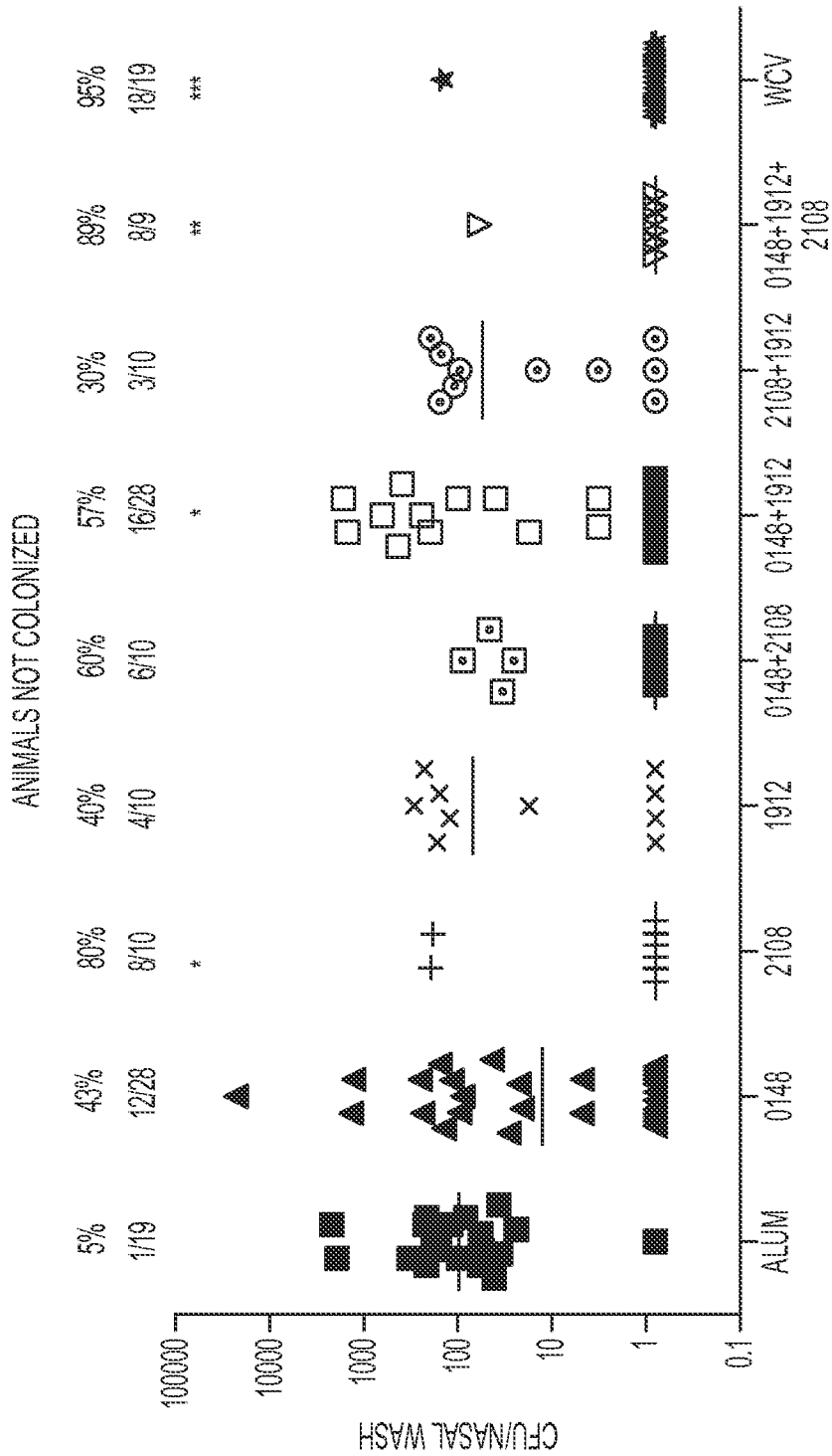
FIG. 12 shows the number of *S. pneumoniae* colonies obtained from a nasal wash in mice that were immunized with the indicated proteins and alum or with killed, unencapsulated whole cell *S. pneumoniae* plus alum (WCV), then challenged with intranasal administration of *S. pneumoniae*, in two pooled studies as described in Example 10.

In two separate studies, animals were subcutaneously immunized three times, two weeks apart with vaccine formulations comprising the polypeptides SP0148 (SEQ ID NO: 2) and SP0148 plus SP1912 (SEQ ID NO: 9), or additionally with SP2108 (SEQ ID NO: 6), SP2108 plus SP0148, and SP2108 plus SP1912, adsorbed to alum. Control animals were immunized with killed, unencapsulated whole cell *S. pneumoniae* plus alum (WCV), or alum alone. Immunized animals were challenged intranasally with $10^7$ live type 6B *S. pneumoniae* four weeks after the last immunization. Seven days after challenge, animals were euthanized and the nasopharyngeal cavities lavaged and cultured on permissive media to evaluate the *S. pneumoniae* titers. Pooled results of the two studies are shown in FIG. 12 as the colony forming units of bacteria (CFU) per lavage. Each symbol represents a titer from an individual mouse response, and the horizontal line represents the median of the group. The number of animals protected from colonization out of the number of animals in the group and corresponding percentage of animals protected from colonization are indicated at the top of the figure. (*p<0.05, p<0.01, *p<0.001 Dunn's Multiple Comparison Test compared to Alum control)

Example 11

Figure 13:
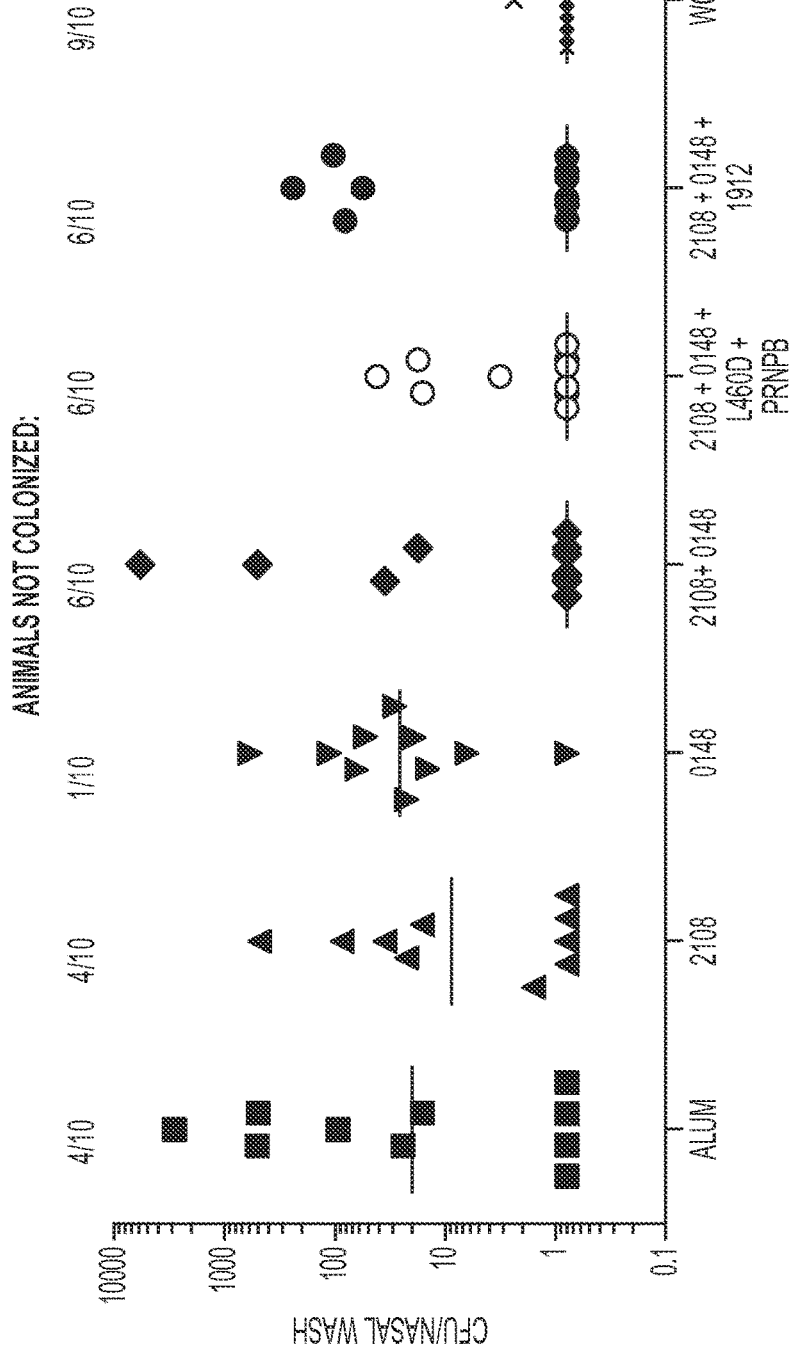
FIG. 13 shows the number of *S. pneumoniae* colonies obtained from a nasal wash in mice that were immunized with the indicated proteins and alum or with killed, unencapsulated whole cell *S. pneumoniae* plus alum (WCB), then challenged with intranasal administration of *S. pneumoniae*, as described in Example 11.

Pneumolysoid L460D, PspA Derivative CD2, SP1912, SP0148, and SP2108 Polypeptides: Colonization Assay Animals were subcutaneously immunized three times, two weeks apart with vaccine formulations comprising the polypeptides SP0148 (SEQ ID NO: 2), SP2108 (SEQ ID NO: 6), SP0148 plus SP2108, and SP0148 plus SP2108 in combination with SP1912 (SEQ ID NO: 9) or known *S. pneumoniae* antigens L460D plus CD2, adsorbed to alum. Two separate studies were conducted. Control animals were immunized with alum alone. Immunized animals were challenged intranasally with $10^7$ live type 6B *S. pneumoniae* four weeks after the last immunization. Seven days after challenge, animals were euthanized and the nasopharyngeal cavities lavaged and cultured on permissive media to evaluate the *S. pneumoniae* titers. Results of the second study are shown in FIG. 13 as the colony forming units of bacteria (CFU) per lavage. Each symbol represents a titer from an individual mouse response, and the horizontal line represents the median of the group. The number of animals protected from colonization out of the number of animals in the group is indicated at the top of the figure.

The chart below shows the absolute number and corresponding percentage of animals protected from colonization in the four studies described in Examples 10 and 11.

| | 1 | 2 | 3 | 4 | # not colonized/ total | % not colonized |
|---|---|---|---|---|---|---|
| Alum | 0/9 | 1/10 | 2/10 | 4/10 | 7/39 | 18% |
| WCV | 9/9 | 9/10 | 9/10 | 9/10 | 36/39 | 92% |
| 0148 | 8/18 | 4/10 | 5/9 | 1/10 | 18/47 | 38% |
| 2108 | | 8/10 | 6/10 | 4/10 | 18/30 | 60% |
| 1912 | | 4/10 | | | 4/10 | 40% |
| 0148 + 2108 | | 6/10 | 3/10 | 6/10 | 15/30 | 50% |
| 0148 + 1912 | 13/18 | 3/10 | | | 16/28 | 57% |
| 2108 + 1912 | | 3/10 | | | 3/10 | 30% |
| 0148 + 2108 + 1912 | | 8/9 | 8/10 | 6/10 | 22/29 | 76% |
| 0148 + 2108 + L460D + CD2 | | | 2/10 | 6/10 | 8/20 | 40% |

Example 12

PspA, SP0148 and SP2108 Passive Antibody Transfer and Aspiration Challenge (Sepsis Assay)

Figure 14:
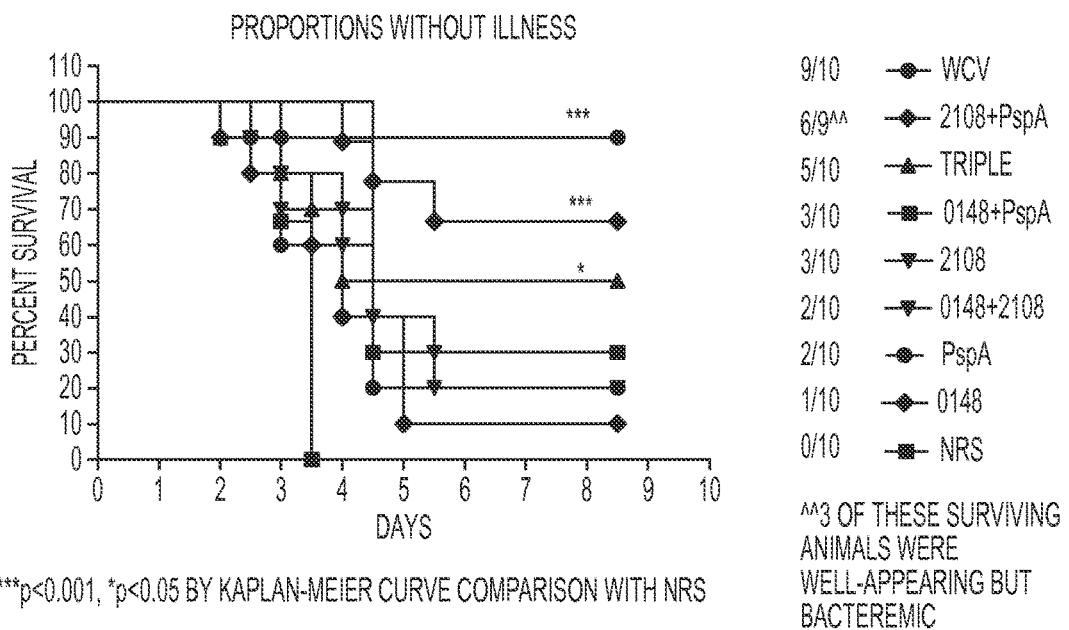
FIG. 14 shows survival of mice that were injected with antibodies or sera specific to the indicated proteins, then underwent aspiration challenge with *S. pneumoniae*, as described in Example 12.

Groups of ten mice were injected with monoclonal antibodies specific for PspA, heat-inactivated rabbit sera specific for SP0148, SP2108, or combinations of these. Antibody and antisera concentrations and total injection volumes were adjusted with normal rabbit serum (NRS) and PBS. Control animals were injected with NRS, or serum against killed, unencapsulated whole cell *S. pneumoniae* (WCV). One day after injection, the mice underwent aspiration challenge with $10^6$ live *S. pneumoniae* type WU-2 (ST-3). Animals were monitored for survival for eight days. The data are shown in FIG. 14 as survival curves for each immunized group.

FIG. 15 shows the percent of animals protected from sepsis in six separate aspiration challenge studies, two of which are described in more detail in Examples 6 and 12.

Example 13

SP0148, SP2108, and SP1912 Fusion Proteins: IL-17A Immunogenicity Assay

Figure 16A:
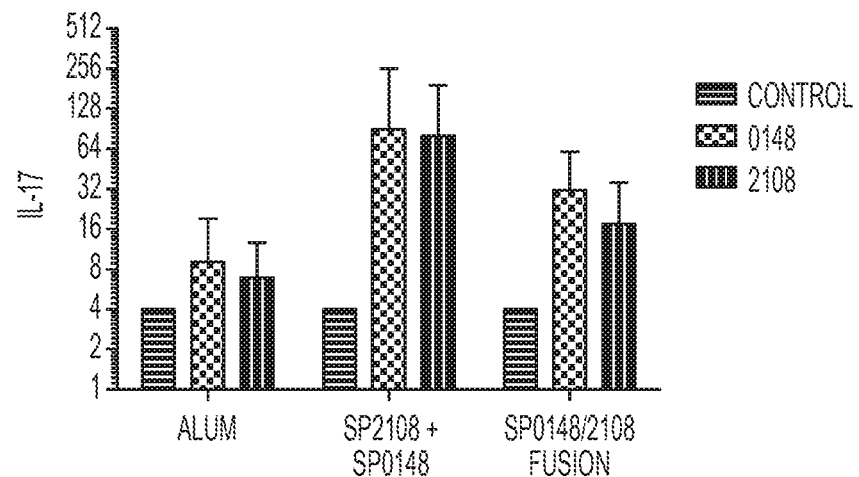
FIGS. 16A-16C show the mean IL-17A response generated by blood samples from mice that were immunized with the indicated proteins and alum, then stimulated with the proteins indicated at upper right, as described in Example 13.
Figure 16B:
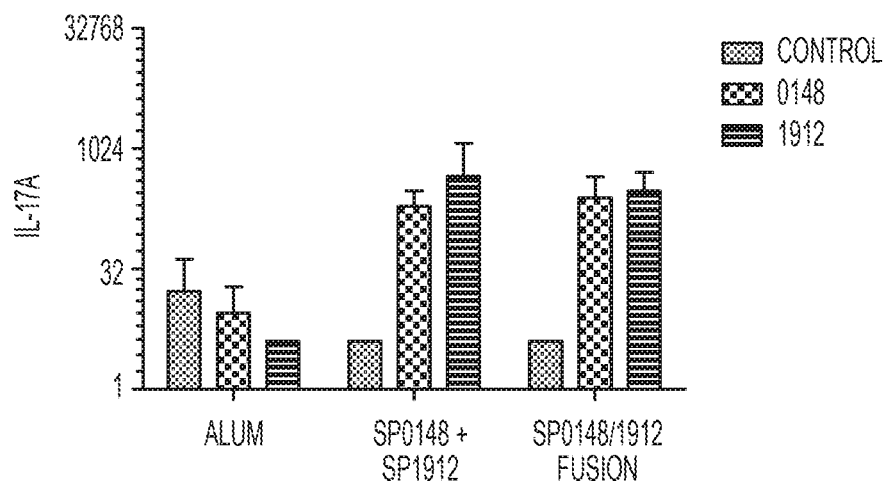
Figure 16C:
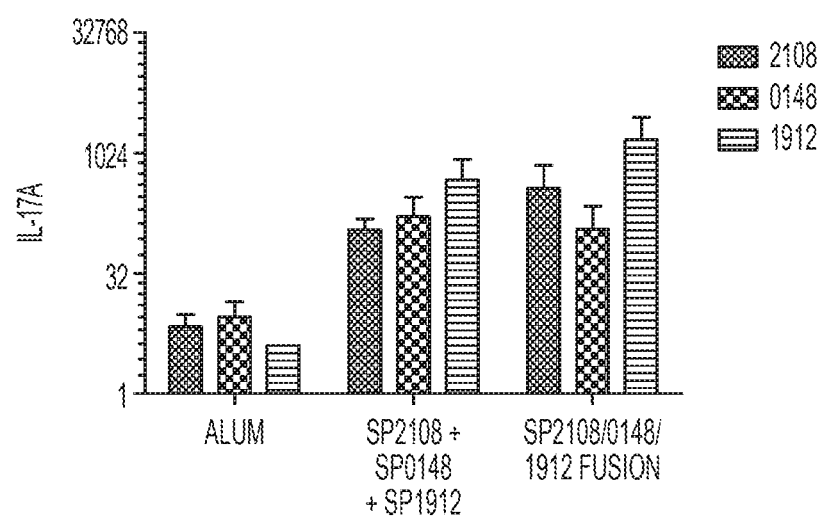

Groups of four mice were subcutaneously immunized three times, two weeks apart with vaccine compositions comprising the fusion proteins SP2108/0148/1912 (SEQ ID NO: 53), SP0148/2108 (SEQ ID NO: 48), SP0148/1912 (SEQ ID NO: 50) or the comparable combinations of the single antigens SP2108 (SEQ ID NO: 6), SP0148 (SEQ ID NO: 2) and SP1912 (SEQ ID NO: 9), adsorbed to alum. Control animals were immunized with alum alone. Two weeks after the last immunization, peripheral blood was collected from the retroorbital sinus and evaluated for IL-17A levels in a whole blood assay. Briefly, the heparizined whole blood was diluted in media and then cultured for six days with single (non-fusion) proteins of immunization. The supernatants were harvested and IL-17A levels measured by ELISA. Results of the IL-17A immunogenicity assay are shown in FIGS. 16A-16C. Each bar represents the mean±SD IL-17A response from each group of four mice in response to the indicated antigen.

Example 14

SP0148, SP2108, and SP1912 Fusion Proteins: IL-17A Immunogenicity Assay

Figure 17A:
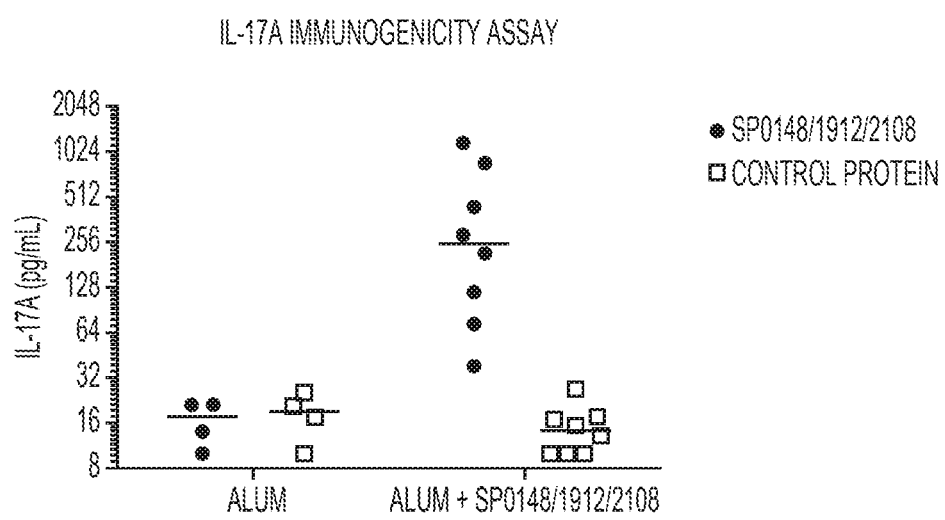
FIGS. 17A and 17B show the concentration of IL-17A generated by blood samples from mice immunized with the indicated fusion proteins and alum, or with alum alone. Blood samples were stimulated with the protein of immunization or a control protein, as indicated at upper right and described in Example 14.
Figure 17B:
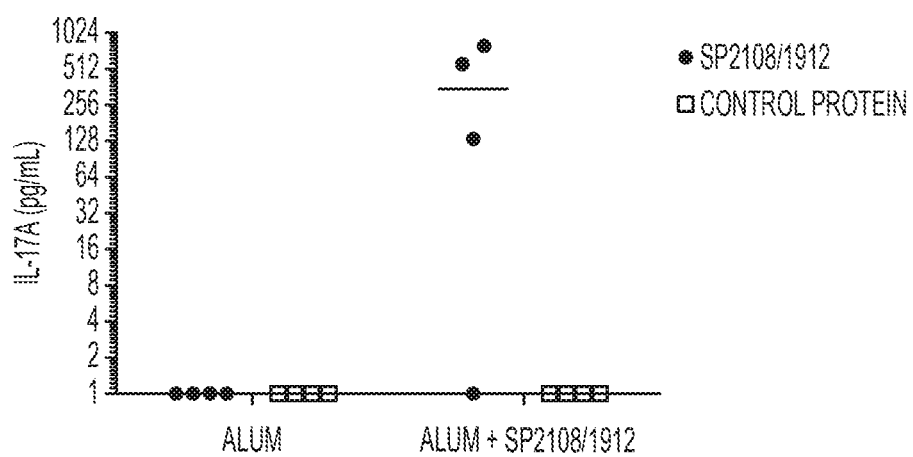

Groups of four to eight mice were subcutaneously immunized three times, two weeks apart, with vaccine compositions comprising the fusion proteins SP0148/1912/2108 (SEQ ID NO: 52) or SP2108/1912 (SEQ ID NO: 49), adsorbed to alum. Control animals were immunized with alum alone. Three weeks after the last immunization, peripheral blood was collected from the retroorbital sinus and evaluated for IL-17A levels in a whole blood assay. Briefly, the heparizined whole blood was diluted in media and then cultured for six days with the protein of immunization, a control protein, or media alone. The cell-free supernatants were harvested and IL-17A concentrations measured by ELISA. Results of the IL-17A immunogenicity assay are shown in FIGS. 17A and 17B. Each symbol represents the IL-17A response of an individual mouse, and the line indicates the median response of the group.

Example 15

SP2108 and SP1912 Fusion Proteins: Frequency of T Cell Response

Figure 18:
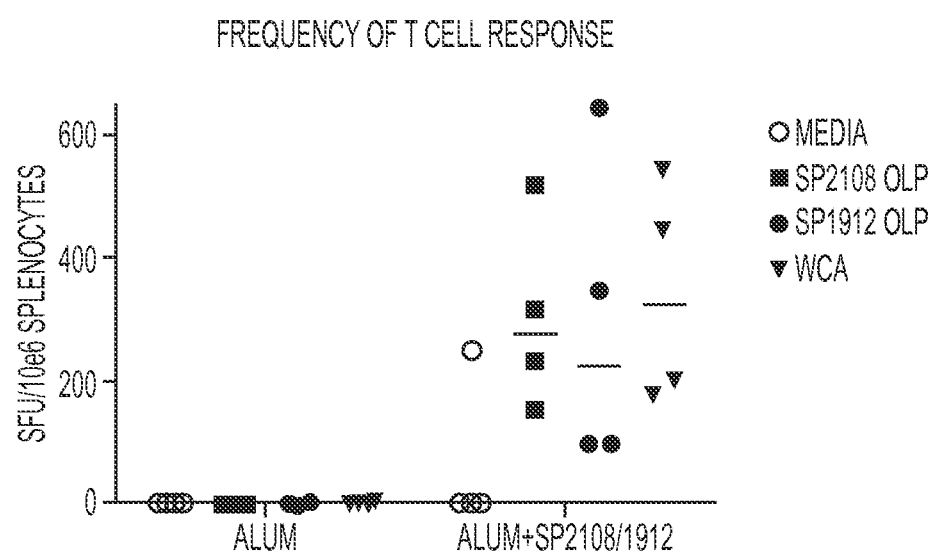
FIG. 18 shows the number of IL-17A spot forming units (SFU) obtained from splenocytes of mice immunized with the indicated fusions proteins and alum, or with alum alone. Splenocytes were stimulated with overlapping peptides (OLP), killed unencapsulated whole cell *S. pneumoniae* (WCA), or media, as indicated at upper right and described in Example 15.

Spleens were collected at the same time as peripheral blood from mice, shown in Example 14, that were immunized with the vaccine composition comprising fusion protein SP2108/1912 (SEQ ID NO: 49), or alum alone. Single cell suspensions were prepared from the spleens. Erythrocytes were lysed, and splenocytes were plated onto ELISpot plates coated with anti-IL-17A capture antibody at 200-800 cells per well and stimulated with overlapping peptides (OLP) spanning SP2108 or SP1912, killed unencapsulated whole-cell *S. pneumoniae* (WCA), or media alone. After two days of incubation, the cells were removed and IL-17A visualized by labeling with biotinylated anti-IL-17A antibody and a horseradish peroxidase substrate. Each colored spot represents a cell that secreted IL-17A. Results of the assay are shown in FIG. 18 as the number of spot forming units (SFU) per $10^6$ splenocytes. Each symbol represents the spot frequency from an individual mouse, and the line indicates the median response of the group.

Example 16

SP0148, SP2108, SP1912 and Fusion Proteins: IL-17A Dose Response Assay

Figure 19A:
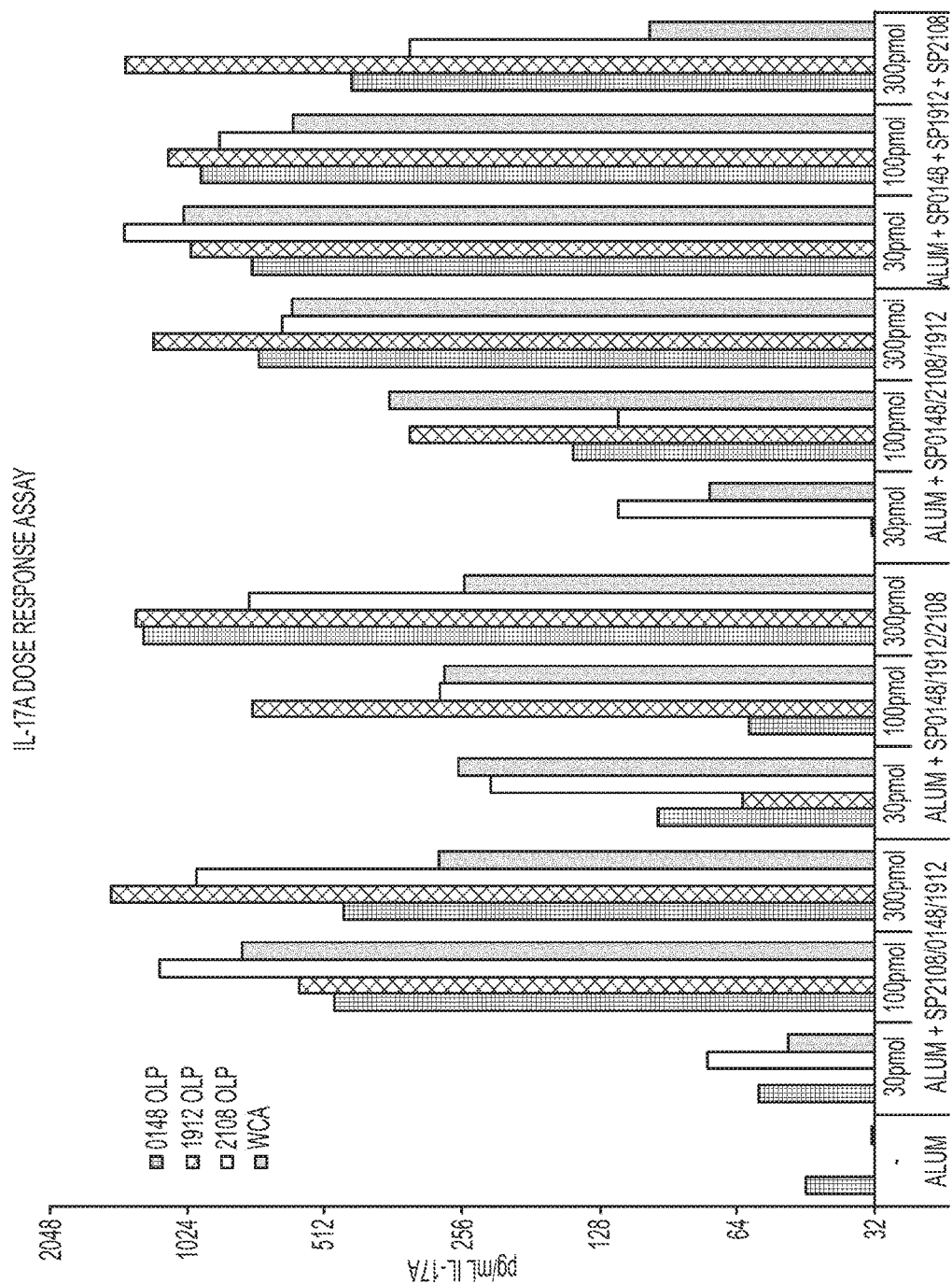

Groups of four mice were subcutaneously immunized three times, two weeks apart, with vaccine compositions comprising 30, 100, or 300 pmol of the fusion proteins SP0148/1912/2108 (SEQ ID NO: 52), SP0148/2108/1912 (SEQ ID NO: 54), SP2108/0148/1912 (SEQ ID NO: 53), SP0148/1912 (SEQ ID NO: 50), SP2108/1912 (SEQ ID NO: 49), or indicated admixtures of SP0148 (SEQ ID NO: 2), SP2108 (SEQ ID NO: 6), and SP1912 (SEQ ID NO: 9), adsorbed to alum. Control animals were immunized with alum alone. Two weeks after the last immunization, peripheral blood was collected from the retroorbital sinus and evaluated for IL-17A levels in a whole blood assay. Briefly, the heparizined whole blood was diluted in media and then cultured for six days with overlapping peptides (OLP) spanning SP0148, SP1912 or SP2108, killed unencapsulated whole-cell *S. pneumoniae* (WCA), or media alone. The cell-free supernatants were harvested and IL-17A concentrations measured by ELISA. Results of the IL-17A dose response assays are shown in FIGS. 19A and 19B. Each bar represents the mean specific IL-17A response of a group of mice with the media-induced (non-specific) background subtracted.

Example 17

SP0148, SP2108, SP1912, and Fusion Proteins: IL-17A Immunogenicity Assay

Figure 20:
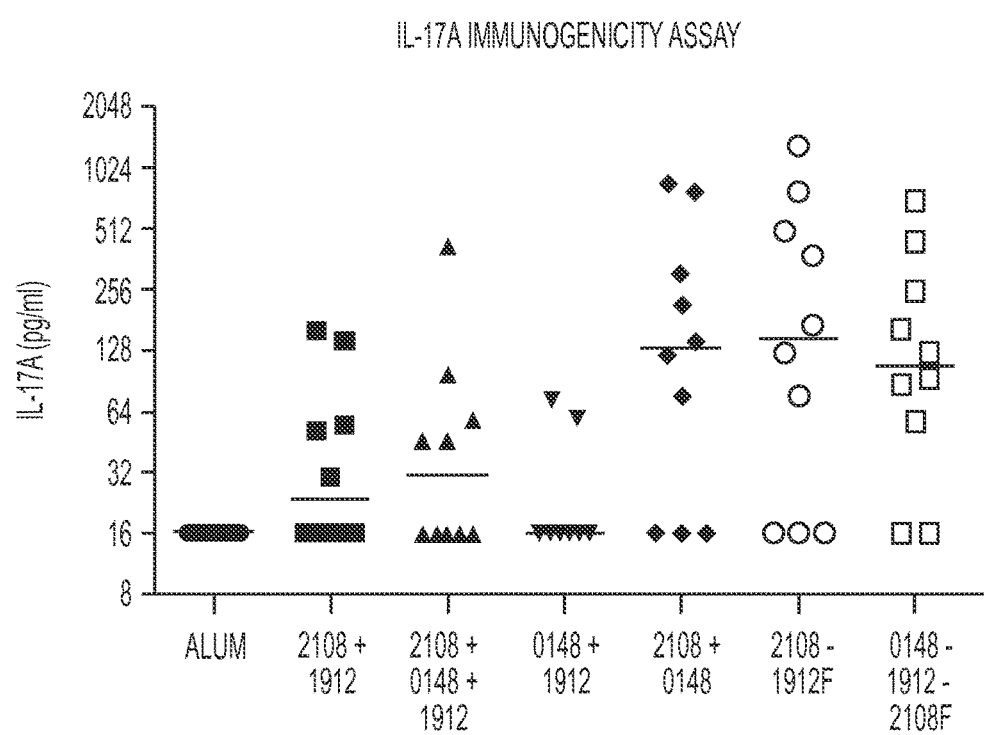
FIG. 20 shows the concentration of IL-17A generated by blood samples from mice immunized with the indicated proteins and alum, or with alum alone. Blood samples were stimulated with killed unencapsulated whole cell *S. pneumoniae* as described in Example 17.

Groups of ten mice were subcutaneously immunized three times, two weeks apart, with vaccine compositions comprising the fusion proteins SP2108/1912 (SEQ ID NO: 49) or SP0148/1912/2108 (SEQ ID NO: 52), or indicated admixtures of SP0148 (SEQ ID NO: 2), SP2108 (SEQ ID NO: 6), and SP1912 (SEQ ID NO: 9), adsorbed to alum. Control animals were immunized with alum alone. Three weeks after the last immunization, peripheral blood was collected from the retroorbital sinus and evaluated for IL-17A levels in a whole blood assay. Briefly, the heparizined whole blood was diluted in media and then cultured for six days with killed unencapsulated whole-cell *S. pneumoniae* (WCA). The cell-free supernatants were harvested and IL-17A levels measured by ELISA. Results of the IL-17A immunogenicity assay are shown in FIG. 20. Each symbol represents the IL-17A response of an individual mouse, and the line indicates the median response of the group.

Example 18

Figure 21A:
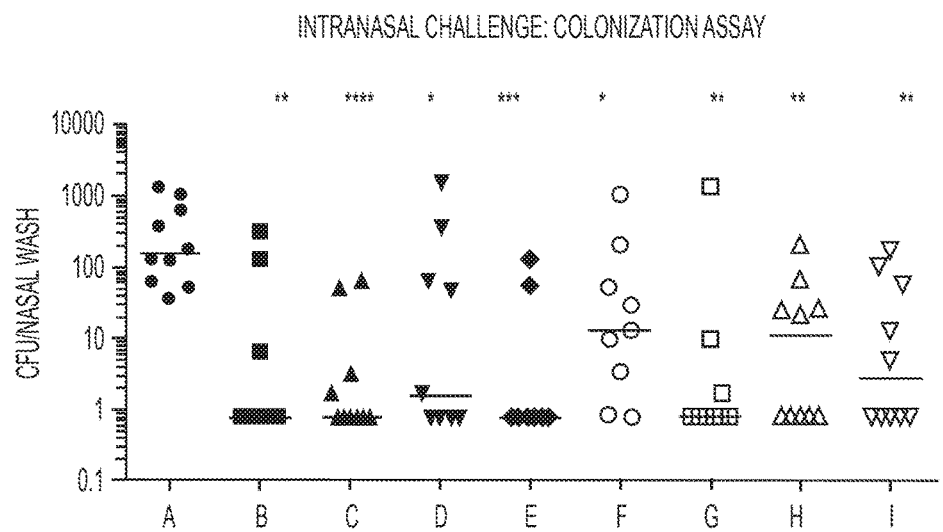
FIGS. 21A-21D show the number of *S. pneumoniae* colonies (CFU) obtained from nasal washes of mice immunized with the indicated proteins and alum, or alum alone, then challenged by intranasal administration of *S. pneumoniae*, as described in Example 18.
Figure 21B:
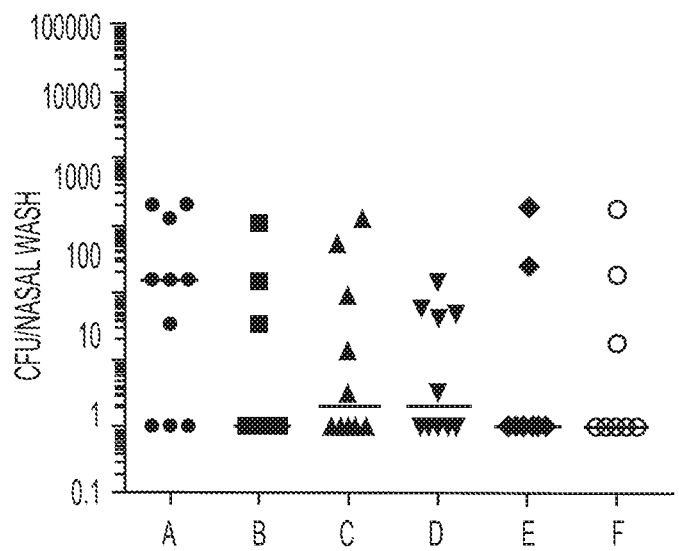
Figure 21C:
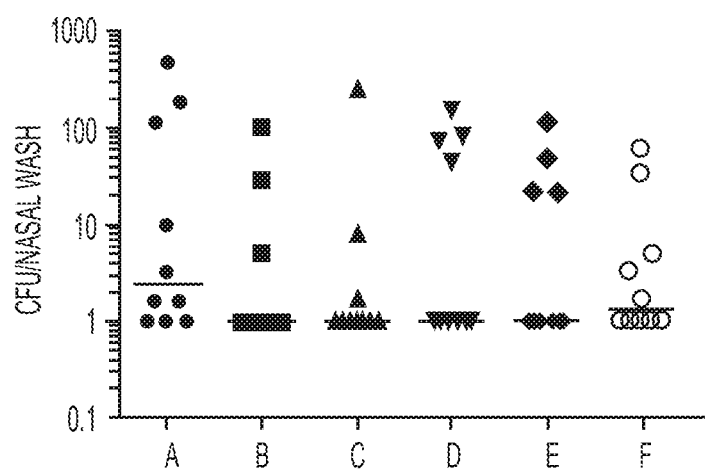
Figure 21D:
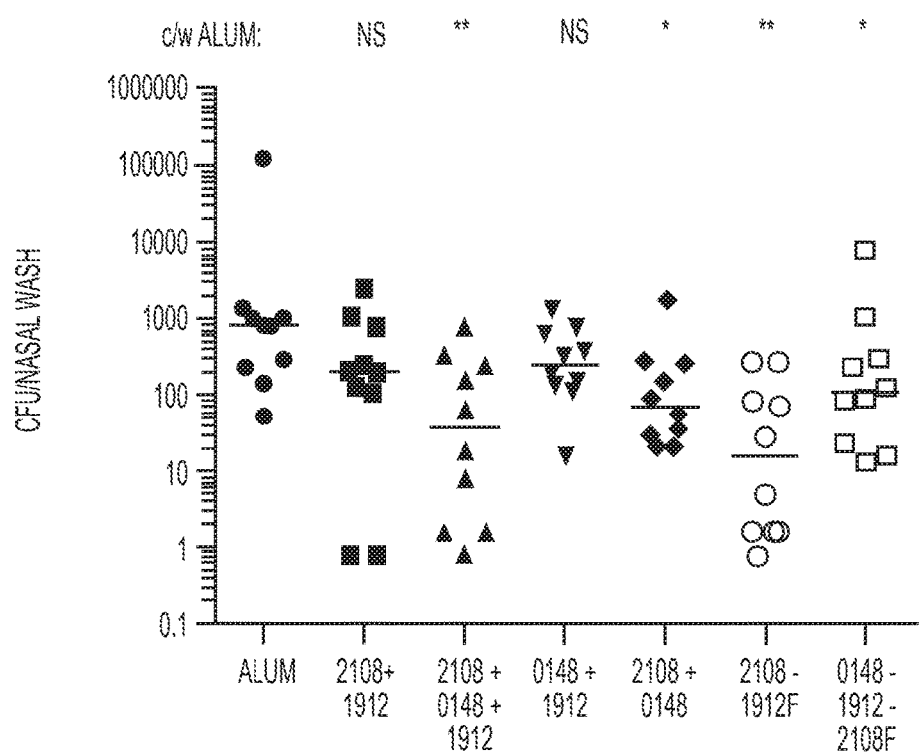

SP0148, SP2108, and SP1912 Fusion Proteins: Intranasal Challenge and Colonization Assay Animals were subcutaneously immunized three times, two weeks apart at the indicated doses with vaccine formulations comprising the fusion proteins SP2108/1912 (SEQ ID NO: 49), SP0148/1912 (SEQ ID NO: 50), SP0148/2108/1912 (SEQ ID NO: 54), SP0148/1912/2108 (SEQ ID NO: 52), or SP2108/0148/1912 (SEQ ID NO: 53), or an admixture of SP0148 (SEQ ID NO: 2), SP2108 (SEQ ID NO: 6) and SP1912 (SEQ ID NO: 9), adsorbed to alum. Control animals were immunized with alum alone Immunized animals were challenged intranasally with $10^6$ to $10^7$ colony forming units (CFU) live strain 0603M20 *S. pneumoniae* twenty-five days after the last immunization. Ten days after challenge, animals were euthanized, the nasopharynx lavaged (nasal wash) and the fluid cultured on permissive media to evaluate the *S. pneumoniae* titers. Results of the colonization assays are shown in FIGS. 21A-21D, as CFU per nasal wash. Each symbol represents the colonization density from an individual mouse, and the horizontal line represents the median of the group. In FIG. 21A, stars indicate statistical significance by Mann-Whitney U test; the absolute number of mice protected and corresponding median log reduction in bacterial colonization are also indicated. (* $p<0.05$;  $p<0.005$; * $p<0.001$; **** $p<0.0005$)

Example 19

SP0148, SP2108, and SP1912 Fusion Proteins: Aspiration Challenge and Sepsis Assay Groups of ten mice are subcutaneously immunized three times, two weeks apart with vaccine compositions comprising the fusion proteins SP2108/0148 (SEQ ID NO: 47), SP0148/2108 (SEQ ID NO: 48), SP2108/1912 (SEQ ID NO: 49), SP0148/1912 (SEQ ID NO: 50), SP2108/1912/0148 (SEQ ID NO: 51), SP0148/1912/2108 (SEQ ID NO: 52), SP2108/0148/1912 (SEQ ID NO: 53), or SP0148/2108/1912 (SEQ ID NO: 54), adsorbed to alum. Control animals are immunized with killed, unencapsulated whole cell *S. pneumoniae* plus alum (WCV), or alum alone. Three weeks after the final immunization, blood is collected for evaluation of IL-17A and antibody, and then one week later, the mice undergo aspiration challenge with $10^7$ live strain WU-2 (serotype 3) *S. pneumoniae*. Animals are monitored for survival for eight days. Results are reported as survival curves for each immunized group.

Example 20

Fusion Protein SP2108/1912 Plus B Cell Antigens: IL-17A Immunogenicity Assay

Groups of twenty mice were subcutaneously immunized three times, two weeks apart with vaccine compositions comprising the fusion protein SP2108/1912 (SEQ ID NO: 49) plus either the B cell antigens YLN and H70 (SEQ ID NO: 33), or the B cell antigen PRN-L460D, adsorbed to alum. Control animals were immunized with killed, unencapsulated whole cell *S. pneumoniae* (WCB), or alum alone. Two to three weeks after the last immunization, peripheral blood was collected from the retroorbital sinus and evaluated for IL-17A levels in a whole blood assay. Briefly, the heparizined whole blood was diluted in media and then cultured for six days with overlapping peptides (OLP) spanning SP2108 or SP1912, or killed unencapsulated whole-cell *S. pneumoniae* (WCA). The cell-free supernatants were harvested and IL-17A concentrations measured by ELISA. Results of the IL-17A immunogenicity assay are shown in FIGS. 22A and 22B (duplicate experiments). Each symbol represents the IL-17A response of an individual mouse, and the line indicates the median response of the group.

Example 21

Fusion Protein SP2108/1912 Plus B Cell Antigens: Intranasal Challenge Followed by Colonization Assay Groups of twenty mice were subcutaneously immunized three times, two weeks apart with vaccine compositions comprising killed, unencapsulated whole cell *S. pneumoniae* (WCB), fusion protein SP2108/1912 (SEQ ID NO: 49) plus either the B cell antigens YLN and H70 (SEQ ID NO: 33), or the B cell antigen PRN-L460D, adsorbed to alum. Control animals were immunized with alum alone Immunized animals were challenged intranasally with $10^7$ live strain 0603M20 *S. pneumoniae* three to five weeks after the last immunization. Ten days after challenge, animals were euthanized and the nasopharynx lavaged (nasal wash) and the fluid cultured on permissive media to evaluate the *S. pneumoniae* titers. Results of the colonization assays are shown in FIGS. 23A and 23B (duplicate experiments), as colony forming units of bacteria (CFU) per nasal wash. Each symbol represents the colonization density from an individual mouse, and the horizontal line represents the median of the group.

Example 22

Fusion Protein SP2108/1912 Plus B Cell Antigens: Intravenous Challenge Followed by Sepsis Assay Groups of twenty mice were subcutaneously immunized three times, two weeks apart with vaccine compositions comprising B cell antigens YLN plus H70 (SEQ ID NO: 33), fusion protein SP2108/1912 (SEQ ID NO: 49) plus B cell antigens YLN and H70 (SEQ ID NO: 33), or fusion protein SP2108/1912 (SEQ ID NO: 49) plus B cell antigen PRN-L460D, adsorbed to alum. Control animals were immunized with alum alone Immunized animals with injected intravenously with $3.6 \times 10^6$ live strain DBL6A *S. pneumoniae* three weeks after last immunization. Animals were monitored for survival for twenty-one days. Results are shown in FIGS. 24A and 24B (duplicate experiments), as hours elapsed until each mouse reaches a moribund state or death. Each symbol represents the response of an individual mouse, and the line indicates the median response of the group.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCES

SP0148 lacking signal sequence

SEQ ID NO: 1

MCSGGAKKEGEAASKKEIIVATNGSPKPFIYEENGELTGYEIEVVRAIFKDSDKYDVKFEKTEWSGVFAGLDADR

YNMAVNNLSYTKERAEKYLYAAPIAQNPNVLVVKKDDSSIKSLDDIGGKSTEVVQATTSAKQLEAYNAEHTDNPT

ILNYTKADFQQIMVRLSDGQFDYKIFDKIGVETVIKNQGLDNLKVIELPSDQQPYVYPLLAQGQDELKSFVDKRI

KELYKDGTLEKLSKQFFGDTYLPAEADIKE

SP0148 including signal sequence (277 amino acids with N-terminal E)

SEQ ID NO: 2

MKKIVKYSSLAALALVAAGVLAACSGGAKKEGEAASKKEIIVATNGSPKPFIYEENGELTGYEIEVVRAIFKDSD

KYDVKFEKTEWSGVFAGLDADRYNMAVNNLSYTKERAEKYLYAAPIAQNPNVLVVKKDDSSIKSLDDIGGKSTEV

VQATTSAKQLEAYNAEHTDNPTILNYTKADFQQIMVRLSDGQFDYKIFDKIGVETVIKNQGLDNLKVIELPSDQQ

PYVYPLLAQGQDELKSFVDKRIKELYKDGTLEKLSKQFFGDTYLPAEADIKE

SP0148 consensus lacking signal sequence

SEQ ID NO: 3

MCSGGAKKEGEAASKKEIIVATNGSPKPFIYEENGELTGYEIEVVRAIFKDSDKYDVKFE
          Q        S R N                                N X

KTEWSGVFAGLDADRYNMAVNNLSYTKERAEKYLYAAPIAQNPNVLVVKKDDSSIKSLDD
                 I                         E

IGGKSTEVVQATTSAKQLEAYNAEHTDNPTILNYTKADLQQIMVRLSDGQFDYKIFDKIG
                                     F

VETVIKNQGLDNLKVIELPSDQQPYVYPLLAQGQDELKSFVDKRIKELYKDGTLEKLSKQ
                         Y       S

FFGDTYLPAEADIK(E)

SP0148 consensus including signal sequence

SEQ ID NO: 4

MKKIVKYSSLAALALVAAGVLAACSGGAKKEGEAASKKEIIVATNGSPKPFIYEENGELT
       G    L          Q              S R N

GYEIEVVRAIFKDSDKYDVKFEKTEWSGVFAGLDADRYNMAVNNLSYTKERAEKYLYAAP
             N X                       I

IAQNPNVLVVKKDDSSIKSLDDIGGKSTEVVQATTSAKQLEAYNAEHTDNPTILNYTKAD
            E

LQQIMVRLSDGQFDYKIFDKIGVETVIKNQGLDNLKVIELPSDQQPYVYPLLAQGQDELK
F                                             Y       S

SFVDKRIKELYKDGTLEKLSKQFFGDTYLPAEADIK(E)

SP2108 lacking signal sequence

SEQ ID NO: 5

MCGSKTADKPADSGSSEVKELTVYVDEGYKSYIEEVAKAYEKEAGVKVTLKTGDALGGLDKLSLDNQSGNVPDVM

MAPYDRVGSLGSDGQLSEVKLSDGAKTDDTTKSLVTAANGKVYGAPAVIESLVMYYNKDLVKDAPKTFADLENLA

KDSKYAFAGEDGKTTAFLADWTNFYYTYGLLAGNGAYVFGQNGKDAKDIGLANDGSIVGINYAKSWYEKWPKGMQ

DTEGAGNLIQTQFQEGKTAAIIDGEWKAQAFKDAKVNYGVATIPTLENGKEYAAFGGGKAWVIPQAVKNLEASQK

FVDFLVATEQQKVLYDKTNEIPANTEARSYAEGKNDELTTAVIKQFKNTQPLENISQMSAVWDPAKNMLFDAVSG

QKDAKTAANDAVTLIKETIKQKFGE

SP2108 including signal sequence

SEQ ID NO: 6

>gi|14973620|gb|AAK76167.1| maltose/maltodextrin ABC transporter,
maltose/maltodextrin-binding protein (*Streptococcus pneumoniae* TIGR4)
MSSKFMKSAAVLGTATLASLLLVACGSKTADKPADSGSSEVKELTVYVDEGYKSYIEEVAKAYEKEAGVKVTLKT

GDALGGLDKLSLDNQSGNVPDVMMAPYDRVGSLGSDGQLSEVKLSDGAKTDDTTKSLVTAANGKVYGAPAVIESL

VMYYNKDLVKDAPKTFADLENLAKDSKYAFAGEDGKTTAFLADWTNFYYTYGLLAGNGAYVFGQNGKDAKDIGLA

NDGSIVGINYAKSWYEKWPKGMQDTEGAGNLIQTQFQEGKTAAIIDGPWKAQAFKDAKVNYGVATIPTLPNGKEY

| SEQUENCES |
|---|
| AAFGGGKAWVIPQAVKNLEASQKFVDFLVATEQQKVLYDKTNEIPANTEARSYAEGKNDELTTAVIKQFKNTQPL |
| PNISQMSAVWDPAKNMLFDAVSGQKDAKTAANDAVTLIKETIKQKFGE |

SP2108 consensus lacking signal sequence  SEQ ID NO: 7

```
MCGSKTADKPADSGSSEVKELTVYVDEGYKSYIEEVAKAYEKEAGVKVTLKTGDALGGLD
          A                                I

KLSLDNQSGNVPDVMMAPYDRVGSLGSDGQLSEVKLSDGAKTDDTTKSLVTAANGKVYGA
    I            X                T

PAVIESLVMYYNKDLVKDAPKTFADLENLAKDSKYAFAGEDGKTTAFLADWTNFYYTYGL
                                                          A

LAGNGAYVFGQNGKDAKDIGLANDSIVGINYAKSWYEKWPKGMQDTEGAGNLIQTQFQE
       G      P        A      X                          H

GKTAAIIDGPWKAQAFKDAKVNYGVATIPTLPNGKEYAAFGGGKAWVIPQAVKNLEASQK
                                             A

FVDFLVATEQQKVLYDKTNEIPANTEARSYAEGKNDELTTAVIKQFKNTQPLPNISQMSA
     S      A                                S

VWDPAKNMLFDAVSGQKDAKTAANDAVTLIKETIKQKFGE
```

SP2108 consensus including signal sequence  SEQ ID NO: 8

```
MSSKFMKSAAVLGTATLASLLLVACGSKTADKPADSGSSEVKELTVYVDEGYKSYIEEVA
    T T      V                                  A

KAYEKEAGVKVTLKTGDALGGLDKLSLDNQSGNVPDVMMAPYDRVGSLGSDGQLSEVKLS
         I                  I            X

DGAKTDDTTKSLVTAANGKVYGAPAVIESLVMYYNKDLVKDAPKTFADLENLAKDSKYAF
     T

AGEDGKTTAFLADWTNFYYTYGLLAGNGAYVFGQNGKDAKDIGLANDSIVGINYAKSWY
              A            G      P        A      X

EKWPKGMQDTEGAGNLIQTQFQEGKTAAIIDGPWKAQAFKDAKVNYGVATIPTLPNGKEY
         H

AAFGGGKAWVIPQAVKNLEASQKFVDFLVATEQQKVLYDKTNEIPANTEARSYAEGKNDE
               A         S      A

LTTAVIKQFKNTQPLPNISQMSAVWDPAKNMLFDAVSGQKDAKTAANDAVTLIKETIKQK
         S

FGE
```

SP1912  SEQ ID NO: 9

```
MNGMKAKKMWMAGLALLGIGSLALATKKVADDRKLMKTQEELTEIVRDHFSDMGEIATLYVQVYESSLESLVGGV
IFEDGRHYTFVYENEDLVYEEEVL
```

SP1912L  SEQ ID NO: 10

```
MRYLATLLLSLAVLITAGCKKVADDRKLMKTQEELTEIVRDHFSDMGEIATLYVQVYESSLESLVGGVIFEDGRH
YTFVYENEDLVYEEEVL
```

SP1912 consensus  SEQ ID NO: 11

```
MNGMKAKKMWMAGLALLGIGSLALATKKVADDRKLMKTQEELTEIVRDHFSDMGEIATLYVQVYESSLESLVGGV
IF
            H       A   L           I           L S

EDGRHYTFVYENEDLVYEEEVL
    I
```

| SEQUENCES |
| --- |

SP0641
>gi|14972117|gb|AAK74791.1| serine protease, subtilase family
[*Streptococcus pneumoniae* TIGR4]

SEQ ID NO: 12

MKKSTVLSLTTAAVILAAYAPNEVVLADTSSSEDALNISDKEKVAENKEKHENIHSAMETSQDFKEKKTAVIKEK

EVVSKNPVIDNNTSNEEAKIKEENSNKSQGDYTDSFVNKNTENPKKEDKVVYIAEFKDKESGEKAIKELSSLKNT

KVLYTYDRIENGSAIETTPDNLDKIKQIEGISSVERAQKVQPMMNHARKEIGVEEAIDYLKSINAPFGKNEDGRG

MVISNIDTGTDYRHKAMRIDDDAKASMRFKKEDLKGTDKNYWLSDKIPHAFNYYNGGKITVEKYDDGRDYFDPHG

MHIAGILAGNDTEQDIKNENGIDGIAPNAQIFSYKMYSDAGSGFAGDETMEHAIEDSIKHNVDVVSVSSGFTGTG

LVGEKYWQAIRALRKAGIPMVVATGNYATSASSSWDLVANNHLKMTDTGNVTRTAAHEDAIAVASAKNQTVEFD

KVNIGGESFKYRNIGAFFDKSKITTNEDGTKAPSKLKEVYIGKGQDQDLIGLDLRGKIAVMDRIYTKDLKNAFKK

AMDKGARAIMVVNTVNYYNRDNWTELPAMGYEADEGTKSQVFSISGDDGVKLWNMINPDKKTEVKRNNKEDFKDK

LEQYYPIDMESFNSNKPNVGDEKEIDFKFAPDTDKELYKEDIIVPAGSTSWGPRIDLLLKPDVSAPGKNIKSTLN

VINGKSTYGYMSGTSMATPIVAASTVLIRPKLKEMLERPVLKNLKGDDKIDLTSLTKIALQNTARPMMDATSWKE

KSQYFASPRQQGAGLINVANALRNEVVATEKNTDSKGLVNSYGSISLKEIKGDKKYFTIKLHNTSNRPLTEKVSA

SAITTDSLTDRLKLDETYKDEKSPDGKQIVPEIHPEKVKGANITFEHDTFTIGANSSFDLNAVINVGEAKNKNKF

VESFIHFESVEEMEALNSNGKKINFQPSLSMPLMGFAGNWNHEPILDKWAWEEGSRSKTLGGYDDDGKPKIPGTL

NKGIGGEHGIDKENPAGVIQNRKDKNTTSLDQNPELFAENNEGINAPSSSGSKIANIYPLDSNGNPQDAQLERGL

TPSPLVLRSAEEGLISIVNTNKEGENQRDLKVISREHFIRGILNSKSNDAKGIKSSKLKVWGDLKWDGLIYNPRG

REENAPESKDNQDPATKIRGQFEPIAEGQYFYKFKYRLTKDYPWQVSYIPVKIDNTAPKIVSVDFSNPEKIKLIT

KDTYHKVKDQYKNETLFARDQKEHPEKEDEIANEVWYAGAALVNEDGEVEKNLEVTYAGEGQGRNRKLDKDGNTI

YEIKGAGDLRGKIIEVIALDGSSNETKIHRIKFANQADEKGMISYYLVDPDQDSSKYQKLGEIAESKEKNLGNGK

EGSLKKDTTGVEHHHQENEESIKEKSSFTIDRNISTIRDFENKDLKKLIKKKFREVDDFTSETGKRMEEYDYKYD

DKGNIIAYDDGTDLEYETEKLDEIKSKIYGVLSPSKDGHFEILGKISNVSKNAKVYYGNNYKSIEIKATKYDFHS

KTMTFDLYANINDIVDGLAFAGDMRLFVKDNDQKKAEIKIRMPEKIKETKSEYPYVSSYGNVIELGEGDLSKNKP

DNLTKMESGKIYSDSEKQQYLLKDNIILRKGYALKVTTYNPGKTDMLEGNGVYSKEDIAKIQKANPNLRALSETT

IYADSRNVEDGRSTQSVLMSALDGENIIRYQVFTFKMNDKGEAIDKDGNLVTDSSKLVLEGKDDKEYTGEDKENV

EAIKEDGSMLFIDTKPVNLSMDKNYENPSKSNKIYVRNPEFYLRGKISDKGGENWELRVNESVVDNYLIYGDLHI

DNTRDFNIKLNVKDGDIMDWGMKDYKANGFPDKVTDMDGNVYLQTGYSDLNAKAVGVHYQFLYDNVKPEVNIDPK

GNTSIEYADGKSVVFNINDKRNNGEDGEIQEQHIYINGKEYTSENDIKQIIDKTLNIKIVVKDFARNTTVKEFIL

NKDTGEVSELKPHRVTVTIQNGKEMSSTIVSEEDFILPVYKGELEKGYQFDGWEISGFEGKKDAGYVINLSKDTF

IKPVFKKIEEKKEEENKPTFDVSKKKDNPQVNHSQLNESHRKEDLQREEHSQKSDSTKDVTATVLDKNNISSKST

TNNPNKLPKTGTASGAQTLLAAGIMFIVGIFLGLKKKNQD

SP0641N

SEQ ID NO: 13

MVVLADTSSSEDALNISDKEKVAENKEKHENIHSAMETSQDFKEKKTAVIKEKEVVSKNPVIDNNTSNEEAKIKE

ENSNKSQGDYTDSFVNKNTENPKKEDKVVYIAEFKDKESGEKAIKELSSLKNTKVLYTYDRIENGSAIETTPDNL

DKIKQIEGISSVERAQKVQPMMNHARKEIGVEEAIDYLKSINAPFGKNEDGRGMVISNIDTGTDYRHKAMRIDDD

AKASMRFKKEDLKGTDKNYWLSDKIPHAFNYYNGGKITVEKYDDGRDYFDPHGMHIAGILAGNDTEQDIKNENGI

DGIAPNAQIFSYKMYSDAGSGFAGDETMEHAIEDSIKHNVDVVSVSSGFTGTGLVGEKYWQAIRALRKAGIPMVV

ATGNYATSASSSWDLVANNHLKMTDTGNVTRTAAHEDAIAVASAKNQTVEFDKVNIGGESFKYRNIGAFFDKSK

ITTNEDGTKAPSKLKFVYIGKGQDQDLIGLDLRGKIAVMDRIYTKDLKNAFKKAMDKGARAIMVVNTVNYYNRDN

| SEQUENCES |
|---|
| WTELPAMGYEADEGTKSQVFSISGDDGVKLWNMINPDKKTEVKRNNKEDFKDKLEQYYPIDMESENSNKPNVGDE |
| KEIDFKFAPDTDKELYKEDIIVPAGSTSWGPRIDLLLKPDVSAPGKNIKSTLNVINGKSTYG |

SP0641M                                                                 SEQ ID NO: 14
MSGTSMATPIVAASTVLIRPKLKEMLERPVLKNLKGDDKIDLTSLTKIALQNTARPMMDATSWKEKSQYFASPRQ
QGAGLINVANALRNEVVATEKNTDSKGLVNSYGSISLKEIKGDKKYFTIKLHNTSNRPLTEKVSASAITTDSLTD
RLKLDETYKDEKSPDGKQIVPEIHPEKVKGANITFEHDTFTIGANSSFDLNAVINVGEAKNKNKFVESFIHFESV
EEMEALNSNGKKINFQPSLSMPLMGFAGNWNHEPILDKWAWEEGSRSKTLGGYDDDGKPKIPGTLNKGIGGEHGI
DKFNPAGVIQNRKDKNTTSLDQNPELFAFNNEGINAPSSSGSKIANIYPLDSNGNPQDAQLERGLTPSPLVLRSA
EEGLISIVNTNKEGENQRDLKVISREHFIRGILNSKSNDAKGIKSSKLKVWGDLKWDGLIYNPRGREENAPESKD
NQDPATKIRGQFEPIAEGQYFYKFKYRLTKDYPWQVSYIPVKIDNTAPKIVSVDFSNPEKIKLITKDTYHKVKDQ
YKNETLFARDQKEHPEKFDEIANEVWYAGAALVNEDGEVEKNLEVTYAGEGQGRNRKLDKDGNTIYEIKGAGDLR
GKIIEVIALDGSSNFTKIHRIKFANQADEKGMISYYLVDPDQDSSKYQ

SP641N consensus                                                        SEQ ID NO: 15
MVVLADTSSSEDALNISDKEKVA-----
ENKEKHENIHSAMETSQDFKEKKTAVIKEKEVVSKNPVIDNNTSNEEAK        -       N       S
VVDKET       KD   N   I    K TE      TI EG A       T  TK      R
                                L IKEENSNKSQGDYTDSFVNKNTENPKKEDKVVYIAEFKDKESGEKAIKELSSLKNTKVLYTYDRIFNGSAIETTP
DN
    D-    Q      H          Q             S       Q  N            G      Q
          NAH SA  G          RL              G LDKIKQIEGISSVERAQKVQPMMNHARKEIGVEEAIDYLKSINAPFGKNEDGRGMVISNIDTGTDYRHKAMRIDD
DA
         T I

KASMRFKKEDLKGTDKNYWLSDKIPHAFNYYNGGKITVEKYDDGRDYFDPHGMHIAGILAGNDTEQDIKNENGID
GI

APNAQIFSYKMYSDAGSGFAGDETMEHAIEDSIKHNVDVVSVSSGFTGTGLVGEKYWQAIRALRKAGIPMVVATG
NY

ATSASSSSWDLVANNHLKMTDTGNVTRTAAHEDAIAVASAKNQTVEFDKVNIGGESFKYRNIGAFFDKSKITTNE
DG
                                                              Q            N

TKAPSKLKEVYIGKGQDQDLIGLDLRGKIAVMDRIYTKDLKNAFKKAMDKGARAIMVVNTVNYYNRDNWTELPAM
GY

EADEGTKSQVFSISGDDGVKLWNMINPDKKTEVKRNNKEDFKDKLEQYYPIDMESENSNKPNVGDEKEIDEKFAP
DT
                                   N

DKELYKEDIIVPAGSTSWGPRIDLLLKPDVSAPGKNIKSTLNVINGKSTYG

SP641M consensus                                                        SEQ ID NO: 16
MSGTSMATPIVAASTVLIRPKLKEMLERPVLKNLKGDDKIDLTSLTKIALQNTARPMMDATSWKEKSQYFASPRQ
QG                                                                       K
T AGLINVANALRNEVVATFKNTDSKGLVNSYGSISLKEIKGDKKYFTIKLHNTSNRPLTFKVSASAITTDSLTDRL
KL
                                                                  V DETYKDEKSPDGKQIVPEIHPEKVKGANITFEHDTFTIGANSSFDLNAVINVGEAKNKNKFVESFIHFESVEEME
AL
        Y                                              R          A

| SEQUENCES |
|---|
| NSNGKKINFQPSLSMPLMGFAGNWNHEPILDKWAWEEGSRSKTLGGYDDDGKPKIPGTLNKGIGGEHGIDKFNPA<br>GV<br>S       TD                                           K   ME |
| IQNRKDKNTTSLDQNPELFAFNNEGINAPSSSGSKIANIYPLDSNGNPQDAQLERGLTPSPLVLRSAEEGLISIV<br>NT<br>          R     D  D       Q VH E  T |
| NKEGENQRDLKVISREHFIRGILNSKSNDAKGIKSSKLKVWGDLKWDGLIYNPRGREENAPESKDNQDPATKIRG<br>QF<br>      K     V            G |
| EPIAEGQYFYKFKYRLTKDYPWQVSYIPVKIDNTAPKIVSVDFSNPEKIKLITKDTYHKVKDQYKNETLFARDQK<br>EH |
| PEKFDEIANEVWYAGAALVNEDGEVEKNLEVTYAGEGQGRNRKLDKDGNTIYEIKGAGDLRGKIIEVIALDGSSN<br>FT<br>                                                                S                  A |
| KIHRIKFANQADEKGMISYYLVDPDQDSSKYQ<br>        DH            KA    E |

SP0882
>gi|14972356|gb|AAK75009.1| conserved hypothetical protein
(*Streptococcus pneumoniae* TIGR4)

SEQ ID NO: 17

MNQSYFYLKMKEHKLKVPYTGKERRVRILLPKDYEKDTDRSYPVVYFHDGQNVENSKESFIGHSWKIIPAIKRNP

DISRMIVVAIDNDGMGRMNEYAAWKFQESPIPGQQFGGKGVEYAEFVMEVVKPFIDETYRTKADCQHTAMIGSSL

GGNITQFIGLEYQDQIGCLGVESSANWLHQEAFNRYFECQKLSPDQRIFIYVGTEEADDTDKTLMDGNIKQAYID

SSLCYYHDLIAGGVHLDNLVLKVQSGAIHSEIPWSENLPDCLRFFAEKW

SP0882N

SEQ ID NO: 18

MNQSYFYLKMKEHKLKVPYTGKERRVRILLPKDYEKDTDRSYPVVYFHDGQNVENSKESFIGHSWKIIPAIKRNP

DISRMIVVAIDNDGMGRMNEYAAWKFQESPIPGQQFGGKGVEYAEFVMEVVKPFI

SP0882 with exogenous signal sequence

SEQ ID NO: 19

MSSKFMKSAAVLGTATLASLLLVACMNQSYFYLKMKEHKLKVPYTGKERRVRILLPKDYEKDTDRSYPVVYFHDG

QNVENSKESFIGHSWKIIPAIKRNPDISRMIVVAIDNDGMGRMNEYAAWKFQESPIPGQQFGGKGVEYAEFVMEV

VKPFIDETYRTKADCQHTAMIGSSLGGNITQFIGLEYQDQIGCLGVESSANWLHQEAFNRYFECQKLSPDQRIFI

YVGTEEADDTDKTLMDGNIKQAYIDSSLCYYHDLIAGGVHLDNLVLKVQSGAIHSEIPWSENLPDCLRFFAEKW

SP0882N with exogenous signal sequence

SEQ ID NO: 20

MSSKFMKSAAVLGTATLASLLLVACMNQSYFYLKMKEHKLKVPYTGKERRVRILLPKDYEKDTDRSYPVVYFHDG

QNVENSKESFIGHSWKIIPAIKRNPDISRMIVVAIDNDGMGRMNEYAAWKFQESPIPGQQFGGKGVEYAEFVMEV

VKPFI

SP0882 consensus

SEQ ID NO: 21

| MNQSYFYLKMKEHKLKVPYTGKERRVRILLPKDYEKDTDRSYPVVYFHDGQNVFNSKESF<br>I                                                                                       Y |
| IGHSWKIIPAIKRNPDISRMIVVAIDNDGMGRMNEYAAWKFQESPIPGQQFGGKGVEYAE<br>   Y                H                     E           E |
| FVMEVVKPFIDETYRTKADCQHTAMIGSSLGGNITQFIGLEYQDQIGCLGVFSSANWLHQ<br>                                                     EK |
| EAFNRYFECQKLSPDQRIFIYVGTEEADDTDKTLMDGNIKQAYIDSSLCYYHDLIAGGVH<br>    I       H                                                                R |

LDNLVLKVQSGAIHSEIPWSENLPDCLRFFAEKW

| SEQUENCES | |
|---|---|
| SP0882N consensus<br><br>MNQSYFYLKMKEHKLKVPYTGKERRVRILLPKDYEKDTDRSYPVVYFHDGQNVFNSKESF<br>I                                                                                         Y<br><br>IGHSWKIIPAIKRNPDISRMIVVAIDNDGMGRMNEYAAWKFQESPIPGQQFGGKGVEYAE<br>  Y            H               E        E<br><br>FVMEVVKPFI | SEQ ID NO: 22 |
| SP0882 consensus with exogenous signal sequence<br><br>MSSKFMKSAAVLGTATLASLLLVACMNQSYFYLKMKEHKLKVPYTGKERRVRILLPKDYE<br>    T   T     V        I<br><br>KDTDRSYPVVYFHDGQNVFNSKESFIGHSWKIIPAIKRNPDISRMIVVAIDNDGMGRMNE<br>              Y         Y                H<br><br>YAAWKFQESPIPGQQFGGKGVEYAEFVMEVVKPFIDETYRTKADCQHTAMIGSSLGGNIT<br>   E         E<br><br>QFIGLEYQDQIGCLGVFSSANWLHQEAFNRYFECQKLSPDQRIFIYVGTEEADDTDKTLM<br>    EK                       I         H<br><br>DGNIKQAYIDSSLCYYHDLIAGGVHLDNLVLKVQSGAIHSEIPWSENLPDCLRFFAEKW<br>                     R | SEQ ID NO: 23 |
| SP0882N consensus with exogenous signal sequence<br><br>MSSKFMKSAAVLGTATLASLLLVACMNQSYFYLKMKEHKLKVPYTGKERRVRILLPKDYE<br>    T   T     V        I<br><br>KDTDRSYPVVYFHDGQNVFNSKESFIGHSWKIIPAIKRNPDISRMIVVAIDNDGMGRMNE<br>              Y         Y                H<br><br>YAAWKFQESPIPGQQFGGKGVEYAEFVMEVVKPFI<br>   E         E | SEQ ID NO: 24 |
| SP1634<br>>gi\|14973124\|gb\|AAK75714.1\| hypothetical protein SP 1634<br>Streptococcus pneumoniae TIGR4<br><br>MANIFDYLKDVAYDSYYDLPLNELDILTLIEITYLSEDNLVSTLPQRLLDLAPQVPRDPTMLTSKNRLQLLDELA<br><br>QHKRFKNCKLSHFINDIDPELQKQFAAMTYRVSLDTYLIVERGTDDSIIGWKEDFHLTYMKEIPAQKHALRYLKN<br><br>FFAHHPKQKVILAGHSKGGNLAIYAASQIEQSLQNQITAVYTFDAPGLHQELTQTAGYQRIMDRSKIFIPQGSII<br><br>GMMLEIPAHQIIVQSTALGGIAQHDTFSWQIEDKHFVQLDKTNSDSQQVDTTFKEWVATVPDEELQLYFDLFFGT<br><br>ILDAGISSINDLASLKALEYIHHLFVQAQSLTPEERETLGRLTQLLIDTRYQAWKNR | SEQ ID NO: 25 |
| SP0314<br>>gi\|14971788\|gb\|AAK74491.1\| hyaluronidase Streptococcus pneumoniae<br>TIGR4MQTKTKKLIVSLSSLVLSGFLLNHYMTIGAEETTTNTIQQSQKEVQYQQRDTKNLVENGDFGQTEDGSSP<br><br>WTGSKAQGWSAWVDQKNSADASTRVIEAKDGAITISSHEKLRAALHRMVPIEAKKKYKLRFKIKTDNKIGIAKVR<br><br>IIEESGKDKRLWNSATTSGTKDWQTIEADYSPTLDVDKIKLELFYETGTGTVSFKDIELVEVADQLSEDSQTDKQ<br><br>LEEKIDLPIGKKHVESLADYTYKVENPDVASVKNGILEPLKEGTTNVIVSKDGKEVKKIPLKILASVKDAYTDRL<br><br>DDWNGIIAGNQYYDSKNEQMAKLNQELEGKVADSLSSISSQADRTYLWEKFSNYKTSANLTATYRKLEEMAKQVT<br><br>NPSSRYYQDETVVRTVRDSMEWMHKHVYNSEKSIVGNWWDYEIGTPRAINNTLSLMKEYFSDEEIKKYTDVIEKF<br><br>VPDPEHERKTTDNPFKALGGNLVDMGRVKVIAGLLRKDDQEISSTIRSIEQVFKLVDQGEGFYQDGSYIDHTNVA<br><br>YTGAYGNVLIDGLSQLLPVIQKTKNPIDKDKMQTMYHWIDKSFAPLLVNGELMDMSRGRSISRANSEGHVAAVEV<br><br>LRGIHRIADMSEGETKQCLQSLVKTIVQSDSYYDVFKNLKTYKDISLMQSLLSDAGVASVPRPSYLSAFNKMDKT<br><br>AMYNAEKGFGEGLSLESSRTLNYEHMNKENKRGWYTSDGMFYLYNGDLSHYSDGYWPTVNPYKMPGTTETDAKRA<br><br>DSDTGKVLPSAFVGTSKLDDANATATMDFTNWNQTLTAHKSWFMLKDKIAFLGSNIQNTSTDTAATTIDQRKLES | SEQ ID NO: 26 |

| SEQUENCES |
|---|
| GNPYKVYVNDKEASLTEQEKDYPETQSVFLESFDSKKNIGYFFFKKSSISMSKALQKGAWKDINEGQSDKEVENE |
| FLTISQAHKQNRDSYGYMLIPNVDRATFNQMIKELESSLIENNETLQSVYDAKQGVWGIVKYDDSVSTISNQFQV |
| LKRGVYTIRKEGDEYKIAYYNPETQESAPDQEVFKKLEQAAQPQVQNSKEKEKSEEEKNHSDQKNLPQTGEGQSI |
| LAS LGFLLLGAFYLFRRGKNN |
| PspA SEQ ID NO: 27 |
| MNKKKMILTSLASVAILGAGEVASSPTEVRAEEAPVANQSKAEKDYDAAVKKSEAAKKDYETAKKKAEDA |
| QKKYDEDQKKTEAKAEKERKASEKIAEATKEVQQAYLAYLQASNESQRKEADKKIKEATQRKDEAEAAFA |
| TIRTTIVVPEPSELAETKKKAEEATKEAEVAKKKSEEAAKEVEVEKNKILEQDAENEKKIDVLQNKVADL |
| EKGIAPYQNEVAELNKEIARLQSDLKDAEENNVEDYIKEGLEQAITNKKAELATTQQNIDKTQKDLEDAE |
| LELEKVLATLDPEGKTQDELDKEAAEAELNEKVEALQNQVAELEEELSKLEDNLKDAETNNVEDYIKEGL |
| EEATATKKAELEKTQKELDAALNELGPDGDEEETPAPAPQPEKPAEEPENPAPAPKPEKSADQQAEEDYA |
| RRSEEEYNRLTQQQPPKAEKPAPAPQPEQPAPAPKIGWKQENGMWYFYNTDGSMATGWLQNNGSWYYLNS |
| NGAMATGWLQYNGSWYYLNANGAMATGWLQYNGSWYYLNANGAMATGWLQYNGSWYYLNANGDMATGWLQ |
| YNGSWYYLNANGDMATGWAKVHGSWYYLNANGSMATGWVKDGETWYYLEASGSMKANQWFQVSDKWYYVN |
| GLGSLSVNTTVDGYKVNANGEWV |
| Immunogenic PspA/PspC polypeptides including the coiled-coil structure (PR + NPB) SEQ ID NO: 28 |
| MSDKIIHLTDDSFDTDVLKADGAILVDFWAEWCGPCKMIAPILDEIADEYQGKLTVA |
| KLNIDQNPGTAPKYGIRGIPTLLLFKNGEVAATKVGALSKGQLKEFLDANLAGSGSG |
| HMHHHHHHSSGLVPRGSGMKETAAAKFERQHMDSPDLGTDDDDKAMADLKKAVNE |
| PEKPAEEPENPAPAPKPAPAPQPEKPAPAPAPKPEKSADQQAEEDYARRSEEEYNRLTQQ |
| QPPKAEKPAPAPVPKPEQPAPAPKTGWGQENGMWCRQACGRTRAPPPPPLRSGC |
| Immunogenic PspA/PspC polypeptide CD2 SEQ ID NO: 29 |
| ADLKKAVNEPEKPAEEPENPAPAPKPAPAPQPEKPAPAPAPKPEKSADQQAEEDYARR |
| SEEEYNRLTQQQPPKAEKPAPAPVPKPEQPAPAPKTGWGQENGMW |
| Immunogenic PspA/PspC polypeptides lacking the coiled-coil structure (PR + NPB) SEQ ID NO: 30 |
| MAKKAELEKTPEKPAEEPENPAPAPQPEKSADQQAEEDYARRSEEEYNRLTQQQPPKA |
| Immunogenic PspA/PspC polypeptides including the coiled-coil structure (PR only) SEQ ID NO: 31 |
| MSDKIIHLTDDSFDTDVLKADGAILVDFWAEWCGPCKMIAPILDEIADEYQGKLTVA |
| KLNIDQNPGTAPKYGIRGIPTLLLFKNGEVAATKVGALSKGQLKEFLDANLAGSGSG |
| HMHHHHHHSSGLVPRGSGMKETAAAKFERQHMDSPDLGTDDDDKAMADLKKAVNE |
| PET PAPAPAPAPAPAPTPEAPAPAPAPAPAPKPAPAPKPAPAPKPAPAPKPAPAPKPAPAPKP |
| APA PAPAPKPEKPAEKPAPAPKPETPKTGWKQENGMWCRQACGRTRAPPPPPLRSG |
| Immunogenic PspA/PspC polypeptides lacking the coiled-coil structure (PR only) SEQ ID NO: 32 |
| DLKKAVNEPETPAPAPAPAPAPAPTPEAPAPAPAPAPAPKPAPAPKPAPAPKPAPAPKPA |
| PAPKPAPAPKPAPAPAPAPKPEKPAEKPAPAPKPETPKTGWKQENGMW |

| SEQUENCES |
| --- |

Immunogenic PspA/PspC polypeptide H70 (aa 290-410 of PspA)
SEQ ID NO: 33

YFKEGLEKTIAAKKAELEKTEADLKKAVNEPEKPAPAPETPAPEAPAEQPKPAPAPQPAPAPK

PEKPAEQPKPEKTDDQQAEEDYARRSEEEYNRLTQQQPPKAEKPAPAPKTGWKQENGM

Non-proline Block (NPB)
SEQ ID NO: 34

EKSADQQAEEDYARRSEEEYNRLTQQQ

Non-proline Block (NPB)
SEQ ID NO: 35

DQQAEEDYARRSEEEYNRLTQQQ

Non-proline Block (NPB)
SEQ ID NO: 36

MEKSADQQAEEDYARRSEEEYNRLTQQQ

SP0148 lacking signal sequence (nucleotides)
SEQ ID NO: 37

ATGTGCTCAGGGGGTGCTAAGAAAGAAGGAGAAGCAGCTAGCAAGAAAGAAATCATCGTTGCAACCAATGGATCA

CCAAAGCCATTTATCTATGAAGAAAATGGCGAATTGACTGGTTACGAGATTGAAGTCGTTCGCGCTATCTTTAAA

GATTCTGACAAATATGATGTCAAGTTTGAAAAGACAGAATGGTCAGGTGTCTTTGCTGGTCTTGACGCTGATCGT

TACAATATGGCTGTCAACAATCTTAGCTACACTAAAGAACGTGCGGAGAAATACCTCTATGCCGCACCAATTGCC

CAAAATCCTAATGTCCTTGTCGTGAAGAAAGATGACTCTAGTATCAAGTCTCTCGATGATATCGGTGGAAAATCG

ACGGAAGTCGTTCAAGCCACTACATCAGCTAAGCAGTTAGAAGCATACAATGCTGAACACACGGACAACCCAACT

ATCCTTAACTATACTAAGGCAGACTTCCAACAAATCATGGTACGTTTGAGCGATGGACAATTTGACTATAAGATT

TTTGATAAAATCGGTGTTGAAACAGTGATCAAGAACCAAGGTTTGGACAACTTGAAAGTTATCGAACTTCCAAGC

GACCAACAACCGTACGTTTACCCACTTCTTGCTCAGGGTCAAGATGAGTTGAAATCGTTTGTAGACAAACGCATC

AAAGAACTTTATAAAGATGGAACTCTTGAAAAATTGTCTAAACAATTCTTCGGAGACACTTATCTACCGGCAGAA

GCTGATATTAAAGAGTAA

SP0148 including signal sequence (nucleotides)
SEQ ID NO: 38

ATGAAAAAAATCGTTAAATACTCATCTCTTGCAGCCCTTGCTCTTGTTGCTGCAGGTGTGCTTGCGGCTTGCTCA

GGGGGTGCTAAGAAAGAAGGAGAAGCAGCTAGCAAGAAAGAAATCATCGTTGCAACCAATGGATCACCAAAGCCA

TTTATCTATGAAGAAAATGGCGAATTGACTGGTTACGAGATTGAAGTCGTTCGCGCTATCTTTAAAGATTCTGAC

AAATATGATGTCAAGTTTGAAAAGACAGAATGGTCAGGTGTCTTTGCTGGTCTTGACGCTGATCGTTACAATATG

GCTGTCAACAATCTTAGCTACACTAAAGAACGTGCGGAGAAATACCTCTATGCCGCACCAATTGCCCAAAATCCT

AATGTCCTTGTCGTGAAGAAAGATGACTCTAGTATCAAGTCTCTCGATGATATCGGTGGAAAATCGACGGAAGTC

GTTCAAGCCACTACATCAGCTAAGCAGTTAGAAGCATACAATGCTGAACACACGGACAACCCAACTATCCTTAAC

TATACTAAGGCAGACTTCCAACAAATCATGGTACGTTTGAGCGATGGACAATTTGACTATAAGATTTTTGATAAA

ATCGGTGTTGAAACAGTGATCAAGAACCAAGGTTTGGACAACTTGAAAGTTATCGAACTTCCAAGCGACCAACAA

CCGTACGTTTACCCACTTCTTGCTCAGGGTCAAGATGAGTTGAAATCGTTTGTAGACAAACGCATCAAAGAACTT

TATAAAGATGGAACTCTTGAAAAATTGTCTAAACAATTCTTCGGAGACACTTATCTACCGGCAGAAGCTGATATT

AAAGAGTAA

SP2108 lacking signal sequence (nucleotides)
SEQ ID NO: 39

ATGTGCGGAAGCAAAACTGCTGATAAGCCTGCTGATTCTGGTTCATCTGAAGTCAAAGAACTCACTGTATATGTA

GACGAGGGATATAAGAGCTATATTGAAGAGGTTGCTAAAGCTTATGAAAAAGAAGCTGGAGTAAAAGTCACTCTT

AAAACTGGTGATGCTCTAGGAGGTCTTGATAAACTTTCTCTTGACAACCAATCTGGTAATGTCCCTGATGTTATG

ATGGCTCCATACGACCGTGTAGGTAGCCTTGGTTCTGACGGACAACTTTCAGAAGTGAAATTGAGCGATGGTGCT

| SEQUENCES |
| --- |

AAAACAGACGACACAACTAAATCTCTTGTAACAGCTGCTAATGGTAAAGTTTACGGTGCTCCTGCCGTTATCGAG

TCACTTGTTATGTACTACAACAAAGACTTGGTGAAAGATGCTCCAAAAACATTTGCTGACTTGGAAAACCTTGCT

AAAGATAGCAAATACGCATTCGCTGGTGAAGATGGTAAAACTACTGCCTTCCTAGCTGACTGGACAAACTTCTAC

TATACATATGGACTTCTTGCCGGTAACGGTGCTTACGTCTTTGGCCAAAACGGTAAAGACGCTAAAGACATCGGT

CTTGCAAACGACGGTTCTATCGTAGGTATCAACTACGCTAAATCTTGGTACGAAAAATGGCCTAAAGGTATGCAA

GATACAGAAGGTGCTGGAAACTTAATCCAAACTCAATTCCAAGAAGGTAAAACAGCTGCTATCATCGACGGACCT

TGGAAAGCTCAAGCCTTTAAAGATGCTAAAGTAAACTACGGAGTTGCAACTATCCCAACTCTTCCAAATGGAAAA

GAATATGCTGCATTCGGTGGTGGTAAAGCTTGGGTCATTCCTCAAGCCGTTAAGAACCTTGAAGCTTCTCAAAAA

TTTGTAGACTTCCTTGTTGCAACTGAACAACAAAAAGTATTATATGATAAGACTAACGAAATCCCAGCTAATACT

GAGGCTCGTTCATACGCTGAAGGTAAAAACGATGAGTTGACAACAGCTGTTATCAAACAGTTCAAGAACACTCAA

CCACTGCCAAACATCTCTCAAATGTCTGCAGTTTGGGATCCAGCGAAAAATATGCTCTTTGATGCTGTAAGTGGT

CAAAAAGATGCTAAAACAGCTGCTAACGATGCTGTAACATTGATCAAAGAAACAATCAAACAAAAATTTGGTGAA

TAA

SP1912 (nucleotides)

SEQ ID NO: 40

ATGAATGGTATGAAAGCTAAAAAAATGTGGATGGCAGGCTTGGCTCTGCTAGGTATCGGAAGCCTTGCTCTTGCT

ACGAAAAAAGTTGCAGATGACCGTAAGCTCATGAAGACTCAGGAAGAGTTGACAGAGATTGTGCGAGACCATTTT

TCCGACATGGGGGAAATTGCGACCCTTTATGTTCAAGTTTACGAAAGCAGTCTGGAGAGCTTGGTTGGTGGCGTC

ATTTTTGAGGATGGCCGTCATTATACCTTTGTCTATGAAAATGAAGACCTAGTCTATGAGGAGGAAGTCTTATGA

SP1912L (nucleotides)

SEQ ID NO: 41

ATGAGATACCTGGCAACATTGTTGTTATCTCTGGCGGTGTTAATCACCGCCGGGTGCAAAAAAGTTGCAGATGAC

CGTAAGCTCATGAAGACTCAGGAAGAGTTGACAGAGATTGTGCGAGACCATTTTTCCGACATGGGGGAAATTGCG

ACCCTTTATGTTCAAGTTTACGAAAGCAGTCTGGAGAGCTTGGTTGGTGGCGTCATTTTTGAGGATGGCCGTCAT

TATACCTTTGTCTATGAAAATGAAGACCTAGTCTATGAGGAGGAAGTCTTATGA

SP0641N (nucleotides)

SEQ ID NO: 42

ATGGTAGTCTTAGCAGACACATCTAGCTCTGAAGATGCTTTAAACATCTCTGATAAAGAAAAAGTAGCAGAAAAT

AAAGAGAAACATGAAAATATCCATAGTGCTATGGAAACTTCACAGGATTTTAAAGAGAAGAAAACAGCAGTCATT

AAGGAAAAAGAAGTTGTTAGTAAAAATCCTGTGATAGACAATAACACTAGCAATGAAGAAGCAAAAATCAAAGAA

GAAAATTCCAATAAATCCCAAGGAGATTATACGGACTCATTTGTGAATAAAAACACAGAAAATCCCAAAAAAGAA

GATAAAGTTGTCTATATTGCTGAATTTAAAGATAAAGAATCTGGAGAAAAAGCAATCAAGGAACTATCCAGTCTT

AAGAATACAAAAGTTTTATATACTTATGATAGAATTTTTAACGGTAGTGCCATAGAAACAACTCCAGATAACTTG

GACAAAATTAAACAAATAGAAGGTATTTCATCGGTTGAAAGGGCACAAAAAGTCCAACCCATGATGAATCATGCC

AGAAAGGAAATTGGAGTTGAGGAAGCTATTGATTACCTAAAGTCTATCAATGCTCCGTTTGGGAAAAATTTTGAT

GGTAGAGGTATGGTCATTTCAAATATCGATACTGGAACAGATTATAGACATAAGGCTATGAGAATCGATGATGAT

GCCAAAGCCTCAATGAGATTTAAAAAAGAAGACTTAAAAGGCACTGATAAAAATTATTGGTTGAGTGATAAAATC

CCTCATGCGTTCAATTATTATAATGGTGGCAAAATCACTGTAGAAAAATATGATGATGGAAGGGATTATTTTGAC

CCACATGGGATGCATATTGCAGGGATTCTTGCTGGAAATGATACTGAACAAGACATCAAAAACTTTAACGGCATA

GATGGAATTGCACCTAATGCACAAATTTTCTCTTACAAAATGTATTCTGACGCAGGATCTGGGTTTGCGGGTGAT

GAAACAATGTTTCATGCTATTGAAGATTCTATCAAACACAACGTTGATGTTGTTTCGGTATCATCTGGTTTTACA

| SEQUENCES |
|---|
| GGAACAGGTCTTGTAGGTGAGAAATATTGGCAAGCTATTCGGGCATTAAGAAAAGCAGGCATTCCAATGGTTGTC |
| GCTACGGGTAACTATGCGACTTCTGCTTCAAGTTCTTCATGGGATTTAGTAGCAAATAATCATCTGAAAATGACC |
| GACACTGGAAATGTAACACGAACTGCAGCACATGAAGATGCGATAGCGGTCGCTTCTGCTAAAAATCAAACAGTT |
| GAGTTTGATAAAGTTAACATAGGTGGAGAAAGTTTTAAATACAGAAATATAGGGGCCTTTTTCGATAAGAGTAAA |
| ATCACAACAAATGAAGATGGAACAAAAGCTCCTAGTAAATTAAAATTTGTATATATAGGCAAGGGGCAAGACCAA |
| GATTTGATAGGTTTGGATCTTAGGGGCAAAATTGCAGTAATGGATAGAATTTATACAAAGGATTTAAAAAATGCT |
| TTTAAAAAAGCTATGGATAAGGGTGCACGCGCCATTATGGTTGTAAATACTGTAAATTACTACAATAGAGATAAT |
| TGGACAGAGCTTCCAGCTATGGGATATGAAGCGGATGAAGGTACTAAAAGTCAAGTGTTTTCAATTTCAGGAGAT |
| GATGGTGTAAAGCTATGGAACATGATTAATCCTGATAAAAAAACTGAAGTCAAAAGAAATAATAAAGAAGATTTT |
| AAAGATAAATTGGAGCAATACTATCCAATTGATATGGAAAGTTTTAATTCCAACAAACCGAATGTAGGTGACGAA |
| AAAGAGATTGACTTTAAGTTTGCACCTGACACAGACAAAGAACTCTATAAAGAAGATATCATCGTTCCAGCAGGA |
| TCTACATCTTGGGGGCCAAGAATAGATTTACTTTTAAAACCCGATGTTTCAGCACCTGGTAAAAATATTAAATCC |
| ACGCTTAATGTTATTAATGGCAAATCAACTTATGGC |

SP0882N DNA
SEQ ID NO: 43
ATGAATCAATCCTACTTTTATCTAAAAATGAAAGAACACAAACTCAAGGTTCCTTATACAGGTAAGGAGCGCCGT
GTACGTATTCTTCTTCCTAAAGATTATGAGAAAGATACAGACCGTTCCTATCCTGTTGTATACTTTCATGACGGG
CAAAATGTTTTTAATAGCAAAGAGTCTTTCATTGGACATTCATGGAAGATTATCCCAGCTATCAAACGAAATCCG
GATATCAGTCGCATGATTGTCGTTGCTATTGACAATGATGGTATGGGCGGATGAATGAGTATGCGGCTTGGAAG
TTCCAAGAATCTCCTATCCCAGGGCAGCAGTTTGGTGGTAAGGGTGTGGAGTATGCTGAGTTTGTCATGGAGGTG
GTCAAGCCTTTTATC

SP0882 with exogenous signal sequence (nucleotides)
SEQ ID NO: 44
ATGTCATCTAAATTTATGAAGAGCGCTGCGGTGCTTGGAACTGCTACACTTGCTAGCTTGCTTTTGGTAGCTTGC
ATGAATCAATCCTACTTTTATCTAAAAATGAAAGAACACAAACTCAAGGTTCCTTATACAGGTAAGGAGCGCCGT
GTACGTATTCTTCTTCCTAAAGATTATGAGAAAGATACAGACCGTTCCTATCCTGTTGTATACTTTCATGACGGG
CAAAATGTTTTTAATAGCAAAGAGTCTTTCATTGGACATTCATGGAAGATTATCCCAGCTATCAAACGAAATCCG
GATATCAGTCGCATGATTGTCGTTGCTATTGACAATGATGGTATGGGCGGATGAATGAGTATGCGGCTTGGAAG
TTCCAAGAATCTCCTATCCCAGGGCAGCAGTTTGGTGGTAAGGGTGTGGAGTATGCTGAGTTTGTCATGGAGGTG
GTCAAGCCTTTTATCGATGAGACCTATCGTACAAAAGCAGACTGCCAGCATACGGCTATGATTGGTTCCTCACTA
GGAGGCAATATTACCCAGTTTATCGGTTTGGAATACCAAGACCAAATTGGTTGCTTGGGCGTTTTTTCATCTGCA
AACTGGCTCCACCAAGAAGCCTTTAACCGCTATTTCGAGTGCCAGAAACTATCGCCTGACCAGCGCATCTTCATC
TATGTAGGAACAGAAGAAGCAGATGATACAGACAAGACCTTGATGGATGGCAATATCAAACAAGCCTATATCGAC
TCGCTTTGCTATTACCATGATTTGATAGCAGGGGAGTACATCTGGATAATCTTGTGCTAAAAGTTCAGTCT
GGTGCCATCCATAGTGAAATCCCTTGGTCAGAAAATCTACCAGATTGTCTGAGATTTTTTGCAGAAAAATGGTAA SP0882N with exogenous signal sequence (nucleotides)
SEQ ID NO: 45
ATGTCATCTAAATTTATGAAGAGCGCTGCGGTGCTTGGAACTGCTACACTTGCTAGCTTGCTTTTGGTAGCTTGC
ATGAATCAATCCTACTTTTATCTAAAAATGAAAGAACACAAACTCAAGGTTCCTTATACAGGTAAGGAGCGCCGT
GTACGTATTCTTCTTCCTAAAGATTATGAGAAAGATACAGACCGTTCCTATCCTGTTGTATACTTTCATGACGGG
CAAAATGTTTTTAATAGCAAAGAGTCTTTCATTGGACATTCATGGAAGATTATCCCAGCTATCAAACGAAATCCG

GATATCAGTCGCATGATTGTCGTTGCTATTGACAATGATGGTATGGGCGGATGAATGAGTATGCGGCTTGGAAG

TTCCAAGAATCTCCTATCCCAGGGCAGCAGTTTGGTGGTAAGGGTGTGGAGTATGCTGAGTTTGTCATGGAGGTG

GTCAAGCCTTTTATC

PSPA (nucleotides)

SEQ ID NO: 46

TTGACAAATATTTACGGAGGAGGCTTATGCTTAATATAAGTATAGGCTAAAAATGATTATCAGAAAAGAG

GTAAATTTAGATGAATAAGAAAAAAATGATTTTAACAAGCCTAGCCAGCGTCGCTATCTTAGGGGCTGGT

TTTGTTGCGTCTTCGCCTACTTTTGTAAGAGCAGAAGAAGCTCCTGTAGCTAACCAGTCTAAAGCTGAGA

AGACTATGATGCAGCAGTGAAAAAATCTGAAGCTGCTAAGAAAGATTACGAAACGGCTAAAAAGAAAGC

AGAAGACGCTCAGAAGAAATATGATGAGGATCAGAAGAAACTGAGGCAAAAGCGGAAAAAGAAAGAAAA

GCTTCTGAAAAGATAGCTGAGGCAACAAAAGAAGTTCAACAAGCGTACCTAGCTTATCTACAAGCTAGCA

ACGAAAGTCAGAGAAAAGAGGCAGATAAGAAGATAAAAGAAGCTACGCAACGCAAAGATGAGGCGGAAGC

TGCATTTGCTACTATTCGAACAACAATTGTAGTTCCTGAACCAAGTGAGTTAGCTGAGACTAAGAAAAAA

GCAGAAGAGGCAACAAAAGAAGCAGAAGTAGCTAAGAAAAAATCTGAAGAGGCAGCTAAAGAGGTAGAAG

TAGAGAAAAATAAAATACTTGAACAAGATGCTGAAAACGAAAAGAAAATTGACGTACTTCAAAACAAAGT

CGCTGATTTAGAAAAAGGAATTGCTCCTTATCAAAACGAAGTCGCTGAATTAAATAAAGAAATTGCTAGA

CTTCAAAGCGATTTAAAAGATGCTGAAGAAAATAATGTAGAAGACTACATTAAAGAAGGTTTAGAGCAAG

CTATCACTAATAAAAAAGCTGAATTAGCTACAACTCAACAAAACATAGATAAAACTCAAAAAGATTTAGA

GGATGCTGAATTAGAACTTGAAAAAGTATTAGCTACATTAGACCCTGAAGGTAAAACTCAAGATGAATTA

GATAAAGAAGCTGCTGAAGCTGAGTTGAATGAAAAAGTTGAAGCTCTTCAAAACCAAGTTGCTGAATTAG

AAGAAGAACTTTCAAAACTTGAAGATAATCTTAAAGATGCTGAAACAAACAACGTTGAAGACTACATTAA

AGAAGGTTTAGAAGAAGCTATCGCGACTAAAAAAGCTGAATTGGAAAAAACTCAAAAAGAATTAGATGCA

GCTCTTAATGAGTTAGGCCCTGATGGAGATGAAGAAGAGACTCCAGCGCCGGCTCCTCAACCAGAAAAAC

CAGCTGAAGAGCCTGAGAATCCAGCTCCAGCACCAAAACCAGAGAAGTCAGCAGATCAACAAGCTGAAGA

AGACTATGCTCGTAGATCAGAAGAAGAATATAATCGCTTGACCCAACAGCAACCGCCAAAAGCAGAAAAA

CCAGCTCCTGCACCACAACCAGAGCAACCAGCTCCTGCACCAAAAATAGGTTGGAAACAAGAAAACGGTA

TGTGGTACTTCTACAATACTGATGGTTCAATGGCGACAGGTTGGCTACAAAACAACGGTTCATGGTACTA

CCTCAACAGCAATGGCGCTATGGCTACAGGTTGGCTCCAATACAATGGTTCATGGTATTACCTAAACGCT

AACGGCGCTATGGCGACAGGCTGGCTCCAATACAATGGCTCATGGTACTACCTCAACGCTAACGGCGCTA

TGGCGACAGGCTGGCTCCAATACAATGGCTCATGGTACTACCTCAACGCTAATGGTGATATGGCGACAGG

ATGGCTCCAATACAACGGTTCATGGTATTACCTCAACGCTAATGGTGATATGGCTACAGGTTGGGCTAAA

GTCCACGGTTCATGGTACTACCTCAACGCTAACGGTTCAATGGCAACAGGTTGGGTGAAAGATGGAGAAA

CCTGGTACTATCTTGAAGCATCAGGTTCTATGAAAGCAAACCAATGGTTCCAAGTATCAGATAAATGGTA

CTATGTCAATGGTTTAGGTTCCCTTTCAGTCAACACAACTGTAGATGGCTATAAAGTCAATGCCAATGGT

GAATGGGTTTAAGCCG

SP2108/SP0148 fusion protein (675 amino acids)

SEQ ID NO: 47

MSSKFMKSAAVLGTATLASLLLVACGSKTADKPADSGSSEVKELTVYVDEGYKSYIEEVAKAYEKEAGVKVTLKT

GDALGGLDKLSLDNQSGNVPDVMMAPYDRVGSLGSDGQLSEVKLSDGAKTDDTTKSLVTAANGKVYGAPAVIESL

VMYYNKDLVKDAPKTFADLENLAKDSKYAFAGEDGKTTAFLADWTNFYYTYGLLAGNGAYVFGQNGKDAKDIGLA

NDGSIVGINYAKSWYEKWPKGMQDTEGAGNLIQTQFQEGKTAAIIDGPWKAQAFKDAKVNYGVATIPTLPNGKEY

AAFGGGKAWVIPQAVKNLEASQKFVDFLVATEQQKVLYDKTNEIPANTEARSYAEGKNDELTTAVIKQFKNTQPL
PNISQMSAVWDPAKNMLFDAVSGQKDAKTAANDAVTLIKETIKQKFGESGGAKKEGEAASKKEIIVATNGSPKPF
IYEENGELTGYEIEVVRAIFKDSDKYDVKFEKTEWSGVFAGLDADRYNMAVNNLSYTKERAEKYLYAAPIAQNPN
VLVVKKDDSSIKSLDDIGGKSTEVVQATTSAKQLEAYNAEHTDNPTILNYTKADFQQIMVRLSDGQFDYKIFDKI
GVETVIKNQGLDNLKVIELPSDQQPYVYPLLAQGQDELKSFVDKRIKELYKDGTLEKLSKQFFGDTYLPAEADIK

SP0148/SP2108 fusion protein (674 amino acids)

SEQ ID NO: 48

MKKIVKYSSLAALALVAAGVLAACSGGAKKEGEAASKKEIIVATNGSPKPFIYEENGELTGYEIEVVRAIFKDSD
KYDVKFEKTEWSGVFAGLDADRYNMAVNNLSYTKERAEKYLYAAPIAQNPNVLVVKKDDSSIKSLDDIGGKSTEV
VQATTSAKQLEAYNAEHTDNPTILNYTKADFQQIMVRLSDGQFDYKIFDKIGVETVIKNQGLDNLKVIELPSDQQ
PYVYPLLAQGQDELKSFVDKRIKELYKDGTLEKLSKQFFGDTYLPAEADIKGSKTADKPADSGSSEVKELTVYVD
EGYKSYIEEVAKAYEKEAGVKVTLKTGDALGGLDKLSLDNQSGNVPDVMMAPYDRVGSLGSDGQLSEVKLSDGAK
TDDTTKSLVTAANGKVYGAPAVIESLVMYYNKDLVKDAPKTFADLENLAKDSKYAFAGEDGKTTAFLADWTNFYY
TYGLLAGNGAYVFGQNGKDAKDIGLANDGSIVGINYAKSWYEKWPKGMQDTEGAGNLIQTQFQEGKTAAIIDGPW
KAQAFKDAKVNYGVATIPTLPNGKEYAAFGGGKAWVIPQAVKNLEASQKFVDFLVATEQQKVLYDKTNEIPANTE
ARSYAEGKNDELTTAVIKQFKNTQPLPNISQMSAVWDPAKNMLFDAVSGQKDAKTAANDAVTLIKETIKQKFGE

SP2108/SP1912 fusion protein (521 amino acids)

SEQ ID NO: 49

MSSKFMKSAAVLGTATLASLLLVACGSKTADKPADSGSSEVKELTVYVDEGYKSYIEEVAKAYEKEAGVKVTLKT
GDALGGLDKLSLDNQSGNVPDVMMAPYDRVGSLGSDGQLSEVKLSDGAKTDDTTKSLVTAANGKVYGAPAVIESL
VMYYNKDLVKDAPKTFADLENLAKDSKYAFAGEDGKTTAFLADWTNFYYTYGLLAGNGAYVFGQNGKDAKDIGLA
NDGSIVGINYAKSWYEKWPKGMQDTEGAGNLIQTQFQEGKTAAIIDGPWKAQAFKDAKVNYGVATIPTLPNGKEY
AAFGGGKAWVIPQAVKNLEASQKFVDFLVATEQQKVLYDKTNEIPANTEARSYAEGKNDELTTAVIKQFKNTQPL
PNISQMSAVWDPAKNMLFDAVSGQKDAKTAANDAVTLIKETIKQKFGENGMKAKKMWMAGLALLGIGSLALATKK
VADDRKLMKTQE ELTEIVRDHFSDMGEIATLYVQVYESSLESLVGGVIFEDGRHYTFVYENEDLVYEEEVL

SP0148/SP1912 fusion protein (374 amino acids)

SEQ ID NO: 50

MKKIVKYSSLAALALVAAGVLAACSGGAKKEGEAASKKEIIVATNGSPKPFIYEENGELTGYEIEVVRAIFKDSD
KYDVKFEKTEWSGVFAGLDADRYNMAVNNLSYTKERAEKYLYAAPIAQNPNVLVVKKDDSSIKSLDDIGGKSTEV
VQATTSAKQLEAYNAEHTDNPTILNYTKADFQQIMVRLSDGQFDYKIFDKIGVETVIKNQGLDNLKVIELPSDQQ
PYVYPLLAQGQDELKSFVDKRIKELYKDGTLEKLSKQFFGDTYLPAEADIKNGMKAKKMWMAGLALLGIGSLALA
TKKVADDRKLMKTQEELTEIVRDHFSDMGEIATLYVQVYESSLESLVGGVIFEDGRHYTFVYENEDLVYEEEVL

SP2108/SP1912/SP0148 fusion protein (773 amino acids)

SEQ ID NO: 51

MSSKFMKSAAVLGTATLASLLLVACGSKTADKPADSGSSEVKELTVYVDEGYKSYIEEVAKAYEKEAGVKVTLKT
GDALGGLDKLSLDNQSGNVPDVMMAPYDRVGSLGSDGQLSEVKLSDGAKTDDTTKSLVTAANGKVYGAPAVIESL
VMYYNKDLVKDAPKTFADLENLAKDSKYAFAGEDGKTTAFLADWTNFYYTYGLLAGNGAYVFGQNGKDAKDIGLA
NDGSIVGINYAKSWYEKWPKGMQDTEGAGNLIQTQFQEGKTAAIIDGPWKAQAFKDAKVNYGVATIPTLPNGKEY
AAFGGGKAWVIPQAVKNLEASQKFVDFLVATEQQKVLYDKTNEIPANTEARSYAEGKNDELTTAVIKQFKNTQPL
PNISQMSAVWDPAKNMLFDAVSGQKDAKTAANDAVTLIKETIKQKFGENGMKAKKMWMAGLALLGIGSLALATKK
VADDRKLMKTQE

| SEQUENCES |
| --- |
| ELTEIVRDHFSDMGEIATLYVQVYESSLESLVGGVIFEDGRHYTFVYENEDLVYEEEVLSGGAKKEGEAASKKEI IVATNGSPKPFIYEENGELTGYEIEVVRAIFKDSDKYDVKFEKTEWSGVFAGLDADRYNMAVNNLSYTKERAEKY LYAAPIAQNPNVLVVKKDDSSIKSLDDIGGKSTEVVQATTSAKQLEAYNAEHTDNPTILNYTKADFQQIMVRLSD GQFDYKIFDKIGVETVIKNQGLDNLKVIELPSDQQPYVYPLLAQGQDELKSFVDKRIKELYKDGTLEKLSKQFFG DTYLPAEADIK |

SP0148/SP1912/SP2108 fusion protein (772 amino acids)

SEQ ID NO: 52

MKKIVKYSSLAALALVAAGVLAACSGGAKKEGEAASKKEIIVATNGSPKPFIYEENGELTGYEIEVVRAIFKDSD KYDVKFEKTEWSGVFAGLDADRYNMAVNNLSYTKERAEKYLYAAPIAQNPNVLVVKKDDSSIKSLDDIGGKSTEV VQATTSAKQLEAYNAEHTDNPTILNYTKADFQQIMVRLSDGQFDYKIFDKIGVETVIKNQGLDNLKVIELPSDQQ PYVYPLLAQGQDELKSFVDKRIKELYKDGTLEKLSKQFFGDTYLPAEADIKNGMKAKKMWMAGLALLGIGSLALA TKKVADDRKLMKTQEELTEIVRDHFSDMGEIATLYVQVYESSLESLVGGVIFEDGRHYTFVYENEDLVYEEEVLG SKTADKPADSGSSEVKELTVYVDEGYKSYIEEVAKAYEKEAGVKVTLKTGDALGGLDKLSLDNQSGNVPDVMMAP YDRVGSLGSDGQLSEVKLSDGAKTDDTTKSLVTAANGKVYGAPAVIESLVMYYNKDLVKDAPKTFADLENLAKDS KYAFAGEDGKTTAFLADWTNFYYTYGLLAGNGAYVFGQNGKDAKDIGLANDGSIVGINYAKSWYEKWPKGMQDTE GAGNLIQTQFQEGKTAAIIDGPWKAQAFKDAKVNYGVATIPTLPNGKEYAAFGGGKAWVIPQAVKNLEASQKFVD FLVATEQQKVLYDKTNEIPANTEARSYAEGKNDELTTAVIKQFKNTQPLPNISQMSAVWDPAKNMLFDAVSGQKD AKTAANDAVTLIKETIKQKFGE

SP2108/SP0148/SP1912 fusion protein (773 amino acids)

SEQ ID NO: 53

MSSKFMKSAAVLGTATLASLLLVACGSKTADKPADSGSSEVKELTVYVDEGYKSYIEEVAKAYEKEAGVKVTLKT GDALGGLDKLSLDNQSGNVPDVMMAPYDRVGSLGSDGQLSEVKLSDGAKTDDTTKSLVTAANGKVYGAPAVIESL VMYYNKDLVKDAPKTFADLENLAKDSKYAFAGEDGKTTAFLADWTNFYYTYGLLAGNGAYVFGQNGKDAKDIGLA NDGSIVGINYAKSWYEKWPKGMQDTEGAGNLIQTQFQEGKTAAIIDGPWKAQAFKDAKVNYGVATIPTLPNGKEY AAFGGGKAWVIPQAVKNLEASQKFVDFLVATEQQKVLYDKTNEIPANTEARSYAEGKNDELTTAVIKQFKNTQPL PNISQMSAVWDPAKNMLFDAVSGQKDAKTAANDAVTLIKETIKQKFGESGGAKKEGEAASKKEIIVATNGSPKPF IYEENGELTGYEIEVVRAIFKDSDKYDVKFEKTEWSGVFAGLDADRYNMAVNNLSYTKERAEKYLYAAPIAQNPN VLVVKKDDSSIKSLDDIGGKSTEVVQATTSAKQLEAYNAEHTDNPTILNYTKADFQQIMVRLSDGQFDYKIFDKI GVETVIKNQGLDNLKVIELPSDQQPYVYPLLAQGQDELKSFVDKRIKELYKDGTLEKLSKQFFGDTYLPAEADIK NGMKAKKMWMAGLALLGIGSLALATKKVADDRKLMKTQEELTEIVRDHFSDMGEIATLYVQVYESSLESLVGGVI FEDGRHYTFVYENEDLVYEEEVL

SP0148/SP2108/SP1912 fusion protein (772 amino acids)

SEQ ID NO: 54

MKKIVKYSSLAALALVAAGVLAACSGGAKKEGEAASKKEIIVATNGSPKPFIYEENGELTGYEIEVVRAIFKDSD KYDVKFEKTEWSGVFAGLDADRYNMAVNNLSYTKERAEKYLYAAPIAQNPNVLVVKKDDSSIKSLDDIGGKSTEV VQATTSAKQLEAYNAEHTDNPTILNYTKADFQQIMVRLSDGQFDYKIFDKIGVETVIKNQGLDNLKVIELPSDQQ PYVYPLLAQGQDELKSFVDKRIKELYKDGTLEKLSKQFFGDTYLPAEADIKGSKTADKPADSGSSEVKELTVYVD EGYKSYIEEVAKAYEKEAGVKVTLKTGDALGGLDKLSLDNQSGNVPDVMMAPYDRVGSLGSDGQLSEVKLSDGAK TDDTTKSLVTAANGKVYGAPAVIESLVMYYNKDLVKDAPKTFADLENLAKDSKYAFAGEDGKTTAFLADWTNFYY TYGLLAGNGAYVFGQNGKDAKDIGLANDGSIVGINYAKSWYEKWPKGMQDTEGAGNLIQTQFQEGKTAAIIDGPW KAQAFKDAKVNYGVATIPTLPNGKEYAAFGGGKAWVIPQAVKNLEASQKFVDFLVATEQQKVLYDKTNEIPANTE ARSYAEGKNDELTTAVIKQFKNTQPLPNISQMSAVWDPAKNMLFDAVSGQKDAKTAANDAVTLIKETIKQKFGEN

GMKAKKMWMAGLALLGIGSLALATKKVADDRKLMKTQEELTEIVRDHFSDMGEIATLYVQVYESSLESLVGGVIF
EDGRHYTFVYENEDLVYEEEVL

L460D (471 amino acids)
SEQ ID NO: 55
MANKAVNDFILAMNYDKKKLLTHQGESIENRFIKEGNQLPDEFVVIERKKRSLSTNTSDISVTATNDSRLYPGAL
LVVDETLLENNPTLLAVDRAPMTYSIDLPGLASSDSFLQVEDPSNSSVRGAVNDLLAKWHQDYGQVNNVPARMQY
EKITAHSMEQLKVKFGSDFEKTGNSLDIDFNSVHSGEKQIQIVNFKQIYYTVSVDAVKNPGDVFQDTVTVEDLKQ
RGISAERPLVYISSVAYGRQVYLKLETTSKSDEVEAAFEALIKGVKVAPQTEWKQILDNTEVKAVILGGDPSSGA
RVVTGKVDMVEDLIQEGSRFTADHPGLPISYTTSFLRDNVVATFQNSTDYVETKVTAYRNGDLLLDHSGAYVAQY
YITWDELSYDHQGKEVLTPKAWDRNGQDLTAHFTTSIPLKGNVRNLSVKIRECTGLAWEWWRTVYEKTDLPLVRK
RTISIWGTTDYPQVEDKVEND SP2108/SP0148 fusion (nucleotides)
SEQ ID NO: 56
ATGTCATCTAAATTTATGAAGAGCGCTGCGGTGCTTGGAACTGCTACACTTGCTAGCTTGCTTTTGGTAGCTTGC
GGAAGCAAAACTGCTGATAAGCCTGCTGATTCTGGTTCATCTGAAGTCAAAGAACTCACTGTATATGTAGACGAG
GGATATAAGAGCTATATTGAAGAGGTTGCTAAAGCTTATGAAAAAGAAGCTGGAGTAAAAGTCACTCTTAAAACT
GGTGATGCTCTAGGAGGTCTTGATAAACTTTCTCTTGACAACCAATCTGGTAATGTCCCTGATGTTATGATGGCT
CCATACGACCGTGTAGGTAGCCTTGGTTCTGACGGACAACTTTCAGAAGTGAAATTGAGCGATGGTGCTAAAACA
GACGACACAACTAAATCTCTTGTAACAGCTGCTAATGGTAAAGTTTACGGTGCTCCTGCCGTTATCGAGTCACTT
GTTATGTACTACAACAAAGACTTGGTGAAAGATGCTCCAAAAACATTTGCTGACTTGGAAAACCTTGCTAAAGAT
AGCAAATACGCATTCGCTGGTGAAGATGGTAAAACTACTGCCTTCCTAGCTGACTGGACAAACTTCTACTATACA
TATGGACTTCTTGCCGGTAACGGTGCTTACGTCTTTGGCCAAAACGGTAAAGACGCTAAAGACATCGGTCTTGCA
AACGACGGTTCTATCGTAGGTATCAACTACGCTAAATCTTGGTACGAAAATGGCCTAAAGGTATGCAAGATACA
GAAGGTGCTGGAAACTTAATCCAAACTCAATTCCAAGAAGGTAAAACAGCTGCTATCATCGACGGACCTTGGAAA
GCTCAAGCCTTTAAAGATGCTAAAGTAAAACTACGGAGTTGCAACTATCCCAACTCTTCCAAATGGAAAAGAATAT
GCTGCATTCGGTGGTGGTAAAGCTTGGGTCATTCCTCAAGCCGTTAAGAACCTTGAAGCTTCTCAAAAATTTGTA
GACTTCCTTGTTGCAACTGAACAACAAAAAGTATTATATGATAAGACTAACGAAATCCCAGCTAATACTGAGGCT
CGTTCATACGCTGAAGGTAAAAACGATGAGTTGACAACAGCTGTTATCAAACAGTTCAAGAACACTCAACCACTG
CCAAACATCTCTCAAATGTCTGCAGTTTGGGATCCAGCGAAAAATATGCTCTTTGATGCTGTAAGTGGTCAAAAA
GATGCTAAAACAGCTGCTAACGATGCTGTAACATTGATCAAAGAAACAATCAAACAAAAATTTGGTGAATCAGGG
GGTGCTAAGAAAGAAGGAGAAGCAGCTAGCAAGAAAGAAATCATCGTTGCAACCAATGGATCACCAAAGCCATTT
ATCTATGAAGAAATGGCGAATTGACTGGTTACGAGATTGAAGTCGTTCGCGCTATCTTTAAAGATTCTGACAAA
TATGATGTCAAGTTTGAAAAGACAGAATGGTCAGGTGTCTTTGCTGGTCTTGACGCTGATCGTTACAATATGGCT
GTCAACAATCTTAGCTACACTAAAGAACGTGCGGAGAAATACCTCTATGCCGCACCAATTGCCCAAAATCCTAAT
GTCCTTGTCGTGAAGAAAGATGACTCTAGTATCAAGTCTCTCGATGATATCGGTGGAAAATCGACGGAAGTCGTT
CAAGCCACTACATCAGCTAAGCAGTTAGAAGCATACAATGCTGAACACACGGACAACCCAACTATCCTTAACTAT
ACTAAGGCAGACTTCCAACAAATCATGGTACGTTTGAGCGATGGACAATTTGACTATAAGATTTTTGATAAAATC

| SEQUENCES |
| --- |
| GGTGTTGAAACAGTGATCAAGAACCAAGGTTTGGACAACTTGAAAGTTATCGAACTTCCAAGCGACCAACAACCG |
| TACGTTTACCCACTTCTTGCTCAGGGTCAAGATGAGTTGAAATCGTTTGTAGACAAACGCATCAAAGAACTTTAT |
| AAAGATGGAACTCTTGAAAAATTGTCTAAACAATTCTTCGGAGACACTTATCTACCGGCAGAAGCTGATATTAAA |

SP0148/SP2108 fusion (nucleotides)

SEQ ID NO: 57

ATGAAAAAAATCGTTAAATACTCATCTCTTGCAGCCCTTGCTCTTGTTGCTGCAGGTGTGCTTGCGGCTTGCTCA

GGGGGTGCTAAGAAAGAAGGAGAAGCAGCTAGCAAGAAAGAAATCATCGTTGCAACCAATGGATCACCAAAGCCA

TTTATCTATGAAGAAATGGCGAATTGACTGGTTACGAGATTGAAGTCGTTCGCGCTATCTTTAAAGATTCTGAC

AAATATGATGTCAAGTTTGAAAAGACAGAATGGTCAGGTGTCTTTGCTGGTCTTGACGCTGATCGTTACAATATG

GCTGTCAACAATCTTAGCTACACTAAAGAACGTGCGGAGAAATACCTCTATGCCGCACCAATTGCCCAAAATCCT

AATGTCCTTGTCGTGAAGAAAGATGACTCTAGTATCAAGTCTCTCGATGATATCGGTGGAAAATCGACGGAAGTC

GTTCAAGCCACTACATCAGCTAAGCAGTTAGAAGCATACAATGCTGAACACACGGACAACCCAACTATCCTTAAC

TATACTAAGGCAGACTTSCAACAAATCATGGTACGTTTGAGCGATGGACAATTTGACTATAAGATTTTTGATAAA

ATCGGTGTTGAAACAGTGATCAAGAACCAAGGTTTGGACAACTTGAAAGTTATCGAACTTCCAAGCGACCAACAA

CCGTACGTTTACCCACTTCTTGCTCAGGGTCAAGATGAGTTGAAATCGTTTGTAGACAAACGCATCAAAGAACTT

TATAAAGATGGAACTCTTGAAAAATTGTCTAAACAATTCTTCGGAGACACTTATCTACCGGCAGAAGCTGATATT

AAAGGAAGCAAAACTGCTGATAAGCCTGCTGATTCTGGTTCATCTGAAGTCAAAGAACTCACTGTATATGTAGAC

GAGGGATATAAGAGCTATATTGAAGAGGTTGCTAAAGCTTATGAAAAAGAAGCTGGAGTAAAAGTCACTCTTAAA

ACTGGTGATGCTCTAGGAGGTCTTGATAAACTTTCTCTTGACAACCAATCTGGTAATGTCCCTGATGTTATGATG

GCTCCATACGACCGTGTAGGTAGCCTTGGTTCTGACGGACAACTTTCAGAAGTGAAATTGAGCGATGGTGCTAAA

ACAGACGACACAACTAAATCTCTTGTAACAGCTGCTAATGGTAAAGTTTACGGTGCTCCTGCCGTTATCGAGTCA

CTTGTTATGTACTACAACAAAGACTTGGTGAAAGATGCTCCAAAAACATTTGCTGACTTGGAAAACCTTGCTAAA

GATAGCAAATACGCATTCGCTGGTGAAGATGGTAAAACTACTGCCTTCCTAGCTGACTGGACAAACTTCTACTAT

ACATATGGACTTCTTGCCGGTAACGGTGCTTACGTCTTTGGCCAAAACGGTAAAGACGCTAAAGACATCGGTCTT

GCAAACGACGGTTCTATCGTAGGTATCAACTACGCTAAATCTTGGTACGAAAAATGGCCTAAAGGTATGCAAGAT

ACAGAAGGTGCTGGAAACTTAATCCAAACTCAATTCCAAGAAGGTAAAACAGCTGCTATCATCGACGGACCTTGG

AAAGCTCAAGCCTTTAAAGATGCTAAAGTAAACTACGGAGTTGCAACTATCCCCAACTCTTCCAAATGGAAAAGAA

TATGCTGCATTCGGTGGTGGTAAAGCTTGGGTCATTCCTCAAGCCGTTAAGAACCTTGAAGCTTCTCAAAAATTT

GTAGACTTCCTTGTTGCAACTGAACAACAAAAAGTATTATATGATAAGACTAACGAAATCCCAGCTAATACTGAG

GCTCGTTCATACGCTGAAGGTAAAAACGATGAGTTGACAACAGCTGTTATCAAACAGTTCAAGAACACTCAACCA

CTGCCAAACATCTCTCAAATGTCTGCAGTTTGGGATCCAGCGAAAAATATGCTCTTTGATGCTGTAAGTGGTCAA

AAAGATGCTAAAACAGCTGCTAACGATGCTGTAACATTGATCAAAGAAACAATCAAACAAAAATTTGGTGAA

SP2108/SP1912 fusion (nucleotides)

SEQ ID NO: 58

ATGTCATCTAAATTTATGAAGAGCGCTGCGGTGCTTGGAACTGCTACACTTGCTAGCTTGCTTTTGGTAGCTTGC

GGAAGCAAAACTGCTGATAAGCCTGCTGATTCTGGTTCATCTGAAGTCAAAGAACTCACTGTATATGTAGACGAG

GGATATAAGAGCTATATTGAAGAGGTTGCTAAAGCTTATGAAAAAGAAGCTGGAGTAAAAGTCACTCTTAAAACT

GGTGATGCTCTAGGAGGTCTTGATAAACTTTCTCTTGACAACCAATCTGGTAATGTCCCTGATGTTATGATGGCT

CCATACGACCGTGTAGGTAGCCTTGGTTCTGACGGACAACTTTCAGAAGTGAAATTGAGCGATGGTGCTAAAACA

GACGACACAACTAAATCTCTTGTAACAGCTGCTAATGGTAAAGTTTACGGTGCTCCTGCCGTTATCGAGTCACTT

GTTATGTACTACAACAAAGACTTGGTGAAAGATGCTCCAAAAACATTTGCTGACTTGGAAAACCTTGCTAAAGAT

| SEQUENCES |
| --- |

AGCAAATACGCATTCGCTGGTGAAGATGGTAAAACTACTGCCTTCCTAGCTGACTGGACAAACTTCTACTATACA

TATGGACTTCTTGCCGGTAACGGTGCTTACGTCTTTGGCCAAAACGGTAAAGACGCTAAAGACATCGGTCTTGCA

AACGACGGTTCTATCGTAGGTATCAACTACGCTAAATCTTGGTACGAAAAATGGCCTAAAGGTATGCAAGATACA

GAAGGTGCTGGAAACTTAATCCAAACTCAATTCCAAGAAGGTAAAACAGCTGCTATCATCGACGGACCTTGGAAA

GCTCAAGCCTTTAAAGATGCTAAAGTAAACTACGGAGTTGCAACTATCCCAACTCTTCCAAATGGAAAAGAATAT

GCTGCATTCGGTGGTGGTAAAGCTTGGGTCATTCCTCAAGCCGTTAAGAACCTTGAAGCTTCTCAAAAATTTGTA

GACTTCCTTGTTGCAACTGAACAACAAAAAGTATTATATGATAAGACTAACGAAATCCCAGCTAATACTGAGGCT

CGTTCATACGCTGAAGGTAAAAACGATGAGTTGACAACAGCTGTTATCAAACAGTTCAAGAACACTCAACCACTG

CCAAACATCTCTCAAATGTCTGCAGTTTGGGATCCAGCGAAAAATATGCTCTTTGATGCTGTAAGTGGTCAAAAA

GATGCTAAAACAGCTGCTAACGATGCTGTAACATTGATCAAAGAAACAATCAAACAAAAATTTGGTGAAAATGGT

ATGAAAGCTAAAAAAATGTGGATGGCAGGCTTGGCTCTGCTAGGTATCGGAAGCCTTGCTCTTGCTACGAAAAAA

GTTGCAGATGACCGTAAGCTCATGAAGACTCAGGAAGAGTTGACAGAGATTGTGCGAGACCATTTTTCCGACATG

GGGGAAATTGCGACCCTTTATGTTCAAGTTTACGAAAGCAGTCTGGAGAGCTTGGTTGGTGGCGTCATTTTTGAG

GATGGCCGTCATTATACCTTTGTCTATGAAAATGAAGACCTAGTCTATGAGGAGGAAGTCTTA

SP0148/SP1912 fusion (nucleotides)

SEQ ID NO: 59

ATGAAAAAAATCGTTAAATACTCATCTCTTGCAGCCCTTGCTCTTGTTGCTGCAGGTGTGCTTGCGGCTTGCTCA

GGGGGTGCTAAGAAAGAAGGAGAAGCAGCTAGCAAGAAAGAAATCATCGTTGCAACCAATGGATCACCAAAGCCA

TTTATCTATGAAGAAATGGCGAATTGACTGGTTACGAGATTGAAGTCGTTCGCGCTATCTTTAAAGATTCTGAC

AAATATGATGTCAAGTTTGAAAAGACAGAATGGTCAGGTGTCTTTGCTGGTCTTGACGCTGATCGTTACAATATG

GCTGTCAACAATCTTAGCTACACTAAAGAACGTGCGGAGAAATACCTCTATGCCGCACCAATTGCCCAAAATCCT

AATGTCCTTGTCGTGAAGAAAGATGACTCTAGTATCAAGTCTCTCGATGATATCGGTGGAAAATCGACGGAAGTC

GTTCAAGCCACTACATCAGCTAAGCAGTTAGAAGCATACAATGCTGAACACACGGACAACCCAACTATCCTTAAC

TATACTAAGGCAGACTTCCAACAAATCATGGTACGTTTGAGCGATGGACAATTTGACTATAAGATTTTTGATAAA

ATCGGTGTTGAAACAGTGATCAAGAACCAAGGTTTGGACAACTTGAAAGTTATCGAACTTCCAAGCGACCAACAA

CCGTACGTTTACCCACTTCTTGCTCAGGGTCAAGATGAGTTGAAATCGTTTGTAGACAAACGCATCAAAGAACTT

TATAAAGATGGAACTCTTGAAAAATTGTCTAAACAATTCTTCGGAGACACTTATCTACCGGCAGAAGCTGATATT

AAAAATGGTATGAAAGCTAAAAAAATGTGGATGGCAGGCTTGGCTCTGCTAGGTATCGGAAGCCTTGCTCTTGCT

ACGAAAAAAGTTGCAGATGACCGTAAGCTCATGAAGACTCAGGAAGAGTTGACAGAGATTGTGCGAGACCATTTT

TCCGACATGGGGGAAATTGCGACCCTTTATGTTCAAGTTTACGAAAGCAGTCTGGAGAGCTTGGTTGGTGGCGTC

ATTTTTGAGGATGGCCGTCATTATACCTTTGTCTATGAAAATGAAGACCTAGTCTATGAGGAGGAAGTCTTA

SP2108/SP1912/SP0148 fusion (nucleotides)

SEQ ID NO: 60

ATGTCATCTAAATTTATGAAGAGCGCTGCGGTGCTTGGAACTGCTACACTTGCTAGCTTGCTTTTGGTAGCTTGC

GGAAGCAAAACTGCTGATAAGCCTGCTGATTCTGGTTCATCTGAAGTCAAAGAACTCACTGTATATGTAGACGAG

GGATATAAGAGCTATATTGAAGAGGTTGCTAAAGCTTATGAAAAGAAGCTGGAGTAAAAGTCACTCTTAAAACT

GGTGATGCTCTAGGAGGTCTTGATAAACTTTCTCTTGACAACCAATCTGGTAATGTCCCTGATGTTATGATGGCT

CCATACGACCGTGTAGGTAGCCTTGGTTCTGACGGACAACTTTCAGAAGTGAAATTGAGCGATGGTGCTAAAACA

GACGACACAACTAAATCTCTTGTAACAGCTGCTAATGGTAAAGTTTACGGTGCTCCTGCCGTTATCGAGTCACTT

GTTATGTACTACAACAAAGACTTGGTGAAAGATGCTCCAAAAACATTTGCTGACTTGGAAAACCTTGCTAAAGAT

| SEQUENCES |
| --- |
| AGCAAATACGCATTCGCTGGTGAAGATGGTAAAACTACTGCCTTCCTAGCTGACTGGACAAACTTCTACTATACA |
| TATGGACTTCTTGCCGGTAACGGTGCTTACGTCTTTGGCCAAAACGGTAAAGACGCTAAAGACATCGGTCTTGCA |
| AACGACGGTTCTATCGTAGGTATCAACTACGCTAAATCTTGGTACGAAAAATGGCCTAAAGGTATGCAAGATACA |
| GAAGGTGCTGGAAACTTAATCCAAACTCAATTCCAAGAAGGTAAAACAGCTGCTATCATCGACGGACCTTGGAAA |
| GCTCAAGCCTTTAAAGATGCTAAAGTAAACTACGGAGTTGCAACTATCCCAACTCTTCCAAATGGAAAAGAATAT |
| GCTGCATTCGGTGGTGGTAAAGCTTGGGTCATTCCTCAAGCCGTTAAGAACCTTGAAGCTTCTCAAAAATTTGTA |
| GACTTCCTTGTTGCAACTGAACAACAAAAAGTATTATATGATAAGACTAACGAAATCCCAGCTAATACTGAGGCT |
| CGTTCATACGCTGAAGGTAAAAACGATGAGTTGACAACAGCTGTTATCAAACAGTTCAAGAACACTCAACCACTG |
| CCAAACATCTCTCAAATGTCTGCAGTTTGGGATCCAGCGAAAAATATGCTCTTTGATGCTGTAAGTGGTCAAAAA |
| GATGCTAAAACAGCTGCTAACGATGCTGTAACATTGATCAAAGAAACAATCAAACAAAAATTTGGTGAAAATGGT |
| ATGAAAGCTAAAAAAATGTGGATGGCAGGCTTGGCTCTGCTAGGTATCGGAAGCCTTGCTCTTGCTACGAAAAAA |
| GTTGCAGATGACCGTAAGCTCATGAAGACTCAGGAAGAGTTGACAGAGATTGTGCGAGACCATTTTTCCGACATG |
| GGGGAAATTGCGACCCTTTATGTTCAAGTTTACGAAAGCAGTCTGGAGAGCTTGGTTGGTGGCGTCATTTTTGAG |
| GATGGCCGTCATTATACCTTTGTCTATGAAAATGAAGACCTAGTCTATGAGGAGGAAGTCTTATGCTCAGGGGGT |
| GCTAAGAAAGAAGGAGAAGCAGCTAGCAAGAAAGAAATCATCGTTGCAACCAATGGATCACCAAAGCCATTTATC |
| TATGAAGAAAATGGCGAATTGACTGGTTACGAGATTGAAGTCGTTCGCGCTATCTTTAAAGATTCTGACAAATAT |
| GATGTCAAGTTTGAAAAGACAGAATGGTCAGGTGTCTTTGCTGGTCTTGACGCTGATCGTTACAATATGGCTGTC |
| AACAATCTTAGCTACACTAAAGAACGTGCGGAGAAATACCTCTATGCCGCACCAATTGCCCAAAATCCTAATGTC |
| CTTGTCGTGAAGAAAGATGACTCTAGTATCAAGTCTCTCGATGATATCGGTGGAAAATCGACGGAAGTCGTTCAA |
| GCCACTACATCAGCTAAGCAGTTAGAAGCATACAATGCTGAACACACGGACAACCCAACTATCCTTAACTATACT |
| AAGGCAGACTTCCAACAAATCATGGTACGTTTGAGCGATGGACAATTTGACTATAAGATTTTTGATAAAATCGGT |
| GTTGAAACAGTGATCAAGAACCAAGGTTTGGACAACTTGAAAGTTATCGAACTTCCAAGCGACCAACAACCGTAC |
| GTTTACCCACTTCTTGCTCAGGGTCAAGATGAGTTGAAATCGTTTGTAGACAAACGCATCAAAGAACTTTATAAA |
| GATGGAACTCTTGAAAAATTGTCTAAACAATTCTTCGGAGACACTTATCTACCGGCAGAAGCTGATATTAAA |

SP0148/SP1912/SP2108 fusion (nucleotides)
SEQ ID NO: 61

| |
| --- |
| ATGAAAAAAATCGTTAAATACTCATCTCTTGCAGCCCTTGCTCTTGTTGCTGCAGGTGTGCTTGCGGCTTGCTCA |
| GGGGGTGCTAAGAAAGAAGGAGAAGCAGCTAGCAAGAAAGAAATCATCGTTGCAACCAATGGATCACCAAAGCCA |
| TTTATCTATGAAGAAAATGGCGAATTGACTGGTTACGAGATTGAAGTCGTTCGCGCTATCTTTAAAGATTCTGAC |
| AAATATGATGTCAAGTTTGAAAAGACAGAATGGTCAGGTGTCTTTGCTGGTCTTGACGCTGATCGTTACAATATG |
| GCTGTCAACAATCTTAGCTACACTAAAGAACGTGCGGAGAAATACCTCTATGCCGCACCAATTGCCCAAAATCCT |
| AATGTCCTTGTCGTGAAGAAAGATGACTCTAGTATCAAGTCTCTCGATGATATCGGTGGAAAATCGACGGAAGTC |
| GTTCAAGCCACTACATCAGCTAAGCAGTTAGAAGCATACAATGCTGAACACACGGACAACCCAACTATCCTTAAC |
| TATACTAAGGCAGACTTCCAACAAATCATGGTACGTTTGAGCGATGGACAATTTGACTATAAGATTTTTGATAAA |
| ATCGGTGTTGAAACAGTGATCAAGAACCAAGGTTTGGACAACTTGAAAGTTATCGAACTTCCAAGCGACCAACAA |
| CCGTACGTTTACCCACTTCTTGCTCAGGGTCAAGATGAGTTGAAATCGTTTGTAGACAAACGCATCAAAGAACTT |
| TATAAAGATGGAACTCTTGAAAAATTGTCTAAACAATTCTTCGGAGACACTTATCTACCGGCAGAAGCTGATATT |
| AAAAATGGTATGAAAGCTAAAAAAATGTGGATGGCAGGCTTGGCTCTGCTAGGTATCGGAAGCCTTGCTCTTGCT |
| ACGAAAAAAGTTGCAGATGACCGTAAGCTCATGAAGACTCAGGAAGAGTTGACAGAGATTGTGCGAGACCATTTT |
| TCCGACATGGGGGAAATTGCGACCCTTTATGTTCAAGTTTACGAAAGCAGTCTGGAGAGCTTGGTTGGTGGCGTC |

| SEQUENCES |
|---|

ATTTTTGAGGATGGCCGTCATTATACCTTTGTCTATGAAAATGAAGACCTAGTCTATGAGGAGGAAGTCTTAGGA
AGCAAAACTGCTGATAAGCCTGCTGATTCTGGTTCATCTGAAGTCAAAGAACTCACTGTATATGTAGACGAGGGA
TATAAGAGCTATATTGAAGAGGTTGCTAAAGCTTATGAAAAAGAAGCTGGAGTAAAAGTCACTCTTAAAACTGGT
GATGCTCTAGGAGGTCTTGATAAACTTTCTCTTGACAACCAATCTGGTAATGTCCCTGATGTTATGATGGCTCCA
TACGACCGTGTAGGTAGCCTTGGTTCTGACGGACAACTTTCAGAAGTGAAATTGAGCGATGGTGCTAAAACAGAC
GACACAACTAAATCTCTTGTAACAGCTGCTAATGGTAAAGTTTACGGTGCTCCTGCCGTTATCGAGTCACTTGTT
ATGTACTACAACAAAGACTTGGTGAAAGATGCTCCAAAAACATTTGCTGACTTGGAAAACCTTGCTAAAGATAGC
AAATACGCATTCGCTGGTGAAGATGGTAAAACTACTGCCTTCCTAGCTGACTGGACAAACTTCTACTATACATAT
GGACTTCTTGCCGGTAACGGTGCTTACGTCTTTGGCCAAAACGGTAAAGACGCTAAAGACATCGGTCTTGCAAAC
GACGGTTCTATCGTAGGTATCAACTACGCTAAATCTTGGTACGAAAAATGGCCTAAAGGTATGCAAGATACAGAA
GGTGCTGGAAACTTAATCCAAACTCAATTCCAAGAAGGTAAAACAGCTGCTATCATCGACGGACCTTGGAAAGCT
CAAGCCTTTAAAGATGCTAAAGTAAACTACGGAGTTGCAACTATCCCAACTCTTCCAAATGGAAAAGAATATGCT
GCATTCGGTGGTGGTAAAGCTTGGGTCATTCCTCAAGCCGTTAAGAACCTTGAAGCTTCTCAAAAATTTGTAGAC
TTCCTTGTTGCAACTGAACAACAAAAAGTATTATATGATAAGACTAACGAAATCCCAGCTAATACTGAGGCTCGT
TCATACGCTGAAGGTAAAAACGATGAGTTGACAACAGCTGTTATCAAACAGTTCAAGAACACTCAACCACTGCCA
AACATCTCTCAAATGTCTGCAGTTTGGGATCCAGCGAAAAATATGCTCTTTGATGCTGTAAGTGGTCAAAAAGAT
GCTAAAACAGCTGCTAACGATGCTGTAACATTGATCAAAGAAACAATCAAACAAAAATTTGGTGAACACCACCAC
CACCACCACTGA

SP2108/SP0148/SP1912 fusion (nucleotides)  
SEQ ID NO: 62  
ATGTCATCTAAATTTATGAAGAGCGCTGCGGTGCTTGGAACTGCTACACTTGCTAGCTTGCTTTTGGTAGCTTGC
GGAAGCAAAACTGCTGATAAGCCTGCTGATTCTGGTTCATCTGAAGTCAAAGAACTCACTGTATATGTAGACGAG
GGATATAAGAGCTATATTGAAGAGGTTGCTAAAGCTTATGAAAAAGAAGCTGGAGTAAAAGTCACTCTTAAAACT
GGTGATGCTCTAGGAGGTCTTGATAAACTTTCTCTTGACAACCAATCTGGTAATGTCCCTGATGTTATGATGGCT
CCATACGACCGTGTAGGTAGCCTTGGTTCTGACGGACAACTTTCAGAAGTGAAATTGAGCGATGGTGCTAAAACA
GACGACACAACTAAATCTCTTGTAACAGCTGCTAATGGTAAAGTTTACGGTGCTCCTGCCGTTATCGAGTCACTT
GTTATGTACTACAACAAAGACTTGGTGAAAGATGCTCCAAAAACATTTGCTGACTTGGAAAACCTTGCTAAAGAT
AGCAAATACGCATTCGCTGGTGAAGATGGTAAAACTACTGCCTTCCTAGCTGACTGGACAAACTTCTACTATACA
TATGGACTTCTTGCCGGTAACGGTGCTTACGTCTTTGGCCAAAACGGTAAAGACGCTAAAGACATCGGTCTTGCA
AACGACGGTTCTATCGTAGGTATCAACTACGCTAAATCTTGGTACGAAAAATGGCCTAAAGGTATGCAAGATACA
GAAGGTGCTGGAAACTTAATCCAAACTCAATTCCAAGAAGGTAAAACAGCTGCTATCATCGACGGACCTTGGAAA
GCTCAAGCCTTTAAAGATGCTAAAGTAAACTACGGAGTTGCAACTATCCCAACTCTTCCAAATGGAAAAGAATAT
GCTGCATTCGGTGGTGGTAAAGCTTGGGTCATTCCTCAAGCCGTTAAGAACCTTGAAGCTTCTCAAAAATTTGTA
GACTTCCTTGTTGCAACTGAACAACAAAAAGTATTATATGATAAGACTAACGAAATCCCAGCTAATACTGAGGCT
CGTTCATACGCTGAAGGTAAAAACGATGAGTTGACAACAGCTGTTATCAAACAGTTCAAGAACACTCAACCACTG
CCAAACATCTCTCAAATGTCTGCAGTTTGGGATCCAGCGAAAAATATGCTCTTTGATGCTGTAAGTGGTCAAAAA
GATGCTAAAACAGCTGCTAACGATGCTGTAACATTGATCAAAGAAACAATCAAACAAAAATTTGGTGAATCAGGG
GGTGCTAAGAAAGAAGGAGAAGCAGCTAGCAAGAAAGAAATCATCGTTGCAACCAATGGATCACCAAAGCCATTT
ATCTATGAAGAAAATGGCGAATTGACTGGTTACGAGATTGAAGTCGTTCGCGCTATCTTTAAAGATTCTGACAAA

| SEQUENCES |
|---|
| TATGATGTCAAGTTTGAAAAGACAGAATGGTCAGGTGTCTTTGCTGGTCTTGACGCTGATCGTTACAATATGGCT |
| GTCAACAATCTTAGCTACACTAAAGAACGTGCGGAGAAATACCTCTATGCCGCACCAATTGCCCAAAATCCTAAT |
| GTCCTTGTCGTGAAGAAAGATGACTCTAGTATCAAGTCTCTCGATGATATCGGTGGAAAATCGACGGAAGTCGTT |
| CAAGCCACTACATCAGCTAAGCAGTTAGAAGCATACAATGCTGAACACACGGACAACCCAACTATCCTTAACTAT |
| ACTAAGGCAGACTTCCAACAAATCATGGTACGTTTGAGCGATGGACAATTTGACTATAAGATTTTTGATAAAATC |
| GGTGTTGAAACAGTGATCAAGAACCAAGGTTTGGACAACTTGAAAGTTATCGAACTTCCAAGCGACCAACAACCG |
| TACGTTTACCCACTTCTTGCTCAGGGTCAAGATGAGTTGAAATCGTTTGTAGACAAACGCATCAAAGAACTTTAT |
| AAAGATGGAACTCTTGAAAAATTGTCTAAACAATTCTTCGGAGACACTTATCTACCGGCAGAAGCTGATATTAAA |
| AATGGTATGAAAGCTAAAAAAATGTGGATGGCAGGCTTGGCTCTGCTAGGTATCGGAAGCCTTGCTCTTGCTACG |
| AAAAAAGTTGCAGATGACCGTAAGCTCATGAAGACTCAGGAAGAGTTGACAGAGATTGTGCGAGACCATTTTTCC |
| GACATGGGGGAAATTGCGACCCTTTATGTTCAAGTTTACGAAAGCAGTCTGGAGAGCTTGGTTGGTGGCGTCATT |
| TTTGAGGATGGCCGTCATTATACCTTTGTCTATGAAAATGAAGACCTAGTCTATGAGGAGGAAGTCTTA |

SP0148/SP2108/SP1912 fusion (nucleotides)

SEQ ID NO: 63

| ATGAAAAAAATCGTTAAATACTCATCTCTTGCAGCCCTTGCTCTTGTTGCTGCAGGTGTGCTTGCGGCTTGCTCA |
|---|
| GGGGGTGCTAAGAAAGAAGGAGAAGCAGCTAGCAAGAAAGAAATCATCGTTGCAACCAATGGATCACCAAAGCCA |
| TTTATCTATGAAGAAATGGCGAATTGACTGGTTACGAGATTGAAGTCGTTCGCGCTATCTTTAAAGATTCTGAC |
| AAATATGATGTCAAGTTTGAAAAGACAGAATGGTCAGGTGTCTTTGCTGGTCTTGACGCTGATCGTTACAATATG |
| GCTGTCAACAATCTTAGCTACACTAAAGAACGTGCGGAGAAATACCTCTATGCCGCACCAATTGCCCAAAATCCT |
| AATGTCCTTGTCGTGAAGAAAGATGACTCTAGTATCAAGTCTCTCGATGATATCGGTGGAAAATCGACGGAAGTC |
| GTTCAAGCCACTACATCAGCTAAGCAGTTAGAAGCATACAATGCTGAACACACGGACAACCCAACTATCCTTAAC |
| TATACTAAGGCAGACTTCCAACAAATCATGGTACGTTTGAGCGATGGACAATTTGACTATAAGATTTTTGATAAA |
| ATCGGTGTTGAAACAGTGATCAAGAACCAAGGTTTGGACAACTTGAAAGTTATCGAACTTCCAAGCGACCAACAA |
| CCGTACGTTTACCCACTTCTTGCTCAGGGTCAAGATGAGTTGAAATCGTTTGTAGACAAACGCATCAAAGAACTT |
| TATAAAGATGGAACTCTTGAAAAATTGTCTAAACAATTCTTCGGAGACACTTATCTACCGGCAGAAGCTGATATT |
| AAAGGAAGCAAAACTGCTGATAAGCCTGCTGATTCTGGTTCATCTGAAGTCAAAGAACTCACTGTATATGTAGAC |
| GAGGGATATAAGAGCTATATTGAAGAGGTTGCTAAAGCTTATGAAAAGAAGCTGGAGTAAAAGTCACTCTTAAA |
| ACTGGTGATGCTCTAGGAGGTCTTGATAAACTTTCTCTTGACAACCAATCTGGTAATGTCCCTGATGTTATGATG |
| GCTCCATACGACCGTGTAGGTAGCCTTGGTTCTGACGGACAACTTTCAGAAGTGAAATTGAGCGATGGTGCTAAA |
| ACAGACGACACAACTAAATCTCTTGTAACAGCTGCTAATGGTAAAGTTTACGGTGCTCCTGCCGTTATCGAGTCA |
| CTTGTTATGTACTACAACAAAGACTTGGTGAAAGATGCTCCAAAAACATTTGCTGACTTGGAAAACCTTGCTAAA |
| GATAGCAAATACGCATTCGCTGGTGAAGATGGTAAAACTACTGCCTTCCTAGCTGACTGGACAAACTTCTACTAT |
| ACATATGGACTTCTTGCCGGTAACGGTGCTTACGTCTTTGGCCAAAACGGTAAAGACGCTAAAGACATCGGTCTT |
| GCAAACGACGGTTCTATCGTAGGTATCAACTACGCTAAATCTTGGTACGAAAATGGCCTAAAGGTATGCAAGAT |
| ACAGAAGGTGCTGGAAACTTAATCCAAACTCAATTCCAAGAAGGTAAAACAGCTGCTATCATCGACGGACCTTGG |
| AAAGCTCAAGCCTTTAAAGATGCTAAAGTAAACTACGGAGTTGCAACTATCCCAACTCTTCCAAATGGAAAAGAA |
| TATGCTGCATTCGGTGGTGGTAAAGCTTGGGTCATTCCTCAAGCCGTTAAGAACCTTGAAGCTTCTCAAAAATTT |
| GTAGACTTCCTTGTTGCAACTGAACAACAAAAAGTATTATATGATAAGACTAACGAAATCCCAGCTAATACTGAG |
| GCTCGTTCATACGCTGAAGGTAAAAACGATGAGTTGACAACAGCTGTTATCAAACAGTTCAAGAACACTCAACCA |
| CTGCCAAACATCTCTCAAATGTCTGCAGTTTGGGATCCAGCGAAAAATATGCTCTTTGATGCTGTAAGTGGTCAA |

-continued

| SEQUENCES |
|---|

AAAGATGCTAAAACAGCTGCTAACGATGCTGTAACATTGATCAAAGAAACAATCAAACAAAAATTTGGTGAAAAT
GGTATGAAAGCTAAAAAAATGTGGATGGCAGGCTTGGCTCTGCTAGGTATCGGAAGCCTTGCTCTTGCTACGAAA
AAAGTTGCAGATGACCGTAAGCTCATGAAGACTCAGGAAGAGTTGACAGAGATTGTGCGAGACCATTTTTCCGAC
ATGGGGGAAATTGCGACCCTTTATGTTCAAGTTTACGAAAGCAGTCTGGAGAGCTTGGTTGGTGGCGTCATTTTT
GAGGATGGCCGTCATTATACCTTTGTCTATGAAAATGAAGACCTAGTCTATGAGGAGGAAGTCTTA

SEQ ID NO: 64

HHHHHH

SEQ ID NO: 65

MSYYHHHHHH

Canonical lipobox motif

SEQ ID NO: 66

[LIVMFESTAGPC]-[LVIAMFTG]-[IVMSTAGCP]-[AGS]-C

SP2108 signal sequence

SEQ ID NO: 67

MSSKFMKSAAVLGTATLASLLLVAC

*E. coli* RlpB signal sequence

SEQ ID NO: 68

MRYLATLLLSLAVLITAG[C]

Fusion protein linker (19-mer)

SEQ ID NO: 69

LGGGGSGGGGSGGGGSAAA

Fusion protein LR linker (20-mer)

SEQ ID NO: 70

LAEATAKEATAKEATAKATA

Fusion protein LC linker (14-mer)

SEQ ID NO: 71

GPKPHRIQSTPKGS

Amino-terminal boundary to the PR-region

SEQ ID NO: 72

DLKKAVNE

Carboxy-terminal boundary to the PR-region

SEQ ID NO: 73

(K/G)TGW(K/G)QENGMW

---

We claim:

1. A fusion protein comprising:
 a first polypeptide comprising an amino acid sequence with at least 95% sequence identity to the amino acid sequence of SEQ ID NO: 6 or to the amino acid sequence of SEQ ID NO: 5; and
 a second polypeptide comprising an amino acid sequence with at least 95% sequence identity to the amino acid sequence of SEQ ID NO: 9.

2. The fusion protein of claim 1, wherein the first polypeptide comprises the amino acid sequence of SEQ ID NO: 6 or comprises the amino acid sequence of SEQ ID NO: 5, and the second polypeptide comprises the amino acid sequence of SEQ ID NO: 9.

3. The fusion protein of claim 1, wherein the first polypeptide consists of the amino acid sequence of SEQ ID NO: 6 or consists of the amino acid sequence of SEQ ID NO: 5.

4. The fusion protein of claim 1, wherein the second polypeptide consists of the amino acid sequence of SEQ ID NO: 9.

5. The fusion protein of claim 1, wherein the fusion protein comprises the amino acid sequence of SEQ ID NO: 49.

6. The fusion protein of claim 1, wherein the fusion protein consists of the amino acid sequence of SEQ ID NO: 49.

7. The fusion protein of claim 1, further comprising a third polypeptide comprising an amino acid sequence with at least 95% sequence identity to the amino acid sequence of SEQ ID NO: 2 or to the amino acid sequence of SEQ ID NO: 1.

8. The fusion protein of claim 7, wherein the third polypeptide comprises the amino acid sequence of SEQ ID NO: 2 or comprises the amino acid sequence of SEQ ID NO: 1.

9. The fusion protein of claim 7, wherein the third polypeptide consists of the amino acid sequence of SEQ ID NO: 2 or consists of the amino acid sequence of SEQ ID NO: 1.

10. The fusion protein of claim 7, wherein the fusion protein comprises the amino acid sequence of SEQ ID NO:53.

11. The fusion protein of claim 7, wherein the fusion protein consists of the amino acid sequence of SEQ ID NO:53.

12. The fusion protein of claim 7, wherein the fusion protein comprises the amino acid sequence of SEQ ID NO: 52.

13. The fusion protein of claim 7, wherein the fusion protein consists of the amino acid sequence of SEQ ID NO: 52.

14. The fusion protein of claim 1, wherein the fusion protein is lipidated.

15. An immunogenic composition comprising a pharmaceutically acceptable carrier and the fusion protein of claim 1.

16. The immunogenic composition of claim 15, further comprising an adjuvant.

17. The immunogenic composition of claim 15, wherein the immunogenic composition comprises 1-1000 µg of the fusion protein.

18. The fusion protein of claim 1, wherein the fusion protein comprises an amino acid sequence with at least 95% sequence identity to the amino acid sequence of SEQ ID NO: 49.

19. The fusion protein of claim 7, wherein the fusion protein comprises an amino acid sequence with at least 95% sequence identity to the amino acid sequence of SEQ ID NO: 53.

20. The fusion protein of claim 7, wherein the fusion protein comprises an amino acid sequence with at least 95% sequence identity to the amino acid sequence of SEQ ID NO: 52.

* * * * *